United States Patent
Sapieha et al.

(10) Patent No.: US 12,031,137 B2
(45) Date of Patent: *Jul. 9, 2024

(54) COMPOSITIONS COMPRISING SASP MODULATORS AND SENESCENCE ATTENUATORS AND USES THEREOF FOR MODULATING CELLULAR SENESCENCE

(71) Applicant: RSEM, LIMITED PARTNERSHIP, Montreal (CA)

(72) Inventors: Przemyslaw Sapieha, Beaconsfield (CA); Frédérick Antoine Mallette, Montreal (CA); Malika Oubaha, Montreal (CA); Normand Beaulieu, Montreal (CA); Ariel Wilson, Montreal (CA)

(73) Assignee: RSEM, LIMITED PARTNERSHIP, Montreal (CA)

( * ) Notice: Subject to any disclaimer, the term of this patent is extended or adjusted under 35 U.S.C. 154(b) by 188 days.

This patent is subject to a terminal disclaimer.

(21) Appl. No.: 17/302,113

(22) Filed: Apr. 23, 2021

(65) Prior Publication Data

US 2022/0098594 A1 Mar. 31, 2022

Related U.S. Application Data

(63) Continuation of application No. 16/335,896, filed as application No. PCT/CA2017/051120 on Sep. 9, 2017, now abandoned.

(Continued)

(51) Int. Cl.
A61K 47/68 (2017.01)
A61K 31/155 (2006.01)
(Continued)

(52) U.S. Cl.
CPC ........ *C12N 15/1138* (2013.01); *A61K 31/155* (2013.01); *A61K 31/7088* (2013.01);
(Continued)

(58) Field of Classification Search
None
See application file for complete search history.

(56) References Cited

U.S. PATENT DOCUMENTS

2016/0002641 A1 1/2016 Sapieha

FOREIGN PATENT DOCUMENTS

| EP | 1306093 A1 | 5/2003 | |
| EP | 2497498 A1 * | 9/2012 | ............... A61P 1/02 |

(Continued)

OTHER PUBLICATIONS

Jiang et al., Neuropilin 1 directly interacts with Fer Kinase to mediate Semaphorin 3A-induced death of cortical neurons. J. Biol> Chem. 2010, 285; 9908-9918 (Year: 2010).*

(Continued)

*Primary Examiner* — Aurora M Fontainhas
(74) *Attorney, Agent, or Firm* — Lavery, de Billy, L.L.P.; Alain Dumont

(57) ABSTRACT

Described herein are compositions and methods for modulating cellular senescence of a cell or induction of the senescence-associated secretory phenotype (SASP) in a cell. The methods generally comprise modulating the level or activity of IRE1a as a mean to control cellular senescence and induction of the SASP. Also described are methods for treating and preventing ocular vascular diseases comprising contacting cells in an eye of a subject with a biguanide compound and ophthalmic compositions comprising a biguanide compound.

12 Claims, 47 Drawing Sheets

Specification includes a Sequence Listing.

Related U.S. Application Data

(60) Provisional application No. 62/398,797, filed on Sep. 23, 2016, provisional application No. 62/398,819, filed on Sep. 23, 2016, provisional application No. 62/398,183, filed on Sep. 22, 2016.

(51) Int. Cl.

| | | |
|---|---|---|
| *A61K 31/7088* | (2006.01) | |
| *A61K 38/17* | (2006.01) | |
| *A61P 3/04* | (2006.01) | |
| *C07K 16/28* | (2006.01) | |
| *C12N 15/113* | (2010.01) | |
| *C12N 15/62* | (2006.01) | |

(52) U.S. Cl.
CPC .............. *A61K 38/179* (2013.01); *A61P 3/04* (2018.01); *C07K 16/2863* (2013.01); *C07K 2319/30* (2013.01); *C12N 2310/111* (2013.01); *C12N 2310/122* (2013.01); *C12N 2310/531* (2013.01)

(56) References Cited

FOREIGN PATENT DOCUMENTS

| | | |
|---|---|---|
| WO | 2015/070280 A1 | 5/2015 |
| WO | 2015/138634 A1 | 9/2015 |
| WO | 2016/033699 A1 | 3/2016 |

OTHER PUBLICATIONS

Cerani, Neuron-Derived Semaphorin 3A is an Early Inducer of Vascular Permeability in Diabetic Retinopathy. University of Montreal Thesis 2012 (Year: 2012).*
Gu et al., 2002 Characterization of Neuropilin-1 Structural Features That Confer Binding to Semaphorin3A and Vascular Endothelial Growth Factor 165. The Journal of Biological Chemistry 277, 18069-18076. (Year: 2002).*
Qiu, Q. et al., "Toll-like receptor-mediated IRE1alpha activation as a therapeutic target for inflammatory arthritis", EMBO J 32, 2477-2490 (2013).
Sapieha, P. et al., "Retinopathy of prematurity: understanding ischemic retinal vasculopathies at an extreme of life", J Clin Invest 120, 3022-3032 (2010).
Sapieha, P. et al., "Omega-3 polyunsaturated fatty acids preserve retinal function in type 2 diabetic mice", Nutr Diabetes 2, e36 (2012).
Sapieha, P., "Eyeing central neurons in vascular growth and reparative angiogenesis", Blood 120, 2182-2194 (2012).
Stahl, A. et al., "Postnatal Weight Gain Modifies Severity and Functional Outcome of Oxygen-Induced Proliferative Retinopathy", Am J Pathol. vol. 177, No. 6, Dec. 2010.
Stahl, A. et al., "Computer-aided quantification of retinal neovascularization", Angiogenesis 12, 297-301 (2009).
Stahl, A. et al., "The mouse retina as an angiogenesis model", Invest Ophthalmol Vis Sci 51, 2813-2826 (2010).
Shirvan, A. et al., "Anti-semaphorin 3A Antibodies Rescue Retinal Ganglion Cells from Cell Death following Optic Nerve Axotomy", JBC 277 (51): 49799-49807(2002).
Smith, L.E. et al., "Oxygen-induced retinopathy in the mouse", Invest Ophthalmol Vis Sci 35, 101-111 (1994).
Storer, M. et al., "Senescence is a developmental mechanism that contributes to embryonic growth and patterning", Cell 155, 1119-1130 (2013).
Tabas, I., et al., "Integrating the mechanisms of apoptosis induced by endoplasmic reticulum stress", Nat Cell Biol 13, 184-190 (2011).
Thompson, A.F., et al., "Induction of Neuronal Morphology in the 661W Cone Photoreceptor Cell Line with Staurosporine", PLoS One 10, e0145270 (2015).
Usui, Y. et al., "Neurovascular crosstalk between interneurons and capillaries is required for vision", J Clin Invest 125, 2335-2346 (2015).
Wajapeyee, N. et al., "Oncogenic BRAF induces senescence and apoptosis through pathways mediated by the secreted protein IGFBP7", Cell 132, 363-374 (2008).
Wei, Y. et al., "Nrf2 in ischemic neurons promotes retinal vascular regeneration through regulation of semaphorin 6A", Proceedings of the National Academy of Sciences of the United States of America 112, E6927-30 6936 (2015).
Wiley, C.D. et al., "From Ancient Pathways to Aging Cells-Connecting Metabolism and Cellular Senescence", Cell Metab 23, 1013-1021 (2016).
Zhang, K. et al., "The unfolded protein response transducer IRE1a prevents ER stress-induced hepatic steatosis", EMBO Journal 30, 1357-1375 (2011).
International Search Report and Written Opinion in respect of PCT Application No. PCT/CA2017/051120.
Erika Check Hayden, "Aging pushed as treatable condition", Nature, vol. 522, p. 265, Jun. 18, 2015.
Acosta, J. et al., "A complex secretory program orchestrated by the inflammasome controls paracrine senescence", Nature Cell Biology 15, 978-990 (2013).
Acosta, J. et al., "Chemokine signaling via the CXCR2 receptor reinforces senescence", Cell 133, 1006-1018 (2008).
Aiello, L. P. et al., "Suppression of retinal neovascularization in vivo by inhibition of vascular endothelial growth factor (VEGF) using soluble VEGF-receptor chimeric proteins", Proc Natl Acad Sci US A 92, 10457-10461 (1995).
Aiello, L, "Perspectives on diabetic retinopathy", American journal of ophthalmology 136, 122-135 (2003) (Abstract only).
Antipenko, A. et al., "Structure of the semaphorin-3A receptor binding module", Neuron 39: 589-598 (2003).
Asnaghi, V. C. et al., "A role for the polyol pathway in the early neuroretinal apoptosis and glial changes induced by diabetes in the rat", Diabetes 52, 506-511 (2003).
Bai, Y. et al., "Effects of semaphorin 3A on retinal pigment epithelial cell activity. Investigative ophthalmology & visual science 54", 6628-6638 (2013).
Baker, D.J. et al., "Clearance of p16Ink4a-positive senescent cells delays ageing-associated disorders", Nature 479, 232-236 (2011).
Baker D.J. et al., "Naturally occurring p16(Ink4a)-positive cells shorten healthy lifespan", Nature 530, 184-189 (2016).
Barber, A.J. et al., "Neural apoptosis in the retina during experimental and human diabetes", Early onset and effect of insulin. J Clin Invest 102, 783-791 (1998).
Barber, A.J. et al., "The Ins2Akita mouse as a model of early retinal complications in diabetes", Invest Ophthalmol Vis Sci 46, 2210-2218 (2005).
Beausejour, C.M. et al., "Reversal of human cellular senescence: roles of the p53 and p16 pathways", EMBO J 22, 4212-4222 (2003).
Binet. F. et al., "Neuronal ER Stress Impedes Myeloid-Cell-Induced Vascular Regeneration through IRE1alpha Degradation of Netrin-1", Cell Metab 17, 353-371 (2013).
Binet, F. et al., "ER Stress and Angiogenesis", Cell Metab, (2015).
Cao, R. et al., "VEGFR1-mediated pericyte ablation links VEGF and PlGF to cancer-associated retinopathy", Proc Natl Acad Sci US A 107, 856-861 (2010).
Cerani, A. et al., "Neuron-derived semaphorin 3A is an early inducer of vascular permeability in diabetic retinopathy via neuropilin-1", Cell metabolism 18, 505-518 (2013).
Childs, B.G. et al., "Cellular senescence in aging and age-related disease: from mechanisms to therapy", Nat Med 21, 1424-1435 (2015).
Chopp, M. et al., "Neurogenesis, angiogenesis, and MRI indices of functional recovery from stroke", Stroke 38, 827-831 (2007).
Clausen, B.E. et al., "Conditional gene targeting in macrophages and granulocytes using LysMcre mice", Transgenic Res 8, 265-277 (1999).
Collado, M. et al., "Tumour biology: senescence in premalignant tumours", Nature 436, 642 (2005).
Coppe, J-P. et al., "Secretion of vascular endothelial growth factor by primary human fibroblasts at senescence", J Biol Chem 281, 29568-29574 (2006).

(56) References Cited

OTHER PUBLICATIONS

Coppe, J.-P. et al., "The senescence-associated secretory phenotype: the dark side of tumor suppression", Annual review of pathology 5, 99-118 (2010).
Dejda, A. et al., "Neuropilin-1 mediates myeloid cell chemoattraction and influences retinal neuroimmune crosstalk", Journal of Clinical Investigation 124, 4807-4822 (2014).
Demaria, M. et al., "An essential role for senescent cells in optimal wound healing through secretion of PDGF-AA", Dev Cell 31, 722-733 (2014).
Dimri, G.P. et al., "A biomarker that identifies senescent human cells in culture and in aging skin in vivo", Proc Natl Acad Sci U S A 92, 9363-9367 (1995).
Dorfman, A. et al., "Early manifestations of postnatal hyperoxia on the retinal structure and function of the neonatal rat", Invest Ophthalmol Vis Sci 49, 458-466 (2008).
Dull, T. et al., "A third-generation lentivirus vector with a conditional packaging system", J Virol 72, 8463-8471 (1998).
Edwards, M.M. et al., "The deletion of Math5 disrupts retinal blood vessel and glial development in mice", Exp Eye Res, (2011).
Gastinger, M.J. et al., "Dendrite remodeling and other abnormalities in the retinal ganglion cells of Ins2 Akita diabetic mice", Invest Ophthalmol Vis Sci 49, 2635-2642 (2008).
Hancock, H.A. et al., "Oscillatory potential analysis and ERGs of normal and diabetic rats", Invest Ophthalmol Vis Sci 45, 1002-1008 (2004).
Hartnett, M.E. et al., "Mechanisms and management of retinopathy of prematurity", The New England Journal of Medicine 367, 2515-2526 (2012).
Hasan et al., "Inhibition of VEGF induces cellular senescence in colorectal cancer cells", International Journal of Cancer, 129, 2115-2123 (2011).
Hellstrom, A. et al., "Retinopathy of prematurity", The Lancet—British Edition 382, 1445-1457 (2013).
Holash, J. et al., "VEGF-Trap: a VEGF blocker with potent anti-tumor effects", Proc Natl Acad Sci U S A 99, 11393-11398 (2002).
Honek, J. et al., "Modulation of age-related insulin sensitivity by VEGF-dependent vascular plasticity in adipose tissues", Proc Natl Acad Sci US A 111, 14906-14911 (2014).
Joyal, J.-S. et al., "Ischemic neurons prevent vascular regeneration of neural tissue by secreting semaphorin 3A", Blood 117, 6024-6035 (2011).
Kern, T.S. et al., "Retinal ganglion cells in diabetes", J Physiol 586, 4401-4408 (2008).
Krizhanovsky, V. et al., "Senescence of activated stellate cells limits liver fibrosis", Cell 134, 657-667 (2008).
Kuilman, T. et al., "Oncogene-induced senescence relayed by an interleukin-dependent inflammatory network", Cell 133, 1019-1031 (2008).
Laberge, R.-M. et al., "MTOR regulates the pro-tumorigenic senescence-associated secretory phenotype by promoting L1A translation", Nature Cell Biology, Aug. 2015 (Aug. 2015), vol. 17(8), pp. 1049-1061, ISSN:1576-1479.
Li, L. et al., "Angiogenesis and improved cerebral blood flow in the ischemic boundary area detected by MRI after administration of sildenafil to rats with embolic stroke", Brain Res 1132, 185-192 (2007).
Mallette, F.A. et al., "The DNA damage signaling pathway is a critical mediator of oncogene-induced senescence", Genes Dev 21, 43-48 (2007).
Martinon, F. et al., "TLR activation of the transcription factor XBP1 regulates innate immune responses in macrophages", Nat Immunol 11, 411-418 (2010).
Moiseeva, O. et al., "Metformin, aging and cancer", Aging 5, 330-331 (2013).
Moiseeva, O. et al., "Metformin inhibits the senescence-associated secretory phenotype by interfering with IKK/NF-KB activation", Aging cell 12, 489-498 (2013).
Morishige, N. et al., "Expression pf semaphorin 3A in the rat corneal epithelium during wound healing", Biochemical and Biophysical Research Communication, May 14, 2010 (May 14, 2010), vol. 395(4), pp. 451-457, ISSN: 1090-2104, Abstract, pp. 453-455.
Munoz-Espin, D. et al., "Programmed cell senescence during mammalian embryonic development", Cell 35 155, 1104-1118 (2013).
Okabe, K. et al., "Neurons limit angiogenesis by titrating VEGF in retina", Cell 159, 584-596 (2014).
Oubaha, M. et al., "Senescence-associated secretary phenotype contributes to pathological angiogenesis in retinopathy", Science Translational Medicine, Oct. 26, 2016 (Oct. 26, 2016), vol. 8(362). pp. 362ra144, ISSN:1946-6242.
Qahar, M. et al., "Semaphorin 3A promotes activtion of Pax7, Myl5, and MyoD through inhibition of emerin expression in activated satellite cells", FEBS Open Bio, Apr. 27, 2016 (Apr. 27, 2016), vol. 6(6), pp. 529-539, ISSN:2211-5463, pp. 535 and 537.
Katarzyna A. Uniewicz et al: "Exogenous Recombinant Dimeric Neuropilin-1 Is Sufficient to Drive Angiogenesis", Journal of Biological Chemistry, vol. 286, No. 1, Oct. 18, 2010 (Oct. 18, 2010), pp. 12-23.
European Search Report and Written Opinion dated Apr. 14, 2020 in respect of EP Patent application No. 17852040.
Office Action dated Sep. 14, 2021 in respect of JP Patent application No. 2019-536626.
Examination Report dated Feb. 29, 2024, issued by the European Patent Office (EPO) in respect of corresponding EP applicaiton No. 17 852 040.9.
Shirvan et al., Anti-semaphorin 3A Antibodies Rescue Retinal Ganglion Cells from Cell Death following Optic Nerve Axotomy. The Journal of Biological Chemistry, vol. 277, No. 51, 49799-49807, 2002.
Soilomon AS et al., Up-regulation of semaphorin expression in retina of glaucomatous rabbits. Graefe's Arch Clin Exp Ophthalmol (2003) 241: 673-681.

* cited by examiner

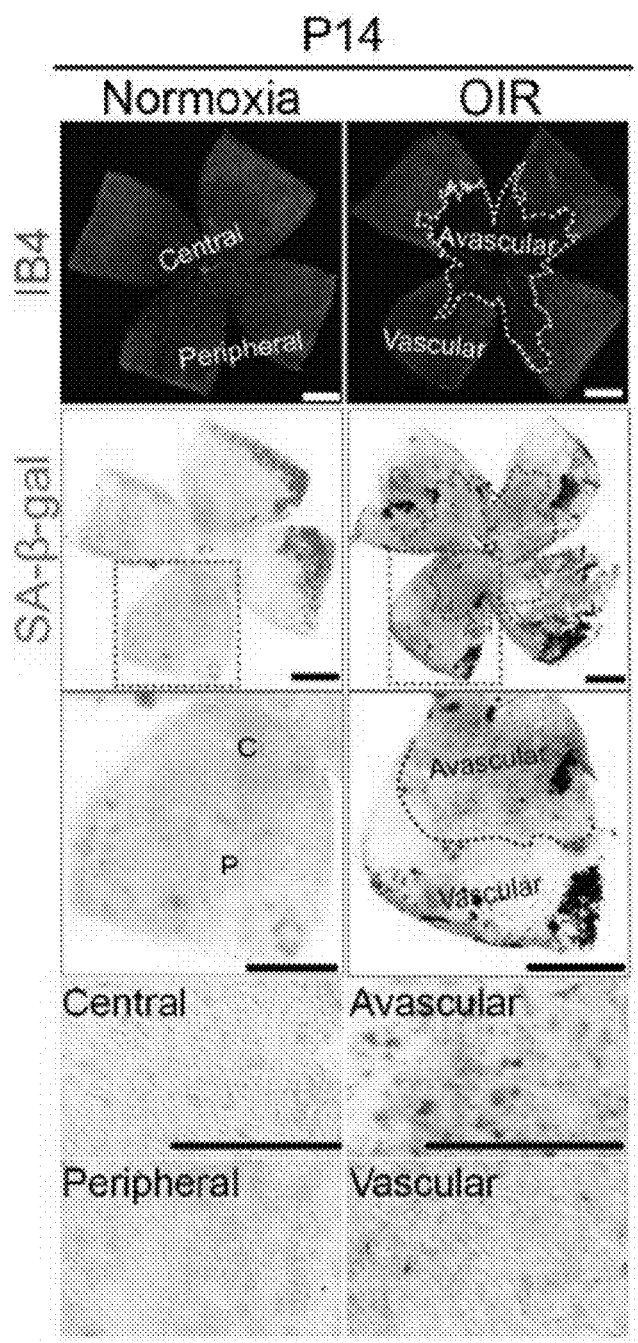
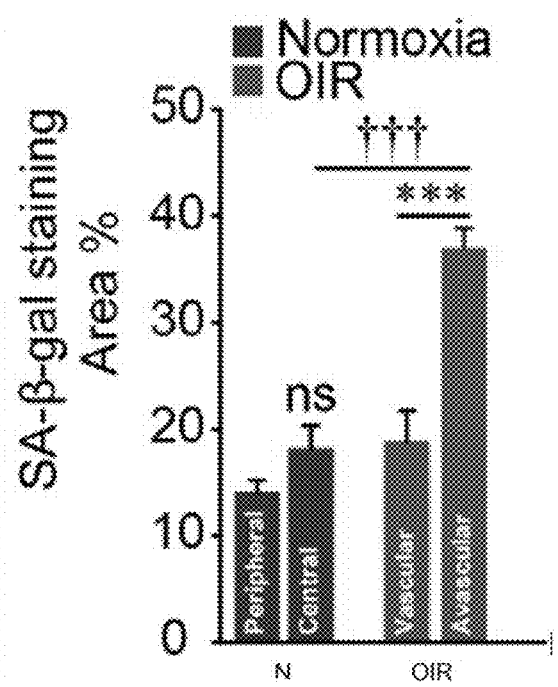
FIG. 1G
FIG. 1F

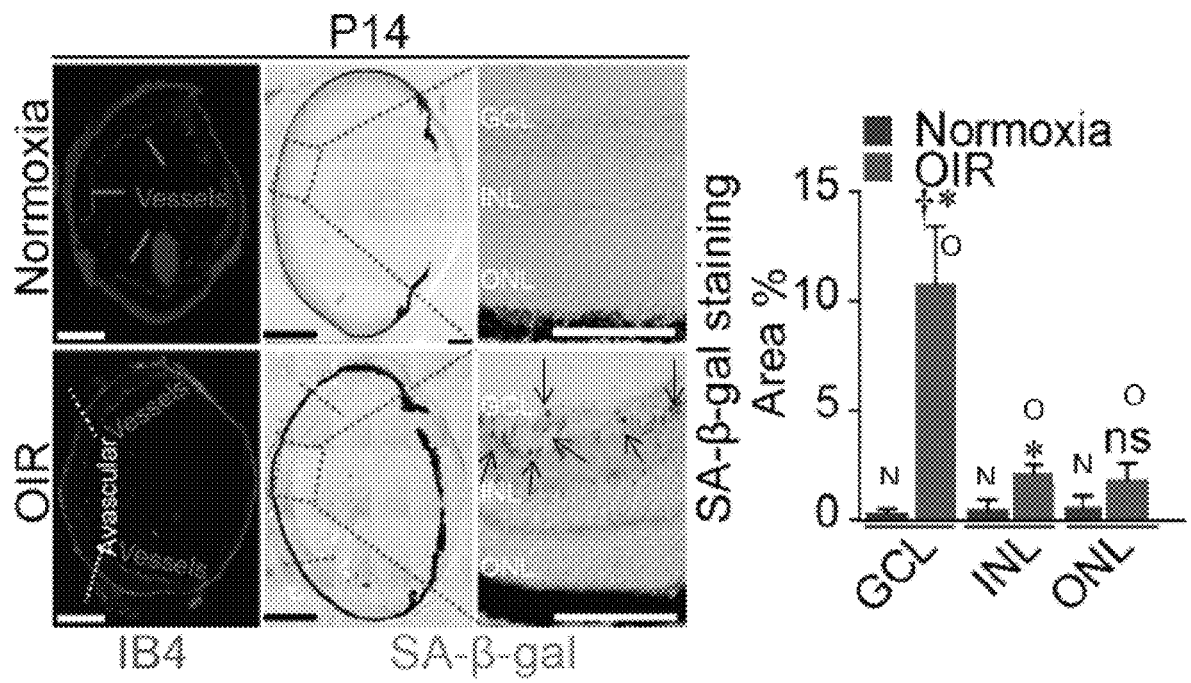
FIG. 1H  FIG. 1I
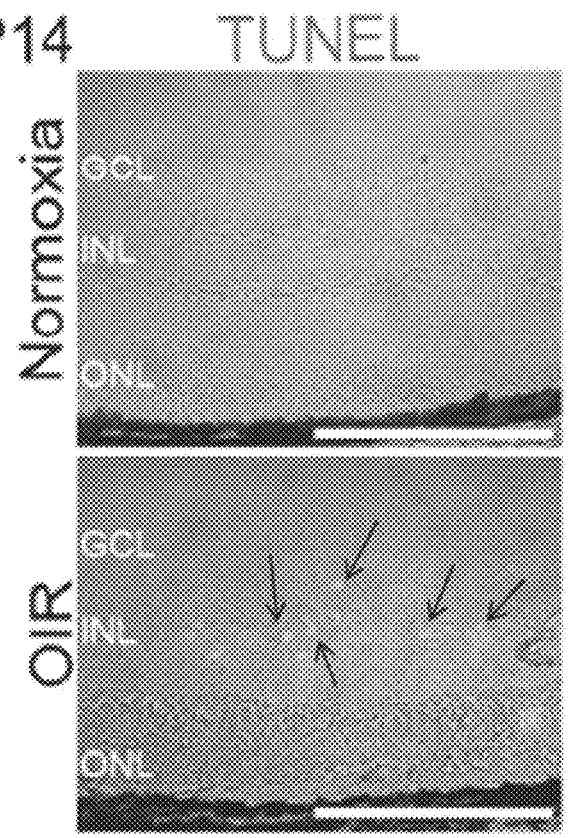
FIG. 1J

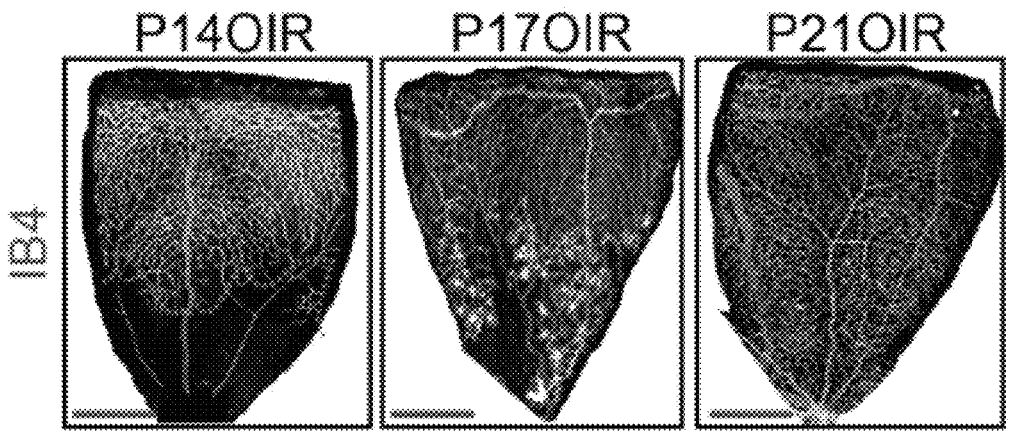
FIG. 2A
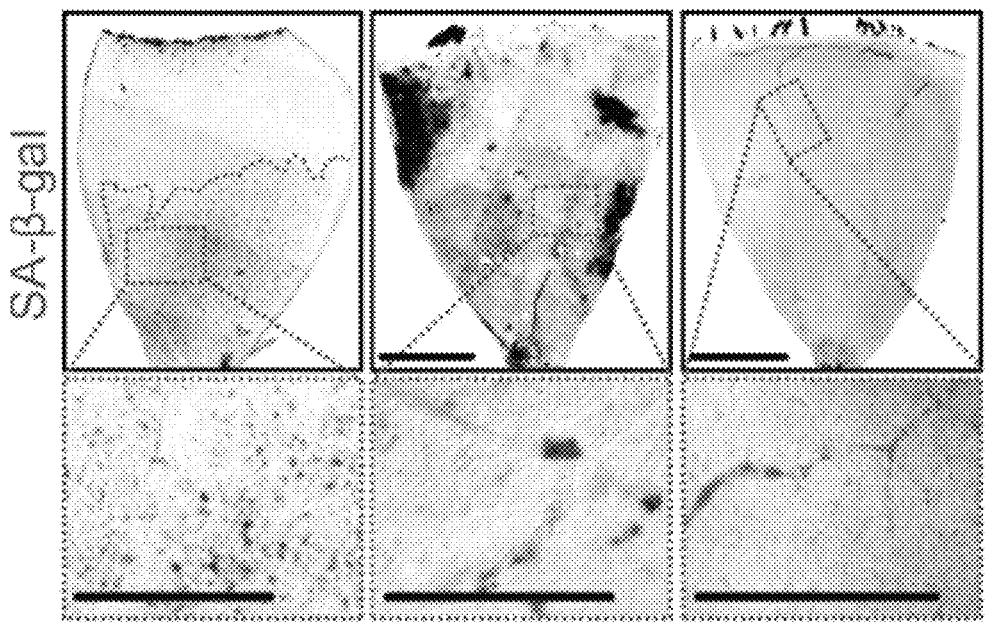
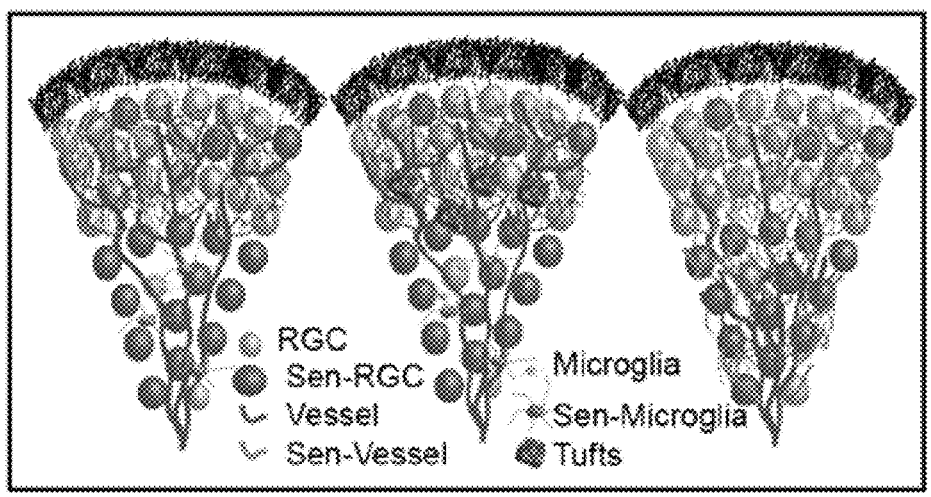
FIG. 2B

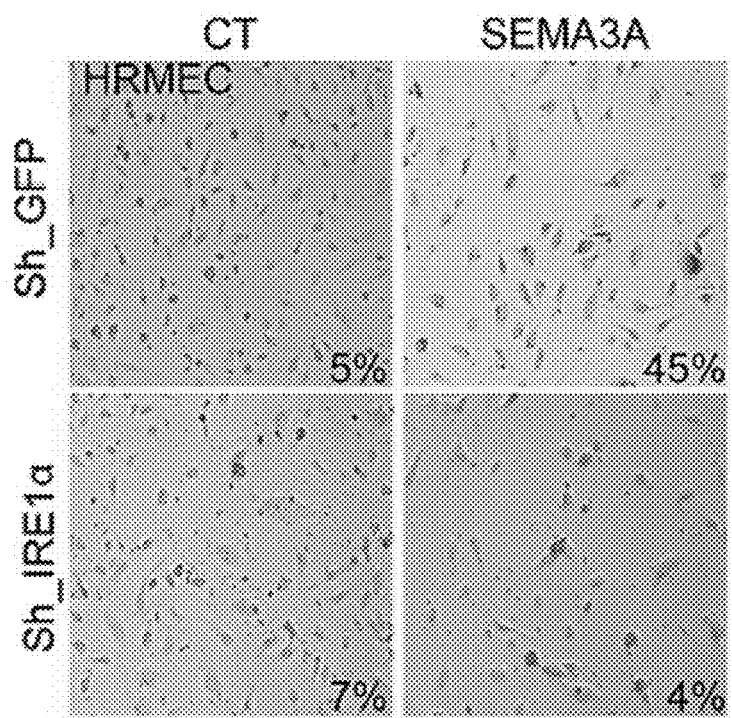
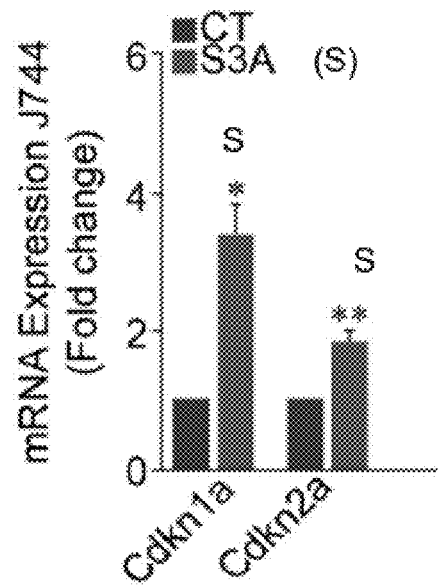
FIG. 6E
FIG. 6F
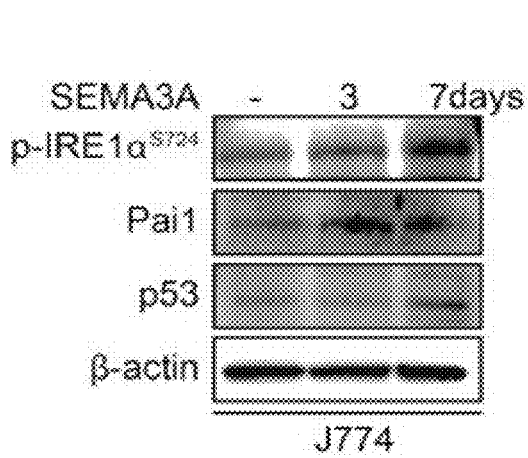
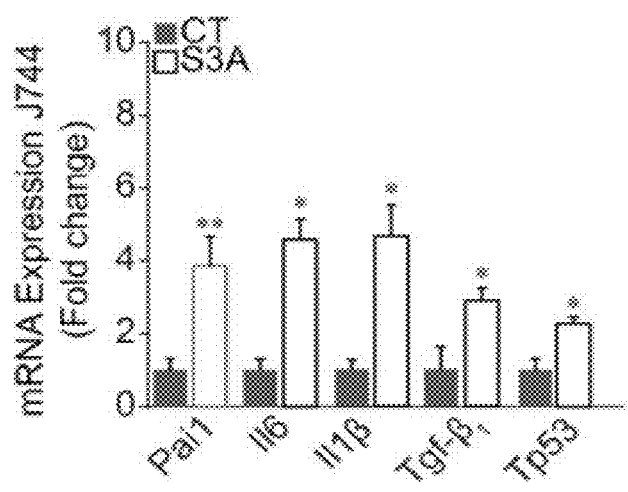
FIG. 7A
FIG. 7B

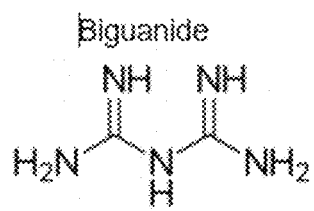
FIG. 15A

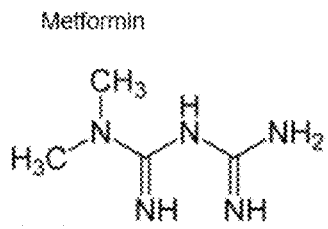
FIG. 15B

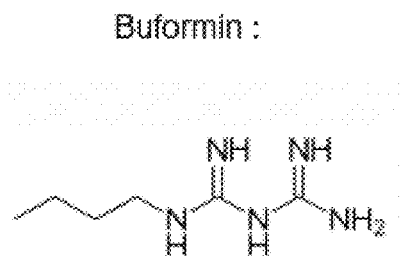
FIG. 15C

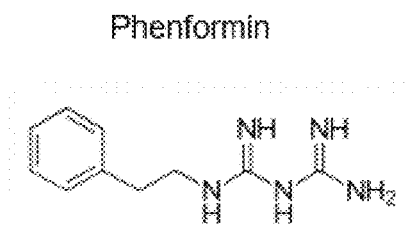
FIG. 15D

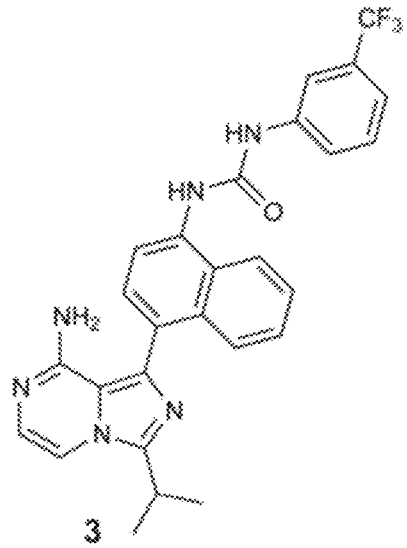
FIG. 15E

MGWLTRIVCLFWGVLLTARANYQNGKNNVPRLKLSYKEMLESNNVITFNGLANSSSYHTFLLDEERSRLYVGAKDHIF
SFDLVNIKDFQKIVWPVSYTRRDECKWAGKDILKECANFIKVLKAYNQTHLYACGTGAFHPICTYIEIGHHPEDNIFK
LENSHFENGRGKSPYDPKLLTASLLIDGELYSGTAADFMGRDFAIFRTLGHHHPIRTEQHDSRWLNDPKFISAHLISE
SDNPEDDKVYFFFRENAIDGEHSGKATHARIGQICKNDFGGHRSLVNKWTTFLKARLICSVPGPNGIDTHFDELQDVF
LMNFKDPKNPVVYGVFTTSSNIFKGSAVCMYSMSDVRRVFLGPYAHRDGPNYQWVPYQGRVPYPRPGTCPSKTFGGFD
STKDLPDDVITFARSHPAMYNPVFPMNNRPIVIKTDVNYQFTQIVVDRVDAEDGQYDVMFIGTDVGTVLKVVSIPKET
WYDLEEVLLEEMTVFREPTAISAMELSTKQQQLYIGSTAGVAQLPLHRCDIYGKACAECCLARDPYCAWDGSACSRYF
PTAKRRTRRQDIRNGDPLTHCSDLHHDNHHGHSPEERIIYGVENSSTFLECSPKSQRALVYWQFQRRNEERKEEIRVD
DHIIRTDQGLLLRSLQQKDSGNYLCHAVEHGFIQTLLKVTLEVIDTEHLEELLHKDDDGDGSKTKEMSNSMTPSQKVW
YRDFMQLINHPNLNTMDEFCEQVWKRDRKQRRQRPGHTPGNSNKWKHLQENKKGRNRRTHEFERAPRSV

FIG. 16

```
                         ┌──── Signal ────┐┌─ a1
                    10         20         30         40         50         60         70
Rat          MERGLPLLCA TLALALALAG AFRSDKCGGT IKIENPGYLT SPGYPHSYHP SEKCEWLIQA PEPYQRIMIN
Human        MERGLPLLCA VLALVLAPAG AFRSDKCGDT IKIESPGYLT SPGYPHSYHP SEKCEWLIQA PDPYQRIMIN
Mouse        MERGLPLLCA TLALALALAG AFRSDKCGGT IKIENPGYLT SPGYPHSYHP SEKCEWLIQA PEPYQRIMIN
Consensus    MERGLPLLCA .LAL.LA.AG AFR.DKCG.T IKIE.PGYLT SPGYPHSYHP SEKCEWLIQA P.PYQRIMIN 80         90        100        110        120        130        140
Rat          FNPHFDLEDR DCKYDYVEVI DGENEGGRLN GKFCGKIAPS PVVSSGPFLF IKFVSDYETH GAGFSIRYEI
Human        FNPHFDLEDR DCKYDYVEVF DGENENGHFR GKFCGKIAPP PVVSSGPFLF IKFVSDYETH GAGFSIRYEL
Mouse        FNPHFDLEDR DCKYDYVEVI DGENEGGRLN GKFCGKIAPS PVVSSGPFLF IKFVSDYETH GAGFSIRYEI
Consensus    FNPHFDLEDR DCKYDYVEV. DGENE.G... GKFCGKIAP. PVVSGPFLF IKFVSDYETH GAGFSIRYE.

┐┌─ a2
                   150        160        170        180        190        200        210
Rat          FKRGPECSQN YTAPTGVIKS PGFPEKYPNS LECTYIIFAP KMSEIILEFE SFDLEQDSNP PGGVFCRYDR
Human        FKRGPECSQN YITPSGVIKS PGFPEKYPNS LECTYIVFAP KMSEIILEFE SFDLEPDSNP PGGMFCRYDR
Mouse        FKRGPECSQN YTAPTGVIKS PGFPEKYPNS LECTYIIFAP KMSEIILEFE SFDLEQDSNP PGGMFCRYDR
Consensus    FKRGPECSQN YT.P.GVIKS PGFPEKYPNS LECTYI.FAP KMSEIILEFE SFDLE.DSNP PGG.FCRYDR ┐┌─ b1
                   220        230        240        250        260        270        280
Rat          LEIWDGFPEV GPHIGRYCGQ KTPGRIRSSS GILSMVFYTD SAIAKEGFSA NYSVLQSSIS EDFKCMEALG
Human        LEIWDGFPDV GPHIGRYCGQ KTPGRIRSSS GILSMVFYTD SAIAKEGFSA NYSVLQSSVS EDFKCMEALG
Mouse        LEIWDGFPEV GPHIGRYCGQ KTPGRIRSSS GVLSMVFYTD SAIAKEGFSA NYSVLQSSIS EDFKCMEALG
Consensus    LEIWDGFP.V GPHIGRYCGQ KTPGRIRSSS G.LSMVFYTD SAIAKEGFSA NYSVLQSS.S EDFKCMEALG 290        300        310        320        330        340        350
Rat          MESGEIHSDQ ITASSQYGTN WSVERSRLNY PENGWTPGED SYREWIQVDL GLLRFVTAVG TQGAISKETK
Human        MESGEIHSDQ ITASSQYSTN WSAERSRLNY PENGWTPGED SYREWIQVDL GLLRFVTAVG TQGAISKETK
Mouse        MESGEIHSDQ ITASSQYGTN WSVERSRLNY PENGWTPGED SYKEWIQVDL GLLRFVTAVG TQGAISKETK
Consensus    MESGEIHSDQ ITASSQY.TN WS.ERSRLNY PENGWTPGED SY.EWIQVDL GLLRFVTAVG TQGAISKETK 360        370        380        390        400        410        420
Rat          KKYYVKTYRV DISSNGEDWI TLKEGNKAII FQGNINPIDV VFGVFPKPLI IRFVRIKPAS WEIGISMRFE
Human        KKYYVKTYKI DVSSNGEDWI TIKEGNKPVL FQGNINPIDV VVAVFPKPLI IRFVRIKPAT WEIGISMRFE
Mouse        KKYYVKTYRV DISSNGEDWI SLKEGNKAII FQGNINPIDV VLGVFSKPLI IRFVRIKPVS WEIGISMRFE
Consensus    KKYYVKTY.. D.SSNGEDWI ..KEGNK... FQGNINPIDV V..VF.KPLI IRFVRIKP.. WEIGISMRFE ┐┌─ b2
                   430        440        450        460        470        480        490
Rat          VYGCKITDYP CSGMLGMVSG LISDSQITAS NQGDRNWMPE NIRLVTSRTG WALPPSPHPY INEWLQVDLG
Human        VYGCKITDYP CSGMLGMVSG LISDSQITAS NQGDRNWMPE NIRLVTSRSG WALPPAPHSY INEWLQIDLG
Mouse        VYGCKITDYP CSGMLGMVSG LISDSQITAS NQADRNWMPE NIRLVTSRTG WALPPSPHPY TNEWLQVDLG
Consensus    VYGCKITDYP CSGMLGMVSG LISDSQIT.S NQ.DRNWMPE NIRLVTSR.G WALPP.PH.Y .NEWLQ.DLG 500        510        520        530        540        550        560
Rat          DEKIVRGVII QGGKHRENKV FMRKFKIAYS NNGSDWKMIM DDSKRKAKSF EGNNNYDTPE LRAFTPLSTR
Human        EEKIVRGIII QGGKHRENKV FMRKFKIGYS NNGSDWKMIM DDSKRKAKSF EGNNNYDTPE LRTFPALSTR
Mouse        DEKIVRGVII QGGKHRENKV FMRKFKIAYS NNGSDWKTIM DDSKRKAKSF EGNNNYDTPE LRTFSPLSTR
Consensus    .EKIVRG.II QGGKHRENKV FMRKFKI.YS NNGSDWK.IM DDSKRKAKSF EGNNNYDTPE LR.F..LSTR ┐┌─ c
                   570        580        590        600        610        620        630
Rat          FIRIYPERAT HSGLGLRMEL LGCEVEVPTA GPTTPNGNFV DECDDDQANC HSGTGDDFQL TGGTTVLATE
Human        FIRIYPERAT HGGLGLRMEL LGCEVEAPTA GPTTPNGNLV DECDDDQANC HSGTGDDFQL TGGTTVLATE
Mouse        FIRIYPERAT HSGLGLRMEL LGCEVEAPTA GPTTPNGNFV DECDDDQANC HSGTGDDFQL TGGTTVLATE
Consensus    FIRIYPERAT H.GLGLRMEL LGCEVE.PTA GPTTPNGN.V DECDDDQANC HSGTGDDFQL TGGTTVLATE
```

FIG. 17A

```
                640        650        660        670        680        690        700
Rat       KPTIIDSTIQ SEFPTYGFNC EFGWGSHKTF CHWEHDSHAQ LRWRVLTSKI GPIQDHTGDG NFIYSQADEN
Human     KPTVIDSTIQ SEFPTYGFNC EFGWGSHKTF CHWEHDNHVQ LKWSVLTSKI GPIQDHTGDG NFIYSQADEN
Mouse     KPTIIDSTIQ SEFPTYGFNC EFGWGSHKTF CHWEHDSHAQ LRWSVLTSKI GPIQDHTGDG NFIYSQADEN
Consensus KPT.IDSTIQ SEFPTYGFNC EFGWGSHKTF CHWEHD.H.Q L.W.VLTSKI GPIQDHTGDG NFIYSQADEN 710        720        730        740        750        760        770
Rat       QKGKVARLVS PVVYSQSSAH CMTFWYHMSG SHVGTLRVKL HYQKPEEYDQ LVWMVVGHQG DHWKEGRVLL
Human     QKGKVARLVS PVVYSQNSAH CMTFWYHMSG SHVGTLRVKL RYQKPEEYDQ LVWMAIGHQG DHWKEGRVLL
Mouse     QKGKVARLVS PVVYSQSSAH CMTFWYHMSG SHVGTLRVKL RYQKPEEYDQ LVWMVVGHQG DHWKEGRVLL
Consensus QKGKVARLVS PVVYSQ.SAH CMTFWYHMSG SHVGTLRVKL .YQKPEEYDQ LVWM..GHQG DHWKEGRVLL 780        790        800        810        820        830        840
Rat       HKSLKLYQVI FEGEIGKGNL GGIAVDDISI NNHIPQEDCA KPTDLDKKNT EIKIDETGST PGYEeEGKGD
Human     HKSLKLYQVI FEGEIGKGNL GGIAVDDISI NMHISQEDCA KPAELDKKNP EIKIDETGST PGYEGEGEGD
Mouse     HKSLKLYQVI FEGEIGKGNL GGIAVDDISI NNHISQEDCA KPTDLDKKNT EIKIDETGST PGYEGEGEGD
Consensus HKSLKLYQVI FEGEIGKGNL GGIAVDDISI NNHI.QEDCA KP.DLDKKN. EIKIDETGST PGYE.EG.GD TM                  Cytoplasmic domain
                850        860        870        880        890        900        910
Rat       KNISRKPGNV LKTLDPILIT IIAMSALGVL LGAVCGVVLY CACWHNGMSE RNLSALENYN FELVDGVKLK
Human     KNISRKPGNV LKTLDPILII IIAMSALGVL LGAVCGVVLY CACWHNGMSE RNLSALENYN FELVDGVKLK
Mouse     KNISRKPGNV LKTLDPILIT IIAMSALGVL LGAVCGVVLY CACWHNGMSE RNLSALENYN FELVDGVKLK
Consensus KNISRKPGNV LKTLDPILIT IIAMSALGVL LGAVCGVVLY CACWHNGMSE RNLSALENYN FELVDGVKLK 920
Rat       KDKLNPQSNY SEA
Human     KDKLNIQSTY SEA
Mouse     KDKLNPQSNY SEA
Consensus KDKLN.QS.Y SEA
```

FIG. 17B

NRP-1 Traps
```
               10         20         30         40         50         60         70
NRP-1     MERGLPLLCA VLALVLAPAG AFRNDKCGDT IKIESPGYLT SPGYPHSYHP SEKCEWLIQA PDPYQRIMIN
Trap G    MERGLPLLCA VLALVLAPAG AFRNDKCGDT IKIESPGYLT SPGYPHSYHP SEKCEWLIQA PDPYQRIMIN
Trap R    MERGLPLLCA VLALVLAPAG AFRNDKCGDT IKIESPGYLT SPGYPHSYHP SEKCEWLIQA PDPYQRIMIN
Trap Z    MERGLPLLCA VLALVLAPAG AFRNDKCGDT IKIESPGYLT SPGYPHSYHP SEKCEWLIQA PDPYQRIMIN
Trap AB   MERGLPLLCA VLALVLAPAG AFRNDKCGDT IKIESPGYLT SPGYPHSYHP SEKCEWLIQA PDPYQRIMIN
Trap AC   MERGLPLLCA VLALVLAPAG AFRNDKCGDT IKIESPGYLT SPGYPHSYHP SEKCEWLIQA PDPYQRIMIN
Trap O    MERGLPLLCA VLALVLAPAG AFRNDKCGDT IKIESPGYLT SPGYPHSYHP SEKCEWLIQA PDPYQRIMIN
Trap Q    MERGLPLLCA VLALVLAPAG AFRNDKCGDT IKIESPGYLT SPGYPHSYHP SEKCEWLIQA PDPYQRIMIN
Trap M    MERGLPLLCA VLALVLAPAG AFRNDKCGDT IKIESPGYLT SPGYPHSYHP SEKCEWLIQA PDPYQRIMIN
Trap P    MERGLPLLCA VLALVLAPAG AFRNDKCGDT IKIESPGYLT SPGYPHSYHP SEKCEWLIQA PDPYQRIMIN
Trap N    MERGLPLLCA VLALVLAPAG AFRNDKCGDT IKIESPGYLT SPGYPHSYHP SEKCEWLIQA PDPYQRIMIN
Trap W    MERGLPLLCA VLALVLAPAG AFRNDKCGDT IKIESPGYLT SPGYPHSYHP SEKCEWLIQA PDPYQRIMIN
Trap X    MERGLPLLCA VLALVLAPAG AFRNDKCGDT IKIESPGYLT SPGYPHSYHP SEKCEWLIQA PDPYQRIMIN
Trap Y    MERGLPLLCA VLALVLAPAG AFRNDKCGDT IKIESPGYLT SPGYPHSYHP SEKCEWLIQA PDPYQRIMIN
Trap S    MERGLPLLCA VLALVLAPAG AFRNDKCGDT IKIESPGYLT SPGYPHSYHP SEKCEWLIQA PDPYQRIMIN
Trap AD   MERGLPLLCA VLALVLAPAG AFRNDKCGDT IKIESPGYLT SPGYPHSYHP SEKCEWLIQA PDPYQRIMIN
Trap AE   MERGLPLLCA VLALVLAPAG AFRNDKCGDT IKIESPGYLT SPGYPHSYHP SEKCEWLIQA PDPYQRIMIN
Trap AF   MERGLPLLCA VLALVLAPAG AFRNDKCGDT IKIESPGYLT SPGYPHSYHP SEKCEWLIQA PDPYQRIMIN
Trap AG   MERGLPLLCA VLALVLAPAG AFRNDKCGDT IKIESPGYLT SPGYPHSYHP SEKCEWLIQA PDPYQRIMIN
Trap AJ   MERGLPLLCA VLALVLAPAG AFRNDK
Trap AK   MERGLPLLCA VLALVLAPAG AFRNDK
Trap AR   MERGLPLLCA VLALVLAPAG AFRNDK
Trap AS   MERGLPLLCA VLALVLAPAG AFRNDK 80         90        100        110        120        130        140
NRP-1     FNPHFDLEDR DCKYDYVEVF DGENENGHFR GKFCGKIAPP PVVSSGPFLF IKFVSDYETH GAGFSIRYEL
Trap G    FNPHFDLEDR DCKYDYVEVF DGENENGHFR GKFCGKIAPP PVVSSGPFLF IKFVSDYETH GAGFSIRYEL
Trap R    FNPHFDLEDR DCKYDYVEVF DGENENGHFR GKFCGKIAPP PVVSSGPFLF IKFVSDYETH GAGFSIRYEL
Trap Z    FNPHFDLEDR DCKYDYVEVF DGENENGHFR GKFCGKIAPP PVVSSGPFLF IKFVSDYETH GAGFSIRYEL
Trap AB   FNPHFDLEDR DCKYDYVEVF DGENENGHFR GKFCGKIAPP PVVSSGPFLF IKFVSDYETH GAGFSIRYEL
Trap AC   FNPHFDLEDR DCKYDYVEVF DGENENGHFR GKFCGKIAPP PVVSSGPFLF IKFVSDYETH GAGFSIRYEL
Trap O    FNPHFDLEDR DCKYDYVEVF DGENENGHFR GKFCGKIAPP PVVSSGPFLF IKFVSDYETH GAGFSIRYEL
Trap Q    FNPHFDLEDR DCKYDYVEVF DGENENGHFR GKFCGKIAPP PVVSSGPFLF IKFVSDYETH GAGFSIRYEL
Trap M    FNPHFDLEDR DCKYDYVEVF DGENENGHFR GKFCGKIAPP PVVSSGPFLF IKFVSDYETH GAGFSIRYEL
Trap P    FNPHFDLEDR DCKYDYVEVF DGENENGHFR GKFCGKIAPP PVVSSGPFLF IKFVSDYETH GAGFSIRYEL
Trap N    FNPHFDLEDR DCKYDYVEVF DGENENGHFR GKFCGKIAPP PVVSSGPFLF IKFVSDYETH GAGFSIRYEL
Trap W    FNPHFDLEDR DCKYDYVEVF DGENENGHFR GKFCGKIAPP PVVSSGPFLF IKFVSDYETH GAGFSIRYEL
Trap X    FNPHFDLEDR DCKYDYVEVF DGENENGHFR GKFCGKIAPP PVVSSGPFLF IKFVSDYETH GAGFSIRYEL
Trap Y    FNPHFDLEDR DCKYDYVEVF DGENENGHFR GKFCGKIAPP PVVSSGPFLF IKFVSDYETH GAGFSIRYEL
Trap S    FNPHFDLEDR DCKYDYVEVF DGENENGHFR GKFCGKIAPP PVVSSGPFLF IKFVSDYETH GAGFSIRYEL
Trap AD   FNPHFDLEDR DCKYDYVEVF DGENENGHFR GKFCGKIAPP PVVSSGPFLF IKFVSDYETH GAGFSIRYEL
Trap AE   FNPHFDLEDR DCKYDYVEVF DGENENGHFR GKFCGKIAPP PVVSSGPFLF IKFVSDYETH GAGFSIRYEL
Trap AF   FNPHFDLEDR DCKYDYVEVF DGENENGHFR GKFCGKIAPP PVVSSGPFLF IKFVSDYETH GAGFSIRYEL
Trap AG   FNPHFDLEDR DCKYDYVEVF DGENENGHFR GKFCGKIAPP PVVSSGPFLF IKFVSDYETH GAGFSIRYEL
Trap AJ
Trap AK
Trap AR
Trap AS
```

FIG. 18A

```
              150        160        170        180        190        200        210
NRP-1    FKRGPECSQN YTTPSGVIKS PGFPEKYPNS LECTYIVFAP KMSEIILEFE SFDLEPDSNP PGGMFCRYDR
Trap G   FKRGPECSQN YTTPSGVIKS PGFPEKYPNS LECTYIVFAP KMSEIILEFE SFDLEPDSNP PGGMFCRYDR
Trap R   FKRGPECSQN YTTPSGVIKS PGFPEKYPNS LECTYIVFAP KMSEIILEFE SFDLEPDSNP PGGMFCRYDR
Trap Z   FKRGPECSQN YTTPSGVIKS PGFPEKYPNS LECTYIVFAP KMSEIILEFE SFDLEPDSNP PGGMFCRYDR
Trap AB  FKRGPECSQN YTTPSGVIKS PGFPEKYPNS LECTYIVFAP KMSEIILEFE SFDLEPDSNP PGGMFCRYDR
Trap AC  FKRGPECSQN YTTPSGVIKS PGFPEKYPNS LECTYIVFAP KMSEIILEFE SFDLEPDSNP PGGMFCRYDR
Trap O   FKRGPECSQN YTTPSGVIKS PGFPEKYPNS LECTYIVFAP KMSEIILEFE SFDLEPDSNP PGGMFCRYDR
Trap Q   FKRGPECSQN YTTPSGVIKS PGFPEKYPNS LECTYIVFAP KMSEIILEFE SFDLEPDSNP PGGMFCRYDR
Trap M   FKRGPECSQN YTTPSGVIKS PGFPEKYPNS LECTYIVFAP KMSEIILEFE SFDLEPDSNP PGGMFCRYDR
Trap P   FKRGPECSQN YTTPSGVIKS PGFPEKYPNS LECTYIVFAP KMSEIILEFE SFDLEPDSNP PGGMFCRYDR
Trap N   FKRGPECSQN YTTPSGVIKS PGFPEKYPNS LECTYIVFAP KMSEIILEFE SFDLEPDSNP PGGMFCRYDR
Trap W   FKRGPECSQN YTTPSGVIKS PGFPEKYPNS LECTYIVFAP KMSEIILEFE SFDLEPDSNP PGGMFCRYDR
Trap X   FKRGPECSQN YTTPSGVIKS PGFPEKYPNS LECTYIVFAP KMSEIILEFE SFDLEPDSNP PGGMFCRYDR
Trap Y   FKRGPECSQN YTTPSGVIKS PGFPEKYPNS LECTYIVFAP KMSEIILEFE SFDLEPDSNP PGGMFCRYDR
Trap S   FKRGPECSQN YTTPSGVIKS PGFPEKYPNS LECTYIVFAP KMSEIILEFE SFDLEPDSNP PGGMFCRYDR
Trap AD  FKRGPECSQN YTTPSGVIKS PGFPEKYPNS LECTYIVFAP KMSEIILEFE SFDLEPDSNP PGGMFCRYDR
Trap AE  FKRGPECSQN YTTPSGVIKS PGFPEKYPNS LECTYIVFAP KMSEIILEFE SFDLEPDSNP PGGMFCRYDR
Trap AF  FKRGPECSQN YTTPSGVIKS PGFPEKYPNS LECTYIVFAP KMSEIILEFE SFDLEPDSNP PGGMFCRYDR
Trap AG  FKRGPECSQN YTTPSGVIKS PGFPEKYPNS LECTYIVFAP KMSEIILEFE SFDLEPDSNP PGGMFCRYDR
Trap AJ    RGPECSQN YTTPSGVIKS PGFPEKYPNS LECTYIVFAP KMSEIILEFE SFDLEPDSNP PGGMFCRYDR
Trap AK    RGPECSQN YTTPSGVIKS PGFPEKYPNS LECTYIVFAP KMSEIILEFE SFDLEPDSNP PGGMFCRYDR
Trap AR    RGPECSQN YTTPSGVIKS PGFPEKYPNS LECTYIVFAP KMSEIILEFE SFDLEPDSNP PGGMFCRYDR
Trap AS    RGPECSQN YTTPSGVIKS PGFPEKYPNS LECTYIVFAP KMSEIILEFE SFDLEPDSNP PGGMFCRYDR 220        230        240        250        260        270        280
NRP-1    LEIWDGFPDV GPHIGRYCGQ KTPGRIRSSS GILSMVFYTD SAIAKEGFSA NYSVLQSSVS EDFKCMEALG
Trap G   LEIWDGFPDV GPHIGRYCGQ KTPGRIRSSS GILSMVFYTD SAIAKEGFSA NYSVLQSSVS EDFKCMEALG
Trap R   LEIWDGFPDV GPHIGRYCGQ KTPGRIRSSS GILSMVFYTD SAIAKEGFSA NYSVLQSSVS EDFKCMEALG
Trap Z   LEIWDGFPDV GPHIGRYCGQ KTPGRIRSSS GILSMVFYTD SAIAKEGFSA NYSVLQSSVS EDFKCMEALG
Trap AB  LEIWDGFPDV GPHIGRYCGQ KTPGRIRSSS GILSMVFYTD SAIAKEGFSA NYSVLQSSVS EDFKCMEALG
Trap AC  LEIWDGFPDV GPHIGRYCGQ KTPGRIRSSS GILSMVFYTD SAIAKEGFSA NYSVLQSSVS EDFKCMEALG
Trap O   LEIWDGFPDV GPHIGRYCGQ KTPGRIRSSS GILSMVFYTD SAIAKEGFSA NYSVLQSSVS EDFKCMEALG
Trap Q   LEIWDGFPDV GPHIGRYCGQ KTPGRIRSSS GILSMVFYTD SAIAKEGFSA NYSVLQSSVS EDFKCMEALG
Trap M   LEIWDGFPDV GPHIGRYCGQ KTPGRIRSSS GILSMVFYTD SAIAKEGFSA NYSVLQSSVS EDFKCMEALG
Trap P   LEIWDGFPDV GPHIGRYCGQ KTPGRIRSSS GILSMVFYTD SAIAKEGFSA NYSVLQSSVS EDFKCMEALG
Trap N   LEIWDGFPDV GPHIGRYCGQ KTPGRIRSSS GILSMVFYTD SAIAKEGFSA NYSVL
Trap W   LEIWDGFPDV GPHIGRYCGQ KTPGRIRSSS GILSMVFYTD SAIAKEGFSA NYSVLQSSVS EDFKCMEALG
Trap X   LEIWDGFPDV GPHIGRYCGQ KTPGRIRSSS GILSMVFYTD SAIAKEGFSA NYSVLQSSVS EDFKCMEALG
Trap Y   LEIWDGFPDV GPHIGRYCGQ KTPGRIRSSS GILSMVFYTD SAIAKEGFSA NYSVLQSSVS EDFK
Trap S   LEIWDGFPDV GPHIGRYCGQ KTPGRIRSSS GILSMVFYTD SAIAKEGFSA NYSVLQSSVS EDFKCMEALG
Trap AD  LEIWDGFPDV GPHIGRYCGQ KTPGRIRSSS GILSMVFYTD SAIAKEGFSA NYSVLQSSVS EDFKCMEALG
Trap AE  LEIWDGFPDV GPHIGRYCGQ KTPGRIRSSS GILSMVFYTD SAIAKEGFSA NYSVLQSSVS EDFKCMEALG
Trap AF  LEIWDGFPDV GPHIGRYCGQ KTPGRIRSSS GILSMVFYTD SAIAKEGFSA NYSVLQSSVS EDFKKITDYP
Trap AG  LEIWDGFPDV GPHIGRYCGQ KTPGRIRSSS GILSMVFYTD SAIAKEGFSA NYSVLQSSVS EDFKKITDYP
Trap AJ  LEIWDGFPDV GPHIGRYCGQ KTPGRIRSSS GILSMVFYTD SAIAKEGFSA NYSVLQSSVS EDFKCMEALG
Trap AK  LEIWDGFPDV GPHIGRYCGQ KTPGRIRSSS GILSMVFYTD SAIAKEGFSA NYSVLQSSVS EDFKCMEALG
Trap AR  LEIWDGFPDV GPHIGRYCGQ KTPGRIRSSS GILSMVFYTD SAIAKEGFSA NYSVLQSSVS EDFKCMEALG
Trap AS  LEIWDGFPDV GPHIGRYCGQ KTPGRIRSSS GILSMVFYTD SAIAKEGFSA NYSVLQSSVS EDFKCMEALG
```

FIG. 18B

```
              290        300        310        320        330        340        350
NRP-1    MESGEIHSDQ ITASSQYSTN WSAERSRLNY PENGWIPGED SYREWIQVDL GLLRFVTAVG TQGAISKETK
Trap G   MESGEIHSDQ ITASSQYSTN WSAERSRLNY PENGWIPGED SYREWIQVDL GLLRFVTAVG TQGAISKETK
Trap R   MESGEIHSDQ ITASSQASTN WSAERSRLNY PENGWIPGED SYREWIQVDL GLLRFVTAVG TQGAISKETK
Trap Z   MESGEIHSDQ ITASSQYSTN WSAERSRLNY PENGWIPGKK SYREWIQVDL GLLRFVTAVG TQGAISKETK
Trap AB  MESGEIHSDQ ITASSQYSTN WSAERSRLNY PENGWIPGED SYREWIQVDL GLLRFVTAVG TQGAIAKKTK
Trap AC  MESGEIHSDQ ITASSQYSTN WSAERSRLNY PENGWIPGEK SYREWIQVDL GLLRFVTAVG TQGAISKETK
Trap O   MESGEIHSDQ ITASSQYSTN WSAERSRLNY PENGWIPGED SYREWIQVDL GLLRFVTAVG TQGAISKETK
Trap Q   MESGEIHSDQ ITASSQASTN WSAERSRLNY PENGWIPGED SYREWIQVDL GLLRFVTAVG TQGAISKETK
Trap M   MESGEIHSDQ ITASSQYSTN WSAERSRLNY PENGWIPGED SYREWIQVDL GLLRFVTAVG TQGAISKETK
Trap P   MESGEIHSDQ ITASSQASTN WSAERSRLNY PENGWIPGED SYREWIQVDL GLLRFVTAVG TQGAISKETK
Trap N
Trap W   MESGEIHSDQ ITASSQYSTN WSAERSRLNY PENGWIPGED SYREWIQVDL GLLRFVTAVG TQGAISKETK
Trap X   MESGEIHSDQ ITASSQASTN WSAERSRLNY PENGWIPGED SYREWIQVDL GLLRFVTAVG TQGAISKETK
Trap Y
Trap S   MESGEIHSDQ ITASSQYSTN WSAERSRLNY PENGWIPGED SYREWIQVDL GLLRFVTAVG TQGAISKETK
Trap AD  MESGEIHSDQ ITASSQYSTN WSAERSRLNY PENGWIPGEK SYREWIQVDL GLLRFVTAVG TQGAISKETK
Trap AE  MESGEIHSDQ ITASSQYSTN WSAERSRLNY PENGWIPGEK SYREWIQVDL GLLRFVTAVG TQGAISKETK
Trap AF
Trap AG
Trap AJ  MESGEIHSDQ ITASSQYSTN WSAERSRLNY PENGWIPGED SYREWIQVDL GLLRFVTAVG TQGAISKETK
Trap AK  MESGEIHSDQ ITASSQYSTN WSAERSRLNY PENGWIPGED SYREWIQVDL GLLRFVTAVG TQGAISKETK
Trap AR  MESGEIHSDQ ITASSQYSTN WSAERSRLNY PENGWIPGED SYREWIQVDL GLLRFVTAVG TQGAISKETK
Trap AS  MESGEIHSDQ ITASSQYSTN WSAERSRLNY PENGWIPGED SYREWIQVDL GLLRFVTAVG TQGAISKETK 360        370        380        390        400        410        420
NRP-1    KKYYVKTYKI DVSSNGEDWI TIKEGNKPVL FQGNTNPTDV VVAVFPKPLI TRFVRIKPAT WETGISMRFE
Trap G   KKYYVKTYKI DVSSNGEDWI TIKEGNKPVL FQGNTNPTDV VVAVFPKPLI TRFVRIKPAT WETGISMRFE
Trap R   KKYYVKTYKI DVSSNGEDWI TIKEGNKPVL FQGNTNPTDV VVAVFPKPLI TRFVRIKPAT WETGISMRFE
Trap Z   KKYYVKTYKI DVSSNGEDWI TIKEGNKPVL FQGNTNPTDV VVAVFPKPLI TRFVRIKPAT WETGISMRFE
Trap AB  KKYYVKTYKI DVSSNGEDWI TIKEGNKPVL FQGNTNPTDV VVAVFPKPLI TRFVRIKPAT WETGISMRFE
Trap AC  KKYYVKTYKI DVSSNGEDWI TIKEGNKPVL FQGNTNPTDV VVAVFPKPLI TRFVRIKPAT WETGISMRFE
Trap O   KKYYVKTYKI DVSSNGEDWI TIKEGNKPVL FQGNTNPTDV VVAVFPKPLI TRFVRIKPAT WETGISMRFE
Trap Q   KKYYVKTYKI DVSSNGEDWI TIKEGNKPVL FQGNTNPTDV VVAVFPKPLI TRFVRIKPAT WETGISMRFE
Trap M   KKYYVKTYKI DVSSNGEDWI TIKEGNKPVL FQGNTNPTDV VVAVFPKPLI TRFVRIKPAT WETGISMRFE
Trap P   KKYYVKTYKI DVSSNGEDWI TIKEGNKPVL FQGNTNPTDV VVAVFPKPLI TRFVRIKPAT WETGISMRFE
Trap N
Trap W   KKYYVKTYKI DVSSNGEDWI TIKEGNKPVL FQGNTNPTDV VVAVFPKPLI TRFVRIKPAT WETGISMRFE
Trap X   KKYYVKTYKI DVSSNGEDWI TIKEGNKPVL FQGNTNPTDV VVAVFPKPLI TRFVRIKPAT WETGISMRFE
Trap Y
Trap S   KKYYVKTYKI DVSSNGEDWI TIKEGNKPVL FQGNTNPTDV VVAVFPKPLI TRFVRIKPAT WETGISMRFE
Trap AD  KKYYVKTYKI DVSSNGEDWI TIKEGNKPVL FQGNTNPTDV VVAVFPKPLI TRFVRIKPAT WETGISMRFE
Trap AE  KKYYVKTYKI DVSSNGEDWI TIKEGNKPVL FQGNTNPTDV VVAVFPKPLI TRFVRIKPAT WETGISMRFE
Trap AF
Trap AG
Trap AJ  KKYYVKTYKI DVSSNGEDWI TIKEGNKPVL FQGNTNPTDV VVAVFPKPLI TRFVRIKPAT WETGISMRFE
Trap AK  KKYYVKTYKI DVSSNGEDWI TIKEGNKPVL FQGNTNPTDV VVAVFPKPLI TRFVRIKPAT WETGISMRFE
Trap AR  KKYYVKTYKI DVSSNGEDWI TIKEGNKPVL FQGNTNPTDV VVAVFPKPLI TRFVRIKPAT WETGISMRFE
Trap AS  KKYYVKTYKI DVSSNGEDWI TIKEGNKPVL FQGNTNPTDV VVAVFPKPLI TRFVRIKPAT WETGISMRFE
```

FIG. 18C

```
             430        440        450        460        470        480        490
NRP-1    VYGCKITDYP CSGMLGMVSG LISDSQITSS NQGDRNWMPE NIRLVTSRSG WALPPAPHSY INEWLQIDLG
Trap G   VYGCKITDYP CSGMLGMVSG LISDSQITSS NQGDRNWMPE NIRLVTSRSG WALPPAPHSY INEWLQIDLG
Trap R   VYGCKITDYP CSGMLGMVSG LISDSQITSS NQGDRNWMPE NIRLVTSRSG WALPPAPHSY INEWLQIDLG
Trap Z   VYGCKITDYP CSGMLGMVSG LISDSQITSS NQGDRNWMPE NIRLVTSRSG WALPPAPHSY INEWLQIDLG
Trap AB  VYGCKITDYP CSGMLGMVSG LISDSQITSS NQGDRNWMPE NIRLVTSRSG WALPPAPHSY INEWLQIDLG
Trap AC  VYGCKITDYP CSGMLGMVSG LISDSQITSS NQGDRNWMPE NIRLVTSRSG WALPPAPHSY INEWLQIDLG
Trap O   VYGCKITDYP CSGMLGMVSG LISDSQITSS NQGDRNWMPE NIRLVTSRSG WALPPAPHSY INEWLQIDLG
Trap Q   VYGCKITDYP CSGMLGMVSG LISDSQITSS NQGDRNWMPE NIRLVTSRSG WALPPAPHSY INEWLQIDLG
Trap M   VYGC
Trap P   VYGC
Trap N
Trap W   VYGCKITDYP
Trap X   VYGCKITDYP
Trap Y
Trap S   VYGCKITDYP
Trap AD  VYGC
Trap AE  VYGCKITDYP CSGMLGMVSG LISDSQITSS NQGDRNWMPE NIRLVTSRSG WALPPAPHSY INEWLQIDLG
Trap AF             CSGMLGMVSG LISDSQITSS NQGDRNWMPE NIRLVTSRSG WALPPAPHSY INEWLQIDLG
Trap AG            CSGMLGMVSG LISDSQITSS NQGDRNWMPE NIRLVTSRSG WALPPAPHSY INEWLQIDLG
Trap AJ  VYGCKITDYP CSGMLGMVSG LISDSQITSS NQGDRNWMPE NIRLVTSRSG WALPPAPHSY INEWLQIDLG
Trap AK  VYGCKITDYP CSGMLGMVSG LISDSQITSS NQGDRNWMPE NIRLVTSRSG WALPPAPHSY INEWLQIDLG
Trap AR  VYGC
Trap AS  VYGCKITDYP 500        510        520        530        540        550        560
NRP-1    EEKIVRGIII QGGKHRENKV FMRKFKIGYS NNGSDWKMIM DDSKRKAKSF EGNNNYDTPE LRTFPALSTR
Trap G   EEKIVRGIII QGGKHRENKV FMRKFKIGYS NNGSDWKMIM DDSKRKAKSF EGNNNYDTPE LRTFPALSTR
Trap R   EEKIVRGIII QGGKHRENKV FMRKFKIGYS NNGSDWKMIM DDSKRKAKSF EGNNNYDTPE LRTFPALSTR
Trap Z   EEKIVRGIII QGGKHRENKV FMRKFKIGYS NNGSDWKMIM DDSKRKAKSF EGNNNYDTPE LRTFPALSTR
Trap AB  EEKIVRGIII QGGKHRENKV FMRKFKIGYS NNGSDWKMIM DDSKRKAKSF EGNNNYDTPE LRTFPALSTR
Trap AC  EEKIVRGIII QGGKHRENKV FMRKFKIGYS NNGSDWKMIM DDSKRKAKSF EGNNNYDTPE LRTFPALSTR
Trap O   EEKIVRGIII QGGKHRENKV FMRKFKIGYS NNGSDWKMIM DDSKRKAKSF EGNNNYDTPE LRTFPALSTR
Trap Q   EEKIVRGIII QGGKHRENKV FMRKFKIGYS NNGSDWKMIM DDSKRKAKSF EGNNNYDTPE LRTFPALSTR
Trap M
Trap P
Trap N
Trap W
Trap X
Trap Y
Trap S
Trap AD
Trap AE  EEKIVRGIII QGGKHRENKV FMRKFKIGYS NNGSDWKMIM DDSKRKAKSF EGNNNYDTPE LRTFPALSTR
Trap AF  EEKIVRGIII QGGKHRENKV FMRKFKIGYS NNGSDWKMIM DDSKRKAKSF EGNNNYDTPE LRTFPALSTR
Trap AG  EEKIVRGIII QGGKHRENKV FMRKFKIGYS NNGSDWKMIM DDSKRKAKSF EGNNNYDTPE LRTFPALSTR
Trap AJ  EEKIVRGIII QGGKHRENKV FMRKFKIGYS NNGSDWKMIM DDSKRKAKSF EGNNNYDTPE LRTFPALSTR
Trap AK  EEKIVRGIII QGGKHRENKV FMRKFKIGYS NNGSDWKMIM DDSKRKAKSF EGNNNYDTPE LRTFPALSTR
Trap AR
Trap AS
```

FIG. 18D

```
          570        580        590        600        610        620        630
NRP-1    FIRIYPERAI HGGLGLRMEL LGCEVEAPTA GPTTPNGNLV DECDDQANC  HSGTGDDFQL TGGTTVLATE
Trap G   FIRIYPERAI HGGLGLRMEL LGCEVEAPTA GPTTPNGNLV DECDDQANC  HSGTGDDFQL TGGTTVLATE
Trap R   FIRIYPERAI HGGLGLRMEL LGCEVEAPTA GPTTPNGNLV DECDDQANC  HSGTGDDFQL TGGTTVLATE
Trap Z   FIRIYPERAI HGGLGLRMEL LGCEVEAPTA GPTTPNGNLV DECDDQANC  HSGTGDDFQL TGGTTVLATE
Trap AB  FIRIYPERAI HGGLGLRMEL LGCEVEAPTA GPTTPNGNLV DECDDQANC  HSGTGDDFQL TGGTTVLATE
Trap AC  FIRIYPERAI HGGLGLRMEL LGCEVEAPTA GPTTPNGNLV DECDDQANC  HSGTGDDFQL TGGTTVLATE
Trap O   FIRIYPERAI HGGLGLRMEL LGC
Trap Q   FIRIYPERAI HGGLGLRMEL LGC
Trap M
Trap P
Trap N
Trap W                         EVEAPTA GPTTPNGNLV DECDDQANC  HSGTGDDFQL TGGTTVLATE
Trap X                         EVEAPTA GPTTPNGNLV DECDDQANC  HSGTGDDFQL TGGTTVLATE
Trap Y                         EVEAPTA GPTTPNGNLV DECDDQANC  HSGTGDDFQL TGGTTVLATE
Trap S                         EVEAPTA GPTTPNGNLV DECDDQANC  HSGTGDDFQL TGGTTVLATE
Trap AD  FIRIYPERAI HGGLGLRMEL LGC
Trap AE
Trap AF  FIRIYPERAI HGGLGLRMEL LGCEVEAPTA GPTTPNGNLV DECDDQANC  HSGTGDDFQL TGGTTVLATE
Trap AG  FIRIYPERAI HGGLGLRMEL LGC
Trap AJ  FIRIYPERAI HGGLGLRMEL LGCEVEAPTA GPTTPNGNLV DECDDQANC  HSGTGDDFQL TGGTTVLATE
Trap AK  FIRIYPERAI HGGLGLRMEL LGC
Trap AR
Trap AS                        EVEAPTA GPTTPNGNLV DECDDQANC  HSGTGDDFQL TGGTTVLATE 640        650        660        670        680        690        700
NRP-1    KPTVIDSTIQ SEFPTYGFNC EFGWGSHKTF CHWEHDNHVQ LKWSVLTSKT GPIQDHTGDG NFIYSQADEN
Trap G   KPTVIDSTIQ SEFPTYGFNC EFGWGSHKTF CHWEHDNHVQ LKWSVLTSKT GPIQDHTGDG NFIYSQADEN
Trap R   KPTVIDSTIQ SEFPTYGFNC EFGWGSHKTF CHWEHDNHVQ LKWSVLTSKT GPIQDHTGDG NFIYSQADEN
Trap Z   KPTVIDSTIQ SEFPTYGFNC EFGWGSHKTF CHWEHDNHVQ LKWSVLTSKT GPIQDHTGDG NFIYSQADEN
Trap AB  KPTVIDSTIQ SEFPTYGFNC EFGWGSHKTF CHWEHDNHVQ LKWSVLTSKT GPIQDHTGDG NFIYSQADEN
Trap AC  KPTVIDSTIQ SEFPTYGFNC EFGWGSHKTF CHWEHDNHVQ LKWSVLTSKT GPIQDHTGDG NFIYSQADEN
Trap O
Trap Q
Trap M
Trap P
Trap N
Trap W   KPTVIDSTIQ SEFPTYGFNC EFGWGSHKTF CHWEHDNHVQ LKWSVLTSKT GPIQDHTGDG NFIYSQADEN
Trap X   KPTVIDSTIQ SEFPTYGFNC EFGWGSHKTF CHWEHDNHVQ LKWSVLTSKT GPIQDHTGDG NFIYSQADEN
Trap Y   KPTVIDSTIQ SEFPTYGFNC EFGWGSHKTF CHWEHDNHVQ LKWSVLTSKT GPIQDHTGDG NFIYSQADEN
Trap S   KPTVIDSTIQ SEFPTYGFNC EFGWGSHKTF CHWEHDNHVQ LKWSVLTSKT GPIQDHTGDG NFIYSQADEN
Trap AD
Trap AE
Trap AF  KPTVIDSTIQ SEFPTYGFNC EFGWGSHKTF CHWEHDNHVQ LKWSVLTSKT GPIQDHTGDG NFIYSQADEN
Trap AG  KPTVIDSTIQ SEFPTYGFNC EFGWGSHKTF CHWEHDNHVQ LKWSVLTSKT GPIQDHTGDG NFIYSQADEN
Trap AJ
Trap AK
Trap AR
Trap AS  KPTVIDSTIQ SEFPTYGFNC EFGWGSHKTF CHWEHDNHVQ LKWSVLTSKT GPIQDHTGDG NFIYSQADEN
```

FIG. 18E

```
        710        720        730        740        750        760        770
NRP-1   QKGKVARLVS PVVYSQNSAH CMTFWYHMSG SHVGTLRVKL RYQKPEEYDQ LVWMAIGHQG DHWKEGRVLL
Trap G  QKGKVARLVS PVVYSQNSAH CMTFWYHMSG SHVGTLRVKL RYQKPEEYDQ LVWMAIGHQG DHWKEGRVLL
Trap R  QKGKVARLVS PVVYSQNSAH CMTFWYHMSG SHVGTLRVKL RYQKPEEYDQ LVWMAIGHQG DHWKEGRVLL
Trap Z  QKGKVARLVS PVVYSQNSAH CMTFWYHMSG SHVGTLRVKL RYQKPEEYDQ LVWMAIGHQG DHWKEGRVLL
Trap AB QKGKVARLVS PVVYSQNSAH CMTFWYHMSG SHVGTLRVKL RYQKPEEYDQ LVWMAIGHQG DHWKEGRVLL
Trap AC QKGKVARLVS PVVYSQNSAH CMTFWYHMSG SHVGTLRVKL RYQKPEEYDQ LVWMAIGHQG DHWKEGRVLL
Trap O
Trap Q
Trap M
Trap P
Trap N
Trap W  QKGKVARLVS PVVYSQNSAH CMTFWYHMSG SHVGTLRVKL RYQKPEEYDQ LVWMAIGHQG DHWKEGRVLL
Trap X  QKGKVARLVS PVVYSQNSAH CMTFWYHMSG SHVGTLRVKL RYQKPEEYDQ LVWMAIGHQG DHWKEGRVLL
Trap Y  QKGKVARLVS PVVYSQNSAH CMTFWYHMSG SHVGTLRVKL RYQKPEEYDQ LVWMAIGHQG DHWKEGRVLL
Trap S  QKGKVARLVS PVVYSQNSAH CMTFWYHMSG SHVGTLRVKL RYQKPEEYDQ LVWMAIGHQG DHWKEGRVLL
Trap AD
Trap AE
Trap AF QKGKVARLVS PVVYSQNSAH CMTFWYHMSG SHVGTLRVKL RYQKPEEYDQ LVWMAIGHQG DHWKEGRVLL
Trap AG
Trap AJ QKGKVARLVS PVVYSQNSAH CMTFWYHMSG SHVGTLRVKL RYQKPEEYDQ LVWMAIGHQG DHWKEGRVLL
Trap AK
Trap AR
Trap AS QKGKVARLVS PVVYSQNSAH CMTFWYHMSG SHVGTLRVKL RYQKPEEYDQ LVWMAIGHQG DHWKEGRVLL 780        790        800        810        820        830        840
NRP-1   HKSLKLYQVI FEGEIGKGNL GGIAVDDISI NNHISQEDCA KPADLDKKNP EIKIDETGST PGYEGEGEGD
Trap G  HKSLKLYQVI FEGEIGKGNL GGIAVDDISI NNHISQEDCA KPADLDKKNP EIKIDETGST PGYEGEGEGD
Trap R  HKSLKLYQVI FEGEIGKGNL GGIAVDDISI NNHISQEDCA KPADLDKKNP EIKIDETGST PGYEGEGEGD
Trap Z  HKSLKLYQVI FEGEIGKGNL GGIAVDDISI NNHISQEDCA KPADLDKKNP EIKIDETGST PGYEGEGEGD
Trap AB HKSLKLYQVI FEGEIGKGNL GGIAVDDISI NNHISQEDCA KPADLDKKNP EIKIDETGST PGYEGEGEGD
Trap AC HKSLKLYQVI FEGEIGKGNL GGIAVDDISI NNHISQEDCA KPADLDKKNP EIKIDETGST PGYEGEGEGD
Trap O
Trap Q
Trap M
Trap P
Trap N
Trap W  HKSLKLYQVI FEGEIGKGNL GGIAV
Trap X  HKSLKLYQVI FEGEIGKGNL GGIAVDDISI NNHISQEDCA KPADLDKKNP EIKIDETGST PGYEGEGEGD
Trap Y  HKSLKLYQVI FEGEIGKGNL GGIAVDDISI NNHISQEDCA KPADLDKKNP EIKIDETGST PGYEGEGEGD
Trap S  HKSLKLYQVI FEGEIGKGNL GGIAVDDISI NNHISQEDCA KPADLDKKNP EIKIDETGST PGYEGEGEGD
Trap AD
Trap AE
Trap AF HKSLKLYQVI FEGEIGKGNL GGIAVDDISI NNHISQEDCA KPADLDKKNP EIKIDETGST PGYEGEGEGD
Trap AG
Trap AJ HKSLKLYQVI FEGEIGKGNL GGIAVDDISI NNHISQEDCA KPADLDKKNP EIKIDETGST PGYEGEGEGD
Trap AK
Trap AR
Trap AS HKSLKLYQVI FEGEIGKGNL GGIAVDDISI NNHISQEDCA KPADLDKKNP EIKIDETGST PGYEGEGEGD
```

FIG. 18F

```
                850        860        870        880        890        900        910
NRP-1    KNISRKPGNV LKTLDPILIT IIAMSALGVL LGAVCGVVLY CACWHNGMSE RNLSALENYN FELVDGVKLK
Trap G   KNISRKPGNV LKTLDP
Trap R   KNISRKPGNV LKTLDP
Trap Z   KNISRKPGNV LKTLDP
Trap AB  KNISRKPGNV LKTLDP
Trap AC  KNISRKPGNV LKTLDP
Trap O
Trap Q
Trap M
Trap P
Trap N
Trap W
Trap X   KNISRKPGNV LKTLDP
Trap Y   KNISRKPGNV LKTLDP
Trap S   KNISRKPGNV LKTLDP
Trap AD
Trap AE
Trap AF  KNISRKPGNV LKTLDP
Trap AG
Trap AJ  KNISRKPGNV LKTLDP
Trap AK
Trap AR
Trap AS  KNISRKPGNV LKTLDP

920
NRP-1    KDKLNTQSTY SEA
```

FIG. 18G

MERGLPLLCAVLALVLAPAGAFRNDKCGDTIKIESPGYLTSPGYPHSYHPSEKCEWLIQAPDPYQRIMINFNPHFD
LEDRDCKYDYVEVFDGENENGHFRGKFCGKIAPPPVVSSGPFLFIKFVSDYETHGAGFSIRYEIFKRGPECSQNYT
TPSGVIKSPGFPEKYPNSLECTYIVFVPKMSEIILEFESFDLEPDSNPPGGMFCRYDRLEIWDGFPDVGPHIGRYCG
QKTPGRIRSSSGILSMVFYTDSAIAKEGFSANYSVLQSSVSEDFKCMEALGMESGEIHSDQITASSQYSTNWSAER
SRLNYPENGWTPGEDSYREWIQVDLGLLRFVTAVGTQGAISKETKKKYYVKTYKIDVSSNGEDWITIKEGNKPVLF
QGNTNPTDVVVAVFPKPLITRFVRIKPATWETGISMRFEVYGCKITDYPCSGMLGMVSGLISDSQITSSNQGDRNW
MPENIRLVTSRSGWALPPAPHSYINEWLQIDLGEEKIVRGIIIQGGKHRENKVFMRKFKIGYSNNGSDWKMIMDDS
KRKAKSFEGNNNYDTPELRTFPALSTRFIRIYPERATHGGLGLRMELLGCEVEAPTAGPTTPNGNLVDECDDDQA
NCHSGTGDDFQLTGGTTVLATEKPTVIDSTIQSGIK

FIG. 19A

MERGLPLLCAVLALVLAPAGAFRNDKCGDTIKIESPGYLTSPGYPHSYHPSEKCEWLIQAPDPYQRIMINFNPHFD
LEDRDCKYDYVEVFDGENENGHFRGKFCGKIAPPPVVSSGPFLFIKFVSDYETHGAGFSIRYEIFKRGPECSQNYT
TPSGVIKSPGFPEKYPNSLECTYIVFVPKMSEIILEFESFDLEPDSNPPGGMFCRYDRLEIWDGFPDVGPHIGRYCG
QKTPGRIRSSSGILSMVFYTDSAIAKEGFSANYSVLQSSVSEDFKCMEALGMESGEIHSDQITASSQYSTNWSAER
SRLNYPENGWTPGEDSYREWIQVDLGLLRFVTAVGTQGAISKETKKKYYVKTYKIDVSSNGEDWITIKEGNKPVLF
QGNTNPTDVVVAVFPKPLITRFVRIKPATWETGISMRFEVYGCKITDYPCSGMLGMVSGLISDSQITSSNQGDRNW
MPENIRLVTSRSGWALPPAPHSYINEWLQIDLGEEKIVRGIIIQGGKHRENKVFMRKFKIGYSNNGSDWKMIMDDS
KRKAKSFEGNNNYDTPELRTFPALSTRFIRIYPERATHGGLGLRMELLGCEVEGGTTVLATEKPTVIDSTIQSGIK

FIG. 19B

MERGLPLLCAVLALVLAPAGAFRNDKCGDTIKIESPGYLTSPGYPHSYHPSEKCEWLIQAPDPYQRIMINFNPHFD
LEDRDCKYDYVEVFDGENENGHFRGKFCGKIAPPPVVSSGPFLFIKFVSDYETHGAGFSIRYEIFKRGPECSQNYT
TPSGVIKSPGFPEKYPNSLECTYIVFVPKMSEIILEFESFDLEPDSNPPGGMFCRYDRLEIWDGFPDVGPHIGRYCG
QKTPGRIRSSSGILSMVFYTDSAIAKEGFSANYSVLQSSVSEDFKCMEALGMESGEIHSDQITASSQYSTNWSAER
SRLNYPENGWTPGEDSYREWIQVDLGLLRFVTAVGTQGAISKETKKKYYVKTYKIDVSSNGEDWITIKEGNKPVLF
QGNTNPTDVVVAVFPKPLITRFVRIKPATWETGISMRFEVYGCKITDYPCSGMLGMVSGLISDSQITSSNQGDRNW
MPENIRLVTSRSGWALPPAPHSYINEWLQIDLGEEKIVRGIIIQGGKHRENKVFMRKFKIGYSNNGSDWKMIMDDS
KRKAKSFEGNNNYDTPELRTFPALSTRFIRIYPERATHGGLGLRMELLGCEVEAPTAGPTTPNGNLVDECDDDQA
NCHSGTGDDFQLTG**AETIFIPLLYHFSSCLSWDQLTPVCVLVTPHGRELPRNRSCLARTRASSFPHVIWIDELFLI
ATTICNNNLSHFESQRLGLS**

FIG. 19C

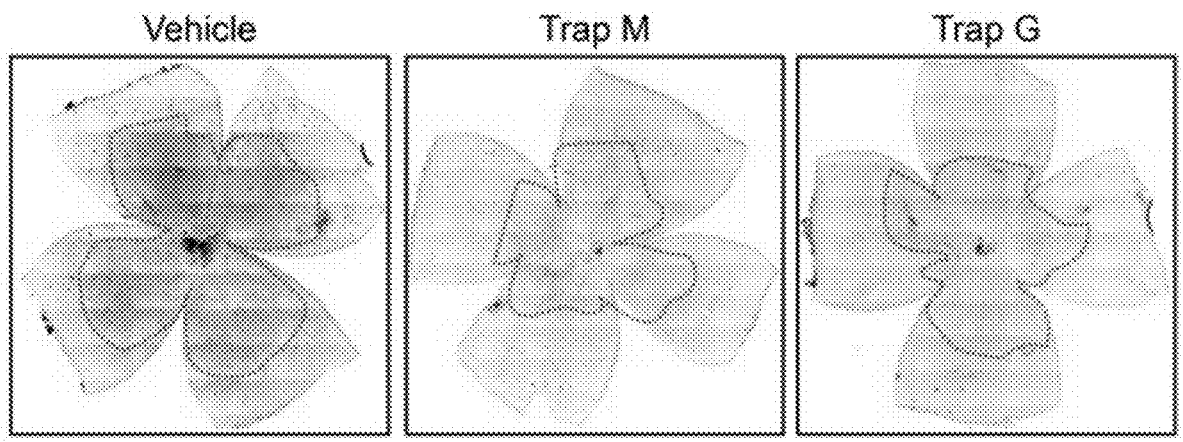

FIG. 20A

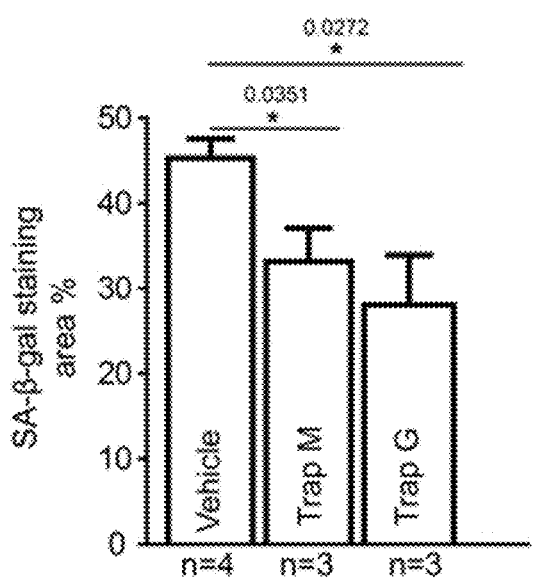

FIG. 20B

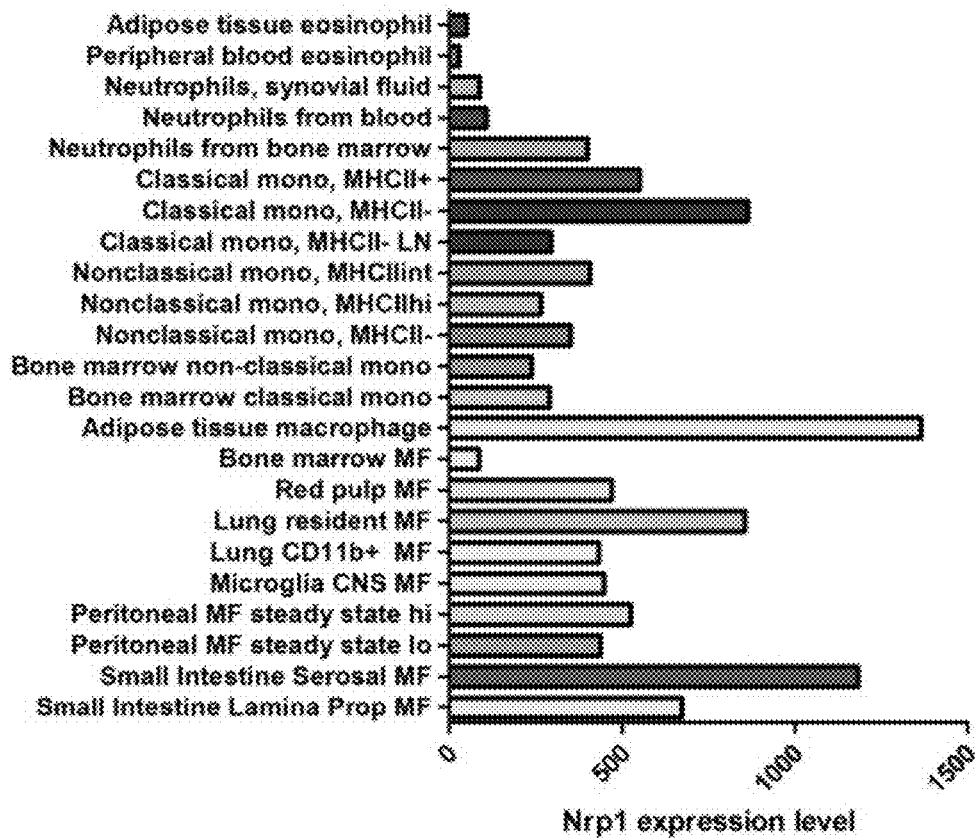
FIG. 21A
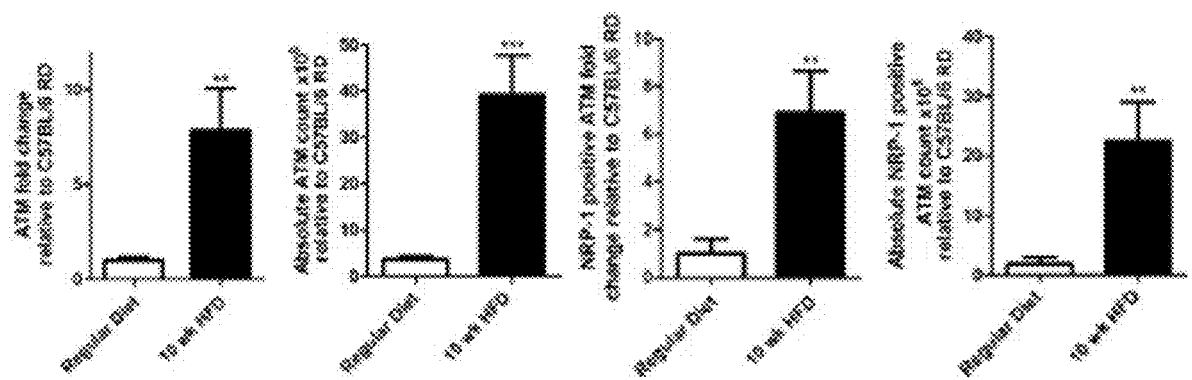
FIG. 21B
FIG. 21C

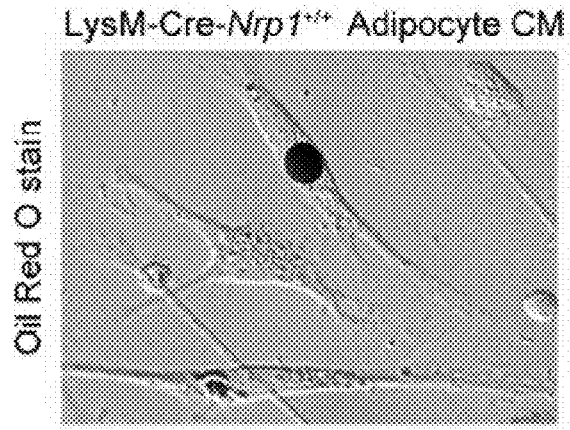
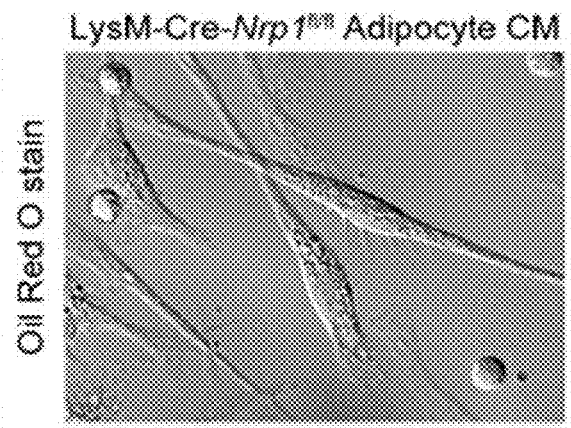
FIG. 22F          FIG. 22G
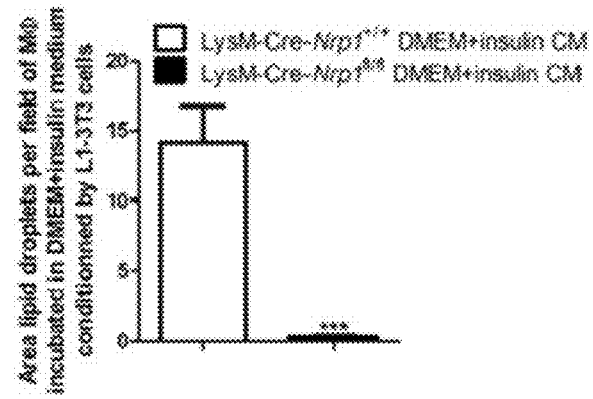
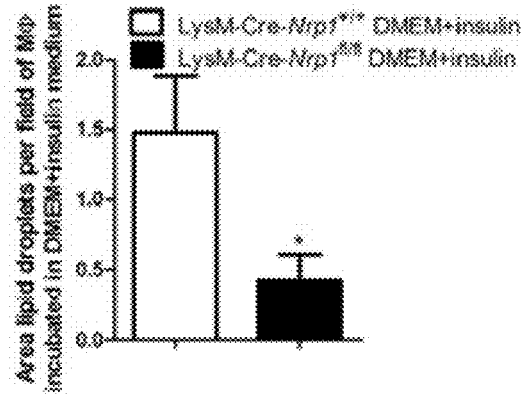
FIG. 22H          FIG. 22I
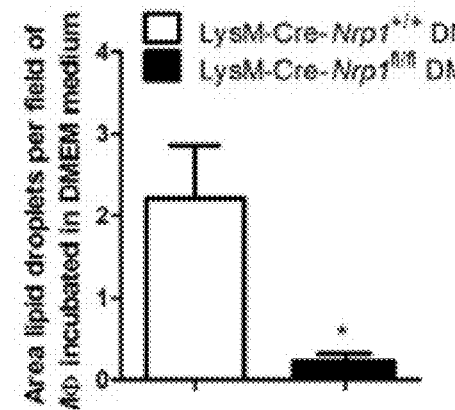
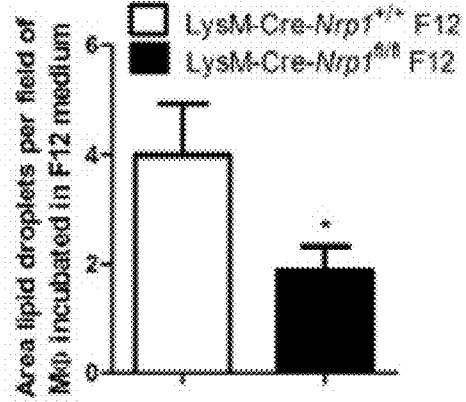
FIG. 22J          FIG. 22K

```
SEQUENCE LISTING

<160> NUMBER OF SEQ ID NOS: 110

<210> SEQ ID NO 1
<211> LENGTH: 22
<212> TYPE: DNA
<213> ORGANISM: Artificial sequence
<220> FEATURE:
<223> OTHER INFORMATION: Synthetic construct

<400> SEQUENCE: 1
gacggccagg tcatcactat tg                                              22

<210> SEQ ID NO 2
<211> LENGTH: 21
<212> TYPE: DNA
<213> ORGANISM: Artificial sequence
<220> FEATURE:
<223> OTHER INFORMATION: Synthetic construct

<400> SEQUENCE: 2
ctggtacatc agcacctcac a                                               21

<210> SEQ ID NO 3
<211> LENGTH: 21
<212> TYPE: DNA
<213> ORGANISM: Artificial sequence
<220> FEATURE:
<223> OTHER INFORMATION: Synthetic construct

<400> SEQUENCE: 3
ctctgggaaa tcgtggaaat g                                               21

<210> SEQ ID NO 4
<211> LENGTH: 22
<212> TYPE: DNA
<213> ORGANISM: Artificial sequence
<220> FEATURE:
<223> OTHER INFORMATION: Synthetic construct

<400> SEQUENCE: 4
```
ccgaacgtga tccgctactt ct                                              22

<210> SEQ ID NO 5
<211> LENGTH: 20
<212> TYPE: DNA
<213> ORGANISM: Artificial sequence
<220> FEATURE:
<223> OTHER INFORMATION: Synthetic construct

<400> SEQUENCE: 5
ggccaatccc aagagcagag                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
ctccactgct gcttcctgag                                                 20

<210> SEQ ID NO 7
<211> LENGTH: 21
<212> TYPE: DNA
<213> ORGANISM: Artificial sequence
<220> FEATURE:
<223> OTHER INFORMATION: Synthetic construct

<400> SEQUENCE: 7
ccgtgttggt tcatccctgt a                                               21

<210> SEQ ID NO 8
<211> LENGTH: 17
<212> TYPE: DNA
<213> ORGANISM: Artificial sequence
<220> FEATURE:
<223> OTHER INFORMATION: Synthetic construct

<400> SEQUENCE: 8
tgacgtcgtg gaactgc                                                    17

<210> SEQ ID NO 9
<211> LENGTH: 22
<212> TYPE: DNA
<213> ORGANISM: Artificial sequence
<220> FEATURE:
<223> OTHER INFORMATION: Synthetic construct

<400> SEQUENCE: 9
gggacttcgc tatcttcaga ac                                              22

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
ggactctcca cctgcaagac                                                 20

<210> SEQ ID NO 11
<211> LENGTH: 21
<212> TYPE: DNA
<213> ORGANISM: Artificial sequence

```
<220> FEATURE:
<223> OTHER INFORMATION: Synthetic construct

<400> SEQUENCE: 11
ctgagtccga atcaggtcca g                                              21

<210> SEQ ID NO 12
<211> LENGTH: 21
<212> TYPE: DNA
<213> ORGANISM: Artificial sequence
<220> FEATURE:
<223> OTHER INFORMATION: Synthetic construct

<400> SEQUENCE: 12
cgcgacgtgg aactggcaga a                                              21

<210> SEQ ID NO 13
<211> LENGTH: 20
<212> TYPE: DNA
<213> ORGANISM: Artificial sequence
<220> FEATURE:
<223> OTHER INFORMATION: Synthetic construct

<400> SEQUENCE: 13
gccctgagtc aagaggacag                                                20

<210> SEQ ID NO 14
<211> LENGTH: 20
<212> TYPE: DNA
<213> ORGANISM: Artificial sequence
<220> FEATURE:
<223> OTHER INFORMATION: Synthetic construct

<400> SEQUENCE: 14
caaggctttt gaaggcaaag                                                20

<210> SEQ ID NO 15
<211> LENGTH: 20
<212> TYPE: DNA
<213> ORGANISM: Artificial sequence
<220> FEATURE:
<223> OTHER INFORMATION: Synthetic construct

<400> SEQUENCE: 15
gtcacagatg tgccgaatgg                                                20

<210> SEQ ID NO 16
<211> LENGTH: 20
<212> TYPE: DNA
<213> ORGANISM: Artificial sequence
<220> FEATURE:
<223> OTHER INFORMATION: Synthetic construct

<400> SEQUENCE: 16
ggcggtggtg acagtatctt                                                20

<210> SEQ ID NO 17
<211> LENGTH: 22
<212> TYPE: DNA
<213> ORGANISM: Artificial sequence
<220> FEATURE:
<223> OTHER INFORMATION: Synthetic construct

<400> SEQUENCE: 17
ccacaggatt ccatacccaa ga                                             22
```

<210> SEQ ID NO 18
<211> LENGTH: 20
<212> TYPE: DNA
<213> ORGANISM: Artificial sequence
<220> FEATURE:
<223> OTHER INFORMATION: Synthetic construct

<400> SEQUENCE: 18
gagctcctta acatgccctg                                        20

<210> SEQ ID NO 19
<211> LENGTH: 24
<212> TYPE: DNA
<213> ORGANISM: Artificial sequence
<220> FEATURE:
<223> OTHER INFORMATION: Synthetic construct

<400> SEQUENCE: 19
aagtgcatca tcgttgttca taca                                   24

<210> SEQ ID NO 20
<211> LENGTH: 22
<212> TYPE: DNA
<213> ORGANISM: Artificial sequence
<220> FEATURE:
<223> OTHER INFORMATION: Synthetic construct

<400> SEQUENCE: 20
cgcaaagtcc ttctgctcca ca                                     22

<210> SEQ ID NO 21
<211> LENGTH: 20
<212> TYPE: DNA
<213> ORGANISM: Artificial sequence
<220> FEATURE:
<223> OTHER INFORMATION: Synthetic construct

<400> SEQUENCE: 21
gccacatgct agacacgcta                                        20

<210> SEQ ID NO 22
<211> LENGTH: 20
<212> TYPE: DNA
<213> ORGANISM: Artificial sequence
<220> FEATURE:
<223> OTHER INFORMATION: Synthetic construct

<400> SEQUENCE: 22
tgctgagctc atgccctttg                                        20

<210> SEQ ID NO 23
<211> LENGTH: 29
<212> TYPE: DNA
<213> ORGANISM: Artificial sequence
<220> FEATURE:
<223> OTHER INFORMATION: Synthetic construct

<400> SEQUENCE: 23
ttttggattt ttaagacaga gtctttgta                              29

<210> SEQ ID NO 24
<211> LENGTH: 20
<212> TYPE: DNA
<213> ORGANISM: Artificial sequence
<220> FEATURE:
<223> OTHER INFORMATION: Synthetic construct

<400> SEQUENCE: 24
gaaagacttg tgaagtcggc                                            20

<210> SEQ ID NO 25
<211> LENGTH: 21
<212> TYPE: DNA
<213> ORGANISM: Artificial sequence
<220> FEATURE:
<223> OTHER INFORMATION: Synthetic construct

<400> SEQUENCE: 25
ggcgtgcttt taggaatgtt g                                          21

<210> SEQ ID NO 26
<211> LENGTH: 20
<212> TYPE: DNA
<213> ORGANISM: Artificial sequence
<220> FEATURE:
<223> OTHER INFORMATION: Synthetic construct

<400> SEQUENCE: 26
catagatggc gttgttgcgg                                            20

<210> SEQ ID NO 27
<211> LENGTH: 21
<212> TYPE: DNA
<213> ORGANISM: Artificial sequence
<220> FEATURE:
<223> OTHER INFORMATION: Synthetic construct

<400> SEQUENCE: 27
gtccatggga agatgttctg g                                          21

<210> SEQ ID NO 28
<211> LENGTH: 24
<212> TYPE: DNA
<213> ORGANISM: Artificial sequence
<220> FEATURE:
<223> OTHER INFORMATION: Synthetic construct

<400> SEQUENCE: 28
cttggtggtt tgctacgacg tggg                                       24

<210> SEQ ID NO 29
<211> LENGTH: 20
<212> TYPE: DNA
<213> ORGANISM: Artificial sequence
<220> FEATURE:
<223> OTHER INFORMATION: Synthetic construct

<400> SEQUENCE: 29
ctcctaggcc cctcagaagt                                            20

<210> SEQ ID NO 30
<211> LENGTH: 20
<212> TYPE: DNA
<213> ORGANISM: Artificial sequence
<220> FEATURE:
<223> OTHER INFORMATION: Synthetic construct

<400> SEQUENCE: 30
agaaggtgtt tgtggctgct                                            20

<210> SEQ ID NO 31

<211> LENGTH: 20
<212> TYPE: DNA
<213> ORGANISM: Artificial sequence
<220> FEATURE:
<223> OTHER INFORMATION: Synthetic construct

<400> SEQUENCE: 31
tgagcgtgat cagctccagg                                              20

<210> SEQ ID NO 32
<211> LENGTH: 20
<212> TYPE: DNA
<213> ORGANISM: Artificial sequence
<220> FEATURE:
<223> OTHER INFORMATION: Synthetic construct

<400> SEQUENCE: 32
gtcactgaca gaggcgatga                                              20

<210> SEQ ID NO 33
<211> LENGTH: 21
<212> TYPE: DNA
<213> ORGANISM: Artificial sequence
<220> FEATURE:
<223> OTHER INFORMATION: Synthetic construct

<400> SEQUENCE: 33
aaatccttga tattaaccag g                                            21

<210> SEQ ID NO 34
<211> LENGTH: 21
<212> TYPE: DNA
<213> ORGANISM: Artificial sequence
<220> FEATURE:
<223> OTHER INFORMATION: Synthetic construct

<400> SEQUENCE: 34
tttcccgtaa atatcacacc g                                            21

<210> SEQ ID NO 35
<211> LENGTH: 21
<212> TYPE: DNA
<213> ORGANISM: Artificial sequence
<220> FEATURE:
<223> OTHER INFORMATION: Synthetic construct

<400> SEQUENCE: 35
ttgaaactac tttaagaacg g                                            21

<210> SEQ ID NO 36
<211> LENGTH: 21
<212> TYPE: DNA
<213> ORGANISM: Artificial sequence
<220> FEATURE:
<223> OTHER INFORMATION: Synthetic construct

<400> SEQUENCE: 36
aaattagcac attcttcag g                                             21

<210> SEQ ID NO 37
<211> LENGTH: 21
<212> TYPE: DNA
<213> ORGANISM: Artificial sequence
<220> FEATURE:
<223> OTHER INFORMATION: Synthetic construct

<400> SEQUENCE: 37

| aaattgccaa taccaagg c | 21 |

<210> SEQ ID NO 38
<211> LENGTH: 21
<212> TYPE: DNA
<213> ORGANISM: Artificial sequence
<220> FEATURE:
<223> OTHER INFORMATION: Synthetic construct

<400> SEQUENCE: 38

| aatgagctgc atgaagtctc g | 21 |

<210> SEQ ID NO 39
<211> LENGTH: 21
<212> TYPE: DNA
<213> ORGANISM: Artificial sequence
<220> FEATURE:
<223> OTHER INFORMATION: Synthetic construct

<400> SEQUENCE: 39

| aaattggcac attctttcag g | 21 |

<210> SEQ ID NO 40
<211> LENGTH: 21
<212> TYPE: DNA
<213> ORGANISM: Artificial sequence
<220> FEATURE:
<223> OTHER INFORMATION: Synthetic construct

<400> SEQUENCE: 40

| ttcattagga atacatcctg c | 21 |

<210> SEQ ID NO 41
<211> LENGTH: 21
<212> TYPE: DNA
<213> ORGANISM: Artificial sequence
<220> FEATURE:
<223> OTHER INFORMATION: Synthetic construct

<400> SEQUENCE: 41

| ttatttatag gaaacactgg g | 21 |

<210> SEQ ID NO 42
<211> LENGTH: 19
<212> TYPE: DNA
<213> ORGANISM: Artificial sequence
<220> FEATURE:
<223> OTHER INFORMATION: Synthetic construct

<400> SEQUENCE: 42

| aacgccaccc atccaacca | 19 |

<210> SEQ ID NO 43
<211> LENGTH: 22
<212> TYPE: DNA
<213> ORGANISM: Artificial sequence
<220> FEATURE:
<223> OTHER INFORMATION: Synthetic construct

<400> SEQUENCE: 43

| gcaagctgac cctgaagttc at | 22 |

<210> SEQ ID NO 44
<211> LENGTH: 644
<212> TYPE: PRT

<213> ORGANISM: Homo sapiens

<400> SEQUENCE: 44

```
Met Glu Arg Gly Leu Pro Leu Leu Cys Ala Val Leu Ala Leu Val Leu
1               5                   10                  15
Ala Pro Ala Gly Ala Phe Arg Asn Asp Lys Cys Gly Asp Thr Ile Lys
            20                  25                  30
Ile Glu Ser Pro Gly Tyr Leu Thr Ser Pro Gly Tyr Pro His Ser Tyr
        35                  40                  45
His Pro Ser Glu Lys Cys Glu Trp Leu Ile Gln Ala Pro Asp Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Pro Val
            100                 105                 110
Val Ser Ser Gly Pro Phe Leu Phe Ile Lys Phe Val Ser Asp Tyr Glu
        115                 120                 125
Thr His Gly Ala Gly Phe Ser Ile Arg Tyr Glu Ile Phe Lys Arg Gly
    130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Val Pro Lys Met Ser Glu Ile Ile Leu Glu Phe Glu Ser Phe
            180                 185                 190
Asp Leu Glu Pro Asp Ser Asn Pro Pro Gly Gly Met Phe Cys Arg Tyr
        195                 200                 205
Asp Arg Leu Glu Ile Trp Asp Gly Phe Pro Asp Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Ser Thr Asn Trp Ser Ala Glu
    290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
        355                 360                 365
Trp Ile Thr Ile Lys Glu Gly Asn Lys Pro Val Leu Phe Gln Gly Asn
    370                 375                 380
Thr Asn Pro Thr Asp Val Val Val Ala Val Phe Pro Lys Pro Leu Ile
385                 390                 395                 400
```

```
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
        515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Leu Val Asp Glu Cys Asp Asp Asp Gln Ala
        595                 600                 605
Asn Cys His Ser Gly Thr Gly Asp Asp Phe Gln Leu Thr Gly Gly Thr
610                 615                 620
Thr Val Leu Ala Thr Glu Lys Pro Thr Val Ile Asp Ser Thr Ile Gln
625                 630                 635                 640
Ser Gly Ile Lys

<210> SEQ ID NO 45
<211> LENGTH: 609
<212> TYPE: PRT
<213> ORGANISM: Homo sapiens

<400> SEQUENCE: 45

Met Glu Arg Gly Leu Pro Leu Leu Cys Ala Val Leu Ala Leu Val Leu
1               5                   10                  15
Ala Pro Ala Gly Ala Phe Arg Asn Asp Lys Cys Gly Asp Thr Ile Lys
            20                  25                  30
Ile Glu Ser Pro Gly Tyr Leu Thr Ser Pro Gly Tyr Pro His Ser Tyr
        35                  40                  45
His Pro Ser Glu Lys Cys Glu Trp Leu Ile Gln Ala Pro Asp Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Pro Val
            100                 105                 110
Val Ser Ser Gly Pro Phe Leu Phe Ile Lys Phe Val Ser Asp Tyr Glu
        115                 120                 125
```

```
Thr His Gly Ala Gly Phe Ser Ile Arg Tyr Glu Ile Phe Lys Arg Gly
    130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Val Pro Lys Met Ser Glu Ile Ile Leu Glu Phe Glu Ser Phe
                180                 185                 190
Asp Leu Glu Pro Asp Ser Asn Pro Pro Gly Met Phe Cys Arg Tyr
            195                 200                 205
Asp Arg Leu Glu Ile Trp Asp Gly Phe Pro Asp Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
Phe Lys Cys Met Glu Ala Leu Gly Met Glu Ser Gly Glu Ile His Ser
    275                 280                 285
Asp Gln Ile Thr Ala Ser Ser Gln Tyr Ser Thr Asn Trp Ser Ala Glu
    290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
    355                 360                 365
Trp Ile Thr Ile Lys Glu Gly Asn Lys Pro Val Leu Phe Gln Gly Asn
    370                 375                 380
Thr Asn Pro Thr Asp Val Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
            435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
    515                 520                 525
Ile Met Asp Asp Ser Lys Arg Lys Ala Lys Ser Phe Glu Gly Asn Asn
    530                 535                 540
Asn Tyr Asp Thr Pro Glu Leu Arg Thr Phe Pro Ala Leu Ser Thr Arg
```

```
                  545                 550                 555                 560
            Phe Ile Arg Ile Tyr Pro Glu Arg Ala Thr His Gly Gly Leu Gly Leu
                              565                 570                 575

Arg Met Glu Leu Leu Gly Cys Glu Val Glu Gly Gly Thr Thr Val Leu
                              580                 585                 590

Ala Thr Glu Lys Pro Thr Val Ile Asp Ser Thr Ile Gln Ser Gly Ile
                              595                 600                 605

Lys

<210> SEQ ID NO 46
<211> LENGTH: 704
<212> TYPE: PRT
<213> ORGANISM: Homo sapiens

<400> SEQUENCE: 46

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Val Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
```

```
                305                 310                 315                 320
        Ser Tyr Arg Glu Trp Ile Gln Val Asp Leu Gly Leu Arg Phe Val
                        325                 330                 335

Thr Ala Val Gly Thr Gln Gly Ala Ile Ser Lys Glu Thr Lys Lys
                        340                 345                 350

Tyr Tyr Val Lys Thr Tyr Lys Ile Asp Val Ser Ser Asn Gly Glu Asp
                        355                 360                 365

Trp Ile Thr Ile Lys Glu Gly Asn Lys Pro Val Leu Phe Gln Gly Asn
        370                 375                 380

Thr Asn Pro Thr Asp Val Val Ala Val Phe Pro Lys Pro Leu Ile
        385                 390                 395                 400

Thr Arg Phe Val Arg Ile Lys Pro Ala Thr Trp Glu Thr Gly Ile Ser
                        405                 410                 415

Met Arg Phe Glu Val Tyr Gly Cys Lys Ile Thr Asp Tyr Pro Cys Ser
                        420                 425                 430

Gly Met Leu Gly Met Val Ser Gly Leu Ile Ser Asp Ser Gln Ile Thr
                        435                 440                 445

Ser Ser Asn Gln Gly Asp Arg Asn Trp Met Pro Glu Asn Ile Arg Leu
        450                 455                 460

Val Thr Ser Arg Ser Gly Trp Ala Leu Pro Pro Ala Pro His Ser Tyr
        465                 470                 475                 480

Ile Asn Glu Trp Leu Gln Ile Asp Leu Gly Glu Glu Lys Ile Val Arg
                        485                 490                 495

Gly Ile Ile Ile Gln Gly Gly Lys His Arg Glu Asn Lys Val Phe Met
                        500                 505                 510

Arg Lys Phe Lys Ile Gly Tyr Ser Asn Asn Gly Ser Asp Trp Lys Met
                        515                 520                 525

Ile Met Asp Asp Ser Lys Arg Lys Ala Lys Ser Phe Glu Gly Asn Asn
                        530                 535                 540

Asn Tyr Asp Thr Pro Glu Leu Arg Thr Phe Pro Ala Leu Ser Thr Arg
        545                 550                 555                 560

Phe Ile Arg Ile Tyr Pro Glu Arg Ala Thr His Gly Gly Leu Gly Leu
                        565                 570                 575

Arg Met Glu Leu Leu Gly Cys Glu Val Glu Ala Pro Thr Ala Gly Pro
                        580                 585                 590

Thr Thr Pro Asn Gly Asn Leu Val Asp Glu Cys Asp Asp Gln Ala
                        595                 600                 605

Asn Cys His Ser Gly Thr Gly Asp Asp Phe Gln Leu Thr Gly Ala Glu
                        610                 615                 620

Thr Ile Phe Ile Pro Leu Leu Tyr His Phe Ser Ser Cys Leu Ser Trp
        625                 630                 635                 640

Asp Gln Leu Thr Pro Val Cys Val Leu Val Thr Pro His Gly Arg Glu
                        645                 650                 655

Leu Pro Arg Asn Arg Ser Cys Leu Ala Arg Thr Arg Ala Ser Ser Phe
                        660                 665                 670

Pro His Val Ile Trp Ile Asp Glu Leu Phe Leu Ile Ala Thr Thr Ile
                        675                 680                 685

Cys Asn Asn Asn Leu Ser His Phe Glu Ser Gln Arg Leu Gly Leu Ser
                        690                 695                 700

<210> SEQ ID NO 47
<211> LENGTH: 923
<212> TYPE: PRT
<213> ORGANISM: artificial sequence
```

```
<220> FEATURE:
<223> OTHER INFORMATION: Synthetic construct
<220> FEATURE:
<221> NAME/KEY: VARIANT
<222> LOCATION: (11)..(11)
<223> OTHER INFORMATION: X is any amino acid
<220> FEATURE:
<221> NAME/KEY: VARIANT
<222> LOCATION: (15)..(15)
<223> OTHER INFORMATION: X is any amino acid
<220> FEATURE:
<221> NAME/KEY: VARIANT
<222> LOCATION: (18)..(18)
<223> OTHER INFORMATION: X is any amino acid
<220> FEATURE:
<221> NAME/KEY: VARIANT
<222> LOCATION: (24)..(24)
<223> OTHER INFORMATION: X is any amino acid
<220> FEATURE:
<221> NAME/KEY: VARIANT
<222> LOCATION: (29)..(29)
<223> OTHER INFORMATION: X is any amino acid
<220> FEATURE:
<221> NAME/KEY: VARIANT
<222> LOCATION: (35)..(35)
<223> OTHER INFORMATION: X is any amino acid
<220> FEATURE:
<221> NAME/KEY: VARIANT
<222> LOCATION: (62)..(62)
<223> OTHER INFORMATION: X is any amino acid
<220> FEATURE:
<221> NAME/KEY: VARIANT
<222> LOCATION: (90)..(90)
<223> OTHER INFORMATION: X is any amino acid
<220> FEATURE:
<221> NAME/KEY: VARIANT
<222> LOCATION: (96)..(96)
<223> OTHER INFORMATION: X is any amino acid
<220> FEATURE:
<221> NAME/KEY: VARIANT
<222> LOCATION: (98)..(98)
<223> OTHER INFORMATION: X is any amino acid
<220> FEATURE:
<221> NAME/KEY: VARIANT
<222> LOCATION: (99)..(99)
<223> OTHER INFORMATION: X is any amino acid
<220> FEATURE:
<221> NAME/KEY: VARIANT
<222> LOCATION: (100)..(100)
<223> OTHER INFORMATION: X is any amino acid
<220> FEATURE:
<221> NAME/KEY: VARIANT
<222> LOCATION: (100)..(100)
<223> OTHER INFORMATION: X is any amino acid
<220> FEATURE:
<221> NAME/KEY: VARIANT
<222> LOCATION: (110)..(110)
<223> OTHER INFORMATION: X is any amino acid
<220> FEATURE:
<221> NAME/KEY: VARIANT
<222> LOCATION: (140)..(140)
<223> OTHER INFORMATION: X is any amino acid
<220> FEATURE:
<221> NAME/KEY: VARIANT
<222> LOCATION: (153)..(153)
<223> OTHER INFORMATION: X is any amino acid
<220> FEATURE:
<221> NAME/KEY: VARIANT
<222> LOCATION: (155)..(155)
<223> OTHER INFORMATION: X is any amino acid
<220> FEATURE:
<221> NAME/KEY: VARIANT
<222> LOCATION: (170)..(170)
<223> OTHER INFORMATION: X is any amino acid
<220> FEATURE:
<221> NAME/KEY: VARIANT
<222> LOCATION: (170)..(170)
<223> OTHER INFORMATION: X is any amino acid
<220> FEATURE:
```

```
<221> NAME/KEY: VARIANT
<222> LOCATION: (177)..(177)
<223> OTHER INFORMATION: X is any amino acid
<220> FEATURE:
<221> NAME/KEY: VARIANT
<222> LOCATION: (196)..(196)
<223> OTHER INFORMATION: X is any amino acid
<220> FEATURE:
<221> NAME/KEY: VARIANT
<222> LOCATION: (204)..(204)
<223> OTHER INFORMATION: X is any amino acid
<220> FEATURE:
<221> NAME/KEY: VARIANT
<222> LOCATION: (219)..(219)
<223> OTHER INFORMATION: X is any amino acid
<220> FEATURE:
<221> NAME/KEY: VARIANT
<222> LOCATION: (242)..(242)
<223> OTHER INFORMATION: X is any amino acid
<220> FEATURE:
<221> NAME/KEY: VARIANT
<222> LOCATION: (269)..(269)
<223> OTHER INFORMATION: X is any amino acid
<220> FEATURE:
<221> NAME/KEY: VARIANT
<222> LOCATION: (298)..(298)
<223> OTHER INFORMATION: X is any amino acid
<220> FEATURE:
<221> NAME/KEY: VARIANT
<222> LOCATION: (303)..(303)
<223> OTHER INFORMATION: X is any amino acid
<220> FEATURE:
<221> NAME/KEY: VARIANT
<222> LOCATION: (323)..(323)
<223> OTHER INFORMATION: X is any amino acid
<220> FEATURE:
<221> NAME/KEY: VARIANT
<222> LOCATION: (359)..(359)
<223> OTHER INFORMATION: X is any amino acid
<220> FEATURE:
<221> NAME/KEY: VARIANT
<222> LOCATION: (360)..(360)
<223> OTHER INFORMATION: X is any amino acid
<220> FEATURE:
<221> NAME/KEY: VARIANT
<222> LOCATION: (362)..(362)
<223> OTHER INFORMATION: X is any amino acid
<220> FEATURE:
<221> NAME/KEY: VARIANT
<222> LOCATION: (371)..(371)
<223> OTHER INFORMATION: X is any amino acid
<220> FEATURE:
<221> NAME/KEY: VARIANT
<222> LOCATION: (372)..(372)
<223> OTHER INFORMATION: X is any amino acid
<220> FEATURE:
<221> NAME/KEY: VARIANT
<222> LOCATION: (378)..(378)
<223> OTHER INFORMATION: X is any amino acid
<220> FEATURE:
<221> NAME/KEY: VARIANT
<222> LOCATION: (379)..(379)
<223> OTHER INFORMATION: X is any amino acid
<220> FEATURE:
<221> NAME/KEY: VARIANT
<222> LOCATION: (380)..(380)
<223> OTHER INFORMATION: X is any amino acid
<220> FEATURE:
<221> NAME/KEY: VARIANT
<222> LOCATION: (392)..(392)
<223> OTHER INFORMATION: X is any amino acid
<220> FEATURE:
<221> NAME/KEY: VARIANT
<222> LOCATION: (393)..(393)
<223> OTHER INFORMATION: X is any amino acid
<220> FEATURE:
<221> NAME/KEY: VARIANT
<222> LOCATION: (393)..(393)
<223> OTHER INFORMATION: X is any amino acid
```

```
<220> FEATURE:
<221> NAME/KEY: VARIANT
<222> LOCATION: (396)..(396)
<223> OTHER INFORMATION: X is any amino acid
<220> FEATURE:
<221> NAME/KEY: VARIANT
<222> LOCATION: (409)..(409)
<223> OTHER INFORMATION: X is any amino acid
<220> FEATURE:
<221> NAME/KEY: VARIANT
<222> LOCATION: (410)..(410)
<223> OTHER INFORMATION: X is any amino acid
<220> FEATURE:
<221> NAME/KEY: VARIANT
<222> LOCATION: (449)..(449)
<223> OTHER INFORMATION: X is any amino acid
<220> FEATURE:
<221> NAME/KEY: VARIANT
<222> LOCATION: (453)..(453)
<223> OTHER INFORMATION: X is any amino acid
<220> FEATURE:
<221> NAME/KEY: VARIANT
<222> LOCATION: (469)..(469)
<223> OTHER INFORMATION: X is any amino acid
<220> FEATURE:
<221> NAME/KEY: VARIANT
<222> LOCATION: (476)..(476)
<223> OTHER INFORMATION: X is any amino acid
<220> FEATURE:
<221> NAME/KEY: VARIANT
<222> LOCATION: (479)..(479)
<223> OTHER INFORMATION: X is any amino acid
<220> FEATURE:
<221> NAME/KEY: VARIANT
<222> LOCATION: (481)..(481)
<223> OTHER INFORMATION: X is any amino acid
<220> FEATURE:
<221> NAME/KEY: VARIANT
<222> LOCATION: (487)..(487)
<223> OTHER INFORMATION: X is any amino acid
<220> FEATURE:
<221> NAME/KEY: VARIANT
<222> LOCATION: (491)..(491)
<223> OTHER INFORMATION: X is any amino acid
<220> FEATURE:
<221> NAME/KEY: VARIANT
<222> LOCATION: (498)..(498)
<223> OTHER INFORMATION: X is any amino acid
<220> FEATURE:
<221> NAME/KEY: VARIANT
<222> LOCATION: (518)..(518)
<223> OTHER INFORMATION: X is any amino acid
<220> FEATURE:
<221> NAME/KEY: VARIANT
<222> LOCATION: (518)..(518)
<223> OTHER INFORMATION: X is any amino acid
<220> FEATURE:
<221> NAME/KEY: VARIANT
<222> LOCATION: (518)..(518)
<223> OTHER INFORMATION: X is any amino acid
<220> FEATURE:
<221> NAME/KEY: VARIANT
<222> LOCATION: (528)..(528)
<223> OTHER INFORMATION: X is any amino acid
<220> FEATURE:
<221> NAME/KEY: VARIANT
<222> LOCATION: (528)..(528)
<223> OTHER INFORMATION: X is any amino acid
<220> FEATURE:
<221> NAME/KEY: VARIANT
<222> LOCATION: (553)..(553)
<223> OTHER INFORMATION: X is any amino acid
<220> FEATURE:
<221> NAME/KEY: VARIANT
<222> LOCATION: (553)..(553)
<223> OTHER INFORMATION: X is any amino acid
<220> FEATURE:
<221> NAME/KEY: VARIANT
<222> LOCATION: (555)..(555)
```

```
<223> OTHER INFORMATION: X is any amino acid
<220> FEATURE:
<221> NAME/KEY: VARIANT
<222> LOCATION: (556)..(556)
<223> OTHER INFORMATION: X is any amino acid
<220> FEATURE:
<221> NAME/KEY: VARIANT
<222> LOCATION: (572)..(572)
<223> OTHER INFORMATION: X is any amino acid
<220> FEATURE:
<221> NAME/KEY: VARIANT
<222> LOCATION: (587)..(587)
<223> OTHER INFORMATION: X is any amino acid
<220> FEATURE:
<221> NAME/KEY: VARIANT
<222> LOCATION: (599)..(599)
<223> OTHER INFORMATION: X is any amino acid
<220> FEATURE:
<221> NAME/KEY: VARIANT
<222> LOCATION: (601)..(601)
<223> OTHER INFORMATION: X is any amino acid
<220> FEATURE:
<221> NAME/KEY: VARIANT
<222> LOCATION: (634)..(634)
<223> OTHER INFORMATION: X is any amino acid
<220> FEATURE:
<221> NAME/KEY: VARIANT
<222> LOCATION: (634)..(634)
<223> OTHER INFORMATION: X is any amino acid
<220> FEATURE:
<221> NAME/KEY: VARIANT
<222> LOCATION: (667)..(667)
<223> OTHER INFORMATION: X is any amino acid
<220> FEATURE:
<221> NAME/KEY: VARIANT
<222> LOCATION: (669)..(669)
<223> OTHER INFORMATION: X is any amino acid
<220> FEATURE:
<221> NAME/KEY: VARIANT
<222> LOCATION: (672)..(672)
<223> OTHER INFORMATION: X is any amino acid
<220> FEATURE:
<221> NAME/KEY: VARIANT
<222> LOCATION: (674)..(674)
<223> OTHER INFORMATION: X is any amino acid
<220> FEATURE:
<221> NAME/KEY: VARIANT
<222> LOCATION: (717)..(717)
<223> OTHER INFORMATION: X is any amino acid
<220> FEATURE:
<221> NAME/KEY: VARIANT
<222> LOCATION: (741)..(741)
<223> OTHER INFORMATION: X is any amino acid
<220> FEATURE:
<221> NAME/KEY: VARIANT
<222> LOCATION: (755)..(755)
<223> OTHER INFORMATION: X is any amino acid
<220> FEATURE:
<221> NAME/KEY: VARIANT
<222> LOCATION: (756)..(756)
<223> OTHER INFORMATION: X is any amino acid
<220> FEATURE:
<221> NAME/KEY: VARIANT
<222> LOCATION: (805)..(805)
<223> OTHER INFORMATION: X is any amino acid
<220> FEATURE:
<221> NAME/KEY: VARIANT
<222> LOCATION: (813)..(813)
<223> OTHER INFORMATION: X is any amino acid
<220> FEATURE:
<221> NAME/KEY: VARIANT
<222> LOCATION: (820)..(820)
<223> OTHER INFORMATION: X is any amino acid
<220> FEATURE:
<221> NAME/KEY: VARIANT
<222> LOCATION: (835)..(835)
<223> OTHER INFORMATION: X is any amino acid
<220> FEATURE:
<221> NAME/KEY: VARIANT
```

```
<222> LOCATION: (838)..(838)
<223> OTHER INFORMATION: X is any amino acid
<220> FEATURE:
<221> NAME/KEY: VARIANT
<222> LOCATION: (916)..(916)
<223> OTHER INFORMATION: X is any amino acid
<220> FEATURE:
<221> NAME/KEY: VARIANT
<222> LOCATION: (919)..(919)
<223> OTHER INFORMATION: X is any amino acid

<400> SEQUENCE: 47

Met Glu Arg Gly Leu Pro Leu Leu Cys Ala Xaa Leu Ala Leu Xaa Leu
1               5                   10                  15

Ala Xaa Ala Gly Ala Phe Arg Xaa Asp Lys Cys Gly Xaa Thr Ile Lys
            20                  25                  30

Ile Glu Xaa Pro Gly Tyr Leu Thr Ser Pro Gly Tyr Pro His Ser Tyr
        35                  40                  45

His Pro Ser Glu Lys Cys Glu Trp Leu Ile Gln Ala Pro Xaa Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Xaa Asp Gly Glu Asn Glu Xaa
                85                  90                  95

Gly Xaa Xaa Xaa Gly Lys Phe Cys Gly Lys Ile Ala Pro Xaa Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Xaa Phe Lys Arg Gly
    130                 135                 140

Pro Glu Cys Ser Gln Asn Tyr Thr Xaa Pro Xaa Gly Val Ile Lys Ser
145                 150                 155                 160

Pro Gly Phe Pro Glu Lys Tyr Pro Asn Ser Leu Glu Cys Thr Tyr Ile
                165                 170                 175

Xaa Phe Ala Pro Lys Met Ser Glu Ile Ile Leu Glu Phe Glu Ser Phe
            180                 185                 190

Asp Leu Glu Xaa Asp Ser Asn Pro Pro Gly Gly Xaa Phe Cys Arg Tyr
        195                 200                 205

Asp Arg Leu Glu Ile Trp Asp Gly Phe Pro Xaa Val Gly Pro His Ile
    210                 215                 220

Gly Arg Tyr Cys Gly Gln Lys Thr Pro Gly Arg Ile Arg Ser Ser Ser
225                 230                 235                 240

Gly Xaa Leu Ser Met Val Phe Tyr Thr Asp Ser Ala Ile Ala Lys Glu
                245                 250                 255

Gly Phe Ser Ala Asn Tyr Ser Val Leu Gln Ser Ser Xaa Ser Glu Asp
            260                 265                 270

Phe Lys Cys Met Glu Ala Leu Gly Met Glu Ser Gly Glu Ile His Ser
    275                 280                 285

Asp Gln Ile Thr Ala Ser Ser Gln Tyr Xaa Thr Asn Trp Ser Xaa Glu
290                 295                 300

Arg Ser Arg Leu Asn Tyr Pro Glu Asn Gly Trp Thr Pro Gly Glu Asp
305                 310                 315                 320

Ser Tyr Xaa Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
        340                 345                 350
```

```
Tyr Tyr Val Lys Thr Tyr Xaa Xaa Asp Xaa Ser Ser Asn Gly Glu Asp
            355                 360                 365

Trp Ile Xaa Xaa Lys Glu Gly Asn Lys Xaa Xaa Xaa Phe Gln Gly Asn
        370                 375                 380

Thr Asn Pro Thr Asp Val Val Xaa Xaa Val Phe Xaa Lys Pro Leu Ile
385                 390                 395                 400

Thr Arg Phe Val Arg Ile Lys Pro Xaa Xaa Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Xaa Ser Asn Gln Xaa Asp Arg Asn Trp Met Pro Glu Asn Ile Arg Leu
450                 455                 460

Val Thr Ser Arg Xaa Gly Trp Ala Leu Pro Pro Xaa Pro His Xaa Tyr
465                 470                 475                 480

Xaa Asn Glu Trp Leu Gln Xaa Asp Leu Gly Xaa Glu Lys Ile Val Arg
                485                 490                 495

Gly Xaa Ile Ile Gln Gly Gly Lys His Arg Glu Asn Lys Val Phe Met
            500                 505                 510

Arg Lys Phe Lys Ile Xaa Tyr Ser Asn Asn Gly Ser Asp Trp Lys Xaa
            515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Xaa Phe Xaa Xaa Leu Ser Thr Arg
545                 550                 555                 560

Phe Ile Arg Ile Tyr Pro Glu Arg Ala Thr His Xaa Gly Leu Gly Leu
            565                 570                 575

Arg Met Glu Leu Leu Gly Cys Glu Val Glu Xaa Pro Thr Ala Gly Pro
            580                 585                 590

Thr Thr Pro Asn Gly Asn Xaa Val Asp Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Xaa Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Xaa His Xaa Gln Leu Xaa
            660                 665                 670

Trp Xaa Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
            690                 695                 700

Val Ala Arg Leu Val Ser Pro Val Val Tyr Ser Gln Xaa Ser Ala His
705                 710                 715                 720

Cys Met Thr Phe Trp Tyr His Met Ser Gly Ser His Val Gly Thr Leu
            725                 730                 735

Arg Val Lys Leu Xaa Tyr Gln Lys Pro Glu Glu Tyr Asp Gln Leu Val
            740                 745                 750

Trp Met Xaa Xaa Gly His Gln Gly Asp His Trp Lys Glu Gly Arg Val
            755                 760                 765

Leu Leu His Lys Ser Leu Lys Leu Tyr Gln Val Ile Phe Glu Gly Glu
```

```
                770                 775                 780
Ile Gly Lys Gly Asn Leu Gly Gly Ile Ala Val Asp Asp Ile Ser Ile
785                 790                 795                 800

Asn Asn His Ile Xaa Gln Glu Asp Cys Ala Lys Pro Xaa Leu Asp Lys
                805                 810                 815

Lys Asn Asn Xaa Glu Ile Lys Ile Asp Glu Thr Gly Ser Thr Pro Gly
                820                 825                 830

Tyr Glu Xaa Glu Gly Xaa Gly Asp Lys Asn Ile Ser Arg Lys Pro Gly
                835                 840                 845

Asn Val Leu Lys Thr Leu Asp Pro Ile Leu Ile Thr Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
                900                 905                 910

Lys Leu Asn Xaa Gln Ser Xaa Tyr Ser Glu Ala
            915                 920

<210> SEQ ID NO 48
<211> LENGTH: 923
<212> TYPE: PRT
<213> ORGANISM: Mus musculus

<400> SEQUENCE: 48

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
                20                  25                  30

Ile Glu Asn Pro Gly Tyr Leu Thr Ser Pro Gly Tyr Pro His Ser Tyr
            35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

Asp Arg Leu Glu Ile Trp Asp Gly Phe Pro Glu Val Gly Pro His Ile
    210                 215                 220
```

```
Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
            245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Gly Thr Asn Trp Ser Val Glu
        290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Arg Val Asp Ile Ser Ser Asn Gly Glu Asp
            355                 360                 365

Trp Ile Ser Leu Lys Glu Gly Asn Lys Ala Ile Ile Phe Gln Gly Asn
370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ala Ser Asn Gln Ala Asp Arg Asn Trp Met Pro Glu Asn Ile Arg Leu
450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
            485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
            565                 570                 575

Arg Met Glu Leu Leu Gly Cys Glu Val Glu Ala Pro Thr Ala Gly Pro
            580                 585                 590

Thr Thr Pro Asn Gly Asn Pro Val Asp Glu Cys Asp Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
```

```
                    645                 650                 655
His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
        915                 920

<210> SEQ ID NO 49
<211> LENGTH: 922
<212> TYPE: PRT
<213> ORGANISM: Ratus norvegicus

<400> SEQUENCE: 49

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95
```

```
Gly Arg Leu Trp Gly Lys Phe Cys Gly Lys Ile Ala Pro Ser Pro Val
                100             105             110

Val Ser Ser Gly Pro Phe Leu Phe Ile Lys Phe Val Ser Asp Tyr Glu
            115             120             125

Thr His Gly Ala Gly Phe Ser Ile Arg Tyr Glu Ile Phe Lys Arg Gly
        130             135             140

Pro Glu Cys Ser Gln Asn Tyr Thr Ala Pro Thr Gly Val Ile Lys Ser
145             150             155             160

Pro Gly Phe Pro Glu Lys Tyr Pro Asn Ser Leu Glu Cys Thr Tyr Ile
                165             170             175

Ile Phe Ala Pro Lys Met Ser Glu Ile Ile Leu Glu Phe Glu Ser Phe
            180             185             190

Asp Leu Glu Gln Asp Ser Asn Pro Pro Gly Gly Val Phe Cys Arg Tyr
        195             200             205

Asp Arg Leu Glu Ile Trp Asp Gly Phe Pro Glu Val Gly Pro His Ile
210             215             220

Gly Arg Tyr Cys Gly Gln Lys Thr Pro Gly Arg Ile Arg Ser Ser Ser
225             230             235             240

Gly Ile Leu Ser Met Val Phe Tyr Thr Asp Ser Ala Ile Ala Lys Glu
            245             250             255

Gly Phe Ser Ala Asn Tyr Ser Val Leu Gln Ser Ser Ile Ser Glu Asp
        260             265             270

Phe Lys Cys Met Glu Ala Leu Gly Met Glu Ser Gly Glu Ile His Ser
            275             280             285

Asp Gln Ile Thr Ala Ser Ser Gln Tyr Gly Thr Asn Trp Ser Val Glu
290             295             300

Arg Ser Arg Leu Asn Tyr Pro Glu Asn Gly Trp Thr Pro Gly Glu Asp
305             310             315             320

Ser Tyr Arg Glu Trp Ile Gln Val Asp Leu Gly Leu Leu Arg Phe Val
            325             330             335

Thr Ala Val Gly Thr Gln Gly Ala Ile Ser Lys Glu Thr Lys Lys Lys
        340             345             350

Tyr Tyr Val Lys Thr Tyr Arg Val Asp Ile Ser Ser Asn Gly Glu Asp
            355             360             365

Trp Ile Thr Leu Lys Glu Gly Asn Lys Ala Ile Ile Phe Gln Gly Asn
370             375             380

Thr Asn Pro Thr Asp Val Val Phe Gly Val Phe Pro Lys Pro Leu Ile
385             390             395             400

Thr Arg Phe Val Arg Ile Lys Pro Ala Ser Trp Glu Thr Gly Ile Ser
            405             410             415

Met Arg Phe Glu Val Tyr Gly Cys Lys Ile Thr Asp Tyr Pro Cys Ser
            420             425             430

Gly Met Leu Gly Met Val Ser Gly Leu Ile Ser Asp Ser Gln Ile Thr
        435             440             445

Ala Ser Asn Gln Gly Asp Arg Asn Trp Met Pro Glu Asn Ile Arg Leu
450             455             460

Val Thr Ser Arg Thr Gly Trp Ala Leu Pro Pro Ser Pro His Pro Tyr
465             470             475             480

Ile Asn Glu Trp Leu Gln Val Asp Leu Gly Asp Glu Lys Ile Val Arg
            485             490             495

Gly Val Ile Ile Gln Gly Gly Lys His Arg Glu Asn Lys Val Phe Met
            500             505             510

Arg Lys Phe Lys Ile Ala Tyr Ser Asn Asn Gly Ser Asp Trp Lys Met
```

```
                515                 520                 525
Ile Met Asp Asp Ser Lys Arg Lys Ala Lys Ser Phe Glu Gly Asn Asn
530                 535                 540

Asn Tyr Asp Thr Pro Glu Leu Arg Ala Phe Thr Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Val Pro Thr Ala Gly Pro
                580                 585                 590

Thr Thr Pro Asn Gly Asn Pro Val Asp Glu Cys Asp Asp Gln Ala
                595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
                660                 665                 670

Trp Arg Val Leu Thr Ser Lys Thr Gly Pro Ile Gln Asp His Thr Gly
                675                 680                 685

Asp Gly Asn Phe Ile Tyr Ser Gln Ala Asp Glu Asn Gln Lys Gly Lys
                690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu His Tyr Gln Lys Pro Glu Glu Tyr Asp Gln Leu Val
                740                 745                 750

Trp Met Val Val Gly His Gln Gly Asp His Trp Lys Glu Gly Arg Val
                755                 760                 765

Leu Leu His Lys Ser Leu Lys Leu Tyr Gln Val Ile Phe Glu Gly Glu
                770                 775                 780

Ile Gly Lys Gly Asn Leu Gly Gly Ile Ala Val Asp Asp Ile Ser Ile
785                 790                 795                 800

Asn Asn His Ile Pro Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
                820                 825                 830

Tyr Glu Glu Gly Lys Gly Asp Lys Asn Ile Ser Arg Lys Pro Gly Asn
                835                 840                 845

Val Leu Lys Thr Leu Asp Pro Ile Leu Ile Thr Ile Ala Met Ser
850                 855                 860

Ala Leu Gly Val Leu Leu Gly Ala Val Cys Gly Val Val Leu Tyr Cys
865                 870                 875                 880

Ala Cys Trp His Asn Gly Met Ser Glu Arg Asn Leu Ser Ala Leu Glu
                885                 890                 895

Asn Tyr Asn Phe Glu Leu Val Asp Gly Val Lys Leu Lys Lys Asp Lys
                900                 905                 910

Leu Asn Pro Gln Ser Asn Tyr Ser Glu Ala
                915                 920

<210> SEQ ID NO 50
```

```
<211> LENGTH: 771
<212> TYPE: PRT
<213> ORGANISM: Homo sapiens

<400> SEQUENCE: 50

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
```

```
            385                 390                 395                 400
        Thr Phe Ala Arg Ser His Pro Ala Met Tyr Asn Pro Val Phe Pro Met
                        405                 410                 415
        Asn Asn Arg Pro Ile Val Ile Lys Thr Asp Val Asn Tyr Gln Phe Thr
                        420                 425                 430
        Gln Ile Val Val Asp Arg Val Asp Ala Glu Asp Gly Gln Tyr Asp Val
                        435                 440                 445
        Met Phe Ile Gly Thr Asp Val Gly Thr Val Leu Lys Val Val Ser Ile
                450                 455                 460
        Pro Lys Glu Thr Trp Tyr Asp Leu Glu Glu Val Leu Leu Glu Glu Met
        465                 470                 475                 480
        Thr Val Phe Arg Glu Pro Thr Ala Ile Ser Ala Met Glu Leu Ser Thr
                        485                 490                 495
        Lys Gln Gln Gln Leu Tyr Ile Gly Ser Thr Ala Gly Val Ala Gln Leu
                        500                 505                 510
        Pro Leu His Arg Cys Asp Ile Tyr Gly Lys Ala Cys Ala Glu Cys Cys
                        515                 520                 525
        Leu Ala Arg Asp Pro Tyr Cys Ala Trp Asp Gly Ser Ala Cys Ser Arg
                530                 535                 540
        Tyr Phe Pro Thr Ala Lys Arg Arg Thr Arg Arg Gln Asp Ile Arg Asn
        545                 550                 555                 560
        Gly Asp Pro Leu Thr His Cys Ser Asp Leu His His Asp Asn His His
                        565                 570                 575
        Gly His Ser Pro Glu Glu Arg Ile Ile Tyr Gly Val Glu Asn Ser Ser
                        580                 585                 590
        Thr Phe Leu Glu Cys Ser Pro Lys Ser Gln Arg Ala Leu Val Tyr Trp
                        595                 600                 605
        Gln Phe Gln Arg Arg Asn Glu Glu Arg Lys Glu Ile Arg Val Asp
                    610                 615                 620
        Asp His Ile Ile Arg Thr Asp Gln Gly Leu Leu Leu Arg Ser Leu Gln
        625                 630                 635                 640
        Gln Lys Asp Ser Gly Asn Tyr Leu Cys His Ala Val Glu His Gly Phe
                        645                 650                 655
        Ile Gln Thr Leu Leu Lys Val Thr Leu Glu Val Ile Asp Thr Glu His
                        660                 665                 670
        Leu Glu Glu Leu Leu His Lys Asp Asp Gly Asp Gly Ser Lys Thr
                675                 680                 685
        Lys Glu Met Ser Asn Ser Met Thr Pro Ser Gln Lys Val Trp Tyr Arg
                690                 695                 700
        Asp Phe Met Gln Leu Ile Asn His Pro Asn Leu Asn Thr Met Asp Glu
        705                 710                 715                 720
        Phe Cys Glu Gln Val Trp Lys Arg Asp Arg Lys Gln Arg Arg Gln Arg
                        725                 730                 735
        Pro Gly His Thr Pro Gly Asn Ser Asn Lys Trp Lys His Leu Gln Glu
                        740                 745                 750
        Asn Lys Lys Gly Arg Asn Arg Arg Thr His Glu Phe Glu Arg Ala Pro
                        755                 760                 765
        Arg Ser Val
                770

<210> SEQ ID NO 51
<211> LENGTH: 1308
<212> TYPE: DNA
<213> ORGANISM: artificial sequence
```

<220> FEATURE:
<223> OTHER INFORMATION: Synthetic construct

<400> SEQUENCE: 51

```
atggagaggg ggctgccgct cctctgcgcc gtgctcgccc tcgtcctcgc cccggccggc      60
gcttttcgca acgataaatg tggcgatact ataaaaattg aaagccccgg taccttaca     120
tctcctggtt atcctcattc ttatcaccca agtgaaaaat gcgaatggct gattcaggct    180
ccggacccat accagagaat tatgatcaac ttcaaccctc acttcgattt ggaggacaga    240
gactgcaagt atgactacgt ggaagtcttc gatggagaaa atgaaaatgg acattttagg    300
ggaaagttct gtggaaagat agcccctcct cctgttgtgt cttcagggcc atttcttttt    360
atcaaatttg tctctgacta cgaaacacat ggtgcaggat tttccatacg ttatgaactt    420
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccaggggga tgttctgtcg ctacgaccgg ctagaaatct gggatggatt ccctgatgtt    660
ggccctcaca ttgggcgtta ctgtggacag aaaacaccag tcgaatccg atcctcatcg    720
ggcattctct ccatggtttt ttacaccgac agcgcgatag caaagaagg tttctcagca    780
aactacagtg tcttgcagag cagtgtctca gaagatttca atgtatgga agctctgggc    840
atggaatcag agaaaattca ttctgaccag atcacagctt cttcccagta tagcaccaac    900
tggtctgcag agcgctcccg cctgaactac cctgagaatg ggtggactcc cggagagaag    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcagatctgg atccaaggaa aacttgtatt ccagggc                 1308
```

<210> SEQ ID NO 52
<211> LENGTH: 436
<212> TYPE: PRT
<213> ORGANISM: artificial sequence
<220> FEATURE:
<223> OTHER INFORMATION: Synthetic construct

<400> SEQUENCE: 52

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110
```

```
Val Ser Ser Gly Pro Phe Leu Phe Ile Lys Phe Val Ser Asp Tyr Glu
    115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Lys
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Arg Ser Gly Ser Lys Glu Asn Leu
            420                 425                 430

Tyr Phe Gln Gly
        435

<210> SEQ ID NO 53
<211> LENGTH: 1785
<212> TYPE: DNA
<213> ORGANISM: artificial sequence
<220> FEATURE:
<223> OTHER INFORMATION: Synthetic construct

<400> SEQUENCE: 53
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
```

```
ccggacccat accagagaat tatgatcaac ttcaaccctc acttcgattt ggaggacaga    240
gactgcaagt atgactacgt ggaagtcttc gatggagaaa atgaaaatgg acattttagg    300
ggaaagttct gtggaaagat agcccctcct cctgttgtgt cttcagggcc atttcttttt    360
atcaaatttg tctctgacta cgaaacacat ggtgcaggat tttccatacg ttatgaactt    420
ttcaagagag gtcctgaatg ttcccagaac tacacaacac ctagtggagt gataaagtcc    480 cccgattcc ctgaaaaata tcccaacagc cttgaatgca cttatattgt ctttgcgcca    540
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag gtcgaatccg atcctcatcg    720
ggcattctct ccatggtttt ttacaccgac agcgcgatag caaaagaagg tttctcagca    780
aactacagtg tcttgcagag cagtgtctca gaagatttca atgtatggaa gctctgggc    840 atggaatcag gagaaattca ttctgaccag atcacagctt cttcccagta tagcaccaac    900
tggtctgcag agcgctcccg cctgaactac cctgagaatg ggtggactcc cggagagaag    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcaagataac agattatcct tgctctggaa tgttgggtat ggtgtctgga   1320
cttatttctg actcccagat cacatcatcc aaccaagggg acagaaactg gatgcctgaa   1380
aacatccgcc tggtaaccag tcgctctggc tgggcacttc cacccgcacc tcattcctac   1440
atcaatgagt ggctccaaat agacctgggg gaggagaaga tcgtgagggg catcatcatt   1500
cagggtggga agcaccgaga gaacaaggtg ttcatgagga agttcaagat cgggtacagc   1560
aacaacggct cggactggaa gatgatcatg gatgacagca acgcaaggc gaagtctttt   1620 gagggcaaca caactatga tacacctgag ctgcggactt tccagctctc tccacgcga    1680 ttcatcagga tctaccccga gagagccact catggcggac tggggctcag aatggagctg   1740
ctgggctgta gatctggatc caaggaaaac ttgtatttcc agggc                  1785
```

<210> SEQ ID NO 54
<211> LENGTH: 595
<212> TYPE: PRT
<213> ORGANISM: artificial sequence
<220> FEATURE:
<223> OTHER INFORMATION: Synthetic construct

<400> SEQUENCE: 54

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80
```

```
Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Lys
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495
```

```
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
        515                 520                 525
Ile Met Asp Asp Ser Lys Arg Lys Ala Lys Ser Phe Glu Gly Asn Asn
    530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Arg Ser Gly Ser Lys Gly Asn Leu Tyr
            580                 585                 590
Phe Gln Gly
        595

<210> SEQ ID NO 55
<211> LENGTH: 2154
<212> TYPE: DNA
<213> ORGANISM: artificial sequence
<220> FEATURE:
<223> OTHER INFORMATION: Synthetic construct

<400> SEQUENCE: 55
atggagaggg ggctgccgct cctctgcgcc gtgctcgccc tcgtcctcgc cccggccggc      60
gcttttcgca acgataaatg tggcgatact ataaaaattg aaagcccgg gtaccttaca     120
tctcctggtt atcctcattc ttatcaccca agtgaaaaat gcgaatggct gattcaggct    180
ccggacccat accagagaat tatgatcaac ttcaaccctc acttcgattt ggaggacaga    240
gactgcaagt atgactacgt ggaagtcttc gatggagaaa atgaaaatgg acattttagg    300
ggaaagttct gtggaaagat agcccctcct cctgttgtgt cttcagggcc atttcttttt    360
atcaaatttg tctctgacta cgaaacacat ggtgcaggat tttccatacg ttatgaactt    420
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccaggggga tgttctgtcg ctacgaccgg ctagaaatct gggatggatt ccctgatgtt    660
ggccctcaca ttgggcgtta ctgtggacag aaaacaccag tcgaatccg atcctcatcg    720
ggcattctct ccatggtttt ttacaccgac agcgcgatag caaaagaagg tttctcagca    780
aactacagtg tcttgcagag cagtgtctca gaagatttca aaaagataac agattatcct    840
tgctctggaa tgtttgggta tgtgtctgga cttatttctg actcccagat cacatcatcc    900
aaccaagggg acagaaactg gatgcctgaa aacatccgcc tggtaaccag tcgctctggc    960
tgggcacttc cacccgcacc tcattcctac atcaatgagt ggctccaaat agacctgggg   1020
gaggagaaga tcgtgagggg catcatcatt caggtgggag agcaccgaga gaacaaggtg   1080
ttcatgagga agttcaagat cgggtacagc aacaacggct cggactggaa gatgatcatg   1140
gatgacagca acgcaaggc gaagtctttt gagggcaaca acaactatga tacacctgag   1200
ctgcggactt ttccagctct ctccacgcga ttcatcagga tctaccccga gagagccact   1260
catggcggac tggggctcag aatggagctg ctgggctgtg aagtggaagc ccctacagct   1320
ggaccgacca ctcccaacgg gaacttggtg atgaatgtg atgacgacca ggccaactgc   1380
cacagtggaa caggtgatga cttccagctc acaggtggca ccactgtgct ggccacagaa   1440
```

-continued

| | |
|---|---|
| aagcccacgg tcatagacag caccatacaa tcagagtttc aacatatgg ttttaactgt | 1500 |
| gaatttggct ggggctctca caagaccttc tgccactggg aacatgacaa tcacgtgcag | 1560 |
| ctcaagtgga gtgtgttgac cagcaagacg ggacccattc aggatcacac aggagatggc | 1620 |
| aacttcatct attcccaagc tgacgaaaat cagaagggca agtggctcg cctggtgagc | 1680 |
| cctgtggttt attcccagaa ctctgcccac tgcatgacct tctggtatca catgtctggg | 1740 |
| tcccacgtcg gcacactcag ggtcaaactg cgctaccaga agccagagga gtacgatcag | 1800 |
| ctggtctgga tggccattgg acaccaaggt gaccactgga aggaagggcg tgtcttgctc | 1860 |
| cacaagtctc tgaaacttta tcaggtgatt ttcgagggcg aaatcggaaa aggaaaccct | 1920 |
| ggtgggattg ctgtggatga cattagtatt aataaccaca tttcacaaga agattgtgca | 1980 |
| aaaccagcag acctggataa aaagaaccca gaaattaaaa ttgatgaaac agggagcacg | 2040 |
| ccaggatacg aaggtgaagg agaaggtgac aagaacatct ccaggaagcc aggcaatgtg | 2100 |
| ttgaagacct tagaccccag atctggatcc aaggaaaact tgtatttcca gggc | 2154 |

```
<210> SEQ ID NO 56
<211> LENGTH: 718
<212> TYPE: PRT
<213> ORGANISM: artificial sequence
<220> FEATURE:
<223> OTHER INFORMATION: Synthetic construct

<400> SEQUENCE: 56
```

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
            245                 250                 255

Gly Phe Ser Ala Asn Tyr Ser Val Leu Gln Ser Ser Val Ser Glu Asp
        260                 265                 270

Phe Lys Lys Ile Thr Asp Tyr Pro Cys Ser Gly Met Leu Gly Met Val
    275                 280                 285

Ser Gly Leu Ile Ser Asp Ser Gln Ile Thr Ser Ser Asn Gln Gly Asp
290                 295                 300

Arg Asn Trp Met Pro Glu Asn Ile Arg Leu Val Thr Ser Arg Ser Gly
305                 310                 315                 320

Trp Ala Leu Pro Pro Ala Pro His Ser Tyr Ile Asn Glu Trp Leu Gln
                325                 330                 335

Ile Asp Leu Gly Glu Glu Lys Ile Val Arg Gly Ile Ile Gln Gly
            340                 345                 350

Gly Lys His Arg Glu Asn Lys Val Phe Met Arg Lys Phe Lys Ile Gly
        355                 360                 365

Tyr Ser Asn Asn Gly Ser Asp Trp Lys Met Ile Met Asp Ser Lys
    370                 375                 380

Arg Lys Ala Lys Ser Phe Glu Gly Asn Asn Asn Tyr Asp Thr Pro Glu
385                 390                 395                 400

Leu Arg Thr Phe Pro Ala Leu Ser Thr Arg Phe Ile Arg Ile Tyr Pro
                405                 410                 415

Glu Arg Ala Thr His Gly Gly Leu Gly Leu Arg Met Glu Leu Leu Gly
            420                 425                 430

Cys Glu Val Glu Ala Pro Thr Ala Gly Pro Thr Thr Pro Asn Gly Asn
        435                 440                 445

Leu Val Asp Glu Cys Asp Asp Gln Ala Asn Cys His Ser Gly Thr
    450                 455                 460

Gly Asp Asp Phe Gln Leu Thr Gly Gly Thr Thr Val Leu Ala Thr Glu
465                 470                 475                 480

Lys Pro Thr Val Ile Asp Ser Thr Ile Gln Ser Glu Phe Pro Thr Tyr
                485                 490                 495

Gly Phe Asn Cys Glu Phe Gly Trp Gly Ser His Lys Thr Phe Cys His
            500                 505                 510

Trp Glu His Asp Asn His Val Gln Leu Lys Trp Ser Val Leu Thr Ser
        515                 520                 525

Lys Thr Gly Pro Ile Gln Asp His Thr Gly Asp Gly Asn Phe Ile Tyr
    530                 535                 540

Ser Gln Ala Asp Glu Asn Gln Lys Gly Lys Val Ala Arg Leu Val Ser
545                 550                 555                 560

Pro Val Val Tyr Ser Gln Asn Ser Ala His Cys Met Thr Phe Trp Tyr
                565                 570                 575

His Met Ser Gly Ser His Val Gly Thr Leu Arg Val Lys Leu Arg Tyr
            580                 585                 590

Gln Lys Pro Glu Glu Tyr Asp Gln Leu Val Trp Met Ala Ile Gly His
        595                 600                 605

Gln Gly Asp His Trp Lys Glu Gly Arg Val Leu Leu His Lys Ser Leu
    610                 615                 620

Lys Leu Tyr Gln Val Ile Phe Glu Gly Glu Ile Gly Lys Gly Asn Leu
625                 630                 635                 640

Gly Gly Ile Ala Val Asp Asp Ile Ser Ile Asn Asn His Ile Ser Gln
                645                 650                 655

Glu Asp Cys Ala Lys Pro Ala Asp Leu Asp Lys Lys Asn Pro Glu Ile

```
                    660              665             670
Lys Ile Asp Glu Thr Gly Ser Thr Pro Gly Tyr Glu Gly Glu Gly Glu
            675             680             685

Gly Asp Lys Asn Ile Ser Arg Lys Pro Gly Asn Val Leu Lys Thr Leu
        690             695             700

Asp Pro Arg Ser Gly Ser Lys Glu Asn Leu Tyr Phe Gln Gly
705             710             715
```

<210> SEQ ID NO 57
<211> LENGTH: 1335
<212> TYPE: DNA
<213> ORGANISM: artificial sequence
<220> FEATURE:
<223> OTHER INFORMATION: Synthetic construct

<400> SEQUENCE: 57

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagccccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtgaaagat | agcccctcct | cctgttgtgt | cttcagggcc | atttctttt | 360 |
| atcaaatttg | tctctgacta | cgaaacacat | ggtgcaggat | tttccatacg | ttatgaactt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccagggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaaagaagg | tttctcagca | 780 |
| aactacagtg | tcttgcagag | cagtgtctca | gaagatttca | aaaagataac | agattatcct | 840 |
| tgctctggaa | tgttgggtat | ggtgtctgga | cttatttctg | actcccagat | cacatcatcc | 900 |
| aaccaagggg | acagaaactg | gatgcctgaa | acatccgcc | tggtaaccag | tcgctctggc | 960 |
| tgggcacttc | cacccgcacc | tcattcctac | atcaatgagt | ggctccaaat | agacctgggg | 1020 |
| gaggagaaga | tcgtgagggg | catcatcatt | cagggtggga | agcaccgaga | gaacaaggtg | 1080 |
| ttcatgagga | agttcaagat | cgggtacagc | aacaacggct | cggactggaa | gatgatcatg | 1140 |
| gatgacagca | aacgcaaggc | gaagtctttt | gagggcaaca | acaactatga | tacacctgag | 1200 |
| ctgcggactt | ttccagctct | ctccacgcga | ttcatcagga | tctaccccga | gagccact | 1260 |
| catggcggac | tggggctcag | aatggagctg | ctgggctgta | gatctggatc | caaggaaaac | 1320 |
| ttgtatttcc | agggc | | | | | 1335 |

<210> SEQ ID NO 58
<211> LENGTH: 445
<212> TYPE: PRT
<213> ORGANISM: artificial sequence
<220> FEATURE:
<223> OTHER INFORMATION: Synthetic construct

<400> SEQUENCE: 58

```
Met Glu Arg Gly Leu Pro Leu Leu Cys Ala Val Leu Ala Leu Val Leu
1               5                   10                  15
```

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Lys Ile Thr Asp Tyr Pro Cys Ser Gly Met Leu Gly Met Val
        275                 280                 285

Ser Gly Leu Ile Ser Asp Ser Gln Ile Thr Ser Ser Asn Gln Gly Asp
    290                 295                 300

Arg Asn Trp Met Pro Glu Asn Ile Arg Leu Val Thr Ser Arg Ser Gly
305                 310                 315                 320

Trp Ala Leu Pro Pro Ala Pro His Ser Tyr Ile Asn Glu Trp Leu Gln
                325                 330                 335

Ile Asp Leu Gly Glu Glu Lys Ile Val Arg Gly Ile Ile Gln Gly
            340                 345                 350

Gly Lys His Arg Glu Asn Lys Val Phe Met Arg Lys Phe Lys Ile Gly
        355                 360                 365

Tyr Ser Asn Asn Gly Ser Asp Trp Lys Met Ile Met Asp Asp Ser Lys
    370                 375                 380

Arg Lys Ala Lys Ser Phe Glu Gly Asn Asn Tyr Asp Thr Pro Glu
385                 390                 395                 400

Leu Arg Thr Phe Pro Ala Leu Ser Thr Arg Phe Ile Arg Ile Tyr Pro
                405                 410                 415

Glu Arg Ala Thr His Gly Gly Leu Gly Leu Arg Met Glu Leu Leu Gly
            420                 425                 430

Cys Arg Ser Gly Ser Lys Glu Asn Leu Tyr Phe Gln Gly
            435                 440                 445

<210> SEQ ID NO 59
<211> LENGTH: 2256
<212> TYPE: DNA
<213> ORGANISM: artificial sequence
<220> FEATURE:
<223> OTHER INFORMATION: Synthetic construct

<400> SEQUENCE: 59

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaaag | aggtcctgaa | tgttcccaga | actacacaac | acctagtgga | 120 |
| gtgataaagt | cccccggatt | ccctgaaaaa | tatcccaaca | gccttgaatg | cacttatatt | 180 |
| gtctttgcgc | aaagatgtc | agagattatc | ctggaatttg | aaagctttga | cctggagcct | 240 |
| gactcaaatc | ctccagggggg | gatgttctgt | cgctacgacc | ggctagaaat | ctgggatgga | 300 |
| ttccctgatg | ttggccctca | cattgggcgt | tactgtggac | agaaaacacc | aggtcgaatc | 360 |
| cgatcctcat | cgggcattct | ctccatggtt | ttttacaccg | acagcgcgat | agcaaaagaa | 420 |
| ggtttctcag | caaactacag | tgtcttgcag | agcagtgtct | cagaagattt | caaatgtatg | 480 |
| gaagctctgg | gcatggaatc | aggagaaatt | cattctgacc | agatcacagc | ttcttcccag | 540 |
| tatagcacca | actggtctgc | agagcgctcc | cgcctgaact | accctgagaa | tgggtggact | 600 |
| cccggagagg | attcctaccg | agagtggata | caggtagact | tgggccttct | cgcctttgtc | 660 |
| acggctgtcg | ggacacaggg | cgccatttca | aaagaaacca | gaagaaata | ttatgtcaag | 720 |
| acttacaaga | tcgacgttag | ctccaacggg | gaagactgga | tcaccataaa | agaaggaaac | 780 |
| aaacctgttc | tctttcaggg | aaacaccaac | cctacagatg | ttgtggttgc | agtattcccc | 840 |
| aaaccactga | taactcgatt | tgtccgaatc | aagcctgcaa | cttgggaaac | tggcatatct | 900 |
| atgagatttg | aagtatatgg | ttgcaagata | acagattatc | cttgctctgg | aatgttgggt | 960 |
| atggtgtctg | gacttatttc | tgactcccag | atcacatcat | ccaaccaagg | ggacagaaac | 1020 |
| tggatgcctg | aaaacatccg | cctggtaacc | agtcgctctg | gctgggcact | tccacccgca | 1080 |
| cctcattcct | acatcaatga | gtggctccaa | atagacctgg | gggaggagaa | gatcgtgagg | 1140 |
| ggcatcatca | ttcagggtgg | gaagcaccga | gagaacaagg | tgttcatgag | gaagttcaag | 1200 |
| atcgggtaca | gcaacaacgg | ctcggactgg | aagatgatca | tggatgacag | caaacgcaag | 1260 |
| gcgaagtctt | ttgagggcaa | caacaactat | gatacacctg | agctgcggac | ttttccagct | 1320 |
| ctctccacgc | gattcatcag | gatctacccc | gagagagcca | ctcatggcgg | actgggctc | 1380 |
| agaatggagc | tgctgggctg | tgaagtggaa | gcccctacag | ctggaccgac | cactcccaac | 1440 |
| gggaacttgg | tggatgaatg | tgatgacgac | caggccaact | gccacagtgg | aacaggtgat | 1500 |
| gacttccagc | tcacaggtgg | caccactgtg | ctggccacag | aaaagcccac | ggtcatagac | 1560 |
| agcaccatac | aatcagagtt | tccaacatat | ggttttaact | gtgaatttgg | ctggggctct | 1620 |
| cacaagacct | tctgccactg | gaacatgac | aatcacgtgc | agctcaagtg | gagtgtgttg | 1680 |
| accagcaaga | cgggacccat | tcaggatcac | acaggagatg | gcaacttcat | ctattcccaa | 1740 |
| gctgacgaaa | atcagaaggg | caaagtggct | cgcctggtga | gcctgtggt | ttattcccag | 1800 |
| aactctgccc | actgcatgac | cttctggtat | cacatgtctg | gtcccacgt | cggcacactc | 1860 |
| agggtcaaac | tgcgctacca | gaagccgag | gagtacgatc | agctggtctg | gatggccatt | 1920 |
| ggacaccaag | gtgaccactg | gaaggaaggg | cgtgtcttgc | tccacaagtc | tctgaaactt | 1980 |

```
tatcaggtga ttttcgaggg cgaaatcgga aaaggaaacc ttggtgggat tgctgtggat    2040
gacattagta ttaataacca catttcacaa gaagattgtg caaaaccagc agacctggat    2100
aaaaagaacc cagaaattaa aattgatgaa acagggagca cgccaggata cgaaggtgaa    2160
ggagaaggtg acaagaacat ctccaggaag ccaggcaatg tgttgaagac cttagacccc    2220
agatctggat ccaaggaaaa cttgtatttc cagggc                              2256
```

<210> SEQ ID NO 60
<211> LENGTH: 752
<212> TYPE: PRT
<213> ORGANISM: artificial sequence
<220> FEATURE:
<223> OTHER INFORMATION: Synthetic construct

<400> SEQUENCE: 60

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Arg Gly Pro Glu Cys Ser
            20                  25                  30

Gln Asn Tyr Thr Thr Pro Ser Gly Val Ile Lys Ser Pro Gly Phe Pro
        35                  40                  45

Glu Lys Tyr Pro Asn Ser Leu Glu Cys Thr Tyr Ile Val Phe Ala Pro
    50                  55                  60

Lys Met Ser Glu Ile Ile Leu Glu Phe Glu Ser Phe Asp Leu Glu Pro
65                  70                  75                  80

Asp Ser Asn Pro Pro Gly Gly Met Phe Cys Arg Tyr Asp Arg Leu Glu
                85                  90                  95

Ile Trp Asp Gly Phe Pro Asp Val Gly Pro His Ile Gly Arg Tyr Cys
            100                 105                 110

Gly Gln Lys Thr Pro Gly Arg Ile Arg Ser Ser Ser Gly Ile Leu Ser
        115                 120                 125

Met Val Phe Tyr Thr Asp Ser Ala Ile Ala Lys Glu Gly Phe Ser Ala
    130                 135                 140

Asn Tyr Ser Val Leu Gln Ser Ser Val Ser Glu Asp Phe Lys Cys Met
145                 150                 155                 160

Glu Ala Leu Gly Met Glu Ser Gly Glu Ile His Ser Asp Gln Ile Thr
                165                 170                 175

Ala Ser Ser Gln Tyr Ser Thr Asn Trp Ser Ala Glu Arg Ser Arg Leu
            180                 185                 190

Asn Tyr Pro Glu Asn Gly Trp Thr Pro Gly Glu Asp Ser Tyr Arg Glu
        195                 200                 205

Trp Ile Gln Val Asp Leu Gly Leu Leu Arg Phe Val Thr Ala Val Gly
    210                 215                 220

Thr Gln Gly Ala Ile Ser Lys Glu Thr Lys Lys Tyr Tyr Val Lys
225                 230                 235                 240

Thr Tyr Lys Ile Asp Val Ser Ser Asn Gly Glu Asp Trp Ile Thr Ile
                245                 250                 255

Lys Glu Gly Asn Lys Pro Val Leu Phe Gln Gly Asn Thr Asn Pro Thr
            260                 265                 270

Asp Val Val Ala Val Phe Pro Lys Pro Leu Ile Thr Arg Phe Val
        275                 280                 285

Arg Ile Lys Pro Ala Thr Trp Glu Thr Gly Ile Ser Met Arg Phe Glu
    290                 295                 300

Val Tyr Gly Cys Lys Ile Thr Asp Tyr Pro Cys Ser Gly Met Leu Gly
305                 310                 315                 320
```

-continued

```
Met Val Ser Gly Leu Ile Ser Asp Ser Gln Ile Thr Ser Ser Asn Gln
                325                 330                 335
Gly Asp Arg Asn Trp Met Pro Glu Asn Ile Arg Leu Val Thr Ser Arg
            340                 345                 350
Ser Gly Trp Ala Leu Pro Pro Ala Pro His Ser Tyr Ile Asn Glu Trp
        355                 360                 365
Leu Gln Ile Asp Leu Gly Glu Glu Lys Ile Val Arg Gly Ile Ile Ile
    370                 375                 380
Gln Gly Gly Lys His Arg Glu Asn Lys Val Phe Met Arg Lys Phe Lys
385                 390                 395                 400
Ile Gly Tyr Ser Asn Asn Gly Ser Asp Trp Lys Met Ile Met Asp Asp
            405                 410                 415
Ser Lys Arg Lys Ala Lys Ser Phe Glu Gly Asn Asn Asn Tyr Asp Thr
        420                 425                 430
Pro Glu Leu Arg Thr Phe Pro Ala Leu Ser Thr Arg Phe Ile Arg Ile
    435                 440                 445
Tyr Pro Glu Arg Ala Thr His Gly Gly Leu Gly Leu Arg Met Glu Leu
    450                 455                 460
Leu Gly Cys Glu Val Glu Ala Pro Thr Ala Gly Pro Thr Thr Pro Asn
465                 470                 475                 480
Gly Asn Leu Val Asp Glu Cys Asp Asp Gln Ala Asn Cys His Ser
            485                 490                 495
Gly Thr Gly Asp Asp Phe Gln Leu Thr Gly Thr Thr Val Leu Ala
        500                 505                 510
Thr Glu Lys Pro Thr Val Ile Asp Ser Thr Ile Gln Ser Glu Phe Pro
    515                 520                 525
Thr Tyr Gly Phe Asn Cys Glu Phe Gly Trp Gly Ser His Lys Thr Phe
    530                 535                 540
Cys His Trp Glu His Asp Asn His Val Gln Leu Lys Trp Ser Val Leu
545                 550                 555                 560
Thr Ser Lys Thr Gly Pro Ile Gln Asp His Thr Gly Asp Gly Asn Phe
            565                 570                 575
Ile Tyr Ser Gln Ala Asp Glu Asn Gln Lys Gly Lys Val Ala Arg Leu
        580                 585                 590
Val Ser Pro Val Val Tyr Ser Gln Asn Ser Ala His Cys Met Thr Phe
    595                 600                 605
Trp Tyr His Met Ser Gly Ser His Val Gly Thr Leu Arg Val Lys Leu
    610                 615                 620
Arg Tyr Gln Lys Pro Glu Glu Tyr Asp Gln Leu Val Trp Met Ala Ile
625                 630                 635                 640
Gly His Gln Gly Asp His Trp Lys Glu Gly Arg Val Leu Leu His Lys
            645                 650                 655
Ser Leu Lys Leu Tyr Gln Val Ile Phe Glu Gly Glu Ile Gly Lys Gly
        660                 665                 670
Asn Leu Gly Gly Ile Ala Val Asp Asp Ile Ser Ile Asn Asn His Ile
    675                 680                 685
Ser Gln Glu Asp Cys Ala Lys Pro Ala Asp Leu Asp Lys Lys Asn Pro
    690                 695                 700
Glu Ile Lys Ile Asp Glu Thr Gly Ser Thr Pro Gly Tyr Glu Gly Glu
705                 710                 715                 720
Gly Glu Gly Asp Lys Asn Ile Ser Arg Lys Pro Gly Asn Val Leu Lys
            725                 730                 735
```

Thr Leu Asp Pro Arg Ser Gly Ser Lys Glu Asn Leu Tyr Phe Gln Gly
            740                 745                 750

<210> SEQ ID NO 61
<211> LENGTH: 1437
<212> TYPE: DNA
<213> ORGANISM: artificial sequence
<220> FEATURE:
<223> OTHER INFORMATION: Synthetic construct

<400> SEQUENCE: 61

```
atggagaggg ggctgccgct cctctgcgcc gtgctcgccc tcgtcctcgc cccggccggc      60
gcttttcgca acgataaaag aggtcctgaa tgttcccaga actacacaac acctagtgga     120
gtgataaagt cccccggatt ccctgaaaaa tatcccaaca gccttgaatg cacttatatt     180
gtctttgcgc aaagatgtc agagattatc ctggaatttg aaagctttga cctggagcct     240
gactcaaatc ctccaggggg gatgttctgt cgctacgacc ggctagaaat ctgggatgga     300
ttccctgatg ttggccctca cattgggcgt tactgtggac agaaaacacc aggtcgaatc     360
cgatcctcat cgggcattct ctccatggtt ttttacaccg acagcgcgat agcaaaagaa     420
ggtttctcag caaactacag tgtcttgcag agcagtgtct cagaagattt caaatgtatg     480
gaagctctgg gcatggaatc aggagaaatt cattctgacc agatcacagc ttcttcccag     540
tatagcacca actggtctgc agagcgctcc cgcctgaact accctgagaa tgggtggact     600
cccggagagg attcctaccg agagtggata caggtagact tgggccttct gcgctttgtc     660
acggctgtcg ggacacaggg cgccatttca aaagaaacca agaagaaata ttatgtcaag     720
acttacaaga tcgacgttag ctccaacggg gaagactgga tcaccataaa agaaggaaac     780
aaacctgttc tctttcaggg aaacaccaac cctacagatg ttgtggttgc agtattcccc     840
aaaccactga taactcgatt tgtccgaatc aagcctgcaa cttgggaaac tggcatatct     900
atgagatttg aagtatatgg ttgcaagata acagattatc cttgctctgg aatgttgggt     960
atggtgtctg gacttatttc tgactcccag atcacatcat ccaaccaagg ggacagaaac    1020
tggatgcctg aaaacatccg cctggtaacc agtcgctctg gctgggcact tccacccgca    1080
cctcattcct acatcaatga gtggctccaa atagacctgg gggaggagaa gatcgtgagg    1140
ggcatcatca ttcagggtgg gaagcaccga gagaacaagg tgttcatgag gaagttcaag    1200
atcgggtaca gcaacaacgg ctcggactgg aagatgatca tggatgacag caaacgcaag    1260
gcgaagtctt tgagggcaa caacaactat gatacacctg agctgcggac ttttccagct    1320
ctctccacgc gattcatcag gatctacccc gagagagcca ctcatggcgg actgggctc    1380
agaatggagc tgctgggctg tagatctgga tccaaggaaa acttgtattt ccagggc     1437
```

<210> SEQ ID NO 62
<211> LENGTH: 479
<212> TYPE: PRT
<213> ORGANISM: artificial sequence
<220> FEATURE:
<223> OTHER INFORMATION: Synthetic construct

<400> SEQUENCE: 62

Met Glu Arg Gly Leu Pro Leu Leu Cys Ala Val Leu Ala Leu Val Leu
1               5                   10                  15

Ala Pro Ala Gly Ala Phe Arg Asn Asp Lys Arg Gly Pro Glu Cys Ser
            20                  25                  30

Gln Asn Tyr Thr Thr Pro Ser Gly Val Ile Lys Ser Pro Gly Phe Pro
        35                  40                  45

```
Glu Lys Tyr Pro Asn Ser Leu Glu Cys Thr Tyr Ile Val Phe Ala Pro
     50                  55                  60
Lys Met Ser Glu Ile Ile Leu Glu Phe Glu Ser Phe Asp Leu Glu Pro
 65                  70                  75                  80
Asp Ser Asn Pro Pro Gly Gly Met Phe Cys Arg Tyr Asp Arg Leu Glu
                 85                  90                  95
Ile Trp Asp Gly Phe Pro Asp Val Gly Pro His Ile Gly Arg Tyr Cys
                100                 105                 110
Gly Gln Lys Thr Pro Gly Arg Ile Arg Ser Ser Gly Ile Leu Ser
             115                 120                 125
Met Val Phe Tyr Thr Asp Ser Ala Ile Ala Lys Glu Gly Phe Ser Ala
     130                 135                 140
Asn Tyr Ser Val Leu Gln Ser Ser Val Ser Glu Asp Phe Lys Cys Met
145                 150                 155                 160
Glu Ala Leu Gly Met Glu Ser Gly Glu Ile His Ser Asp Gln Ile Thr
                165                 170                 175
Ala Ser Ser Gln Tyr Ser Thr Asn Trp Ser Ala Glu Arg Ser Arg Leu
             180                 185                 190
Asn Tyr Pro Glu Asn Gly Trp Thr Pro Gly Glu Asp Ser Tyr Arg Glu
             195                 200                 205
Trp Ile Gln Val Asp Leu Gly Leu Leu Arg Phe Val Thr Ala Val Gly
     210                 215                 220
Thr Gln Gly Ala Ile Ser Lys Glu Thr Lys Lys Tyr Tyr Val Lys
225                 230                 235                 240
Thr Tyr Lys Ile Asp Val Ser Ser Asn Gly Glu Asp Trp Ile Thr Ile
                245                 250                 255
Lys Glu Gly Asn Lys Pro Val Leu Phe Gln Gly Asn Thr Asn Pro Thr
             260                 265                 270
Asp Val Val Val Ala Val Phe Pro Lys Pro Leu Ile Thr Arg Phe Val
             275                 280                 285
Arg Ile Lys Pro Ala Thr Trp Glu Thr Gly Ile Ser Met Arg Phe Glu
     290                 295                 300
Val Tyr Gly Cys Lys Ile Thr Asp Tyr Pro Cys Ser Gly Met Leu Gly
305                 310                 315                 320
Met Val Ser Gly Leu Ile Ser Asp Ser Gln Ile Thr Ser Ser Asn Gln
                325                 330                 335
Gly Asp Arg Asn Trp Met Pro Glu Asn Ile Arg Leu Val Thr Ser Arg
             340                 345                 350
Ser Gly Trp Ala Leu Pro Pro Ala Pro His Ser Tyr Ile Asn Glu Trp
             355                 360                 365
Leu Gln Ile Asp Leu Gly Glu Glu Lys Ile Val Arg Gly Ile Ile Ile
     370                 375                 380
Gln Gly Gly Lys His Arg Glu Asn Lys Val Phe Met Arg Lys Phe Lys
385                 390                 395                 400
Ile Gly Tyr Ser Asn Asn Gly Ser Asp Trp Lys Met Ile Met Asp Asp
                405                 410                 415
Ser Lys Arg Lys Ala Lys Ser Phe Glu Gly Asn Asn Asn Tyr Asp Thr
             420                 425                 430
Pro Glu Leu Arg Thr Phe Pro Ala Leu Ser Thr Arg Phe Ile Arg Ile
             435                 440                 445
Tyr Pro Glu Arg Ala Thr His Gly Gly Leu Gly Leu Arg Met Glu Leu
     450                 455                 460
```

Leu Gly Cys Arg Ser Gly Ser Lys Glu Asn Leu Tyr Phe Gln Gly
465                 470                 475

<210> SEQ ID NO 63
<211> LENGTH: 960
<212> TYPE: DNA
<213> ORGANISM: artificial sequence
<220> FEATURE:
<223> OTHER INFORMATION: Synthetic construct

<400> SEQUENCE: 63

```
atggagaggg ggctgccgct cctctgcgcc gtgctcgccc tcgtcctcgc cccggccggc      60
gcttttcgca acgataaaag aggtcctgaa tgttcccaga actacacaac acctagtgga     120
gtgataaagt cccccggatt ccctgaaaaa tatcccaaca gccttgaatg cacttatatt     180
gtctttgcgc caaagatgtc agagattatc ctggaatttg aaagctttga cctggagcct     240
gactcaaatc ctccaggggg gatgttctgt cgctacgacc ggctagaaat ctgggatgga     300
ttccctgatg ttggccctca cattgggcgt tactgtggac agaaaacacc aggtcgaatc     360
cgatcctcat cgggcattct ctccatggtt ttttacaccg acagcgcgat agcaaaagaa     420
ggtttctcag caaactacag tgtcttgcag agcagtgtct cagaagattt caaatgtatg     480
gaagctctgg gcatggaatc aggagaaatt cattctgacc agatcacagc ttcttcccag     540
tatagcacca actggtctgc agagcgctcc cgcctgaact accctgagaa tgggtggact     600
cccggagagg attcctaccg agagtggata caggtagact tgggccttct cgctttgtc      660
acggctgtcg ggacacaggg cgccatttca aaagaaacca gaagaaata ttatgtcaag      720
acttacaaga tcgacgttag ctccaacggg gaagactgga tcaccataaa agaaggaaac     780
aaacctgttc tctttcaggg aaacaccaac cctacagatg ttgtggttgc agtattcccc     840
aaaccactga taactcgatt tgtccgaatc aagcctgcaa cttgggaaac tggcatatct     900
atgagatttg aagtatatgg ttgcagatct ggatccaagg aaaacttgta tttccagggc     960
```

<210> SEQ ID NO 64
<211> LENGTH: 320
<212> TYPE: PRT
<213> ORGANISM: artificial sequence
<220> FEATURE:
<223> OTHER INFORMATION: Synthetic construct

<400> SEQUENCE: 64

Met Glu Arg Gly Leu Pro Leu Cys Ala Val Leu Ala Leu Val Leu
1               5                   10                  15

Ala Pro Ala Gly Ala Phe Arg Asn Asp Lys Arg Gly Pro Glu Cys Ser
                20                  25                  30

Gln Asn Tyr Thr Thr Pro Ser Gly Val Ile Lys Ser Pro Gly Phe Pro
            35                  40                  45

Glu Lys Tyr Pro Asn Ser Leu Glu Cys Thr Tyr Ile Val Phe Ala Pro
        50                  55                  60

Lys Met Ser Glu Ile Ile Leu Glu Phe Glu Ser Phe Asp Leu Glu Pro
65                  70                  75                  80

Asp Ser Asn Pro Pro Gly Gly Met Phe Cys Arg Tyr Asp Arg Leu Glu
                85                  90                  95

Ile Trp Asp Gly Phe Pro Asp Val Gly Pro His Ile Gly Arg Tyr Cys
            100                 105                 110

Gly Gln Lys Thr Pro Gly Arg Ile Arg Ser Ser Ser Gly Ile Leu Ser
            115                 120                 125

```
Met Val Phe Tyr Thr Asp Ser Ala Ile Ala Lys Glu Gly Phe Ser Ala
130                 135                 140

Asn Tyr Ser Val Leu Gln Ser Ser Val Ser Glu Asp Phe Lys Cys Met
145                 150                 155                 160

Glu Ala Leu Gly Met Glu Ser Gly Glu Ile His Ser Asp Gln Ile Thr
                165                 170                 175

Ala Ser Ser Gln Tyr Ser Thr Asn Trp Ser Ala Glu Arg Ser Arg Leu
            180                 185                 190

Asn Tyr Pro Glu Asn Gly Trp Thr Pro Gly Glu Asp Ser Tyr Arg Glu
            195                 200                 205

Trp Ile Gln Val Asp Leu Gly Leu Leu Arg Phe Val Thr Ala Val Gly
210                 215                 220

Thr Gln Gly Ala Ile Ser Lys Glu Thr Lys Lys Tyr Tyr Val Lys
225                 230                 235                 240

Thr Tyr Lys Ile Asp Val Ser Ser Asn Gly Glu Asp Trp Ile Thr Ile
                245                 250                 255

Lys Glu Gly Asn Lys Pro Val Leu Phe Gln Gly Asn Thr Asn Pro Thr
            260                 265                 270

Asp Val Val Ala Val Phe Pro Lys Pro Leu Ile Thr Arg Phe Val
            275                 280                 285

Arg Ile Lys Pro Ala Thr Trp Glu Thr Gly Ile Ser Met Arg Phe Glu
290                 295                 300

Val Tyr Gly Cys Arg Ser Gly Ser Lys Glu Asn Leu Tyr Phe Gln Gly
305                 310                 315                 320

<210> SEQ ID NO 65
<211> LENGTH: 1797
<212> TYPE: DNA
<213> ORGANISM: artificial sequence
<220> FEATURE:
<223> OTHER INFORMATION: Synthetic construct

<400> SEQUENCE: 65
atggagaggg ggctgccgct cctctgcgcc gtgctcgccc tcgtcctcgc cccggccggc      60
gcttttcgca acgataaaag aggtcctgaa tgttcccaga actacacaac acctagtgga     120
gtgataaagt cccccggatt ccctgaaaaa tatcccaaca gccttgaatg cacttatatt     180
gtctttgcgc aaagatgtc agagattatc ctggaatttg aaagctttga cctggagcct     240
gactcaaatc ctccaggggg gatgttctgt cgctacgacc ggctagaaat ctgggatgga     300
ttccctgatt tggccctca cattgggcgt tactgtggac agaaaacacc aggtcgaatc     360
cgatcctcat cgggcattct ctccatggtt ttttacaccg acagcgcgat agcaaaagaa     420
ggtttctcag caaactacag tgtcttgcag agcagtgtct cagaagattt caaatgtatg     480
gaagctctgg gcatggaatc aggagaaatt cattctgacc agatcacagc ttcttcccag     540
tatagcacca actggtctgc agagcgctcc cgcctgaact accctgagaa tgggtggact     600
cccggagagg attcctaccg agagtggata caggtagact tgggccttct gcgctttgtc     660
acggctgtcg gaacacaggg cgccatttca aaagaaacca gaagaaata ttatgtcaag     720 acttacaaga tcgacgttag ctccaacggg gaagactgga tcaccataaa agaaggaaac     780
aaacctgttc tctttcaggg aaacaccaac cctacagatg ttgtggttgc agtattcccc     840
aaaccactga taactcgatt tgtccgaatc aagcctgcaa cttgggaaac tggcatatct     900
atgagatttg aagtatatgg ttgcaagata acagattatc tgaagtgga agcccctaca     960 gctggaccga ccactcccaa cgggaacttg gtggatgaat gtgatgacga ccaggccaac    1020
```

```
tgccacagtg aacaggtga tgacttccag ctcacaggtg gcaccactgt gctggccaca      1080
gaaaagccca cggtcataga cagcaccata caatcagagt ttccaacata tggttttaac      1140
tgtgaatttg gctggggctc tcacaagacc ttctgccact gggaacatga caatcacgtg      1200
cagctcaagt ggagtgtgtt gaccagcaag acgggaccca ttcaggatca cacaggagat      1260
ggcaacttca tctattccca agctgacgaa aatcagaagg gcaaagtggc tcgcctggtg      1320
agccctgtgg tttattccca gaactctgcc cactgcatga ccttctggta tcacatgtct      1380
gggtcccacg tcggcacact cagggtcaaa ctgcgctacc agaagccaga ggagtacgat      1440
cagctggtct ggatggccat ggacaccaa ggtgaccact ggaaggaagg gcgtgtcttg      1500
ctccacaagt ctctgaaact ttatcaggtg attttcgagg gcgaaatcgg aaaaggaaac      1560
cttggtggga ttgctgtgga tgacattagt attaataacc acatttcaca agaagattgt      1620
gcaaaaccag cagacctgga taaaagaac ccagaaatta aaattgatga aacagggagc      1680
acgccaggat acgaaggtga aggagaaggt gacaagaaca tctccaggaa gccaggcaat      1740
gtgttgaaga ccttagaccc cagatctgga tccaaggaaa acttgtattt ccagggc          1797
```

<210> SEQ ID NO 66
<211> LENGTH: 599
<212> TYPE: PRT
<213> ORGANISM: artificial sequence
<220> FEATURE:
<223> OTHER INFORMATION: Synthetic construct

<400> SEQUENCE: 66

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Arg Gly Pro Glu Cys Ser
            20                  25                  30

Gln Asn Tyr Thr Thr Pro Ser Gly Val Ile Lys Ser Pro Gly Phe Pro
        35                  40                  45

Glu Lys Tyr Pro Asn Ser Leu Glu Cys Thr Tyr Ile Val Phe Ala Pro
    50                  55                  60

Lys Met Ser Glu Ile Ile Leu Glu Phe Glu Ser Phe Asp Leu Glu Pro
65                  70                  75                  80

Asp Ser Asn Pro Pro Gly Gly Met Phe Cys Arg Tyr Asp Arg Leu Glu
                85                  90                  95

Ile Trp Asp Gly Phe Pro Asp Val Gly Pro His Ile Gly Arg Tyr Cys
            100                 105                 110

Gly Gln Lys Thr Pro Gly Arg Ile Arg Ser Ser Ser Gly Ile Leu Ser
        115                 120                 125

Met Val Phe Tyr Thr Asp Ser Ala Ile Ala Lys Glu Gly Phe Ser Ala
    130                 135                 140

Asn Tyr Ser Val Leu Gln Ser Ser Val Ser Glu Asp Phe Lys Cys Met
145                 150                 155                 160

Glu Ala Leu Gly Met Glu Ser Gly Glu Ile His Ser Asp Gln Ile Thr
                165                 170                 175

Ala Ser Ser Gln Tyr Ser Thr Asn Trp Ser Ala Glu Arg Ser Arg Leu
            180                 185                 190

Asn Tyr Pro Glu Asn Gly Trp Thr Pro Gly Glu Asp Ser Tyr Arg Glu
        195                 200                 205

Trp Ile Gln Val Asp Leu Gly Leu Leu Arg Phe Val Thr Ala Val Gly
    210                 215                 220
```

```
Thr Gln Gly Ala Ile Ser Lys Glu Thr Lys Lys Tyr Tyr Val Lys
225                 230                 235                 240

Thr Tyr Lys Ile Asp Val Ser Ser Asn Gly Glu Asp Trp Ile Thr Ile
                245                 250                 255

Lys Glu Gly Asn Lys Pro Val Leu Phe Gln Gly Asn Thr Asn Pro Thr
            260                 265                 270

Asp Val Val Ala Val Phe Pro Lys Pro Leu Ile Thr Arg Phe Val
        275                 280                 285

Arg Ile Lys Pro Ala Thr Trp Glu Thr Gly Ile Ser Met Arg Phe Glu
    290                 295                 300

Val Tyr Gly Cys Lys Ile Thr Asp Tyr Pro Glu Val Glu Ala Pro Thr
305                 310                 315                 320

Ala Gly Pro Thr Thr Pro Asn Gly Asn Leu Val Asp Glu Cys Asp Asp
                325                 330                 335

Asp Gln Ala Asn Cys His Ser Gly Thr Gly Asp Asp Phe Gln Leu Thr
            340                 345                 350

Gly Gly Thr Thr Val Leu Ala Thr Glu Lys Pro Thr Val Ile Asp Ser
        355                 360                 365

Thr Ile Gln Ser Glu Phe Pro Thr Tyr Gly Phe Asn Cys Glu Phe Gly
    370                 375                 380

Trp Gly Ser His Lys Thr Phe Cys His Trp Glu His Asp Asn His Val
385                 390                 395                 400

Gln Leu Lys Trp Ser Val Leu Thr Ser Lys Thr Gly Pro Ile Gln Asp
                405                 410                 415

His Thr Gly Asp Gly Asn Phe Ile Tyr Ser Gln Ala Asp Glu Asn Gln
            420                 425                 430

Lys Gly Lys Val Ala Arg Leu Val Ser Pro Val Val Tyr Ser Gln Asn
        435                 440                 445

Ser Ala His Cys Met Thr Phe Trp Tyr His Met Ser Gly Ser His Val
    450                 455                 460

Gly Thr Leu Arg Val Lys Leu Arg Tyr Gln Lys Pro Glu Glu Tyr Asp
465                 470                 475                 480

Gln Leu Val Trp Met Ala Ile Gly His Gln Gly Asp His Trp Lys Glu
                485                 490                 495

Gly Arg Val Leu Leu His Lys Ser Leu Lys Leu Tyr Gln Val Ile Phe
            500                 505                 510

Glu Gly Glu Ile Gly Lys Gly Asn Leu Gly Gly Ile Ala Val Asp Asp
        515                 520                 525

Ile Ser Ile Asn Asn His Ile Ser Gln Glu Asp Cys Ala Lys Pro Ala
    530                 535                 540

Asp Leu Asp Lys Lys Asn Pro Glu Ile Lys Ile Asp Glu Thr Gly Ser
545                 550                 555                 560

Thr Pro Gly Tyr Glu Gly Gly Glu Gly Asp Lys Asn Ile Ser Arg
                565                 570                 575

Lys Pro Gly Asn Val Leu Lys Thr Leu Asp Pro Arg Ser Gly Ser Lys
            580                 585                 590

Glu Asn Leu Tyr Phe Gln Gly
        595

<210> SEQ ID NO 67
<211> LENGTH: 2604
<212> TYPE: DNA
<213> ORGANISM: artificial sequence
<220> FEATURE:
<223> OTHER INFORMATION: Synthetic construct
```

<400> SEQUENCE: 67

```
atggagaggg ggctgccgct cctctgcgcc gtgctcgccc tcgtcctcgc cccggccggc    60
gcttttcgca acgataaatg tggcgatact ataaaaattg aaagccccgg gtaccttaca   120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300
ggaaagttct gtggaaagat agcccctcct cctgttgtgt cttcagggcc atttcttttt   360
atcaaatttg tctctgacta cgaaacacat ggtgcaggat tttccatacg ttatgaactt   420
ttcaagagag gtcctgaatg ttcccagaac tacaacacac tagtggagt gataaagtcc    480
cccggattcc ctgaaaaata tcccaacagc cttgaatgca cttatattgt ctttgcgcca   540
aagatgtcag agattatcct ggaatttgaa agctttgacc tggagcctga ctcaaatcct   600
ccaggggga tgttctgtcg ctacgaccgg ctagaaatct gggatggatt ccctgatgtt   660
ggccctcaca ttgggcgtta ctgtggacag aaaacaccag gtcgaatccg atcctcatcg   720
ggcattctct ccatggtttt ttacaccgac agcgcgatag caaaagaagg tttctcagca   780
aactacagtg tcttgcagag cagtgtctca gaagatttca atgtatgga agctctgggc    840
atggaatcag gagaaattca ttctgaccag atcacagctt cttcccagta tagcaccaac   900
tggtctgcag agcgctcccg cctgaactac cctgagaatg ggtggactcc cggagaggat   960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg gcatatctat gagatttgaa  1260
gtatatggtt gcaagataac agattatcct tgctctggaa tgttgggtat ggtgtctgga  1320
cttatttctg actcccagat cacatcatcc aaccaagggg acagaaactg gatgcctgaa  1380
aacatccgcc tggtaaccag tcgctctggc tgggcacttc cacccgcacc tcattcctac  1440
atcaatgagt ggctccaaat agacctgggg gaggagaaga tcgtgagggg catcatcatt  1500
cagggtggga agcaccgaga gaacaaggtg ttcatgagga gttcaagat cgggtacagc   1560
aacaacggct cggactggaa gatgatcatg gatgacagca acgcaaggc gaagtctttt   1620
gagggcaaca caactatga tacacctgag ctgcggactt tccagctct ctccacgcga   1680
ttcatcagga tctaccccga gagagccact catggcggac tggggctcag aatggagctg  1740
ctgggctgtg aagtggaagc cctacagct ggaccgacca ctcccaacgg aacttggtg    1800
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc aacatatgg ttttaactgt gaatttggct ggggctctca caagaccttc   1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca agtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
```

```
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aagaaccca    2460 gaaattaaaa ttgatgaaac agggagcacg ccaggatacg aaggtgaagg agaaggtgac    2520
aagaacatct ccaggaagcc aggcaatgtg ttgaagacct tagaccccag atctggatcc    2580
aaggaaaact tgtatttcca gggc                                          2604

<210> SEQ ID NO 68
<211> LENGTH: 847
<212> TYPE: PRT
<213> ORGANISM: artificial sequence
<220> FEATURE:
<223> OTHER INFORMATION: Synthetic construct

<400> SEQUENCE: 68
```

| | | | | | | | | | | | | | | |
|---|---|---|---|---|---|---|---|---|---|---|---|---|---|---|
| Phe | Arg | Asn | Asp | Lys | Cys | Gly | Asp | Thr | Ile | Lys | Ile | Glu | Ser | Pro | Gly |
| 1 | | | | 5 | | | | | 10 | | | | | 15 | |

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
290                 295                 300

```
Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
            325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
            370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
            435                 440                 445

Gly Trp Ala Leu Pro Pro Ala Pro His Ser Tyr Ile Asn Glu Trp Leu
450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
            530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
            595                 600                 605

Glu Lys Pro Thr Val Ile Asp Ser Thr Ile Gln Ser Glu Phe Pro Thr
610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
            660                 665                 670

Tyr Ser Gln Ala Asp Glu Asn Gln Lys Gly Lys Val Ala Arg Leu Val
            675                 680                 685

Ser Pro Val Val Tyr Ser Gln Asn Ser Ala His Cys Met Thr Phe Trp
            690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
```

```
                    725                 730                 735
His Gln Gly Asp His Trp Lys Glu Gly Arg Val Leu His Lys Ser
                740                 745                 750

Leu Lys Leu Tyr Gln Val Ile Phe Glu Gly Glu Ile Gly Lys Gly Asn
                755                 760                 765

Leu Gly Gly Ile Ala Val Asp Asp Ile Ser Ile Asn Asn His Ile Ser
                770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
                820                 825                 830

Leu Asp Pro Arg Ser Gly Ser Lys Glu Asn Leu Tyr Phe Gln Gly
                835                 840                 845

<210> SEQ ID NO 69
<211> LENGTH: 2604
<212> TYPE: DNA
<213> ORGANISM: artificial sequence
<220> FEATURE:
<223> OTHER INFORMATION: Synthetic construct

<400> SEQUENCE: 69
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttaatgca cttatattgt ctttgcgcca     540
aagatgtcag agattatcct ggaatttgaa agctttgacc tggagcctga ctcaaatcct     600 ccaggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaagaagg tttctcagca     780 aactacagtg tcttgcagag cagtgtctca gaagatttca atgtatggga agctctgggc     840
atggaatcag agaaaattca ttctgaccag atcacagctt cttcccaggc tagcaccaac     900
tggtctgcag agcgctcccg cctgaactac cctgagaatg ggtggactcc cggagaggat     960
tcctaccgag agtggataca ggtagacttg ggcttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140 tttcaggaa acaccaaccc tacagatgtt gtggttgcag tattccccaa ccactgataa    1200
actcgatttg tccgaatcaa gcctgcaact tgggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
```

```
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca acgcaaggc gaagtctttt     1620 gagggcaaca caactatga tacacctgag ctgcggactt ttccagctct ctccacgcga     1680
ttcatcagga tctaccccga gagagccact catggcggac tggggctcag aatggagctg    1740
ctgggctgtg aagtggaagc ccctacagct ggaccgacca ctcccaacgg aacttggtg     1800 gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc caacatatgg ttttaactgt gaatttggct ggggctctca caagaccttc    1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca agtggctcg cctggtgagc cctgtggttt attcccagaa ctctgcccac     2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aagaaccca    2460 gaaattaaaa ttgatgaaac agggagcacg ccaggatacg aaggtgaagg agaaggtgac    2520
aagaacatct ccaggaagcc aggcaatgtg ttgaagacct agaccccag atctggatcc    2580 aaggaaaact tgtatttcca gggc                                          2604
```

<210> SEQ ID NO 70
<211> LENGTH: 847
<212> TYPE: PRT
<213> ORGANISM: artificial sequence
<220> FEATURE:
<223> OTHER INFORMATION: Synthetic construct

<400> SEQUENCE: 70

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140
```

```
Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
            165                 170                 175

Ser Asn Pro Pro Gly Met Phe Cys Arg Tyr Asp Arg Leu Glu Ile
        180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
        210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
            245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
        290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
            325                 330                 335

Tyr Lys Ile Asp Val Ser Ser Asn Gly Glu Asp Trp Ile Thr Ile Lys
        340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
            405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
        435                 440                 445

Gly Trp Ala Leu Pro Pro Ala Pro His Ser Tyr Ile Asn Glu Trp Leu
        450                 455                 460

Gln Ile Asp Leu Gly Glu Glu Lys Ile Val Arg Gly Ile Ile Gln
465                 470                 475                 480

Gly Gly Lys His Arg Glu Asn Lys Val Phe Met Arg Lys Phe Lys Ile
            485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
        530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
```

-continued

|     |     |     |     |     | 565 |     |     |     |     | 570 |     |     |     |     | 575 |     |
| --- | --- | --- | --- | --- | --- | --- | --- | --- | --- | --- | --- | --- | --- | --- | --- | --- |

Asn Leu Val Asp Glu Cys Asp Asp Gln Ala Asn Cys His Ser Gly
            580                      585                      590

Thr Gly Asp Asp Phe Gln Leu Thr Gly Gly Thr Thr Val Leu Ala Thr
        595                      600                      605

Glu Lys Pro Thr Val Ile Asp Ser Thr Ile Gln Ser Glu Phe Pro Thr
        610                      615                      620

Tyr Gly Phe Asn Cys Glu Phe Gly Trp Gly Ser His Lys Thr Phe Cys
625                      630                      635                      640

His Trp Glu His Asp Asn His Val Gln Leu Lys Trp Ser Val Leu Thr
            645                      650                      655

Ser Lys Thr Gly Pro Ile Gln Asp His Thr Gly Asp Gly Asn Phe Ile
        660                      665                      670

Tyr Ser Gln Ala Asp Glu Asn Gln Lys Gly Lys Val Ala Arg Leu Val
        675                      680                      685

Ser Pro Val Val Tyr Ser Gln Asn Ser Ala His Cys Met Thr Phe Trp
        690                      695                      700

Tyr His Met Ser Gly Ser His Val Gly Thr Leu Arg Val Lys Leu Arg
705                      710                      715                      720

Tyr Gln Lys Pro Glu Glu Tyr Asp Gln Leu Val Trp Met Ala Ile Gly
            725                      730                      735

His Gln Gly Asp His Trp Lys Glu Gly Arg Val Leu Leu His Lys Ser
        740                      745                      750

Leu Lys Leu Tyr Gln Val Ile Phe Glu Gly Glu Ile Gly Lys Gly Asn
        755                      760                      765

Leu Gly Gly Ile Ala Val Asp Asp Ile Ser Ile Asn Asn His Ile Ser
770                      775                      780

Gln Glu Asp Cys Ala Lys Pro Ala Asp Leu Asp Lys Lys Asn Pro Glu
785                      790                      795                      800

Ile Lys Ile Asp Glu Thr Gly Ser Thr Pro Gly Tyr Glu Gly Glu Gly
            805                      810                      815

Glu Gly Asp Lys Asn Ile Ser Arg Lys Pro Gly Asn Val Leu Lys Thr
        820                      825                      830

Leu Asp Pro Arg Ser Gly Ser Lys Glu Asn Leu Tyr Phe Gln Gly
        835                      840                      845

```
<210> SEQ ID NO 71
<211> LENGTH: 2604
<212> TYPE: DNA
<213> ORGANISM: artificial sequence
<220> FEATURE:
<223> OTHER INFORMATION: Synthetic construct

<400> SEQUENCE: 71
```

| | |
|---|---|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatgagaaaa tgaaaatgg acatttttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |

```
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag gtcgaatccg atcctcatcg    720
ggcattctct ccatggtttt ttacaccgac agcgcgatag caaaagaagg tttctcagca    780
aactacagtg tcttgcagag cagtgtctca gaagatttca atgtatgga agctctgggc     840
atggaatcag gagaaattca ttctgaccag atcacagctt cttcccagta tagcaccaac    900
tggtctgcag agcgctcccg cctgaactac cctgagaatg ggtggactcc cggaaagaag    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcaagataac agattatcct tgctctggaa tgttgggtat ggtgtctgga   1320
cttatttctg actcccagat cacatcatcc aaccaagggg acagaaactg gatgcctgaa   1380
aacatccgcc tggtaaccag tcgctctggc tgggcacttc cacccgcacc tcattcctac   1440
atcaatgagt ggctccaaat agacctgggg gaggagaaga tcgtgagggg catcatcatt   1500
cagggtggga agcaccgaga gaacaaggtg ttcatgagga agttcaagat cgggtacagc   1560
aacaacggct cggactggaa gatgatcatg gatgacagca acgcaaggc gaagtctttt    1620
gagggcaaca caactatga tacacctgag ctgcggactt ttccagctct ctccacgcga    1680
ttcatcagga tctaccccga gagagccact catggcggac tggggctcag aatggagctg   1740
ctgggctgtg aagtggaagc ccctacagct ggaccgacca ctcccaacgg gaacttggtg   1800
gatgaatgtg atgacgacca ggccaactgc cacagtggaa caggtgatga cttccagctc   1860
acaggtggca ccactgtgct ggccacagaa aagcccacgg tcatagacag caccatacaa   1920
tcagagtttc caacatatgg ttttaactgt gaatttggct ggggctctca caagaccttc   1980
tgccactggg aacatgacaa tcacgtgcag ctcaagtgga gtgtgttgac cagcaagacg   2040
ggacccattc aggatcacac aggagatggc aacttcatct attcccaagc tgacgaaaat   2100
cagaagggca agtggctcg cctggtgagc cctgtggttt attcccagaa ctctgcccac   2160
tgcatgacct tctggtatca catgtctggg tcccacgtcg gcacactcag ggtcaaactg   2220
cgctaccaga agccagagga gtacgatcag ctggtctgga tggccattgg acaccaaggt   2280
gaccactgga aggaagggcg tgtcttgctc cacaagtctc tgaaacttta tcaggtgatt   2340
ttcgagggcg aaatcggaaa aggaaacctt ggtgggattg ctgtggatga cattagtatt   2400
aataaccaca tttcacaaga agattgtgca aaaccagcag acctggataa aaagaaccca   2460
gaaattaaaa ttgatgaaac agggagcacg ccaggatacg aaggtgaagg agaaggtgac   2520
aagaacatct ccaggaagcc aggcaatgtg ttgaagacct tagaccccag atctggatcc   2580
aaggaaaact tgtatttcca gggc                                          2604
```

<210> SEQ ID NO 72
<211> LENGTH: 847
<212> TYPE: PRT
<213> ORGANISM: artificial sequence
<220> FEATURE:
<223> OTHER INFORMATION: Synthetic construct

<400> SEQUENCE: 72

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
                115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Lys Lys Ser Tyr Arg Glu Trp
290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
```

```
                405                 410                 415
Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
            435                 440                 445

Gly Trp Ala Leu Pro Pro Ala Pro His Ser Tyr Ile Asn Glu Trp Leu
            450                 455                 460

Gln Ile Asp Leu Gly Glu Lys Ile Val Arg Gly Ile Ile Ile Gln
465                 470                 475                 480

Gly Gly Lys His Arg Glu Asn Lys Val Phe Met Arg Lys Phe Lys Ile
            485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
            530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
                595                 600                 605

Glu Lys Pro Thr Val Ile Asp Ser Thr Ile Gln Ser Glu Phe Pro Thr
            610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
                660                 665                 670

Tyr Ser Gln Ala Asp Glu Asn Gln Lys Gly Lys Val Ala Arg Leu Val
            675                 680                 685

Ser Pro Val Val Tyr Ser Gln Asn Ser Ala His Cys Met Thr Phe Trp
            690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Glu Gly Arg Val Leu Leu His Lys Ser
            740                 745                 750

Leu Lys Leu Tyr Gln Val Ile Phe Glu Gly Glu Ile Gly Lys Gly Asn
            755                 760                 765

Leu Gly Gly Ile Ala Val Asp Asp Ile Ser Ile Asn Asn His Ile Ser
            770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
            820                 825                 830
```

Leu Asp Pro Arg Ser Gly Ser Lys Glu Asn Leu Tyr Phe Gln Gly
    835                    840                845

<210> SEQ ID NO 73
<211> LENGTH: 2604
<212> TYPE: DNA
<213> ORGANISM: artificial sequence
<220> FEATURE:
<223> OTHER INFORMATION: Synthetic construct

<400> SEQUENCE: 73

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagcccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtggaaagat | agcccctcct | cctgttgtgt | cttcagggcc | atttcttttt | 360 |
| atcaaatttg | tctctgacta | cgaaacacat | ggtgcaggat | tttccatacg | ttatgaactt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccagggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaaagaagg | tttctcagca | 780 |
| aactacagtg | tcttgcagag | cagtgtctca | gaagatttca | aatgtatgga | agctctgggc | 840 |
| atggaatcag | agaaaattca | ttctgaccag | atcacagctt | cttcccagta | tagcaccaac | 900 |
| tggtctgcag | agcgctcccg | cctgaactac | cctgagaatg | ggtggactcc | cggagaggat | 960 |
| tcctaccgag | agtggataca | ggtagacttg | ggccttctgc | gctttgtcac | ggctgtcggg | 1020 |
| acacagggcg | ccattgccaa | aaagaccaag | aagaaatatt | atgtcaagac | ttacaagatc | 1080 |
| gacgttagct | ccaacgggga | agactggatc | accataaaag | aaggaaacaa | acctgttctc | 1140 |
| tttcagggaa | acaccaaccc | tacagatgtt | gtggttgcag | tattcccaa | accactgata | 1200 |
| actcgatttg | tccgaatcaa | gcctgcaact | tgggaaactg | gcatatctat | gagatttgaa | 1260 |
| gtatatggtt | gcaagataac | agattatcct | tgctctggaa | tgttgggtat | ggtgtctgga | 1320 |
| cttatttctg | actcccagat | cacatcatcc | aaccaagggg | acagaaactg | gatgcctgaa | 1380 |
| aacatccgcc | tggtaaccag | tcgctctggc | tgggcacttc | cacccgcacc | tcattcctac | 1440 |
| atcaatgagt | ggctccaaat | agacctgggg | gaggagaaga | tcgtgagggg | catcatcatt | 1500 |
| cagggtggga | agcaccgaga | gaacaaggtg | ttcatgagga | agttcaagat | cgggtacagc | 1560 |
| aacaacggct | cggactggaa | gatgatcatg | gatgacagca | aacgcaaggc | gaagtctttt | 1620 |
| gagggcaaca | caactatga | tacacctgag | ctgcggactt | ttccagctct | ctccacgcga | 1680 |
| ttcatcagga | tctaccccga | gagagccact | catggcggac | tggggctcag | aatggagctg | 1740 |
| ctgggctgtg | aagtggaagc | ccctacagct | ggaccgacca | ctcccaacgg | gaacttggtg | 1800 |
| gatgaatgtg | atgacgacca | ggccaactgc | cacagtggaa | caggtgatga | cttccagctc | 1860 |
| acaggtggca | ccactgtgct | ggccacagaa | aagcccacgg | tcatagacag | caccataaca | 1920 |
| tcagagtttc | caacatatgg | ttttaactgt | gaatttggct | ggggctctca | caagaccttc | 1980 |

-continued

```
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca agtggctcg cctggtgagc cctgtggttt attcccagaa ctctgcccac     2160
tgcatgacct tctggtatca catgtctggg tcccacgtcg gcacactcag ggtcaaactg    2220
cgctaccaga agccagagga gtacgatcag ctggtctgga tggccattgg acaccaaggt   2280
gaccactgga aggaagggcg tgtcttgctc cacaagtctc tgaaacttta tcaggtgatt   2340
ttcgagggcg aaatcggaaa aggaaacctt ggtgggattg ctgtggatga cattagtatt   2400
aataaccaca tttcacaaga agattgtgca aaaccagcag acctggataa aaagaaccca   2460
gaaattaaaa ttgatgaaac agggagcacg ccaggatacg aaggtgaagg agaaggtgac   2520
aagaacatct ccaggaagcc aggcaatgtg ttgaagacct tagacccag atctggatcc    2580 aaggaaaact tgtatttcca gggc                                          2604
```

<210> SEQ ID NO 74
<211> LENGTH: 847
<212> TYPE: PRT
<213> ORGANISM: artificial sequence
<220> FEATURE:
<223> OTHER INFORMATION: Synthetic construct

<400> SEQUENCE: 74

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
```

```
                    245                 250                 255
Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
            275                 280                 285

Tyr Pro Glu Asn Gly Trp Thr Pro Gly Glu Asp Ser Tyr Arg Glu Trp
        290                 295                 300

Ile Gln Val Asp Leu Gly Leu Leu Arg Phe Val Thr Ala Val Gly Thr
305                 310                 315                 320

Gln Gly Ala Ile Ala Lys Lys Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
        370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
                435                 440                 445

Gly Trp Ala Leu Pro Pro Ala Pro His Ser Tyr Ile Asn Glu Trp Leu
        450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
        530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
        595                 600                 605

Glu Lys Pro Thr Val Ile Asp Ser Thr Ile Gln Ser Glu Phe Pro Thr
        610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
            660                 665                 670
```

| | | | | | | | | | | | |
|---|---|---|---|---|---|---|---|---|---|---|---|
|Tyr|Ser|Gln|Ala|Asp|Glu|Asn|Gln|Lys|Gly|Lys|Val|Ala|Arg|Leu|Val|
| |675| | | |680| | | |685| | |

Ser Pro Val Val Tyr Ser Gln Asn Ser Ala His Cys Met Thr Phe Trp
    690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
            725                 730                 735

His Gln Gly Asp His Trp Lys Glu Gly Arg Val Leu Leu His Lys Ser
        740                 745                 750

Leu Lys Leu Tyr Gln Val Ile Phe Glu Gly Ile Gly Lys Gly Asn
            755                 760                 765

Leu Gly Gly Ile Ala Val Asp Asp Ile Ser Ile Asn Asn His Ile Ser
    770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
            805                 810                 815

Glu Gly Asp Lys Asn Ile Ser Arg Lys Pro Gly Asn Val Leu Lys Thr
        820                 825                 830

Leu Asp Pro Arg Ser Gly Ser Lys Glu Asn Leu Tyr Phe Gln Gly
            835                 840                 845

<210> SEQ ID NO 75
<211> LENGTH: 2604
<212> TYPE: DNA
<213> ORGANISM: artificial sequence
<220> FEATURE:
<223> OTHER INFORMATION: Synthetic construct

<400> SEQUENCE: 75

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acatttttagg     300 ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600 ccaggggga tgttctgtcg ctacgaccgg ctagaaatct gggatggatt ccctgatgtt     660
ggccctcaca ttgggcgtta ctgtggacag aaaacaccag tcgaatccg atcctcatcg     720 ggcattctct ccatggtttt ttacaccgac agcgcgatag caaaagaagg tttctcagca     780
aactacagtg tcttgcagag cagtgtctca gaagatttca atgtatgga agctctgggc     840 atggaatcag agaaattcaa ttctgaccag atcacagctt cttcccagta tagcaccaac     900
tggtctgcag agcgctcccg cctgaactac cctgagaatg gtggactcc cggagagaag     960 tcctaccgag agtggataca ggtagacttg ggccttctgc gctttgtcac ggctgtcggg    1020
acacagggcg ccatttcaaa agaaaccaag aagaatatt atgtcaagac ttacaagatc    1080
```

```
gacgttagct ccaacgggga agactggatc accataaaag aaggaaacaa acctgttctc    1140
tttcagggaa acaccaaccc tacagatgtt gtggttgcag tattcccaa ccactgata     1200 actcgatttg tccgaatcaa gcctgcaact tgggaaactg gcatatctat gagatttgaa   1260
gtatatggtt gcaagataac agattatcct tgctctggaa tgttgggtat ggtgtctgga   1320
cttatttctg actcccagat cacatcatcc aaccaagggg acagaaactg gatgcctgaa   1380
aacatccgcc tggtaaccag tcgctctggc tgggcacttc cacccgcacc tcattcctac   1440
atcaatgagt ggctccaaat agacctgggg gaggagaaga tcgtgagggg catcatcatt   1500
cagggtggga agcaccgaga gaacaaggtg ttcatgagga agttcaagat cgggtacagc   1560
aacaacggct cggactggaa gatgatcatg gatgacagca acgcaaggc gaagtcttt    1620 gagggcaaca caactatga tacacctgag ctgcggactt ttccagctct ctccacgcga    1680
ttcatcagga tctaccccga gagagccact catggcggac tggggctcag aatggagctg   1740
ctgggctgtg aagtggaagc ccctacagct ggaccgacca ctcccaacgg aacttggtg    1800 gatgaatgtg atgacgacca ggccaactgc cacagtggaa caggtgatga cttccagctc   1860
acaggtggca ccactgtgct ggccacagaa aagcccacgg tcatagacag caccatacaa   1920
tcagagtttc caacatatgg tttttaactgt gaatttggct ggggctctca caagaccttc   1980
tgccactggg aacatgacaa tcacgtgcag ctcaagtgga gtgtgttgac cagcaagacg   2040
ggacccattc aggatcacac aggagatggc aacttcatct attcccaagc tgacgaaaat   2100
cagaagggca aagtggctcg cctggtgagc cctgtggttt attcccagaa ctctgcccac   2160
tgcatgacct tctggtatca catgtctggg tcccacgtcg gcacactcag ggtcaaactg   2220
cgctaccaga agccagagga gtacgatcag ctggtctgga tggccattgg acaccaaggt   2280
gaccactgga aggaagggcg tgtcttgctc cacaagtctc tgaaacttta tcaggtgatt   2340
ttcgagggcg aaatcggaaa aggaaacctt ggtgggattg ctgtggatga cattagtatt   2400
aataaccaca tttcacaaga agattgtgca aaaccagcag acctggataa aaagaaccca   2460
gaaattaaaa ttgatgaaac agggagcacg ccaggatacg aaggtgaagg agaaggtgac   2520
aagaacatct ccaggaagcc aggcaatgtg ttgaagacct tagaccccag atctggatcc   2580
aaggaaaact tgtatttcca gggc                                          2604
```

<210> SEQ ID NO 76
<211> LENGTH: 847
<212> TYPE: PRT
<213> ORGANISM: artificial sequence
<220> FEATURE:
<223> OTHER INFORMATION: Synthetic construct

<400> SEQUENCE: 76

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Pro Val Val Ser Ser Gly Pro
```

```
                    85               90                 95
Phe Leu Phe Ile Lys Phe Val Ser Asp Tyr Glu Thr His Gly Ala Gly
                100             105             110

Phe Ser Ile Arg Tyr Glu Leu Phe Lys Arg Gly Pro Glu Cys Ser Gln
            115             120             125

Asn Tyr Thr Thr Pro Ser Gly Val Ile Lys Ser Pro Gly Phe Pro Glu
        130             135             140

Lys Tyr Pro Asn Ser Leu Glu Cys Thr Tyr Ile Val Phe Ala Pro Lys
145             150             155             160

Met Ser Glu Ile Ile Leu Glu Phe Gly Ser Phe Asp Leu Glu Pro Asp
                165             170             175

Ser Asn Pro Pro Gly Gly Met Phe Cys Arg Tyr Asp Arg Leu Glu Ile
            180             185             190

Trp Asp Gly Phe Pro Asp Val Gly Pro His Ile Gly Arg Tyr Cys Gly
        195             200             205

Gln Lys Thr Pro Gly Arg Ile Arg Ser Ser Gly Ile Leu Ser Met
    210             215             220

Val Phe Tyr Thr Asp Ser Ala Ile Ala Lys Glu Gly Phe Ser Ala Asn
225             230             235             240

Tyr Ser Val Leu Gln Ser Ser Val Ser Glu Asp Phe Lys Cys Met Glu
                245             250             255

Ala Leu Gly Met Glu Ser Gly Glu Ile His Ser Asp Gln Ile Thr Ala
            260             265             270

Ser Ser Gln Tyr Ser Thr Asn Trp Ser Ala Glu Arg Ser Arg Leu Asn
        275             280             285

Tyr Pro Glu Asn Gly Trp Thr Pro Gly Glu Lys Ser Tyr Arg Glu Trp
    290             295             300

Ile Gln Val Asp Leu Gly Leu Leu Arg Phe Val Thr Ala Val Gly Thr
305             310             315             320

Gln Gly Ala Ile Ser Lys Glu Thr Lys Lys Tyr Tyr Val Lys Thr
                325             330             335

Tyr Lys Ile Asp Val Ser Ser Asn Gly Glu Asp Trp Ile Thr Ile Lys
            340             345             350

Glu Gly Asn Lys Pro Val Leu Phe Gln Gly Asn Thr Asn Pro Thr Asp
        355             360             365

Val Val Val Ala Val Phe Pro Lys Pro Leu Ile Thr Arg Phe Val Arg
    370             375             380

Ile Lys Pro Ala Thr Trp Glu Thr Gly Ile Ser Met Arg Phe Glu Val
385             390             395             400

Tyr Gly Cys Lys Ile Thr Asp Tyr Pro Cys Ser Gly Met Leu Gly Met
                405             410             415

Val Ser Gly Leu Ile Ser Asp Ser Gln Ile Thr Ser Ser Asn Gln Gly
            420             425             430

Asp Arg Asn Trp Met Pro Glu Asn Ile Arg Leu Val Thr Ser Arg Ser
        435             440             445

Gly Trp Ala Leu Pro Pro Ala Pro His Ser Tyr Ile Asn Glu Trp Leu
    450             455             460

Gln Ile Asp Leu Gly Glu Glu Lys Ile Val Arg Gly Ile Ile Gln
465             470             475             480

Gly Gly Lys His Arg Glu Asn Lys Val Phe Met Arg Lys Phe Lys Ile
                485             490             495

Gly Tyr Ser Asn Asn Gly Ser Asp Trp Lys Met Ile Met Asp Asp Ser
            500             505             510
```

Lys Arg Lys Ala Lys Ser Phe Glu Gly Asn Asn Tyr Asp Thr Pro
            515                 520                 525

Glu Leu Arg Thr Phe Pro Ala Leu Ser Thr Arg Phe Ile Arg Ile Tyr
530                 535                 540

Pro Glu Arg Ala Thr His Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
        595                 600                 605

Glu Lys Pro Thr Val Ile Asp Ser Thr Ile Gln Ser Glu Phe Pro Thr
    610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
            660                 665                 670

Tyr Ser Gln Ala Asp Glu Asn Gln Lys Gly Lys Val Ala Arg Leu Val
        675                 680                 685

Ser Pro Val Val Tyr Ser Gln Asn Ser Ala His Cys Met Thr Phe Trp
    690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Glu Gly Arg Val Leu Leu His Lys Ser
            740                 745                 750

Leu Lys Leu Tyr Gln Val Ile Phe Glu Gly Glu Ile Gly Lys Gly Asn
        755                 760                 765

Leu Gly Gly Ile Ala Val Asp Asp Ile Ser Ile Asn Asn His Ile Ser
    770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
            820                 825                 830

Leu Asp Pro Arg Ser Gly Ser Lys Glu Asn Leu Tyr Phe Gln Gly
        835                 840                 845

<210> SEQ ID NO 77
<211> LENGTH: 1785
<212> TYPE: DNA
<213> ORGANISM: artificial sequence
<220> FEATURE:
<223> OTHER INFORMATION: Synthetic construct

<400> SEQUENCE: 77
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180

```
ccggacccat accagagaat tatgatcaac ttcaaccctc acttcgattt ggaggacaga      240
gactgcaagt atgactacgt ggaagtcttc gatggagaaa atgaaaatgg acattttagg      300
ggaaagttct gtggaaagat agcccctcct cctgttgtgt cttcagggcc atttcttttt      360
atcaaatttg tctctgacta cgaaacacat ggtgcaggat tttccatacg ttatgaactt      420
ttcaagagag gtcctgaatg ttcccagaac tacacaacac ctagtggagt gataaagtcc      480
cccggattcc ctgaaaaata tcccaacagc cttgaatgca cttatattgt ctttgcgcca      540
aagatgtcag agattatcct ggaatttgaa agctttgacc tggagcctga ctcaaatcct      600
ccagggggga tgttctgtcg ctacgaccgg ctagaaatct gggatggatt ccctgatgtt      660
ggccctcaca ttgggcgtta ctgtggacag aaaacaccag gtcgaatccg atcctcatcg      720
ggcattctct ccatggtttt ttacaccgac agcgcgatag caaaagaagg tttctcagca      780
aactacagtg tcttgcagag cagtgtctca gaagatttca atgtatggaa gctctgggc      840 atggaatcag gagaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc tacagatgtt gtggttgcag tattccccaa ccactgata      1200 actcgatttg tccgaatcaa gcctgcaact tgggaaactg gcatatctat gagatttgaa     1260
gtatatggtt gcaagataac agattatcct tgctctggaa tgttgggtat ggtgtctgga     1320
cttatttctg actcccagat cacatcatcc aaccaagggg acagaaactg gatgcctgaa     1380
aacatccgcc tggtaaccag tcgctctggc tgggcacttc cacccgcacc tcattcctac     1440
atcaatgagt ggctccaaat agacctgggg gaggagaaga tcgtgagggg catcatcatt     1500
cagggtggga agcaccgaga gaacaaggtg ttcatgagga agttcaagat cgggtacagc     1560
aacaacggct cggactggaa gatgatcatg gatgacagca acgcaaggc gaagtctttt     1620 gagggcaaca caactatga tacacctgag ctgcggactt tccagctcct ctccacgcga     1680
ttcatcagga tctaccccga gagagccact catggcggac tggggctcag aatggagctg     1740
ctgggctgta gatctggatc caaggaaaac ttgtatttcc aggc                      1785
```

<210> SEQ ID NO 78
<211> LENGTH: 574
<212> TYPE: PRT
<213> ORGANISM: artificial sequence
<220> FEATURE:
<223> OTHER INFORMATION: Synthetic construct

<400> SEQUENCE: 78

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

```
Lys Phe Cys Gly Lys Ile Ala Pro Pro Val Ser Ser Gly Pro
                85                  90              95

Phe Leu Phe Ile Lys Phe Val Ser Asp Tyr Glu Thr His Gly Ala Gly
            100                 105             110

Phe Ser Ile Arg Tyr Glu Leu Phe Lys Arg Gly Pro Glu Cys Ser Gln
            115                 120             125

Asn Tyr Thr Thr Pro Ser Gly Val Ile Lys Ser Pro Gly Phe Pro Glu
        130                 135             140

Lys Tyr Pro Asn Ser Leu Glu Cys Thr Tyr Ile Val Phe Ala Pro Lys
145             150                 155             160

Met Ser Glu Ile Ile Leu Glu Phe Glu Ser Phe Asp Leu Glu Pro Asp
                165                 170             175

Ser Asn Pro Pro Gly Gly Met Phe Cys Arg Tyr Asp Arg Leu Glu Ile
            180                 185             190

Trp Asp Gly Phe Pro Asp Val Gly Pro His Ile Gly Arg Tyr Cys Gly
            195                 200             205

Gln Lys Thr Pro Gly Arg Ile Arg Ser Ser Ser Gly Ile Leu Ser Met
        210                 215             220

Val Phe Tyr Thr Asp Ser Ala Ile Ala Lys Glu Gly Phe Ser Ala Asn
225             230                 235             240

Tyr Ser Val Leu Gln Ser Ser Val Ser Glu Asp Phe Lys Cys Met Glu
                245                 250             255

Ala Leu Gly Met Glu Ser Gly Glu Ile His Ser Asp Gln Ile Thr Ala
            260                 265             270

Ser Ser Gln Tyr Ser Thr Asn Trp Ser Ala Glu Arg Ser Arg Leu Asn
        275                 280             285

Tyr Pro Glu Asn Gly Trp Thr Pro Gly Glu Asp Ser Tyr Arg Glu Trp
        290                 295             300

Ile Gln Val Asp Leu Gly Leu Leu Arg Phe Val Thr Ala Val Gly Thr
305             310                 315             320

Gln Gly Ala Ile Ser Lys Glu Thr Lys Lys Tyr Tyr Val Lys Thr
            325                 330             335

Tyr Lys Ile Asp Val Ser Ser Asn Gly Glu Asp Trp Ile Thr Ile Lys
            340                 345             350

Glu Gly Asn Lys Pro Val Leu Phe Gln Gly Asn Thr Asn Pro Thr Asp
        355                 360             365

Val Val Val Ala Val Phe Pro Lys Pro Leu Ile Thr Arg Phe Val Arg
        370                 375             380

Ile Lys Pro Ala Thr Trp Glu Thr Gly Ile Ser Met Arg Phe Glu Val
385             390                 395             400

Tyr Gly Cys Lys Ile Thr Asp Tyr Pro Cys Ser Gly Met Leu Gly Met
            405                 410             415

Val Ser Gly Leu Ile Ser Asp Ser Gln Ile Thr Ser Ser Asn Gln Gly
            420                 425             430

Asp Arg Asn Trp Met Pro Glu Asn Ile Arg Leu Val Thr Ser Arg Ser
        435                 440             445

Gly Trp Ala Leu Pro Pro Ala Pro His Ser Tyr Ile Asn Glu Trp Leu
    450                 455             460

Gln Ile Asp Leu Gly Glu Glu Lys Ile Val Arg Gly Ile Ile Ile Gln
465             470                 475             480

Gly Gly Lys His Arg Glu Asn Lys Val Phe Met Arg Lys Phe Lys Ile
            485                 490             495
```

```
Gly Tyr Ser Asn Asn Gly Ser Asp Trp Lys Met Ile Met Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
545                 550                 555                 560

Gly Cys Arg Ser Gly Ser Lys Glu Asn Leu Tyr Phe Gln Gly
                565                 570
```

<210> SEQ ID NO 79
<211> LENGTH: 1785
<212> TYPE: DNA
<213> ORGANISM: artificial sequence
<220> FEATURE:
<223> OTHER INFORMATION: Synthetic construct

<400> SEQUENCE: 79

| | | |
|---|---|---|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccagggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgtatg caaaagaagg tttctcagca | 780 |
| aactacagtg tcttgcagag cagtgtctca gaagatttca atgtatggaa agctctgggc | 840 |
| atggaatcag gagaaattca ttctgaccag atcacagctt cttcccaggc tagcaccaac | 900 |
| tggtctgcag agcgctcccg cctgaactac cctgagaatg ggtggactcc ggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |
| tttcagggaa acaccaaccc tacagatgtt gtggttgcag tattccccaa accactgata | 1200 |
| actcgatttg tccgaatcaa gcctgcaact tgggaaactg gcatatctat gagatttgaa | 1260 |
| gtatatggtt gcaagataac agattatcct tgctctggaa tgttgggtat ggtgtctgga | 1320 |
| cttatttctg actcccagat cacatcatcc aaccaagggg acagaaactg gatgcctgaa | 1380 |
| aacatccgcc tggtaaccag tcgctctggc tgggcacttc cacccgcacc tcattcctac | 1440 |
| atcaatgagt ggctccaaat agacctgggg gaggagaaga tcgtgagggg catcatcatt | 1500 |
| cagggtggga gcaccgaga gaacaaggtg ttcatgagga agttcaagat cgggtacagc | 1560 |
| aacaacggct cggactggaa gatgatcatg gatgacagca acgcaaggc gaagtctttt | 1620 |

-continued

```
gagggcaaca caactatga tacacctgag ctgcggactt tccagctct ctccacgcga    1680 ttcatcagga tctaccccga gagagccact catggcggac tggggctcag aatggagctg    1740
ctgggctgta gatctggatc caaggaaaac ttgtatttcc agggc                    1785
```

<210> SEQ ID NO 80
<211> LENGTH: 574
<212> TYPE: PRT
<213> ORGANISM: artificial sequence
<220> FEATURE:
<223> OTHER INFORMATION: Synthetic construct

<400> SEQUENCE: 80

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335
```

```
Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
        435                 440                 445

Gly Trp Ala Leu Pro Pro Ala Pro His Ser Tyr Ile Asn Glu Trp Leu
    450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
545                 550                 555                 560

Gly Cys Arg Ser Gly Ser Lys Glu Asn Leu Tyr Phe Gln Gly
                565                 570
```

<210> SEQ ID NO 81
<211> LENGTH: 1308
<212> TYPE: DNA
<213> ORGANISM: artificial sequence
<220> FEATURE:
<223> OTHER INFORMATION: Synthetic construct

<400> SEQUENCE: 81

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
```

-continued

```
ggcattctct ccatggtttt ttacaccgac agcgcgatag caaaagaagg tttctcagca    780
aactacagtg tcttgcagag cagtgtctca gaagatttca aatgtatgga agctctgggc    840
atggaatcag gagaaattca ttctgaccag atcacagctt cttcccagta tagcaccaac    900
tggtctgcag agcgctcccg cctgaactac cctgagaatg ggtggactcc cggagaggat    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa ccactgata    1200 actcgatttg tccgaatcaa gcctgcaact tgggaaactg gcatatctat gagatttgaa   1260
gtatatggtt gcagatctgg atccaaggaa aacttgtatt ccagggc                 1308
```

<210> SEQ ID NO 82
<211> LENGTH: 415
<212> TYPE: PRT
<213> ORGANISM: artificial sequence
<220> FEATURE:
<223> OTHER INFORMATION: Synthetic construct

<400> SEQUENCE: 82

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
```

```
              260                 265                 270
Ser Ser Gln Tyr Ser Thr Asn Trp Ser Ala Glu Arg Ser Arg Leu Asn
            275                 280                 285

Tyr Pro Glu Asn Gly Trp Thr Pro Gly Glu Asp Ser Tyr Arg Glu Trp
        290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
            370                 375                 380

Ile Lys Pro Ala Thr Trp Glu Thr Gly Ile Ser Met Arg Phe Glu Val
385                 390                 395                 400

Tyr Gly Cys Arg Ser Gly Ser Lys Glu Asn Leu Tyr Phe Gln Gly
                405                 410                 415

<210> SEQ ID NO 83
<211> LENGTH: 1308
<212> TYPE: DNA
<213> ORGANISM: artificial sequence
<220> FEATURE:
<223> OTHER INFORMATION: Synthetic construct

<400> SEQUENCE: 83
atggagaggg ggctgccgct cctctgcgcc gtgctcgccc tcgtcctcgc cccggccggc       60
gcttttcgca acgataaatg tggcgatact ataaaaattg aaagcccgg gtaccttaca      120 tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac tagtggagt gataaagtcc     480 cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag tcgaatccg atcctcatcg      720 gcattctctc catggttttt tacaccgac agcgcgatag caaagaagg tttctcagca     780 aactacagtg tcttgcagag cagtgtctca gaagatttca atgtatgga agctctgggc     840 atggaatcag gagaaattca ttctgaccag atcacagctt cttcccaggc tagcaccaac     900
tggtctgcag agcgctcccg cctgaactac cctgagaatg gtggactcc cggagaggat     960 tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc cataaaaag aaggaaacaa acctgttctc    1140
tttcagggaa acaccaaccc tacagatgtt gtggttgcag tattccccaa accactgata    1200
```

-continued

```
actcgatttg tccgaatcaa gcctgcaact tgggaaactg gcatatctat gagatttgaa     1260
gtatatggtt gcagatctgg atccaaggaa aacttgtatt tccagggc                 1308
```

<210> SEQ ID NO 84
<211> LENGTH: 415
<212> TYPE: PRT
<213> ORGANISM: artificial sequence
<220> FEATURE:
<223> OTHER INFORMATION: Synthetic construct

<400> SEQUENCE: 84

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350
```

Glu Gly Asn Lys Pro Val Leu Phe Gln Gly Asn Thr Asn Pro Thr Asp
              355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Arg Ser Gly Ser Lys Glu Asn Leu Tyr Phe Gln Gly
                405                 410                 415

<210> SEQ ID NO 85
<211> LENGTH: 831
<212> TYPE: DNA
<213> ORGANISM: artificial sequence
<220> FEATURE:
<223> OTHER INFORMATION: Synthetic construct

<400> SEQUENCE: 85
atggagaggg ggctgccgct cctctgcgcc gtgctcgccc tcgtcctcgc cccggccggc      60
gcttttcgca acgataaatg tggcgatact ataaaaattg aaagccccgg taccttaca     120 tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaaagaagg tttctcagca     780
aactacagtg tcttgagatc tggatccaag gaaaacttgt atttccaggg c              831

<210> SEQ ID NO 86
<211> LENGTH: 256
<212> TYPE: PRT
<213> ORGANISM: artificial sequence
<220> FEATURE:
<223> OTHER INFORMATION: Synthetic construct

<400> SEQUENCE: 86

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Pro Val Val Ser Ser Gly Pro
                85                  90                  95

```
Phe Leu Phe Ile Lys Phe Val Ser Asp Tyr Glu Thr His Gly Ala Gly
            100                 105                 110
Phe Ser Ile Arg Tyr Glu Leu Phe Lys Arg Gly Pro Glu Cys Ser Gln
        115                 120                 125
Asn Tyr Thr Thr Pro Ser Gly Val Ile Lys Ser Pro Gly Phe Pro Glu
    130                 135                 140
Lys Tyr Pro Asn Ser Leu Glu Cys Thr Tyr Ile Val Phe Ala Pro Lys
145                 150                 155                 160
Met Ser Glu Ile Ile Leu Glu Phe Glu Ser Phe Asp Leu Glu Pro Asp
                165                 170                 175
Ser Asn Pro Pro Gly Met Phe Cys Arg Tyr Asp Arg Leu Glu Ile
            180                 185                 190
Trp Asp Gly Phe Pro Asp Val Gly Pro His Ile Gly Arg Tyr Cys Gly
        195                 200                 205
Gln Lys Thr Pro Gly Arg Ile Arg Ser Ser Gly Ile Leu Ser Met
    210                 215                 220
Val Phe Tyr Thr Asp Ser Ala Ile Ala Lys Glu Gly Phe Ser Ala Asn
225                 230                 235                 240
Tyr Ser Val Leu Arg Ser Gly Ser Lys Glu Asn Leu Tyr Phe Gln Gly
                245                 250                 255
```

<210> SEQ ID NO 87
<211> LENGTH: 2145
<212> TYPE: DNA
<213> ORGANISM: artificial sequence
<220> FEATURE:
<223> OTHER INFORMATION: Synthetic construct

<400> SEQUENCE: 87

```
atggagaggg ggctgccgct cctctgcgcc gtgctcgccc tcgtcctcgc cccggccggc    60
gcttttcgca acgataaatg tggcgatact ataaaaattg aaagccccgg gtaccttaca   120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300
ggaaagttct gtggaaagat agcccctcct cctgttgtgt cttcagggcc atttcttttt   360
atcaaatttg tctctgacta cgaaacacat ggtgcaggat tttccatacg ttatgaactt   420
ttcaagagag gtcctgaatg ttcccagaac tacacaacac ctagtggagt gataaagtcc   480
cccggattcc ctgaaaaata tcccaacagc ttgaatgca cttatattgt ctttgcgcca   540
aagatgtcag agattatcct ggaatttgaa agctttgacc tggagcctga ctcaaatcct   600
ccagggggga tgttctgtcg ctacgaccgg ctagaaatct gggatggatt ccctgatgtt   660
ggccctcaca ttgggcgtta ctgtggacag aaaacaccag gtcgaatccg atcctcatcg   720
ggcattctct ccatggtttt ttacaccgac agcgcgatag caaaagaagg tttctcagca   780
aactacagtg tcttgcagag cagtgtctca gaagatttca atgtatgga agctctgggc   840
atggaatcag agaaattca ttctgaccag atcacagctt cttcccagta tagcaccaac   900
tggtctgcag agcgctcccg cctgaactac cctgagaatg gtggactcc cggagaggat   960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
```

-continued

```
actcgatttg tccgaatcaa gcctgcaact tgggaaactg gcatatctat gagatttgaa    1260
gtatatggtt gcaagataac agattatcct gaagtggaag cccctacagc tggaccgacc    1320
actcccaacg ggaacttggt ggatgaatgt gatgacgacc aggccaactg ccacagtgga    1380
acaggtgatg acttccagct cacaggtggc accactgtgc tggccacaga aaagcccacg    1440
gtcatagaca gcaccataca atcagagttt ccaacatatg gttttaactg tgaatttggc    1500
tggggctctc acaagacctt ctgccactgg gaacatgaca atcacgtgca gctcaagtgg    1560
agtgtgttga ccagcaagac gggacccatt caggatcaca caggagatgg caacttcatc    1620
tattcccaag ctgacgaaaa tcagaagggc aaagtggctc gcctggtgag ccctgtggtt    1680
tattcccaga actctgccca ctgcatgacc ttctggtatc acatgtctgg gtcccacgtc    1740
ggcacactca gggtcaaact gcgctaccag aagccagagg agtacgatca gctggtctgg    1800
atggccattg acaccaagg tgaccactgg aaggaaggc gtgtcttgct ccacaagtct    1860
ctgaaacttt atcaggtgat tttcgagggc gaaatcggaa aaggaaacct tggtgggatt    1920
gctgtggatg acattagtat taataaccac atttcacaag aagattgtgc aaaaccagca    1980
gacctggata aaagaaccc agaaattaaa attgatgaaa cagggagcac gccaggatac    2040
gaaggtgaag gagaaggtga caagaacatc tccaggaagc caggcaatgt gttgaagacc    2100
ttagacccca gatctggatc caaggaaaac ttgtatttcc agggc                  2145
```

<210> SEQ ID NO 88
<211> LENGTH: 694
<212> TYPE: PRT
<213> ORGANISM: artificial sequence
<220> FEATURE:
<223> OTHER INFORMATION: Synthetic construct

<400> SEQUENCE: 88

```
Phe Arg Asn Asp Lys Cys Gly Asp Thr Ile Lys Ile Glu Ser Pro Gly
1               5                  10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190
```

-continued

Trp Asp Gly Phe Pro Asp Val Gly Pro His Ile Gly Arg Tyr Cys Gly
            195                 200                 205
Gln Lys Thr Pro Gly Arg Ile Arg Ser Ser Gly Ile Leu Ser Met
    210                 215                 220
Val Phe Tyr Thr Asp Ser Ala Ile Ala Lys Glu Gly Phe Ser Ala Asn
225                 230                 235                 240
Tyr Ser Val Leu Gln Ser Ser Val Ser Glu Asp Phe Lys Cys Met Glu
                245                 250                 255
Ala Leu Gly Met Glu Ser Gly Glu Ile His Ser Asp Gln Ile Thr Ala
            260                 265                 270
Ser Ser Gln Tyr Ser Thr Asn Trp Ser Ala Glu Arg Ser Arg Leu Asn
    275                 280                 285
Tyr Pro Glu Asn Gly Trp Thr Pro Gly Glu Asp Ser Tyr Arg Glu Trp
    290                 295                 300
Ile Gln Val Asp Leu Gly Leu Leu Arg Phe Val Thr Ala Val Gly Thr
305                 310                 315                 320
Gln Gly Ala Ile Ser Lys Glu Thr Lys Lys Tyr Tyr Val Lys Thr
            325                 330                 335
Tyr Lys Ile Asp Val Ser Ser Asn Gly Glu Asp Trp Ile Thr Ile Lys
            340                 345                 350
Glu Gly Asn Lys Pro Val Leu Phe Gln Gly Asn Thr Asn Pro Thr Asp
            355                 360                 365
Val Val Val Ala Val Phe Pro Lys Pro Leu Ile Thr Arg Phe Val Arg
    370                 375                 380
Ile Lys Pro Ala Thr Trp Glu Thr Gly Ile Ser Met Arg Phe Glu Val
385                 390                 395                 400
Tyr Gly Cys Lys Ile Thr Asp Tyr Pro Glu Val Glu Ala Pro Thr Ala
            405                 410                 415
Gly Pro Thr Thr Pro Asn Gly Asn Leu Val Asp Glu Cys Asp Asp Asp
            420                 425                 430
Gln Ala Asn Cys His Ser Gly Thr Gly Asp Asp Phe Gln Leu Thr Gly
            435                 440                 445
Gly Thr Thr Val Leu Ala Thr Glu Lys Pro Thr Val Ile Asp Ser Thr
    450                 455                 460
Ile Gln Ser Glu Phe Pro Thr Tyr Gly Phe Asn Cys Glu Phe Gly Trp
465                 470                 475                 480
Gly Ser His Lys Thr Phe Cys His Trp Glu His Asp Asn His Val Gln
            485                 490                 495
Leu Lys Trp Ser Val Leu Thr Ser Lys Thr Gly Pro Ile Gln Asp His
            500                 505                 510
Thr Gly Asp Gly Asn Phe Ile Tyr Ser Gln Ala Asp Glu Asn Gln Lys
            515                 520                 525
Gly Lys Val Ala Arg Leu Val Ser Pro Val Val Tyr Ser Gln Asn Ser
    530                 535                 540
Ala His Cys Met Thr Phe Trp Tyr His Met Ser Gly Ser His Val Gly
545                 550                 555                 560
Thr Leu Arg Val Lys Leu Arg Tyr Gln Lys Pro Glu Glu Tyr Asp Gln
            565                 570                 575
Leu Val Trp Met Ala Ile Gly His Gln Gly Asp His Trp Lys Glu Gly
            580                 585                 590
Arg Val Leu Leu His Lys Ser Leu Lys Leu Tyr Gln Val Ile Phe Glu
    595                 600                 605
Gly Glu Ile Gly Lys Gly Asn Leu Gly Gly Ile Ala Val Asp Asp Ile

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
            645                 650                 655

Pro Gly Tyr Glu Gly Glu Gly Asp Lys Asn Ile Ser Arg Lys
        660                 665                 670

Pro Gly Asn Val Leu Lys Thr Leu Asp Pro Arg Ser Gly Ser Lys Glu
        675                 680                 685

Asn Leu Tyr Phe Gln Gly
    690

<210> SEQ ID NO 89
<211> LENGTH: 2145
<212> TYPE: DNA
<213> ORGANISM: artificial sequence
<220> FEATURE:
<223> OTHER INFORMATION: Synthetic construct

<400> SEQUENCE: 89

| | |
|---|---:|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acatttttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccagggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgatag caaaagaagg tttctcagca | 780 |
| aactacagtg tcttgcagag cagtgtctca gaagatttca atgtatgga gctctgggc | 840 |
| atggaatcag agaaaattca ttctgaccag atcacagctt cttcccaggc tagcaccaac | 900 |
| tggtctgcag agcgctcccg cctgaactac cctgagaatg gtggactcc cggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |
| tttcagggaa acaccaaccc tacagatgtt gtggttgcag tattcccaa ccactgata | 1200 |
| actcgatttg tccgaatcaa gcctgcaact tgggaaactg gcatatctat gagatttgaa | 1260 |
| gtatatggtt gcaagataac agattatcct gaagtggaag cccctacagc tggaccgacc | 1320 |
| actcccaacg ggaacttggt ggatgaatgt gatgacgacc aggccaactg ccacagtgga | 1380 |
| acaggtgatg acttccagct cacaggtggc accactgtgc tggcaacaga aaagcccacg | 1440 |
| gtcatagaca caagcaccata ca atcagagttt ccaacatatg gttttaactg tgaatttggc | 1500 |
| tggggctctc acaagacctt ctgccactgg gaacatgaca atcacgtgca gctcaagtgg | 1560 |

-continued

| | |
|---|---|
| agtgtgttga ccagcaagac gggacccatt caggatcaca caggagatgg caacttcatc | 1620 |
| tattcccaag ctgacgaaaa tcagaagggc aaagtggctc gcctggtgag ccctgtggtt | 1680 |
| tattcccaga actctgccca ctgcatgacc ttctggtatc acatgtctgg gtcccacgtc | 1740 |
| ggcacactca gggtcaaact gcgctaccag aagccagagg agtacgatca gctggtctgg | 1800 |
| atggccattg acaccaagg tgaccactgg aaggaagggc gtgtcttgct ccacaagtct | 1860 |
| ctgaaacttt atcaggtgat tttcgagggc gaaatcggaa aaggaaacct tggtgggatt | 1920 |
| gctgtggatg acattagtat taataaccac atttcacaag aagattgtgc aaaaccagca | 1980 |
| gacctggata aaagaaccc agaaattaaa attgatgaaa cagggagcac gccaggatac | 2040 |
| gaaggtgaag gagaaggtga caagaacatc tccaggaagc aggcaatgt gttgaagacc | 2100 |
| ttagacccca gatctggatc caaggaaaac ttgtatttcc agggc | 2145 |

<210> SEQ ID NO 90
<211> LENGTH: 694
<212> TYPE: PRT
<213> ORGANISM: artificial sequence
<220> FEATURE:
<223> OTHER INFORMATION: Synthetic construct

<400> SEQUENCE: 90

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
```

```
                    260                 265                 270
        Ser Ser Gln Ala Ser Thr Asn Trp Ser Ala Glu Arg Ser Arg Leu Asn
                275                 280                 285

Tyr Pro Glu Asn Gly Trp Thr Pro Gly Glu Asp Ser Tyr Arg Glu Trp
                290                 295                 300

Ile Gln Val Asp Leu Gly Leu Leu Arg Phe Val Thr Ala Val Gly Thr
        305                 310                 315                 320

Gln Gly Ala Ile Ser Lys Glu Thr Lys Lys Tyr Tyr Val Lys Thr
                        325                 330                 335

Tyr Lys Ile Asp Val Ser Ser Asn Gly Glu Asp Trp Ile Thr Ile Lys
                        340                 345                 350

Glu Gly Asn Lys Pro Val Leu Phe Gln Gly Asn Thr Asn Pro Thr Asp
                        355                 360                 365

Val Val Val Ala Val Phe Pro Lys Pro Leu Ile Thr Arg Phe Val Arg
                        370                 375                 380

Ile Lys Pro Ala Thr Trp Glu Thr Gly Ile Ser Met Arg Phe Glu Val
        385                 390                 395                 400

Tyr Gly Cys Lys Ile Thr Asp Tyr Pro Glu Val Glu Ala Pro Thr Ala
                        405                 410                 415

Gly Pro Thr Thr Pro Asn Gly Asn Leu Val Asp Glu Cys Asp Asp Asp
                        420                 425                 430

Gln Ala Asn Cys His Ser Gly Thr Gly Asp Asp Phe Gln Leu Thr Gly
                        435                 440                 445

Gly Thr Thr Val Leu Ala Thr Glu Lys Pro Thr Val Ile Asp Ser Thr
                        450                 455                 460

Ile Gln Ser Glu Phe Pro Thr Tyr Gly Phe Asn Cys Glu Phe Gly Trp
        465                 470                 475                 480

Gly Ser His Lys Thr Phe Cys His Trp Glu His Asp Asn His Val Gln
                        485                 490                 495

Leu Lys Trp Ser Val Leu Thr Ser Lys Thr Gly Pro Ile Gln Asp His
                        500                 505                 510

Thr Gly Asp Gly Asn Phe Ile Tyr Ser Gln Ala Asp Glu Asn Gln Lys
                        515                 520                 525

Gly Lys Val Ala Arg Leu Val Ser Pro Val Val Tyr Ser Gln Asn Ser
                        530                 535                 540

Ala His Cys Met Thr Phe Trp Tyr His Met Ser Gly Ser His Val Gly
        545                 550                 555                 560

Thr Leu Arg Val Lys Leu Arg Tyr Gln Lys Pro Glu Glu Tyr Asp Gln
                        565                 570                 575

Leu Val Trp Met Ala Ile Gly His Gln Gly Asp His Trp Lys Glu Gly
                        580                 585                 590

Arg Val Leu Leu His Lys Ser Leu Lys Leu Tyr Gln Val Ile Phe Glu
                        595                 600                 605

Gly Glu Ile Gly Lys Gly Asn Leu Gly Gly Ile Ala Val Asp Asp Ile
                        610                 615                 620

Ser Ile Asn Asn His Ile Ser Gln Glu Asp Cys Ala Lys Pro Ala Asp
        625                 630                 635                 640

Leu Asp Lys Lys Asn Pro Glu Ile Lys Ile Asp Glu Thr Gly Ser Thr
                        645                 650                 655

Pro Gly Tyr Glu Gly Glu Gly Glu Gly Asp Lys Asn Ile Ser Arg Lys
                        660                 665                 670

Pro Gly Asn Val Leu Lys Thr Leu Asp Pro Arg Ser Gly Ser Lys Glu
                        675                 680                 685
```

Asn Leu Tyr Phe Gln Gly
    690

<210> SEQ ID NO 91
<211> LENGTH: 1677
<212> TYPE: DNA
<213> ORGANISM: artificial sequence
<220> FEATURE:
<223> OTHER INFORMATION: Synthetic construct

<400> SEQUENCE: 91

| | | | |
|---|---|---|---|
| atggagaggg ggctgccgct cctctgcgcc gtgctcgccc tcgtcctcgc cccggccggc | 60 |
| gcttttcgca acgataaatg tggcgatact ataaaaattg aaagcccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg cattttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| tcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccagggggga tgttctgtcg ctacgaccgg ctagaaatct gggatggatt ccctgatgtt | 660 |
| ggccctcaca ttgggcgtta ctgtggacag aaaacaccag tcgaatccg atcctcatcg | 720 |
| ggcattctct ccatggtttt ttacaccgac agcgcgatag caaagaagg tttctcagca | 780 |
| aactacagtg tcttgcagag cagtgtctca gaagatttca agaagtgga agcccctaca | 840 |
| gctggaccga ccactcccaa cgggaacttg gtggatgaat gtgatgacga ccaggccaac | 900 |
| tgccacagtg aacaggtga tgacttccag ctcacaggtg gcaccactgt gctgccaca | 960 |
| gaaaagccca cggtcataga cagcaccata caatcagagt ttccaacata tggttttaac | 1020 |
| tgtgaatttg gctggggctc tcacaagacc ttctgccact gggacatga caatcacgtg | 1080 |
| cagctcaagt ggagtgtgtt gaccagcaag acgggaccca ttcaggatca cacaggagat | 1140 |
| ggcaacttca tctattccca agctgacgaa aatcagaagg gcaaagtggc tcgcctggtg | 1200 |
| agccctgtgg tttattccca gaactctgcc cactgcatga ccttctggta tcacatgtct | 1260 |
| gggtccacg tcggcacact cagggtcaaa ctgcgctacc agaagccaga ggagtacgat | 1320 |
| cagctggtct ggatggccat tggacaccaa ggtgaccact ggaaggaagg gcgtgtcttg | 1380 |
| ctccacaagt ctctgaaact ttatcaggtg attttcgagg gcgaaatcgg aaaaggaaac | 1440 |
| cttggtggga ttgctgtgga tgacattagt attaataacc acatttcaca agaagattgt | 1500 |
| gcaaaaccag cagacctgga taaaagaac ccagaaatta aaattgatga acagggagc | 1560 |
| acgccaggat acgaaggtga aggagaaggt gacaagaaca tctccaggaa gccaggcaat | 1620 |
| gtgttgaaga ccttagaccc cagatctgga tccaaggaaa acttgtattt ccagggc | 1677 |

<210> SEQ ID NO 92
<211> LENGTH: 538
<212> TYPE: PRT
<213> ORGANISM: artificial sequence
<220> FEATURE:
<223> OTHER INFORMATION: Synthetic construct

<400> SEQUENCE: 92

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Glu Val Glu
                245                 250                 255

Ala Pro Thr Ala Gly Pro Thr Thr Pro Asn Gly Asn Leu Val Asp Glu
            260                 265                 270

Cys Asp Asp Asp Gln Ala Asn Cys His Ser Gly Thr Gly Asp Asp Phe
        275                 280                 285

Gln Leu Thr Gly Gly Thr Thr Val Leu Ala Thr Glu Lys Pro Thr Val
    290                 295                 300

Ile Asp Ser Thr Ile Gln Ser Glu Phe Pro Thr Tyr Gly Phe Asn Cys
305                 310                 315                 320

Glu Phe Gly Trp Gly Ser His Lys Thr Phe Cys His Trp Glu His Asp
                325                 330                 335

Asn His Val Gln Leu Lys Trp Ser Val Leu Thr Ser Lys Thr Gly Pro
            340                 345                 350

Ile Gln Asp His Thr Gly Asp Gly Asn Phe Ile Tyr Ser Gln Ala Asp
        355                 360                 365

Glu Asn Gln Lys Gly Lys Val Ala Arg Leu Val Ser Pro Val Val Tyr
    370                 375                 380

Ser Gln Asn Ser Ala His Cys Met Thr Phe Trp Tyr His Met Ser Gly
385                 390                 395                 400

Ser His Val Gly Thr Leu Arg Val Lys Leu Arg Tyr Gln Lys Pro Glu
                405                 410                 415
```

```
Glu Tyr Asp Gln Leu Val Trp Met Ala Ile Gly His Gln Gly Asp His
            420                 425                 430

Trp Lys Glu Gly Arg Val Leu Leu His Lys Ser Leu Lys Leu Tyr Gln
    435                 440                 445

Val Ile Phe Glu Gly Glu Ile Gly Lys Gly Asn Leu Gly Gly Ile Ala
        450                 455                 460

Val Asp Asp Ile Ser Ile Asn Asn His Ile Ser Gln Glu Asp Cys Ala
465                 470                 475                 480

Lys Pro Ala Asp Leu Asp Lys Lys Asn Pro Glu Ile Lys Ile Asp Glu
                485                 490                 495

Thr Gly Ser Thr Pro Gly Tyr Glu Gly Glu Gly Glu Gly Asp Lys Asn
            500                 505                 510

Ile Ser Arg Lys Pro Gly Asn Val Leu Lys Thr Leu Asp Pro Arg Ser
    515                 520                 525

Gly Ser Lys Glu Asn Leu Tyr Phe Gln Gly
    530                 535
```

<210> SEQ ID NO 93
<211> LENGTH: 2115
<212> TYPE: DNA
<213> ORGANISM: artificial sequence
<220> FEATURE:
<223> OTHER INFORMATION: Synthetic construct

<400> SEQUENCE: 93

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccaggggga tgttctgtcg ctacgaccgg ctagaaatct gggatggatt ccctgatgtt     660
ggccctcaca ttgggcgtta ctgtggacag aaaacaccag tcgaatccg atcctcatcg     720
ggcattctct ccatggtttt ttacaccgac agcgcgatag caaaagaagg tttctcagca     780
aactacagtg tcttgcagag cagtgtctca gaagatttca atgtatgga agctctgggc     840
atggaatcag gagaaattca ttctgaccag atcacagctt cttcccagta tagcaccaac     900
tggtctgcag agcgctcccg cctgaactac cctgagaatg ggtggactcc cggagaggat     960
tcctaccgag agtggataca gtagacttg gccttctgc gctttgtcac ggctgtcggg    1020
acacagggcg ccatttcaaa agaaaccaag aagaaatatt atgtcaagac ttacaagatc    1080
gacgttagct ccaacgggga agactggatc cataaaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg catatctat gagatttgaa    1260
gtatatggtt gcaagataac agattatcct gaagtggaag cccctacagc tggaccgacc    1320
actcccaacg ggaacttggt ggatgaatgt gatgacgacc aggccaactg ccacagtgga    1380
```

```
acaggtgatg acttccagct cacaggtggc accactgtgc tggccacaga aaagcccacg    1440
gtcatagaca gcaccataca atcagagttt ccaacatatg gttttaactg tgaatttggc    1500
tggggctctc acaagacctt ctgccactgg aacatgaca atcacgtgca gctcaagtgg     1560
agtgtgttga ccagcaagac gggacccatt caggatcaca caggagatgg caacttcatc    1620
tattcccaag ctgacgaaaa tcagaagggc aaagtggctc gcctggtgag ccctgtggtt    1680
tattcccaga actctgccca ctgcatgacc ttctggtatc acatgtctgg gtcccacgtc    1740
ggcacactca gggtcaaact gcgctaccag aagccagagg agtacgatca gctggtctgg    1800
atggccattg acaccaagg tgaccactgg aaggaagggc gtgtcttgct ccacaagtct     1860
ctgaaacttt atcaggtgat tttcgagggc gaaatcggaa aggaaacct tggtgggatt      1920 gctgtggatg acattagtat taataaccac atttcacaag aagattgtgc aaaaccagca    1980
gacctggata aaagaaccc agaaattaaa attgatgaaa cagggagcac gccaggatac     2040
gaaggtgaag gagaaggtga caagaacatc tccaggaagc caggcaatgt gttgaagacc    2100
ttagacccca gatct                                                    2115
```

<210> SEQ ID NO 94
<211> LENGTH: 682
<212> TYPE: PRT
<213> ORGANISM: artificial sequence
<220> FEATURE:
<223> OTHER INFORMATION: Synthetic construct

<400> SEQUENCE: 94

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Ser Gly Ile Leu Ser Met
    210                 215                 220
```

```
Val Phe Tyr Thr Asp Ser Ala Ile Ala Lys Glu Gly Phe Ser Ala Asn
225                 230                 235                 240

Tyr Ser Val Leu Gln Ser Val Ser Glu Asp Phe Lys Cys Met Glu
            245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
            275                 280                 285

Tyr Pro Glu Asn Gly Trp Thr Pro Gly Glu Asp Ser Tyr Arg Glu Trp
            290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Glu Val Glu Ala Pro Thr Ala
            405                 410                 415

Gly Pro Thr Thr Pro Asn Gly Asn Leu Val Asp Glu Cys Asp Asp Asp
            420                 425                 430

Gln Ala Asn Cys His Ser Gly Thr Gly Asp Asp Phe Gln Leu Thr Gly
            435                 440                 445

Gly Thr Thr Val Leu Ala Thr Glu Lys Pro Thr Val Ile Asp Ser Thr
            450                 455                 460

Ile Gln Ser Glu Phe Pro Thr Tyr Gly Phe Asn Cys Glu Phe Gly Trp
465                 470                 475                 480

Gly Ser His Lys Thr Phe Cys His Trp Glu His Asp Asn His Val Gln
            485                 490                 495

Leu Lys Trp Ser Val Leu Thr Ser Lys Thr Gly Pro Ile Gln Asp His
            500                 505                 510

Thr Gly Asp Gly Asn Phe Ile Tyr Ser Gln Ala Asp Glu Asn Gln Lys
            515                 520                 525

Gly Lys Val Ala Arg Leu Val Ser Pro Val Val Tyr Ser Gln Asn Ser
            530                 535                 540

Ala His Cys Met Thr Phe Trp Tyr His Met Ser Gly Ser His Val Gly
545                 550                 555                 560

Thr Leu Arg Val Lys Leu Arg Tyr Gln Lys Pro Glu Glu Tyr Asp Gln
            565                 570                 575

Leu Val Trp Met Ala Ile Gly His Gln Gly Asp His Trp Lys Glu Gly
            580                 585                 590

Arg Val Leu Leu His Lys Ser Leu Lys Leu Tyr Gln Val Ile Phe Glu
            595                 600                 605

Gly Glu Ile Gly Lys Gly Asn Leu Gly Gly Ile Ala Val Asp Asp Ile
            610                 615                 620

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
```

-continued

```
                645                 650                 655
Pro Gly Tyr Glu Gly Glu Gly Glu Gly Asp Lys Asn Ile Ser Arg Lys
            660                 665                 670
Pro Gly Asn Val Leu Lys Thr Leu Asp Pro
            675                 680

<210> SEQ ID NO 95
<211> LENGTH: 923
<212> TYPE: PRT
<213> ORGANISM: artificial sequence
<220> FEATURE:
<223> OTHER INFORMATION: Synthetic construct

<400> SEQUENCE: 95

Met Glu Arg Gly Leu Pro Leu Leu Cys Ala Thr Leu Ala Leu Ala Leu
1               5                   10                  15
Ala Leu Ala Gly Ala Phe Arg Ser Asp Lys Cys Gly Gly Thr Ile Lys
            20                  25                  30
Ile Glu Asn Pro Gly Tyr Leu Thr Ser Pro Gly Tyr Pro His Ser Tyr
        35                  40                  45
His Pro Ser Glu Lys Cys Glu Trp Leu Ile Gln Ala Pro Glu Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Ile Asp Gly Glu Asn Glu Gly
                85                  90                  95
Gly Arg Leu Trp Gly Lys Phe Cys Gly Lys Ile Ala Pro Ser Pro Val
            100                 105                 110
Val Ser Ser Gly Pro Phe Leu Phe Ile Lys Phe Val Ser Asp Tyr Glu
        115                 120                 125
Thr His Gly Ala Gly Phe Ser Ile Arg Tyr Glu Ile Phe Lys Arg Gly
    130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Ser Leu Glu Cys Thr Tyr Ile
                165                 170                 175
Ile Phe Ala Pro Lys Met Ser Glu Ile Ile Leu Glu Phe Glu Ser Phe
            180                 185                 190
Asp Leu Glu Gln Asp Ser Asn Pro Pro Gly Gly Val Phe Cys Arg Tyr
        195                 200                 205
Asp Arg Leu Glu Ile Trp Asp Gly Phe Pro Glu Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Gly Thr Asn Trp Ser Val Glu
    290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
```

```
            325                 330                 335
Thr Ala Val Gly Thr Gln Gly Ala Ile Ser Lys Glu Thr Lys Lys
            340                 345                 350
Tyr Tyr Val Lys Thr Tyr Arg Val Asp Ile Ser Ser Asn Gly Glu Asp
            355                 360                 365
Trp Ile Thr Leu Lys Glu Gly Asn Lys Ala Ile Ile Phe Gln Gly Asn
            370                 375                 380
Thr Asn Pro Thr Asp Val Val Phe Gly Val Phe Pro Lys Pro Leu Ile
385                 390                 395                 400
Thr Arg Phe Val Arg Ile Lys Pro Ala Ser Trp Glu Thr Gly Ile Ser
                    405                 410                 415
Met Arg Phe Glu Val Tyr Gly Cys Lys Ile Thr Asp Tyr Pro Cys Ser
                    420                 425                 430
Gly Met Leu Gly Met Val Ser Gly Leu Ile Ser Asp Ser Gln Ile Thr
                    435                 440                 445
Ala Ser Asn Gln Gly Asp Arg Asn Trp Met Pro Glu Asn Ile Arg Leu
450                 455                 460
Val Thr Ser Arg Thr Gly Trp Ala Leu Pro Pro Ser Pro His Pro Tyr
465                 470                 475                 480
Ile Asn Glu Trp Leu Gln Val Asp Leu Gly Asp Glu Lys Ile Val Arg
                    485                 490                 495
Gly Val Ile Ile Gln Gly Gly Lys His Arg Glu Asn Lys Val Phe Met
                    500                 505                 510
Arg Lys Phe Lys Ile Ala Tyr Ser Asn Asn Gly Ser Asp Trp Lys Met
                    515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Ala Phe Thr Pro Leu Ser Thr Arg
545                 550                 555                 560
Phe Ile Arg Ile Tyr Pro Glu Arg Ala Thr His Ser Gly Leu Gly Leu
                    565                 570                 575
Arg Met Glu Leu Leu Gly Cys Glu Val Glu Val Pro Thr Ala Gly Pro
                    580                 585                 590
Thr Thr Pro Asn Gly Asn Pro Val Asp Glu Cys Asp Asp Gln Ala
                    595                 600                 605
Asn Cys His Ser Gly Thr Gly Asp Asp Phe Gln Leu Thr Gly Gly Thr
                    610                 615                 620
Thr Val Leu Ala Thr Glu Lys Pro Thr Ile Ile Asp Ser Thr Ile Gln
625                 630                 635                 640
Ser Glu Phe Pro Thr Tyr Gly Phe Asn Cys Glu Phe Gly Trp Gly Ser
                    645                 650                 655
His Lys Thr Phe Cys His Trp Glu His Asp Ser His Ala Gln Leu Arg
                    660                 665                 670
Trp Arg Val Leu Thr Ser Lys Thr Gly Pro Ile Gln Asp His Thr Gly
                    675                 680                 685
Asp Gly Asn Phe Ile Tyr Ser Gln Ala Asp Glu Asn Gln Lys Gly Lys
                    690                 695                 700
Val Ala Arg Leu Val Ser Pro Val Val Tyr Ser Gln Ser Ser Ala His
705                 710                 715                 720
Cys Met Thr Phe Trp Tyr His Met Ser Gly Ser His Val Gly Thr Leu
                    725                 730                 735
Arg Val Lys Leu His Tyr Gln Lys Pro Glu Glu Tyr Asp Gln Leu Val
                    740                 745                 750
```

```
Trp Met Val Val Gly His Gln Gly Asp His Trp Lys Glu Gly Arg Val
            755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800

Asn Asn His Ile Pro Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Glu Gly Lys Gly Asp Lys Asn Ile Ser Arg Lys Pro Gly
            835                 840                 845

Asn Val Leu Lys Thr Leu Asp Pro Ile Leu Ile Thr Ile Ala Met
            850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
            915                 920
```

<210> SEQ ID NO 96
<211> LENGTH: 923
<212> TYPE: PRT
<213> ORGANISM: artificial sequence
<220> FEATURE:
<223> OTHER INFORMATION: Synthetic construct

<400> SEQUENCE: 96

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190
```

```
Asp Leu Glu Pro Asp Ser Asn Pro Pro Gly Gly Met Phe Cys Arg Tyr
    195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
                260                 265                 270

Phe Lys Cys Met Glu Ala Leu Gly Met Glu Ser Gly Glu Ile His Ser
                275                 280                 285

Asp Gln Ile Thr Ala Ser Ser Gln Tyr Ser Thr Asn Trp Ser Ala Glu
                290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
                355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
                435                 440                 445

Ser Ser Asn Gln Gly Asp Arg Asn Trp Met Pro Glu Asn Ile Arg Leu
                450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
                515                 520                 525

Ile Met Asp Asp Ser Lys Arg Lys Ala Lys Ser Phe Glu Gly Asn Asn
                530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
                580                 585                 590

Thr Thr Pro Asn Gly Asn Leu Val Asp Glu Cys Asp Asp Gln Ala
                595                 600                 605
```

```
Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
        915                 920

<210> SEQ ID NO 97
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: VARIANT
<222> LOCATION: (2)..(2)
<223> OTHER INFORMATION: X can be any amino acid
<220> FEATURE:
<221> NAME/KEY: VARIANT
<222> LOCATION: (3)..(3)
<223> OTHER INFORMATION: X can be any amino acid
<220> FEATURE:
<221> NAME/KEY: VARIANT
<222> LOCATION: (5)..(5)
<223> OTHER INFORMATION: X can be any amino acid
```

<400> SEQUENCE: 97

Glu Xaa Xaa Tyr Xaa Gln Gly
1               5

<210> SEQ ID NO 98
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT
<222> LOCATION: (3)..(3)
<223> OTHER INFORMATION: X is any amino acid
<220> FEATURE:
<221> NAME/KEY: VARIANT
<222> LOCATION: (5)..(5)
<223> OTHER INFORMATION: X is any amino acid

<400> SEQUENCE: 98

Glu Xaa Xaa Tyr Xaa Gln Ser
1               5

<210> SEQ ID NO 99
<211> LENGTH: 20
<212> TYPE: DNA
<213> ORGANISM: Artificial Sequence
<220> FEATURE:
<223> OTHER INFORMATION: NRP1 forward primer

<400> SEQUENCE: 99
acccacattt cgatttggag                                          20

<210> SEQ ID NO 100
<211> LENGTH: 20
<212> TYPE: DNA
<213> ORGANISM: Artificial Sequence
<220> FEATURE:
<223> OTHER INFORMATION: NRP1 reverse primer

<400> SEQUENCE: 100
ttcatagcgg atggaaaacc                                          20

<210> SEQ ID NO 101
<211> LENGTH: 20
<212> TYPE: DNA
<213> ORGANISM: Artificial Sequence
<220> FEATURE:
<223> OTHER INFORMATION: SEMA3A forward primer

<400> SEQUENCE: 101
gctcctgctc cgtagcctgc                                          20

<210> SEQ ID NO 102
<211> LENGTH: 20
<212> TYPE: DNA
<213> ORGANISM: Artificial Sequence
<220> FEATURE:
<223> OTHER INFORMATION: SEMA3A Reverse primer

<400> SEQUENCE: 102
tcggcgttgc tttcggtccc                                          20

```
<210> SEQ ID NO 103
<211> LENGTH: 14
<212> TYPE: DNA
<213> ORGANISM: Artificial Sequence
<220> FEATURE:
<223> OTHER INFORMATION: SEMA3e forward primer

<400> SEQUENCE: 103
tctgcaacca tcca                                                        14

<210> SEQ ID NO 104
<211> LENGTH: 22
<212> TYPE: DNA
<213> ORGANISM: Artificial Sequence
<220> FEATURE:
<223> OTHER INFORMATION: SEMA3e reverse primer

<400> SEQUENCE: 104
accacaagag ggaagcacag ac                                               22

<210> SEQ ID NO 105
<211> LENGTH: 20
<212> TYPE: DNA
<213> ORGANISM: Artificial Sequence
<220> FEATURE:
<223> OTHER INFORMATION: TGFb forward primer

<400> SEQUENCE: 105
ggactctcca cctgcaagac                                                  20

<210> SEQ ID NO 106
<211> LENGTH: 20
<212> TYPE: DNA
<213> ORGANISM: Artificial Sequence
<220> FEATURE:
<223> OTHER INFORMATION: TGFb reverse primer

<400> SEQUENCE: 106
catagatggc gttgttgcgg                                                  20

<210> SEQ ID NO 107
<211> LENGTH: 20
<212> TYPE: DNA
<213> ORGANISM: Artificial Sequence
<220> FEATURE:
<223> OTHER INFORMATION: VEGFa forward primer

<400> SEQUENCE: 107
gccctgagtc aagaggacag                                                  20

<210> SEQ ID NO 108
<211> LENGTH: 20
<212> TYPE: DNA
<213> ORGANISM: Artificial Sequence
<220> FEATURE:
<223> OTHER INFORMATION: VEGFa reverse primer

<400> SEQUENCE: 108
ctcctaggcc cctcagaagt                                                  20

<210> SEQ ID NO 109
<211> LENGTH: 20
<212> TYPE: DNA
<213> ORGANISM: Artificial Sequence
<220> FEATURE:
<223> OTHER INFORMATION: VEGFb forward primer
```

```
<400> SEQUENCE: 109
tctgagcatg gaactcatgg                                              20

<210> SEQ ID NO 110
<211> LENGTH: 20
<212> TYPE: DNA
<213> ORGANISM: Artificial Sequence
<220> FEATURE:
<223> OTHER INFORMATION: VEGFb reverse primer

<400> SEQUENCE: 110
tctgcattca cattggctgt                                              20
```

COMPOSITIONS COMPRISING SASP MODULATORS AND SENESCENCE ATTENUATORS AND USES THEREOF FOR MODULATING CELLULAR SENESCENCE

CROSS REFERENCE TO RELATED APPLICATIONS

This application is a continuation application of U.S. application Ser. No. 16/335,896 filed on Mar. 22, 2019, which is a national phase application of PCT application having Serial No PCT/CA2017/051120 filed on Sep. 22, 2017 and published in English under PCT Article 21(2), which itself claims benefit of U.S. provisional application Ser. No. 62/474,827, filed on Sep. 23, 2016, U.S. provisional application Ser. No. 62/398,797, filed on Sep. 23, 2016, and U.S. provisional application Ser. No. 62/398,183 filed on Sep. 22, 2016. All of the above applications are incorporated herein by reference in their entirety.

REFERENCE TO SEQUENCE LISTING

This application contains a Sequence Listing in computer readable form entitled "16761_42_SL_ST25.txt", created on Apr. 20, 2021 and having a size of about 249 KB. The computer readable form is incorporated herein by reference.

FIELD OF THE INVENTION

The present invention relates to compositions and methods for modulating cellular senescence. More specifically, the present invention is concerned with the modulation of the senescence-associated secretory phenotype (SASP) in the prevention and treatment of diseases and conditions associated with cellular senescence such as vascular ocular diseases.

BACKGROUND OF THE INVENTION

Cellular senescence is commonly defined as a condition of a cell in which the cell remains viable and metabolically active but has lost the ability to proliferate. Cellular senescence may be caused by a variety of stimuli or factors including telomere shortening due to DNA end replication, DNA damage, altered activities of tumor suppressor genes and oncogenes, oxidative stress, inflammation, chemotherapeutic agents, and exposure to UV irradiation and ionizing radiation (Kuilman et al., Genes & Development. (2010) 24:2463-2479).

Three types of cellular paths leading to a senescence phenotype have been described: replicative senescence, premature senescence and senescence after differentiation (SAD). Replicative senescence is the type of senescence that occurs following a large number of cell division. For example, when grown in culture, primary cells undergo cellular senescence after approximately 50 cell divisions. This barrier to further proliferation is thought to be due to shortening of the cell's telomeres with each successive cell division, causing cells to reach a point (the so-called "Hayflick limit") at which a DNA damage response is triggered, leading ultimately to induction of proliferation arrest and senescence.

Cellular senescence can also be induced in the absence of telomere loss or dysfunction. This type of cellular senescence is called premature cellular senescence and may result from a variety of stimuli including, for example, DNA damage arising from chemotherapy, radiotherapy, exposure to DNA damaging compounds or stimuli such as sunlight and UV light, oxidative stress, inflammation, strong mitogenic signaling and ribosomal stress. DNA damage may take the form of chromosomal dysfunction such as aneuploidy arising from unequal chromosome segregation during mitosis, DNA strand breaks, or chemical modification of DNA (e.g. alkylation). Premature cellular senescence may also be induced by a DNA damage response (DDR) which may or may not reflect actual DNA damage.

Recently, it has become apparent that the senescence process entails more than a simple cessation of cell growth as terminally differentiated, post-mitotic cells have been shown to acquire a senescence-like phenotype (including the SASP) in several diseases. This third type of senescence has been termed senescence after differentiation (SAD) and can be induced by various stressors including genotoxic, proteotoxic, oxidative and ribosomal stressors (see for example, Naylor R M et al., 2013 Clin. Pharmacol Ther. 93(1):105-116).

Not all senescent cells express all possible senescence makers. Nonetheless, salient features of senescent cells include (i) growth arrest, (ii) enlarged and flatten cell morphology, (iii) DNA damage foci in the nucleus, (iv) secretion of growth factors proteases, cytokines and other factors defined as the senescence-associated secretory phenotypes (SASP), (v) senescence-associated β-galactosidase (SA-β-gal) activity (which partly reflects the increase in lysosomal mass), (vi) expression of the tumor suppressor p16INK4a (which may activate pRB and cause the formation of senescence-associated heterochromatin foci (SAHF)), and (vii) increase in number and size of PML nuclear bodies. Furthermore, although diverse factors are known to induce cellular senescence, two tumor suppressor pathways, p53/p21 and p16INK4/pRB, have been shown to play a critical role in the regulation of cellular senescence.

Recent work has extended the involvement of cellular senescence to complex physiological processes such as embryogenesis and tissue repair (19-22). Conversely, in chronic diseases and aging, accretion of senescent cells aggravates tissue dysfunction (23-25). Depending on the condition, cellular senescence has been shown to be either beneficial or detrimental (see Rodier and Campisi, J C B, 2011, 192(4): 547-556 and Naylor et al., Clin Pharmacol Ther. 2013 93(1): 105-116 for review on cellular senescence).

Cellular senescence has been causally implicated in the pathogenesis of diverse age-related diseases and conditions including thinning of the epidermis, skin wrinkling, hair loss and greying hair, reduction in muscle thickness and muscle strength (sarcopenia), increased incidence of inflammation, metabolic disturbances, loss of endurance, atherosclerosis, chronic obstructive pulmonary disease (COPD), Idiopathic pulmonary fibrosis (IPF), neurodegenerative disease, osteoarthritis, osteoporosis, Parkinson's disease, and cataracts. In addition, cellular senescence is believed to contribute to damage to healthy tissues experienced during and following chemotherapy and/or radiotherapy, and the poor health effects post chemotherapy and/or radiotherapy.

Cellular senescence can also be beneficial. For example, its role as an anticancer mechanism in response to DNA damage has been established for decades. Furthermore, senescent cells have been shown to be important for efficient tissue repair and wound healing. Indeed, many factors of the SASP (e.g., growth factors and proteases that participate in wound healing, attractants for immune cells that kill pathogens and proteins that mobilize stem or progenitor cells) are important for tissue repair. The SASP may thus also serve to communicate cellular damage/dysfunction to the surrounding tissue and stimulate repair, if needed. Recent studies support this concept. For example, studies have shown that senescent cells are quickly established near wounds to help mount an inflammatory response (through the SASP) that initiates the process of healing during the proliferation phase. This rapid boost in senescence attracts and activates immune cells to fight infection and clear dead cells and debris. During the remodeling phase, senescent cells play a role in dissolving the fibrous proteins laid down during the proliferative phase and limit the formation of scars. Beneficial effects of cellular senescence have also been reported in liver fibrosis, myocardial infarction and cardiac fibrosis, atherosclerosis and pulmonary hypertension.

Accordingly, preventing cells from undergoing cellular senescence, or preventing DNA damage, DNA damage response pathways or chromatin changes that would activate senescence (e.g., that could lead to SASP), reversing or limiting cellular senescence and/or reducing paracrine senescence in cells which have undergone cellular senescence, would be advantageous to prevent or treat diseases and conditions in which senescence is detrimental. Conversely, promoting cellular senescence in diseases and conditions which are positively affected by cellular senescence may improve recovery or reduce the severity of such disease or conditions.

Obesity and its ensuing sequelae of metabolic syndrome, type 2 diabetes mellitus (TIIDM) and cardiovascular complications constitute a global pandemic. Worldwide obesity has more than doubled since 1980, and in 2014 more than 1.9 billion adults were overweight—of these 600 million were obese (World Health Organization (WHO), 2015).

Overweight and obesity are defined as abnormal or excessive fat accumulation that may impair health. Body mass index (BMI) is a simple index of weight-for-height that is commonly used to classify overweight and obesity in adults. It is defined as a person's weight in kilograms divided by the square of his height in meters ($kg/m^2$). The WHO definition is: (i) a BMI greater than or equal to 25 $kg/m^2$ is overweight; and (ii) a BMI greater than or equal to 30 $kg/m^2$ is obesity. BMI provides a useful population-level measure of overweight and obesity as it is the same for both sexes and for all ages of adults. However, it is considered a rough guide because it may not correspond to the same degree of fatness in different individuals.

Fat accumulation is observed in a range of conditions such as obesity, non-alcoholic fatty liver disease (NAFLD), metabolic syndrome and lipodystrophy syndrome. Elevated BMI (in excessive weight or obesity) is a major risk factor for diseases and conditions such as: cardiovascular diseases ((CVD), mainly heart diseases and stroke); and insulin resistance (which increases the risk of developing TIIDM). Excessive fat accumulation also increases the risk of suffering from other diseases or conditions including musculoskeletal disorders (especially osteoarthritis); and some cancers (endometrial, breast, and colon). The risk for these diseases generally increases, with an increase in BMI.

Metabolic syndrome, also known as syndrome X, affects persons with obesity as well as those with an increased amount of abdominal fat, and is characterized by insulin resistance, dyslipidemia (hypertriglyceridemia, low serum HDL cholesterol levels, and increased LDL cholesterol levels) and hypertension. These conditions are interrelated and share underlying mediators, mechanisms and pathways. Changes in fat distribution, increased waist to hip ratio (WHR) and central fat accumulation are related to increased metabolic risk indices.

Most of the conditions associated with metabolic syndrome have no symptoms, although a large waist circumference is a visible sign. Several organizations have criteria for diagnosing metabolic syndrome. The NCEP ATP III definition is one of the most widely used criteria of metabolic syndrome. It incorporates the key features of hyperglycemia/insulin resistance, visceral obesity, atherogenic dyslipidemia and hypertension/endothelial dysfunction. According to guidelines used by the National Institutes of Health, a subject has metabolic syndrome if three or more of the following traits are present or if the subject is taking medication to control them: (i) Visceral obesity (i.e., large waist circumference—for example, a waistline that measures at least 35 inches (89 centimeters) for women and 40 inches (102 centimeters) for men); (ii) High triglyceride level—150 milligrams per deciliter (mg/dL), or 1.7 millimoles per liter (mmol/L), or higher of this type of fat found in blood; (iii) Reduced high-density lipoprotein (HDL) cholesterol—less than 40 mg/dL (1.04 mmol/L) in men or less than 50 mg/dL (1.3 mmol/L) in women of this "good" cholesterol; (iv) Increased blood pressure—130/85 millimeters of mercury (mm Hg) or higher; and (v) Elevated fasting blood sugar—100 mg/dL (5.6 mmol/L) or higher.

The currently accepted mechanism of obesity induced-metabolic syndrome is that adipose lipid accumulation triggers cytokine release, inducing M1 activation and systemic inflammation (Olefsky and Glass, 2010). While chronic inflammation and macrophage activation is postulated to cause insulin resistance (Osborn and Olefsky, 2012), it remains controversial whether adipose tissue inflammation is an adaptive response permitting effective storage of excess nutrients (Wernstedt Asterholm et al., 2014) and whether proper angiogenesis is a prerequisite for adipose tissue expansion (Cullberg et al., 2013). Both adipocyte oxygen consumption (Lee et al., 2014) and adipose tissue vascular remodeling (Sung et al., 2013) controls the inflammatory state of adipose tissue, which subsequently lead to insulin insensitivity and hyperglycemia.

Despite increasing social awareness regarding obesity-related problems, the proportion of overweight and obese subjects continues to rise. Thus, in view of their high prevalence and associated morbidity and mortality, there remains a need to develop new approaches for the prevention and/or treatment of diseases and conditions associated with fat accumulation.

The present description refers to a number of documents, the content of which is herein incorporated by reference in their entirety.

SUMMARY OF THE INVENTION

The breakdown of vascular beds in ischemic retinopathies, whether it is glycemia-driven in diabetic retinopathy (DR) or oxygen-driven in retinopathy of prematurity (ROP), yields hypoxic/ischemic central nervous system (CNS) tissue subjected to a collection of biochemical and inflammatory stressors that compromise cellular function (1-3). These avascular zones are the source of pro-angiogenic factors that mediate pathological angiogenesis (4) as evidenced by clinical success of laser photocoagulation therapy that ablate these areas (5). While much effort has been invested in understanding the ensuing wave of pathological pre-retinal angiogenesis, relatively little is known of the cellular processes at play during the precursor state of neural tissue hypoxia. A more thorough understanding of the cellular responses operating during the initial stages of retinal ischemia may provide therapeutic avenues that benefit the portion of the 93 million individuals faced with DR and the 15 million preterm infants born each year that present with neovascular retinal disease (6-8).

Central neurons such as retinal ganglion cells (RGCs), which are directly apposed to degenerating vasculature in ischemic retinopathies, require stable metabolic supply for proper function. Interestingly, during progression of DR there is a disconnect between the extent of overt retinal vascular lesions (9) and the relatively subtle and protracted morphological and functional aberrations observed in RGCs (10-12). Furthermore, while there is evidence supporting RGC apoptosis in DR (13-15) the magnitude and dynamics of neuronal death remain a topic of debate (16-18). The relative resilience of retinal ganglion neurons in DR suggests they either receive metabolic supply from an alternative vascular plexus or initiate a protective mechanism that renders them less susceptible to ischemia-induced cell death.

Mechanisms triggered to preserve nervous tissue integrity during ischemic injury confer a critical survival advantage and allow for timely repair and restoration of function (44, 61, 62). Mechanisms leading to cellular senescence likely evolved parallel to those of apoptosis to limit oncogenesis (21), yet for post-mitotic CNS neurons such as those found in the retina, cellular senescence may prevent stressor-induced neurodegeneration. While studied for close to 60 years (63) in the context of aging and disease, Applicant's studies reported herein present a novel role for cellular senescence in weathering ischemia in the CNS. These studies further revealed a previously undescribed role for SEMA3A in modulating senescence, including paracrine senescence in pathological processes and uncover the therapeutic benefits of modulating SEMA3A activity in diseases and conditions associated with senescence.

More specifically, in an aspect, Applicants have identified an unsuspected mechanism triggered by neurons in devascularized retinal zones where they enter a state of premature cellular senescence and adopt a senescence-associated secretory phenotype (SASP) by activating the endoribonuclease activity of the ER-stress effector Inositol-Requiring Enzyme-1a (IRE-1a). Factors produced through the SASP including the secreted embryonic patterning cue Semaphorin3A (SEMA3A), propagate senescence across the ischemic retina to neurons, microglia and the overlying vasculature (paracrine senescence), contributing to destructive pre-retinal angiogenesis.

1. Compositions Comprising SASP Modulators and Senescence Attenuators and Uses Thereof for Treating and Preventing Ocular Diseases.

In a first aspect, data described herein show that pathways of senescence are initially engaged in the retina as a mechanism of homeostasis in order to weather hypoxic stress. However, when persistent, senescence pathways become pathological and compromise tissue integrity. A consequence of cellular senescence is the SASP that through secretion of inflammatory factors hinders adequate revascularization. Notably, as shown herein, analysis of patients suffering from proliferative diabetic retinopathy, showed SASP-associated cytokines in their vitreous. Furthermore, pharmacological inhibition of the SASP with the well-known biguanide metformin or pharmacological or genetic interference against IRE1α limits senescence, enhances reparative vascular regeneration, prevents destructive neovascularization (FIG. 6H-J), and stalls retinal pathology in vivo. These data provide evidence for a previously undescribed paradigm implicating cellular and paracrine senescence in pathological angiogenesis and uncover the therapeutic benefits of ocular delivery of modulators of the SASP to treat ocular vascular diseases (vasculopathies) such as retinopathies as well as Age-related macular degeneration (AMD) and macular edema.

Thus, in accordance with the present invention, there is provided a method of treating or preventing a vascular eye disease or disorder (an ocular vasculopathy, in particular a senescence-associated eye disease or disorder, e.g., a retinopathy) comprising reducing (attenuating/inhibiting) cellular senescence in the eye of the subject. Reduction of cellular senescence can be made by contacting cells of the subject with one or more compounds which reduce cellular senescence (a senescence inhibitor). In embodiments, the senescence inhibitor reduces or inhibits the SASP in ocular cells.

The present invention further provides a method of inhibiting retinal angiogenesis (pathological neovascularization) comprising administering a senescence inhibitor (e.g., a SASP inhibitor) to a subject. In embodiments, the retinal angiogenesis is secondary to ischemia.

The present invention also provides a method of promoting ocular vascular repair and/or reducing ocular ischemia comprising administering a senescence inhibitor (e.g., a SASP inhibitor) to a subject.

The present invention also provides a method of preventing or reducing ocular cellular senescence comprising administering a senescence inhibitor a subject. In embodiments, the senescence inhibitor is a SASP inhibitor.

The present invention also provides a method of preventing or reducing ocular cellular senescence comprising contacting an ocular cell with a senescence inhibitor. In embodiments, the senescence inhibitor is a SASP inhibitor.

In embodiments, the above-noted senescence is paracrine senescence. In embodiments, the senescence is senescence after differentiation. In embodiments, the senescence is premature senescence. In embodiments, the premature senescence in characterized by an increase in the expression and/or RNAse activity of IRE1α. In embodiments, the senescence is retinal senescence. In embodiments, the senescence is characterized by (i) increased expression and/or activity of P16INK4a, Tp53, IRE1a, Cdkn1a Cdkn2a and/or senescence associated beta-gal activity; (ii) expression of γH2Ax and/or PML; and/or (iii) the expression of the senescence-associated secretory phenotype (SASP). In embodiments, the SASP comprises the secretion of IL-1β, IL-6, Pai1, TGFβ1, IRE1a and/or VEGF-a. In embodiments, the above-mentioned SASP is secondary to cellular ischemia.

In embodiments, the cell is a human cell. In embodiments, the cell is a retinal cell. In embodiments, the cell is an endothelial cell. In embodiments, the cell is a microglial cell. In embodiments, the cell is a neuron. In embodiments, the cell is a retinal ganglion cell. In embodiments, the cell is a retinal ganglion neuron. In embodiments, the cell is a vascular cell. In embodiments, the cell is a vascular endothelial cell. In embodiments, the cell is not a vascular cell (i.e., it is located in an avascular area/region). In embodiments, the cell is a fibroblast. In embodiments, the cell is a macrophage.

In embodiments, the administration is topical or local ocular administration. In embodiments, the local ocular administration is subconjunctival (sub-tenons), intravitreal, retrobulbar, posterior juxtascleral or intracameral administration. In embodiments, the local ocular administration is intravitreal administration. In particular embodiments, the local ocular administration is an intravitreal injection.

The present invention also relates to a composition comprising a senescence inhibitor or a SASP inhibitor for use in the methods of the present invention. In embodiments, the composition is an ophthalmic composition. In embodiments, the composition comprises a suitable pharmaceutical carrier, diluent or excipient. In embodiments, the suitable pharmaceutical carrier, diluent or excipient is not normally found in mixtures with the inhibitors disclosed herein (i.e., is a non-naturally occurring carrier or the composition is not naturally found in nature, i.e., is synthetic or manmade). In embodiments, the composition is for treating or preventing a vascular eye disease or disorder. In embodiments, the composition is for inhibiting retinal angiogenesis. In embodiments, the composition is for promoting ocular vascular repair and/or reducing ocular ischemia. In embodiments, the composition is for preventing or reducing ocular cellular senescence. In embodiments, the composition is for use in the preparation of a medicament for (i) treating or preventing a vascular eye disease or disorder; (ii) inhibiting retinal angiogenesis (e.g., pathological retinal neovascularization); (iii) promoting ocular vascular repair and/or reducing ocular ischemia; and/or (iv) preventing or reducing ocular cellular senescence.

In embodiments, the above-mentioned SASP inhibitor is not an inhibitor of IRE1α. In embodiments, the SASP inhibitor is a biguanide compound. In embodiments, the biguanide compound is metformin, phenformin, buformin, proguanil, chlorproguanil, Synthalin A or Synthalin B. In embodiments, the biguanide compound is metformin. In embodiments, the SASP inhibitor is an inhibitor of IRE1α.

In embodiments, the vascular eye disease or disorder is diabetic retinopathy, retinopathy of prematurity, ischemic retinopathy, hypertensive retinopathy, drug-induced retinal vasculopathy, diabetic macular edema, age-related macular degeneration, juvenile macular degeneration, retinal neovascularisation, central retinal vein occlusion, branched retinal vein occlusion, choroidal neovascularization, polypoidal choroidal vasculopathy, physical injury to the eye, glaucoma, rhegmatogenous retinal detachment (RRD), retinal vasculitis, retinal macroaneurysm, retinal microaneurysm, Fuch's dystrophy, ischemic optic neuropathy, macular telangiectasia, optic neuritis, usher syndrome, retinitis pigmentosa, uveitis, ischemic optic neuropathy (ION) or Stangardt disease. In an embodiment, the vascular eye disease or disorder is diabetic retinopathy, retinopathy of prematurity, diabetic macular edema, age-related macular edema, retinal neovascularization, central retinal vein occlusion, branched retinal vein occlusion or choroidal neovascularization. In an embodiment, the vascular eye disease is diabetic retinopathy, retinopathy of prematurity, Dry (atrophic) Age-related Macular Degeneration, wet (exudative) Age-related Macular Degeneration, Branch Retinal Vein Occlusion, or Macular Talacgiectasia.

In embodiments, the subject treated with a SASP inhibitor or composition of the present invention has been diagnosed with one of the above-noted vascular eye disease or disorder. In embodiments, the subject has been diagnosed with diabetic retinopathy, retinopathy of prematurity, diabetic macular edema, age-related macular degeneration, pathological retinal neovascularisation, central retinal vein occlusion, branched retinal vein occlusion, choroidal neovascularization, polypoidal choroidal vasculopathy or Macular Talacgiectasia.

2. Compositions and Methods for Modulating Cellular Senescence Comprising IRE1α or SEMA3A Modulators.
(i) IRE1α Modulators The present invention also provides a method of inhibiting or preventing (i) cellular senescence of a cell or (ii) the senescence-associated secretory phenotype (and/or the induction thereof) of a cell comprising reducing IRE1α expression, activation or activity. The present invention also concerns a method of inhibiting or preventing (i) cellular senescence of a cell or (ii) induction of the senescence-associated secretory phenotype in a cell of a subject comprising administering to the subject an IRE1α inhibitor. In embodiments, the methods of the present invention reduce IRE1α activation; SA-β-gal activity; and/or the expression of Pai1, IL-6, II-1b, TGF-b, tp53, XBP1(s) and/or Vegfa in the cells.

The present invention further concerns a composition comprising an IRE1α inhibitor for (i) inhibiting or preventing cellular senescence of a cell or (ii) induction of the senescence-associated secretory phenotype in a cell comprising an IRE1α inhibitor. In embodiments, the composition is for (i) inhibiting or preventing cellular senescence of a cell or (ii) induction of the senescence-associated secretory phenotype in a cell. In embodiments, the composition is for use in the preparation of a medicament for (i) inhibiting or preventing cellular senescence of a cell or (ii) induction of the senescence-associated secretory phenotype in a cell.

In embodiments, the IRE1α inhibitor is: an antisens or shRNA against IRE1α, 4u8c, bortezomib, N-[(2-Hydroxy-1-naphthalenyl)methylene]-2-thiophenesulfonamide (STF-083010), or MKC-3946. In embodiments, the inhibitor reduces IRE1α activation; SA-β-gal activity; and/or the expression of Pai1, IL-6, II-1b, TGF-b, tp53, XBP1(s) and/or Vegfa in the cells.

The present invention also provides a method of stimulating or inducing (i) senescence of a cell or (ii) the senescence-associated secretory phenotype (SASP) of a cell (and/or the induction thereof) comprising increasing IRE1α level or activity. The present invention also provides a method of improving wound repair comprising increasing IRE1α level or activity, wherein the method increases or induces (i) cellular senescence of a cell or (ii) the senescence-associated secretory phenotype (SASP) in a cell. The present invention further provides a method of stimulating or inducing (i) cellular senescence of a cell or (ii) the senescence-associated secretory phenotype in a cell of a subject comprising increasing IRE1α level or activity. In embodiments, the above-noted methods comprise contacting the cell with a compound which increases IRE1α level or activity. In embodiments, the above-mentioned methods increase IRE1α activation; SA-β-gal activity; and/or the expression of Pai1, IL-6, II-1 b, TGF-b, tp53, XBP1(s) and/or Vegfa in the cells.

In embodiments, the IRE1α activity comprises IRE1α ribonuclease activity and kinase activity.

The present invention further provides a composition comprising a compound which increases IRE1α level or activity. In embodiments, the composition is for inducing (i) senescence of a cell or (ii) the senescence-associated secretory phenotype in a cell. In embodiments, the composition is for treating or preventing liver fibrosis, renal fibrosis, pulmonary hypertension, myocardial infarction or cardiac fibrosis. In embodiments, the composition is for improving wound healing. In embodiments, the composition is for use in the preparation of a medicament for inducing (i) senescence of a cell or (ii) the senescence-associated secretory phenotype in a cell. In embodiments, the composition is for use in the preparation of a medicament for treating or preventing liver fibrosis, renal fibrosis, pulmonary hypertension, myocardial infarction or cardiac fibrosis. In embodiments, the composition is for use in the preparation of a medicament for improving wound healing.

In embodiments, the compound which increases IRE1α level or activity is Apy29 or Sunitinib.

In embodiments, the above-noted cell is a terminally differentiated cell. In embodiments, the cell is a neuron, a microglial cell or an endothelial cell. In embodiments, the cell is a retinal cell. In embodiments, the cell is a myeloid cell. In embodiments, the cell is a retinal ganglion cell. In embodiments, the cell is a retinal ganglion neuron. In embodiments, the cell is a vascular cell. In embodiments, the cell is a vascular endothelial cell. In embodiments, the cell is not a vascular cell (i.e., it is located in an avascular area/region). In embodiments, the cell is a fibroblast. In embodiments, the cell is a macrophage. In embodiments, the cell is a monocyte. In embodiments, the cell is an hepatic cell. In embodiments, the cell is an hepatic stellate cell. In embodiments, the cell is a human cell. In embodiments, the cell is a human microvascular endothelial cell. In particular embodiments, the cell is not an ocular cell.

In embodiments, the above-mentioned senescence is paracrine senescence. In embodiments, the senescence is senescence after differentiation. In embodiments, the senescence is premature senescence. In embodiments, the premature senescence in characterized by an increase in the expression and/or RNAse activity of IRE1α. In embodiments, the senescence is retinal senescence. In embodiments, the senescence is characterized by (i) increased expression and/or activity of P16INK4a, Tp53, IRE1a, Cdkn1a Cdkn2a and/or senescence associated beta-gal activity; (ii) expression of γH2Ax and/or PML; and/or (iii) the expression of the senescence-associated secretory phenotype (SASP). In embodiments, the SASP comprises the secretion of IL-1β, IL-6, Pai1, TGFβ1, IRE1α and/or VEGFa. In embodiments, the above-mentioned SASP is secondary to cellular ischemia. In embodiments, the cell is from a subject suffering or at risk of suffering from sarcopenia, neurodegeneration, thinning of the epidermis, skin wrinkling, hair loss, chronic obstructive pulmonary disease (COPD), Idiopathic pulmonary fibrosis (IPF), atherosclerosis, osteoarthritis, osteoporosis or Parkinson's disease, intestinal bowel disease, glaucoma, intervertebral disc degeneration, brain aneurysm, aortic aneurysm, pancreatic fibrosis or cystic fibrosis. In embodiments, the cell is from a subject which has undergone cancer treatment or is undergoing cancer treatment. In embodiments, the cell is not a retinal cell. In embodiments, the cellular senescence is not associated with a retinal vascular disease (i.e., it does not arise in the context of a retinal disease). In embodiments, the cellular senescence is not associated with a vascular eye disease (i.e., it does not arise in the context of an eye disease). In embodiments, the cellular senescence is not associated diabetic retinopathy (i.e., it does not arise in the context of diabetic retinopathy). In embodiments, the cellular senescence is not associated with macular degeneration. In embodiments, the cell is from a subject having or at risk of having, liver fibrosis, renal fibrosis, pulmonary hypertension, myocardial infarction or cardiac fibrosis. In embodiments, the subject is wounded (e.g., has a cutaneous/tissue wound (e.g., cut)).

(ii) SEMA3A Modulators

In a further aspect, data presented herein provide evidence for a previously undescribed role for SEMA3A in modulating senescence, including paracrine senescence in pathological processes and uncover the therapeutic benefits of modulating SEMA3A activity in diseases and conditions associated with senescence. Indeed, the data demonstrates that SEMA3A activates the ER-stress effector Inositol-Requiring Enzyme-1α (IRE-1α) and senescence effectors p53 and p16.

Accordingly, in an aspect, the present invention provides a method of modulating (i) senescence of a cell or (ii) the senescence-associated secretory phenotype (SASP) of a cell (and/or the induction thereof) comprising modulating SEMA3A level or activity. In embodiments, modulating SEMA3A level or activity comprises contacting the cell with a SEMA3A antagonist or a SEMA3A agonist.

In a related aspect, the present invention provides a method of inhibiting or preventing (i) senescence of a cell or (ii) the senescence-associated secretory phenotype (SASP) of a cell (and/or the induction thereof) comprising reducing SEMA3A level or activity. In embodiments, reducing SEMA3A level or activity comprises contacting the cell with a SEMA3A antagonist.

The present invention further provides a method of inhibiting or preventing (i) senescence of a cell or (ii) the senescence-associated secretory phenotype of a cell of a subject (and/or the induction thereof) comprising reducing SEMA3A level or activity. In embodiments, reducing SEMA3A level or activity comprises administering to the subject (or contacting the cells of the subject with) a SEMA3A antagonist.

In a further aspect, the present invention concerns a SEMA3A antagonist. In embodiments, the SEMA3A antagonist is (a) a SEMA3A antibody; (b) a SEMA3A antisense or shRNA; and/or (c) a soluble NRP1 polypeptide or functional fragment thereof (NRP1 trap).

The present invention also concerns a composition comprising the above-mentioned SEMA3A antagonist. Such antagonist or composition comprising same may be used in the above-described methods (e.g for use in inhibiting or preventing (i) senescence of a cell or (ii) induction of the senescence-associated secretory phenotype (SASP) of a cell).

In a related aspect, the present invention concerns the use of the SEMA3A antagonist or composition of the present invention in the preparation of a medicament for inhibiting or preventing (i) senescence of a cell or (ii) the senescence-associated secretory phenotype (SASP) in a cell (and/or the induction thereof). In embodiments, the methods and compositions described herein are for treating or preventing a senescence associated disease or condition which is sarcopenia, neurodegeneration (e.g., Alzheimer's disease), thinning of the epidermis, skin wrinkling, hair loss, chronic obstructive pulmonary disease (COPD), Idiopathic pulmonary fibrosis (IPF), atherosclerosis, osteoarthritis, osteoporosis, Parkinson's disease, intestinal bowel disease, glaucoma, intervertebral disc degeneration, brain aneurysm, aortic aneurysm, pancreatic fibrosis or cystic fibrosis, metabolic syndrome and/or obesity. In embodiments, the cell is not a retinal cell. In embodiments, the cell is not a retinal ganglion cell. In embodiments, the cell is not from an eye of a subject (ocular cell). In embodiments, the cellular senescence is not associated with a retinal vascular disease.

In embodiments, the above methods reduce IRE1α activation and the expression of Pai1, IL-6, Il-1b, TGF-b, tp53, XBP1(s) and Vegfa in the cell.

In embodiments, the cell is a terminally differentiated cell. In embodiments, the cell is a neuron, a microglial cell or an endothelial cell. In embodiments, cell is a retinal cell. In embodiments, the cell is a myeloid cell. In embodiments, the cell is a fat tissue cell. In embodiments, the cell is a retinal ganglion cell. In embodiments, the cell is a retinal ganglion neuron. In embodiments, the cell is a vascular cell. In embodiments, the cell is a vascular endothelial cell. In embodiments, the cell is not a vascular cell (i.e., it is located in an avascular area/region). In embodiments, the cell is a fibroblast. In embodiments, the cell is a macrophage. In embodiments, the cell is a monocyte. In embodiments, the cell is an hepatic cell. In embodiments, the cell is an hepatic stellate cell. In embodiments, the cell is a human cell. In embodiments, the cell is a human microvascular endothelial cell. In particular embodiments, the cell is not an ocular cell. In embodiments, the above-mentioned senescence is paracrine senescence. In embodiments the senescence is secondary to cellular ischemia. In embodiments the SASP is secondary to cellular ischemia. In embodiments the senescence is secondary to glucose intolerance. In embodiments the SASP is secondary to glucose intolerance.

In embodiments, the cell is from a subject suffering or at risk of suffering from a senescence associated disease or condition which is sarcopenia, neurodegeneration (e.g., Alzheimer's disease), thinning of the epidermis, skin wrinkling, hair loss, chronic obstructive pulmonary disease (COPD), Idiopathic pulmonary fibrosis (IPF), atherosclerosis, osteoarthritis, osteoporosis, Parkinson's disease, intestinal bowel disease, glaucoma, intervertebral disc degeneration, brain aneurysm, aortic aneurysm, pancreatic fibrosis or cystic fibrosis, metabolic syndrome and/or obesity. In embodiments, the cell is not a retinal cell. In embodiments, the cell is not a retinal ganglion cell. In embodiments, the cell is not from an eye of a subject (ocular cell). In embodiments, the cellular senescence is not associated with a retinal vascular disease. In embodiments, the cellular senescence is not associated with a disease of the eye (ocular cellular senescence). In embodiments, the cellular senescence is not associated with Alzheimer's disease. In embodiments, the cellular senescence is not associated with diabetes. In embodiments, the cellular senescence is not associated with cancer. In embodiments, the cellular senescence is not associated with septic shock.

In another aspect, the present invention concerns a method of stimulating or inducing (i) senescence of a cell or (ii) the senescence-associated secretory phenotype of a cell comprising contacting said cell with a SEMA3A polypeptide or functional variant or fragment thereof.

Also provided is a method of stimulating or inducing (i) cellular senescence of a cell or (ii) the senescence-associated secretory phenotype in a cell of a subject comprising administering to said subject an effective amount of a SEMA3A polypeptide or functional variant or fragment thereof.

In a further aspect, the present invention concerns a method for improving wound healing in a tissue comprising cells, the method comprising contacting the cells with a SEMA3A polypeptide or functional variant or fragment thereof.

In a related aspect, the present invention provides a SEMA3A polypeptide or functional variant or fragment or variant thereof, nucleic acid encoding same, vector for delivering and/or expressing the SEMA3A polypeptide or functional variant or fragment and host cell comprising such polypeptide or functional variant or fragment, nucleic acid and/or vector.

The present invention also concerns compositions comprising the above-mentioned SEMA3A polypeptide or functional variant or fragment thereof, nucleic acid, vector and/or host cell. Such compositions, SEMA3A polypeptide or functional variant or fragment, nucleic acid, vector and host cell may be used in the above-described methods (e.g., (a) for inducing (i) senescence of a cell or (ii) the senescence associated secretory phenotype in a cell, (b) in the preparation of a medicament for inducing (i) senescence of a cell or (ii) the senescence associated secretory phenotype in a cell, or (c) for improving wound healing).

In embodiments, the above-mentioned cell in methods of stimulating or inducing (i) cellular senescence, (ii) the SASP, or (iii) wound healing is a terminally differentiated cell. In embodiments, the cell is a neuron, a microglial cell or an endothelial cell. In embodiments, the above-mentioned senescence is paracrine senescence. In embodiments, the SASP is secondary to cellular ischemia. In embodiments, the cell is from a subject having or at risk of having, liver fibrosis, pulmonary hypertension, myocardial infarction, cancer, renal fibrosis or cardiac fibrosis.

In embodiments, the above-mentioned methods increase IRE1α activation and the expression of Pai1, IL-6, Il-1b, TGF-b, tp53, XBP1(s) and Vegfa in cells.

The present invention also provides nucleic acids encoding polypeptides (e.g., NRP1 traps, SEMA3A, IRE1α etc.) antisense, shRNAs etc. disclosed herein as well as vectors and host cells for delivering and/or expressing the nucleic acids, polypeptides, antisense, shRNAs disclosed herein.

Other objects, advantages and features of the present invention will become more apparent upon reading of the following non-restrictive description of specific embodiments thereof, given by way of example only with reference to the accompanying drawings.

3. Modulation of Lipid Parameters

In another aspect, the present invention concerns a method of altering a lipid parameter in a subject, said method comprising administering to the subject: (a) a soluble NRP1 polypeptide or fragment thereof; (b) an NRP1 antibody; or (c) a composition comprising (a) and/or (b) together with a pharmaceutically acceptable carrier, wherein said altering of a lipid parameter is (a) a decrease in total cholesterol level; (b) a decrease in non-HDL cholesterol level; (c) a decrease in triglycerides level; (d) a decrease in the ratio of total cholesterol:HDL cholesterol; (e) a decrease in circulating free fatty acid; (f) an increase in HDL cholesterol or (f) any combination of (a) to (e).

In another aspect, the present invention concerns a method for preventing or treating a disease or condition associated with fat accumulation in a subject, said method comprising administering to the subject: (a) a soluble NRP1 polypeptide or fragment thereof; (b) an NRP1 antibody; or (c) a composition comprising (a) and/or (b) together with a pharmaceutically acceptable carrier.

In an embodiment, said disease or condition associated with fat accumulation is high body mass index (BMI); obesity; metabolic syndrome; NAFLD; a cardiovascular disease (CVD); hypertension and/or Type II Diabetes mellitus (TIIDM).

In an embodiment, said cardiovascular disease is congestive heart failure, hypercholesterolemia and/or atherosclerosis.

In another aspect, the present invention concerns a method for altering a body composition parameter in a subject comprising administering to the subject (a) a soluble NRP1 polypeptide or fragment thereof; (b) an NRP1 antibody; or (c) a composition comprising (a) and/or (b) together with a pharmaceutically acceptable carrier, wherein said body composition parameter is visceral fat area (VFA), body mass index (BMI), waist to hip ratio (WHR); waist-to-height ratio (WHeR), waist circumference (WC); arm circumference (AC), conicity index, percent body fat (PBF), triceps skin fold, subscapular skin fold, white adipose tissue (WAT) level; and or brown adipose (BAT) tissue level.

In embodiments, said soluble NRP1 polypeptide or fragment thereof comprises or consists of an NRP1 polypeptide trap described in Table 2 or set forth in FIG. 7 or 9A.

In an embodiment, said soluble NRP1 polypeptide or fragment thereof is administered systemically.

In another aspect, the present invention concerns a composition comprising (a) a soluble NRP1 polypeptide or fragment thereof; (b) an NRP1 antibody; or (c) a composition comprising (a) and/or (b), together with a pharmaceutically acceptable carrier, for altering a lipid parameter in a subject, wherein said alteration of a lipid parameter is (a) a decrease in total cholesterol level; (b) a decrease in non-HDL cholesterol level; (c) a decrease in triglycerides level; (d) a decrease in the ratio of total cholesterol:HDL cholesterol; (e) a decrease in circulating free fatty acid; (f) an increase in HDL cholesterol or (f) any combination of (a) to (e).

In another aspect, the present invention concerns a composition comprising (a) a soluble NRP1 polypeptide or fragment thereof; (b) an NRP1 antibody; or (c) a composition comprising (a) and/or (b), together with a pharmaceutically acceptable carrier, for preventing or treating a disease or condition associated with fat accumulation in a subject.

In an embodiment, said disease or condition associated with fat accumulation is high body mass index (BMI); obesity; metabolic syndrome; NAFLD; a cardiovascular disease (CVD); hypertension and/or Type II Diabetes mellitus (TIIDM).

In an embodiment, said cardiovascular disease is congestive heart failure, hypercholesterolemia and/or atherosclerosis.

In another aspect, the present invention concerns a composition comprising (a) a soluble NRP1 polypeptide or fragment thereof; (b) an NRP1 antibody; or (c) a composition comprising (a) and/or (b), together with a pharmaceutically acceptable carrier for altering a body composition parameter in a subject,
wherein said body composition parameter is visceral fat area (VFA), body mass index (BMI), waist to hip ratio (WHR); waist-to-height ratio (WHeR), waist circumference (WC); arm circumference (AC), conicity index, percent body fat (PBF), triceps skin fold, subscapular skin fold, white adipose tissue (WAT) level; and or brown adipose (BAT) tissue level.

In an embodiment, said soluble NRP1 polypeptide or fragment thereof comprises or consists of an NRP1 polypeptide trap described in Table 2 or set forth in FIG. 7 or 9A.

In an embodiment, said soluble NRP1 polypeptide or fragment thereof is for systemic administration.

In another aspect, the present invention concerns a use of (a) a soluble NRP1 polypeptide or fragment thereof; (b) an NRP1 antibody; or (c) a composition comprising (a) and/or (b) together with a pharmaceutically acceptable carrier; for altering a lipid parameter in a subject,
wherein said alteration of a lipid parameter is (a) a decrease in total cholesterol level; (b) a decrease in non-HDL cholesterol level; (c) a decrease in triglycerides level; (d) a decrease in the ratio of total cholesterol:HDL cholesterol; (e) a decrease in circulating free fatty acid; (f) an increase in HDL cholesterol or (f) any combination of (a) to (e).

In another aspect, the present invention concerns a use of a soluble NRP1 polypeptide or fragment thereof; (b) an NRP1 antibody; or (c) a composition comprising (a) and/or (b), together with a pharmaceutically acceptable carrier, for preventing or treating a disease or condition associated with fat accumulation in a subject.

In an embodiment, said disease or condition associated with fat accumulation is high body mass index (BMI); obesity; metabolic syndrome; NAFLD; a cardiovascular disease (CVD); hypertension and/or Type II Diabetes mellitus (TIIDM).

In an embodiment, said cardiovascular disease is congestive heart failure, hypercholesterolemia and/or atherosclerosis.

In another aspect, the present invention concerns a use of (a) a soluble NRP1 polypeptide or fragment thereof; (b) an NRP1 antibody; or (c) a composition comprising (a) and/or (b), together with a pharmaceutically acceptable carrier for altering a body composition parameter in a subject, wherein said body composition parameter is visceral fat area (VFA), body mass index (BMI), waist to hip ratio (WHR); waist-to-height ratio (WHeR), waist circumference (WC); arm circumference (AC), conicity index, percent body fat (PBF), triceps skin fold, subscapular skin fold, white adipose tissue (WAT) level; and or brown adipose (BAT) tissue level.

In an embodiment, said soluble NRP1 polypeptide or fragment thereof comprises or consists of an NRP1 polypeptide trap described in Table 2 or set forth in FIG. 7 or 9A.

In an embodiment, said soluble NRP1 polypeptide or fragment thereof is for systemic administration.

In another aspect, the present invention concerns a use of (a) a soluble NRP1 polypeptide or fragment thereof; (b) an NRP1 antibody; or (c) a composition comprising (a) and/or (b), together with a pharmaceutically acceptable carrier; for the preparation of a medicament for altering a lipid parameter in a subject, wherein said altering of a lipid parameter is (a) a decrease in total cholesterol level; (b) a decrease in non-HDL cholesterol level; (c) a decrease in triglycerides level; (d) a decrease in the ratio of total cholesterol:HDL cholesterol; (e) a decrease in circulating free fatty acid; (f) an increase in HDL cholesterol or (f) any combination of (a) to (e).

In another aspect, the present invention concerns a use of a soluble NRP1 polypeptide or fragment thereof; (b) an NRP1 antibody; or (c) a composition comprising (a) and/or (b), together with a pharmaceutically acceptable carrier, for the preparation of a medicament for preventing or treating a disease or condition associated with fat accumulation in a subject.

In an embodiment, said disease or condition associated with fat accumulation is high body mass index (BMI); obesity; metabolic syndrome; NAFLD; a cardiovascular disease (CVD); hypertension and/or Type II Diabetes mellitus (TIIDM).

In an embodiment, said cardiovascular disease is congestive heart failure, hypercholesterolemia and/or atherosclerosis.

In another aspect, the present invention concerns a use of (a) a soluble NRP1 polypeptide or fragment thereof; (b) an NRP1 antibody; or (c) a composition comprising (a) and/or (b), together with a pharmaceutically acceptable carrier for the preparation of a medicament for altering a body composition parameter in a subject, wherein said body composition parameter is visceral fat area (VFA), body mass index (BMI), waist to hip ratio (WHR); waist-to-height ratio (WHeR), waist circumference (WC); arm circumference (AC), conicity index, percent body fat (PBF), triceps skin fold, subscapular skin fold, white adipose tissue (WAT) level; and or brown adipose (BAT) tissue level.

In an embodiment, said soluble NRP1 polypeptide or fragment thereof comprises or consists of an NRP1 polypeptide trap described in Table 2 or set forth in FIG. 7 or 9A.

In an embodiment, said medicament is for systemic administration.

BRIEF DESCRIPTION OF THE DRAWINGS

In the appended drawings:

FIGS. 1A-J show that retinal ischemia triggers cellular senescence and a senescence-associated secretory phenotype. FIG. 1A: Schematic depiction of the mouse model of oxygen-induced retinopathy (OIR). FIG. 1B: Representative gene set enrichment analysis (GSEA) corresponding to signatures of inflammation and apoptosis from large-scale genome-wide RNA-seq of P14 normoxic and OIR retinas. Gene expression profiles positively and negatively correlated with OIR phenotype are represented. FIG. 1C: Heat map and GSEA cluster of Fridman senescence-associated genes (28) in P14 OIR (left columns) vs normoxic retinas (right columns). (NES=normalized enrichment score, FDRq=false discovery rate), color scale depicting expression of log 2 (fold change) from low (−2, left) to high expression (2, right). FIG. 1D: Immunoblots of retinal cell lysates from P14 OIR and normoxic mice show induction of markers of senescence. FIG. 1E: RT-qPCR shows induction of expression of senescence-associated genes, Cdkn1a (p21) and Cdkn2a (p16) in P14 OIR vs normoxic retinas. FIG. 1F: Representative isolectin B4 (IB4) and senescence-associated β-galactosidase staining (SA-β-gal) of P14 normoxia and OIR flatmount retinas. FIG. 1G: Quantification of percentage of senescence-associated β-galactosidase staining (SA-β-gal) in P14 OIR vs normoxia flatmount retinas. Higher magnification views of boxed central (c)/peripheral (p) and vascular/avascular zones of retinas are shown (***$P<0.0001$ central compared with peripheral OIR retinas (n=10); †††$P<0.0001$ avascular compared to central P14 Normoxia retinas (n=7). FIG. 1H: Representative IB4 and SA-β-gal staining of sagittal section of P14 normoxia and OIR retinas. Higher magnification images of boxed central avascular retinal zones are shown in right panel. Retinal ganglion cells (GCL), inner nuclear layer (INL) and outer nuclear layer (ONL) are shown for orientation. FIG. 1I: Quantification of percent area stained with SA-β-gal in retinal sagittal sections at P14 (*$P<0.05$ compared to normoxic retinas (n=10), †$P<0.05$ compared to other P14 OIR layers of the retinas (n=7); ns=not significant). FIG. 1J: TUNEL staining of P14 OIR and normoxic retinas. Scale bars are 500 μm (H). For higher magnification images and (H, J) scale bars are 200 μm. Data are presented as mean±SEM.

FIGS. 2A-F show that cellular senescence propagates during progression of retinopathy. FIG. 2A: Isolectin B4 (IB4) staining of retinas during progression of OIR (P14, P17 and P21). FIG. 2B: Schematic illustration of propagation of cellular senescence throughout OIR depicting the SA-β-gal stained flatmount OIR retinas in lower panels (scale bars 50 μm). Higher magnification images reveal distinct senescent cell population (scale bars 25 μm). FIG. 2C: Representative confocal micrographs of P14 OIR retinas show robust staining of markers of senescence (γH2AX (top row) and Pai1 (middle row) in RGCs (Brn3a staining (2nd column)). Insets are high magnification images of outlined areas. FIG. 2D: Representative confocal micrographs of P17 OIR flatmount retinas reveal that senescence markers (PML (bottom row) and γH2AX (top row)) co-label with microglia (IBA1) and vessels IB4. FIG. 2E: Heat map and GSEA cluster of paracrine senescence-associated genes in P14 OIR vs normoxic retinas for two different samples. FIG. 2F: RT-qPCRs show induction of expression of Pai1, Il1β, Tgf-β1, Il6, Vegf-a, Ire1α and Tp53 in P14 OIR vs normoxic retinas. β-actin was used as a reference gene. Scale bars are 100 μm for C and D. Data are presented as mean±SEM;

FIG. 3A: Western blot analysis of SEMA3A protein expression level during OIR compared to normoxic controls at P10, P14, P17 and P21. β-actin is used as a loading control.

FIG. 4A: Gene expression profiles positively and negatively correlated with OIR phenotype are represented. FIG. 4B: Representative SA-β-gal and IB4 stains of LysM-Cre/ROSA26EYFP$^{fl/fl}$ retinas at P14 and P17 OIR. FIG. 4C: Representative γH2AX staining and EYFP in central regions from LysM-Cre/ROSA26EYFP$^{fl/fl}$ at P14 and P17 OIR. White arrowheads point to co-labeling of γH2AX and EYFP$^+$ microglia;

FIG. 5C: Western blot analysis of SEMA3A protein expression showing the efficiency of the Sh-RNA downregulation in neuronal cells (661W). FIG. 5D: Schematic illustration explaining conditioned media (CM) experiments to tease out the contribution of paracrine senescence. CM from the retinal neuron precursor cell line expressing sh_GFP or sh_SEMA3A made senescent with $H_2O_2$, and CM was harvested and applied to HRMEC. Induction of paracrine senescence in HRMEC was evaluated after 7 days by SA-β-gal staining. FIG. 5E: Levels of secreted SEMA3A in CM from retinal neuron precursor cell infected with Lv.sh_GFP or Lv.sh_S3A were evaluated by immunoblot. (FIG. 5F) Immunoblot analysis of p53 expression in HRMEC exposed to CM from senescent (or not) retinal neuron precursor cells ($H_2O_2$ or vehicle treated). FIG. 5G: Immunoblot analysis of HRMEC exposed to CM from retinal neuron precursor cells transfected with sh_GFP or sh_SEMA3A (sh_S3A) and treated with $H_2O_2$ or vehicle. FIG. 5H: Immunoblot analysis of ER-stress effector, p-IRE1α$^{S724}$, in HRMECs lysates treated with recombinant SEMA3A (100 ng/ml) or CM from senescent J774 cells (Sen-J774) and harvested after 7 days;

FIGS. 6A-F show that SEMA3A induces senescence in J774 macrophage/monocytes. FIG. 6A: P14 Retinal lysates from mice having received an intravitreal injection of Lv.sh_GFP or Lv.sh-IRE1α were immunoblotted against anti-IRE1α and Cre. FIG. 6B: SA-β-gal staining of J774 macrophages treated with SEMA3A (100 ng/ml, 7 days) or $H_2O_2$ as a positive control. Higher magnification views of the boxed regions are shown. FIG. 6C: Immunoblot analysis of J774 macrophages exposed to SEMA3A (100 ng/ml, 7 days) or $H_2O_2$, as positive control, and HRMEC treated with conditioned media (CM) from respective J774 conditions as indicated by dashed arrows. FIG. 6D: Immunoblot against IRE1α demonstrates efficiency of lentivirus-mediated depletion of IRE1α in HRMECs. FIG. 6E: SA-β-gal staining of HRMEC infected with indicated lentiviral vectors (Lv.sh_GFP and Lv.sh_IRE1α) and then treated with recombinant SEMA3A (100 ng/ml, 7 days) or vehicle (CT). FIG. 6F: Relative mRNA expression levels of Cdkn1a, Cdkn2a in J774 treated with SEMA3A (100 ng/ml, 7 days) or vehicle (CT);

FIGS. 7A-F show that the RNAse activity of IRE1α contributes to senescence. FIG. 7A: Immunoblots for markers of senescence in J774 cell lysates stimulated with SEMA3A (S3A) (100 ng/mL) or vehicle for 3 or 7 days shows induction of p-IRE1α$^{S724}$, p53, Pai1, (n=3). FIG. 7B: RT-qPCR in J774 macrophages revealed mRNA increased expression of Pai1, Il6, Il1β, Tgf-β1 and Tp53 after exposure to SEMA3A (100 ng/mL) for 7 days. FIG. 7C: Representative confocal immunofluorescence staining of γH2AX and DAPI of J774 macrophages stimulated with SEMA3A (100 ng/mL) or vehicle for 7 days (Scale bars are 100 μm). Higher magnification views of the outlined areas are shown (Scale bars are 50 μm). Immunoblots (FIG. 7D) for the XBP1(s) (spliced isoform) and PCR (FIG. 7E) for XBP1(s) and unspliced XBP1 (u) in J774 cell lysates treated with vehicle, S3A (100 ng/ml) and/or 4μ8c (1 ng/ml) at day 7 post-treatment. FIG. 7F: RT-qPCR for levels of Pai1, Il6, Il1β, Tgf-β1, Tp53, Ire1α and Tnfα in J774 stimulated with SEMA3A alone or with 4μ8c. β-actin was used as a reference gene. ***P<0.0001, *P<0.005. Scale bars: 100 μm for C & G. High mag C is 50 μm. Data are presented as mean±SEM;

FIG. 8A: angiography, spectral domain optical coherence tomography (SD-OCT) and 3D retinal maps obtained from patients selected for the study. Control patients (CT) (n=10) with nonvascular ocular pathologies were compared with patients with proliferative diabetic retinopathy (PDR) (n=10) patients. Table 1 (Example 6) shows patients characteristics. FIG. 8B: Multiplex assessment of patient vitreous humor for cytokines involved in paracrine senescence shows induction in VEGF-A, Pai1, IL-6, and IL-8. Results are expressed as fold change normalized to CT patients. Points represent individual values; P<0.001, *P<0.0001. FIG. 8C: Immunoblot analysis for p-NFκB$^{S536}$ and p-IRE1α$^{S724}$ in retinal lysates from P14 and P17 of OIR mice intravitreally injected with metformin or vehicle at P12. FIG. 8D: RT-qPCR for levels of Cdkn1a, Cdkn2a and Il6 measured in retinas of P14 OIR mice intravitreally injected with metformin or vehicle at P12 (β-actin was used as a reference gene). Representative P14 (FIG. 8E) and P17 (FIG. 8F) OIR flatmount retinas labeled with IB4 and SA-β-gal in mice intravitreally injected with metformin or vehicle at P12. (FIG. 8G) Quantification of percentage SA-β-gal stained area in P14 and P17 OIR mice treated as in E and F. (P=0.0042 at P14, (n=9); P=0.0013 at P17 (n=11); metformin compared with vehicle-injected retinas). (FIG. 8H) Representative IB4 stained flatmount retinas of P14 and P17 OIR mice intravitreally injected with metformin or vehicle at P12. Quantification of avascular areas at P14 (FIG. 8I) and P17 (FIG. 8J) of OIR. Pre-retinal neovascularization was assessed at P17 OIR (FIG. 8K). Results are expressed as percentage of avascular or neovascular area versus the whole retinal area (*P<0.0001 and *P<0.001; metformin compared to vehicle-injected retinas (n=13)). Horizontal bars represent mean value of percentage, and dots represent individual values. Scale bars are 500 μm. Data are presented as mean±SEM;

FIG. 10A: Isolectin B4 (IB4) and TUNEL staining of the whole eye cryosections at P14 OIR and normoxia presented in FIG. 1I. FIG. 10B: Representative confocal immunofluorescence of γH2AX (green; left column), p-IRE1α$^{S724}$ (green; middle column) and Pai1 (green; right column), isolectin B4 (IB4) (red), and DAPI (blue) on cryosectionned P14 normoxia and OIR retinas. FIG. 10C: Representative confocal immunofluorescence of PML (green; left column), p16 (green; right column), IB4 and DAPI of cryosectionned P14 OIR eyes. FIG. 10D: Representative confocal immunofluorescence against PML, isolectin B4 (IB4) and DAPI of flatmount retina at P21 OIR. FIG. 10E: Representative SA-β-gal staining of cryosections from citrate and STZ retinas. The retinal ganglion cells (GCL), inner nuclear layer (INL) and outer nuclear layer (ONL) are shown for orientation. FIG. 10F: Representative confocal immunofluorescence of α-SMA or NG2, isolectin B4 (IB4), on flatmount retinas from adult mice citrate (control) or STZ (diabetic);

FIG. 12A: Representative SA-β-gal staining of cryosections from P14 and P17 OIR retinas injected with metformin (10 μg/μl, at P12) or vehicle (PBS). FIG. 12B: Representative confocal immunofluorescence of TUNEL (left) and DAPI (middle) on cryosectionned P14 OIR retinas treated or not with metformin. The retinal ganglion cells (GCL), inner nuclear layer (INL) and outer nuclear layer (ONL) are shown for orientation. FIG. 12C: Western blot analysis of cleaved caspase-3 protein expression level during OIR (P14, P17 and P21). β-actin is used as a loading control. Scale bars are 200 μm;

FIG. 13A: RT-qPCR for levels of Vegf-a, Vegf-c, Vegfr-1 and Vegfr-2 measured in retinas of P14 OIR mice intravitreally injected with metformin or vehicle at P12 (β-actin was used as a reference gene); FIG. 13B: RT-qPCR for levels of Cdkn2a, Tp53, Il1β, Tgf-β1 and Sema3a measured in retinas of P14OIR mice intravitreally injected with Aflibercept or vehicle at P12 (β-actin was used as a reference gene);

FIGS. 15A-E show the structures of exemplary biguanide compounds and inhibitors of IRE1α. FIG. 15A: biguanide (CAS #56-03-1); FIG. 15B: Metformin (N,N-Dimethylimidodicarbonimidic diamide; CAS #657-24-9); FIG. 15C: Buformin (1-butylbiguanide, CAS #692-13-7); and FIG. 15D: Phenformin (2-(N-phenethylcarbamimidoyl)guanidine, CAS #114-86-3); FIG. 15E: "Compound 3" IRE1α inhibitor which inhibits the RNAse activity of IRE1α (Wang et al., 2012, Nat. Chem. Bio. 8(12): 982-989);

FIG. 16 shows the amino acid sequence of human SEMA3A precursor protein. This sequence (SEQ ID NO: 50) is further processed into mature form by removal of the signal peptide (amino acid 1-21);

FIGS. 17A-B show an alignment between rat (Access. Nos. EDL96784, NP_659566, SEQ ID NO: 48), human (Accession No. NM003873, SEQ ID NO: 96) and mouse (Accession No. NP_032763, SEQ ID NO: 48) NRP1 protein sequences together with an NRP1 consensus sequence (SEQ ID NO: 47). The NRP1 signal domain (amino acids 1-20/1-21/1-27), subdomain a1 (from about aa22 to about aa148), subdomain a2 (from about aa149 to about aa275), subdomain b1 (from about aa276 to about aa428) and subdomain b2 (from about aa429 to about aa589), domain c (from about aa590 to about aa859), transmembrane domain (from about aa860 to about aa883) and cytoplasmic domain (from about aa884 to about aa923) are identified;

FIGS. 18A-G show an amino acid sequence alignment between exemplary traps of the present invention (see Tables 2 and 9 for the SEQ ID Nos corresponding to each trap shown);

FIGS. 19A-C show human soluble Neuropilin-1 (NRP1) protein sequences. FIG. 19A: NRP1 isoform b/s12 (644 amino acids; Ref seq: NP_001019799.1; NM_001024628.2; Uniprot: O-14786-2, SEQ ID NO: 44); FIG. 19B: NRP1 isoform c/Siv (609 amino acids; Ref seq: NP_001019800.1; NM001024629.2; Uniprot: 014786, SEQ ID NO: 45); FIG. 19C: NRP1 isoform SIII (704 amino acids; Ensembl: ENSP00000363956, SEQ ID NO: 46); and FIGS. 20A-B show attenuation of cellular senescence by a single injection of an NRP1 trap. FIG. 20A: Representative P17 OIR flatmount retinas labeled with SA-β-gal in mice intravitreally injected with traps M and G at P12. FIG. 20B: Quantification of SA-β-gal staining reveals a significant attenuation of cellular senescence when mice receive a single injection of TrapM or TrapG;

FIGS. 21A-G show that NRP1 expressing macrophages accumulate in adipose tissue during diet-induced obesity. FIG. 21A: NRP1 expression level of eosinophils (adipose tissue, peripheral blood), neutrophils (blood, synovial fluid, bone marrow), monocytes (classical: MHCII+, MHCII−, MHCII− LN, bone marrow; non-classical: MHCII intermediate, MHCII high, MHCII−, bone marrow), and macrophages (adipose tissue, bone marrow, red pulp, lung resident, lung CD11b+, central nervous system, steady state peritoneal (high), steady state peritoneal (low), small intestine serosal, small intestine lamina propria) (n=1-4 per group). FIG. 21B: Adipose tissue macrophage (ATM) population FACS in 10 week high fat diet (HFD), and aged-matched control on regular diet (RD) C57BL/6 in white adipose tissue (WAT); FIG. 21C: NRP1 expression levels (n=9 per group) in macrophage (ATM). (FIGS. 21D-G) mRNA expression of NRP1 ligands: (FIG. 21D) Sema3a; (FIG. 21E) Vegfa; (FIG. 21F) Vegfb; and (FIG. 21G) Tgfb1 in RD and 10 week HFD C57BL/6 retroperitoneal white adipose tissue (RPWAT) (n=5 per group). Data are represented as mean±S.E.M. Student's unpaired t-test (FIGS. 21B-G) *p<0.05, p<0.01, *p<0.001;

FIGS. 22A-K shows that NRP1 promotes FA uptake and phagocytosis. FIG. 22A: Acute BODIPY™ uptake within control and LysM-Cre-NRP1$^{fl/fl}$ macrophages (n=7-8 per group). BODIPY™ uptake within (FIG. 22B) retroperitoneal white adipose tissue (RPWAT), (FIG. 22C) Liver, (FIG. 22D) Plasma and (FIG. 22E) Heart of HFD fed control and LysM-Cre-NRP1$^{fl/fl}$ mice (n=6 per group). FIG. 22F: ORO (Oil red 0) stain of control and (FIG. 22G) LysM-Cre-NRP1$^{fl/fl}$ macrophages incubated in adipocyte conditioned medium, FIG. 22H: Quantification of ORO stain of control and LysM-Cre-NRP1$^{fl/fl}$ macrophages incubated in adipocyte conditioned medium (DMEM and insulin), (FIG. 22I) DMEM and insulin, (FIG. 22J) DMEM, (FIG. 22K) Macrophage medium (F12) (n=18-35 per group). Data are represented as mean±S.E.M. Student's unpaired t-test, *p<0.05, p<0.01, *p<0.001;

FIG. 25A: Glycemia (mM) at different time-points of mice fed a HFD after an intraperitoneal injection of 2 g of glucose/kg mice. C57Bl6/J mice at 6-8 weeks of age were intravenously injected with saline or Adeno-Trap M ($0.25 \times 10^{10}$ PFU/injection). Mice were fed a high fat diet right after injection. Glycemia was assessed at different time-points after the intraperitoneal injection of 2 g of glucose/kg mice. FIG. 25B: Area under the curves shown in FIG. 25A ** $P<0.01$ (Adeno GFP vs Adeno Trap M) in Two-way Anova Bonferroni posttest, wherein N=5;

DESCRIPTION OF ILLUSTRATIVE EMBODIMENTS

Figure 1A:
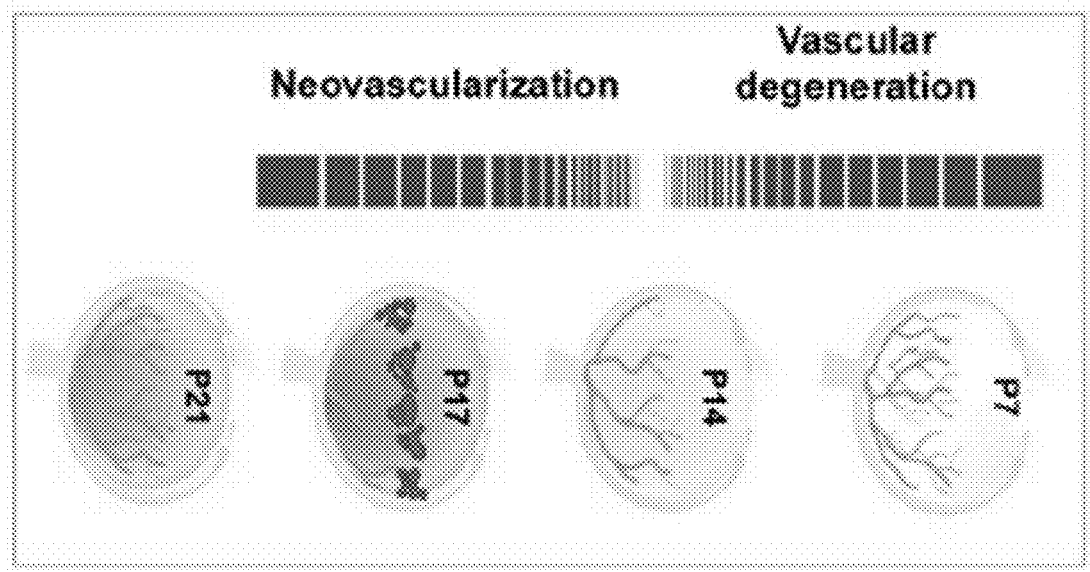

1. Role of Cellular Senescence and SASP in Ocular Vascular Diseases

The data presented herein establish a novel role for cellular senescence in weathering ischemia and modulating angiogenesis in ocular vascular diseases. Indeed a transient accumulation of senescent cells was established in different subcellular populations of the retina in different models of retinopathies. More particularly, it was found that by adopting a SASP, retinal neurons stimulate production of a series of paracrine factors and inflammatory cues that spread senescence to retinal microglia as well as endothelial cells and further exacerbate pathological pre-retinal angiogenesis. Applicants have shown that modulation of cellular senescence through the inhibition of the SASP (e.g., administration of biguanide compounds (e.g., metformin) or pharmacological or genetic inhibition of IRE1α) inhibits ischemia-induced senescence, increases vascular regeneration and suppresses pathological neovascularization in models of vascular ocular diseases. Therefore the SASP was shown to participate in mediating pathological vessel growth, with ischemic cells entering a state of premature senescence and secreting inflammatory cytokines that drive paracrine senescence, exacerbates destructive angiogenesis and hinders reparative vascular regeneration.

Data presented herein support that in the context of ocular vascular diseases such as retinopathies, cellular senescence exerts dichotomous roles within the same disease in that it first likely protects neurons from cell death yet concurrently prevents them from triggering programs of reparative angiogenesis. In addition, the paracrine senescence observed and associated production of vasomodulatory factors in retinopathies, contributes to repelling neovessels to the physiologically avascular vitreous and may promote premature aging-related complication in retinal vasculature. This is particularly relevant in light of the increased incidence of neovascular ocular disease associated with age such as age-related macular degeneration and diabetic retinopathy. Hence preventing cellular senescence during a phase of pathological neovascularization with administration of modulators of senescence could therefore represent a simple therapeutic solution for ocular vascular diseases and disorders such as retinal vasculopathies.

2. Methods of Treating or Preventing Vascular Eye Diseases Involving Cellular Senescence Thus, according to an aspect of the present invention, compositions and methods are provided for treating and/or preventing at least one symptom or indication of a vascular eye disease or disorder in a subject. The methods according to this aspect of the invention comprise administering an inhibitor of the SASP (e.g., a biguanide compound such as metformin) to the subject. In certain aspects the inhibitor of the SASP is administered locally, in the eye of the subject (e.g., topically or intravitreally as opposed to, for example, systemically). Ocular administration is particularly preferred in the case of biguanide compounds such as metformin because systemic administration will generally not allow the compound to reach its target site because of the presence of the blood retinal barrier. In embodiments, the vascular eye disease or disorder is secondary to cellular ischemia.

Vascular eye diseases or conditions that may benefit from inhibition of the SASP in accordance with the present invention include any disease, disorder or condition characterized by abnormal angiogenesis (e.g., pathological neovascularization and/or reduced vascular regeneration). These diseases may be caused by a reduction (transient or sustained/chronic) of metabolic supply (e.g., oxygen, blood, nutrients) to cells which contribute to the normal eye function (e.g., ocular vascular cells, retinal cells, neurons, microglia) leading the presence of senescent cells (or cells harboring a senescence phenotype). Such condition may be present following an ischemic event but is not so limited. As used herein, the term "vascular eye disease or disorder" or "vascular eye disease or condition" thus refers to a disease, disorder or condition that affects the normal physiology of blood vessels in the eye. Non-limiting examples of such ocular eye diseases or conditions comprise: diabetic retinopathy, retinopathy of prematurity, ischemic retinopathy, diabetic macular edema, age-related macular degeneration, retinal neovascularisation, central retinal vein occlusion, branched retinal vein occlusion, choroidal neovascularization, polypoidal choroidal vasculopathy, physical injury to the eye, glaucoma, rhegmatogenous retinal detachment (RRD), retinal vasculitis, retinal macroaneurysm, retinal microaneurysm, Fuch's dystrophy, ischemic optic neuropathy, juvenile macular degeneration, macular telangiectasia, optic neuritis, usher syndrome, retinitis pigmentosa, uveitis, stangardt disease, Leber's congenital amaurosis (LCA). In embodiments, the vascular eye disease or disorder is an ischemic retinopathy. In embodiments, the ischemic retinopathy is associated with diabetic retinopathy, retinopathy or prematurity, ocular vein occlusion, central retinal vein occlusion or branched retinal vein occlusion.

Compounds or agents that inhibit the SASP in accordance with the present invention include biguanide compounds (e.g., metformin), mTor inhibitors (e.g., rapalogue, Torin 1) and/or inhibitors of IRE1α expression (e.g., antisense, shRNAs, etc.), IRE1α activation (S724 phosphorylation) and/or IRE1α RNAse activity (e.g., pharmacological inhibitors/antagonists). Generally, "IRE1α inhibitors" which inhibit the SASP in accordance with the present invention are those which ultimately reduce or abrogate IRE1α RNAse activity.

In particular aspects, compounds and agents that inhibit the SASP and prevent and/or attenuate cellular senescence in the context of vascular eye diseases and disorders (e.g., involving proliferative retinopathies) increase physiological angiogenesis (i.e., beneficial angiogenesis) and reduce pathological angiogenesis (pathological neovascularization) and thus promote tissue repair.

IRE1α is an enzyme that in humans is encoded by the ERN1 gene (Entrez: 2081, Ensembl ENSG00000178607, Uniprot: O75460, Refseq mRNA: NM_152461, NM_001433, Refseq (protein): NP_001424.3). This protein possesses intrinsic kinase activity and an endoribonuclease activity and it is important in altering gene expression as a response to endoplasmic reticulum-based stress signals (mainly the unfolded protein response (UPR)). Two alternatively spliced transcript variants encoding different isoforms have been found for this gene. IRE1α possesses two functional enzymatic domains, an endonuclease and a trans-autophosphorylation kinase domain. Upon activation, IRE1α oligomerizes and carries out an unconventional RNA splicing activity, removing an intron from the X-box binding protein 1 (XBP1) mRNA, and allowing it to become translated into a functional transcription factor, XBP1s. XBP1s upregulates ER chaperones and endoplasmic reticulum associated degradation (ERAD) genes that facilitate recovery from ER stress. Compounds which inhibit IRE1α (i.e., inhibitors) are also known in the art.

As used herein the term "IRE1α inhibitor" or "IRE1α antagonist" refers to an agent able to reduce or block IRE1α-mediated cell signaling associated with cellular senescence and the induction of the SASP (i.e., IRE1α ribonuclease activity and XBP1 processing). Non-limiting examples include an agent which reduces or blocks the expression (transcription or translation) of IRE1α, an agent able to reduce or block IRE1α activation (e.g., S724 phosphorylation and/or IRE1α dimerization). Without being so limited, the agent can be natural or synthetic and can be small molecule or a protein/polypeptide/nucleic acid such as but not limited to an antisense or a shRNA specific to an IRE1α nucleic acid sequence encoding an IRE1α protein or any pharmacological inhibitor described herein. IRE1α inhibitors or IRE1α antagonists of the present invention binds to IRE1α nucleic acid or IRE1α protein to reduce IRE1α expression, activation or activity and ultimately lead to a reduction of IRE1α RNAse activity within the cell.

Inhibitors targeting the catalytic core of the RNase domain and/or the ATP-binding pocket of the kinase domain have been described. Non-limiting examples of inhibitors targeting the RNAse binding pocket include salicylaldehydes (e.g., 3-methoxy-6-bromosalicylaldehyde-Volkmann et al., 2011, JBC 286(14): 12743-12755, PMCID: PMC3069474), 4p8C, MKC-3946, STF-083010, and toyocamycin. Compounds that inhibit IRE1α's RNase activity through the kinase domain have also been identified and named "kinase inhibiting RNase attenuators" (KIRAs) and include KIRA3, and KIRA6 (Cas #1589527-65-0), which inhibit both the kinase and RNAse activities of IRE1α. Sunitinib and APY29 are examples of compounds which inhibit the ATP-binding pocket but allosterically activate the IRE1α RNAse domain (Wang et al., 2012, Nat. Chem. Bio. 8(12): 982-989). Further kinase and/or RNAse inhibitors and activators of IRE1α are described in Wang Supra. In particular embodiment, IRE1α inhibitors which are used in accordance with the present invention inhibit the RNAse activity of IRE1α but not its kinase activity.

Biguanides are a class of organic compound with the formula $HN(C(NH)NH_2)_2$. These compounds were originally discovered in French Lilac (*Galega officinalis*) extracts and showed to lower blood glucose levels. They were thus originally used for the treatment of type 2 diabetes. A variety of derivatives of biguanide are used as pharmaceutical drugs for the treatment of diabetes but also for other diseases and conditions including polycystic ovary syndrome and cancer. Non-limiting examples include, metformin (N,N-Dimethylimidodicarbonimidic diamide (IUPAC name); CAS 657-24-9; DrugBank DB00331; ChemSpider 3949; Glucophage XR™; Carbophage SR™; Riomet™; Fortamet™; Glumetza™; Obimet™; Gluformin™; Dianben™; Diabex™, Diaformin™, Siofor™, and Metfogamma™) buformin (1-butylbiguanide, CAS #692-13-7), Phenformin (2-(N-phenethylcarbamimidoyl)guanidine, CAS #114-86-3), Proguanil, (1-[amino-(4-chloroanilino)methylidene]-2-propan-2-ylguanidine, also known as chloroguanide), Chlorproguanil, Synthalin A, (1,1'-decane-1,10-diyldiguanidine, Cas #111-23-9) and Synthalin B, (1,1'-Dodecamethylene-diguanidinium dichloride, Cas #61167-43-9). FIG. 15 shows the structure of biguanide and some functional derivatives that may be used in accordance with the present invention.

SASP inhibitors of the present invention may be administered in combination with other drugs used to treat vascular eye diseases and disorders including Angiopoietin-2 inhibitors (e.g., described in WO2016/085750), VEGF antagonists (e.g., anti VEGF antibodies (e.g., ranibizumab/ LUCENTIS™)), small molecule VEGF inhibitors (e.g., sunitinib), VEGF-inhibiting fusion proteins (e.g., Aflibercept/EYELEA™)) and/or SEMA3A antagonists (e.g., SEMA3a antibodies or NRP1 traps described below (see Table 2 and FIG. 18) or, for example, in WO 2016/033699).

3. Reduction or Prevention of Cellular Senescence and the SASP by Inhibiting IRE1α

Data presented herein further establish a role for IRE1α in modulating cellular senescence and the SASP. Cellular senescence, (including autocrine and/or paracrine) paracrine senescence can be inhibited or prevented by reducing IRE1α activity (i.e., IRE1α activation and cellular signalling).

IRE1α activity can be inhibited by a number of approaches. Inhibition of IRE1α cellular activity may be done directly by reducing IRE1α (i) nucleic acid or protein expression, (ii) activation (Serine 724 phosphorylation); and/or (iii) RNAse activity (and optionally, its kinase activity) in a cell. As noted above, IRE1α inhibitors are known in the art and include agents which inhibit IRE1α expression (e.g., IRE1α antisense of sh_RNAs), IRE1α activation (e.g., KIRA3, KIRA6) and/or IRE1α ribonuclease (and optionally kinase) activity (e.g., salicylaldehydes, 4p8C, MKC-3946, STF-083010, KIRA3, KIRA6 and toyocamycin).

The present invention thus provides a method of inhibiting or preventing cellular senescence of a cell or induction of the senescence-associated secretory phenotype (SASP) in a cell comprising reducing IRE1α level or activity.

The present invention also concerns a method of inhibiting or preventing cellular senescence of a cell or induction of the senescence-associated secretory phenotype (SASP) in a cell comprising contacting the cell with an inhibitor of IRE1α.

Also provided is a method of inhibiting or preventing cellular senescence of a cell or induction of the senescence-associated secretory phenotype in a cell of a subject comprising administering to the subject an inhibitor of IRE1α.

The above methods may be useful in treating or preventing diseases or conditions in which cellular senescence is detrimental such as various age-related conditions (e.g., sarcopenia, neurodegeneration, thinning of the epidermis, skin wrinkling, hair loss and greying hair, cataract, obesity, metabolic syndrome, and other diseases of old age), chronic obstructive pulmonary disease (COPD), Idiopathic pulmonary fibrosis (IPF), atherosclerosis, osteoarthritis, osteoporosis, glaucoma, Parkinson's disease, intestinal bowel disease, intervertebral disc degeneration, brain aneurysm, aortic aneurysm, pancreatic fibrosis, vascular ocular diseases (e.g., retinal vascular diseases (proliferative retinopathies, diabetic retinopathy, ischemic retinopathies, macular degeneration, glaucoma) and cystic fibrosis. Inhibition or prevention of cellular senescence may also be useful during and/or after cancer treatment to alleviate side effects of chemotherapy/radiotherapy which include for example, metabolic dysfunction, accelerated aging, increased risk of cancer later in life. In embodiments, the senescence-associated diseases or conditions which are encompassed by the present invention exclude one or more vascular ocular diseases (e.g., retinal vascular diseases (proliferative retinopathies, diabetic retinopathy, ischemic retinopathies, macular degeneration, glaucoma)).

Various approaches are available for decreasing IRE1α expression and thus IRE1α-mediated cellular senescence. Non-limiting example includes the use of small hairpin shRNA (RNAi), antisense, ribozymes, TAL effectors targeting the IRE1α promoter or the like. Expression of shRNAs or similar inhibitory RNAs in cells can be obtained by delivery of plasmids or through viral (e.g., lentiviral vector, adenoviral vector, etc.) or bacterial vectors.

Therefore, in alternative embodiments, the invention provides antisense, shRNA molecules and ribozymes for exogenous administration to effect the degradation and/or inhibition of the translation of mRNA of interest. The present invention also provides vectors and host cells for delivering and/or expressing the antisense, shRNA molecules, ribozymes, etc. disclosed herein. The antisense, shRNA molecules and ribozymes preferably target mammalian (preferably human) IRE1α. Examples of therapeutic antisense oligonucleotide applications include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. Nos. 5,276,019 and 5,264,423; BioWorld Today, Apr. 29, 1994, p. 3.

Preferably, in antisense molecules, there is a sufficient degree of complementarity to the mRNA of interest to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as IRE1α inhibitors of the invention is disclosed in U.S. Pat. No. 5,932,435.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In a further embodiment, expression of a nucleic acid encoding a polypeptide of interest (IRE1α), or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example published US patent applications 20020173478 (Gewirtz; published Nov. 21, 2002) and 20020132788 (Lewis et al.; published Nov. 7, 2002). Reagents and kits for performing RNAi are available commercially from for example Ambion Inc. (Austin, TX, USA) and New England Biolabs Inc. (Beverly, MA, USA).

The initial agent for RNAi in some systems is a dsRNA molecule corresponding to a target nucleic acid. The dsRNA (e.g., shRNA) is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector (viral vector such as an adenoviral vector) encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA (shRNAs) or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using E. coli RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods and various methods for introducing such vectors into cells, either in vitro or in vivo (e.g. gene therapy) are known in the art.

Accordingly, in an embodiment expression of a nucleic acid encoding a polypeptide of interest (IRE1α), or a fragment thereof, may be inhibited by introducing into or generating within a cell an siRNA or siRNA-like molecule corresponding to a nucleic acid encoding a polypeptide of interest (e.g. IRE1α), or a fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest.

4. Methods of Promoting Cellular Senescence by Increasing IRE1a Ribonuclease Activity Under certain conditions, stimulation of cellular senescence may be beneficial. Cellular senescence, including autocrine and paracrine senescence can be promoted or induced by stimulating or increasing IRE1α activity (i.e., IRE1α RNAse activity and cellular signaling). IRE1α activity can be increased by a number of approaches including by increasing the expression of IRE1α in a cell or by contacting a cell with a compound which activates IRE1α RNAse activity (e.g., APY29, Sunitinib or compound 3 described in Joshi et al., 2015, 6(15): 1309-1335).

Methods of promoting cellular senescence may be useful in diseases and conditions where senescence has beneficial effects such as tissue repair, wound healing, liver fibrosis, renal fibrosis, myocardial infarction cardiac fibrosis, atherosclerosis, pulmonary hypertension and cancer.

5. Compositions and Methods for Modulating Cellular Senescence Comprising SEMA3A Modulators The Class 3 Semaphorins (Sema3s) are a sub-family of proteins whose known biological roles are varied and growing. The mechanism of action of the Sema3s requires binding to transmembrane receptors that comprise heteromeric complexes of Neuropilins, Plexins and cell adhesion molecules (CAMs). The SEMA3A gene (GeneCard ID: GC07M083955; Entrez Gene ID: 10371; Ensembl: ENSG00000075213) encodes a 771 amino acid protein (NP_006071.1; UniprotKB: Q14563, SEQ ID NO: 50) comprising a signal peptide, an Ig-like C2-type (immunoglobulin-like) domain, a PSI domain and a Sema domain (which is required for signaling). This secreted protein was first described as an axonal guidance cue but it has now been implicated in various physiological and pathological process including organ development, bone metabolism, angiogenesis, vascular permeability, growth cone collapse, myogenic regeneration and formation of neuromuscular junction, regulation of the immune system, inflammation, schizophrenia and retinal diseases such as diabetic retinopathy.

Sema3a generally signals through receptor complexes comprising Neuropilin-1 (NRP1) and a coreceptor (e.g., Class A plexins (e.g., PLXna1-Plxna4, Plxnd1), L1cam, chL1, Robo1). NRP1 (Ensemble; ENSG00000099250; ENST00000265371; Uniprot: 014786; OMIM: 602069; HGNC: 8004; GeneCard ID: GC10M033216, SEQ ID NOs: 44-47, 95 and 96) is a single-pass transmembrane receptor with a large intracellular domain. The basic structure of neuropilin-1 comprises 5 domains: Three extracellular domains (a1a2 (CUB), b1b2 (FV/FVIII) and c (MAM)), a transmembrane domain and a cytoplasmic domain. The a1a2 domain is homologous to complement components C1r and C1s (CUB) which generally contain 4 cysteine residues forming disulfide bridges. This domain binds SEMA3A. Domains b1b2 (FV/FVIII) binds to VEGF. Amino acid Y297 in subdomain b1 is important for binding to VEGF as substitution of Y297 to an alanine significantly reduces VEGF binding to NRP1. Subdomain b1 also contributes to SEMA3A ligand binding. Indeed, Applicants have surprisingly found that substitution of Y297 (Y297A) also significantly reduce SEMA3A binding to NRP1. Crystallographic evidence revealed that VEGF165 and Sema3A do not directly compete for NRP1 but rather can simultaneously bind to NRP1 at distinct, non-overlapping sites.

In addition to the transmembrane form (isoform 1, 923 aa, FIG. 17, SEQ ID NOs: 47, 95 and 96, NM003873; Uniprot: O14786-1), naturally occurring soluble NRP1 proteins (sNRP1) containing only part of the extracellular domain may be secreted by the cells. Different soluble forms have been described ranging from 551 to 704 amino acids (isoforms b/s12 NRP1 (644 aa; RefSeq: NP_001019799.1; NM_001024628.2, SEQ ID NO: 44), s11 NRP1 (704 aa; ENSP00000363956, SEQ ID NO: 46), sIII NRP1 (551 aa) and c/sIV NRP1 (609 aa; RefSeq: NP_001019800.1; NM001024629.2, SEQ ID NO: 45) (Cackowski et al., 2004, Genomics, 84(1): 82-94; Rossignol M et al., Genomics 2000; 70(2):211-222; and Gagnon M L et al., 2000, Proc. Natl. Acad. Sci. USA; 97(6):2573-2578)). The full-length form of the protein contains all 17 exons, whereas soluble isoforms are created by alternative splicing of the NRP1 gene or reading through introns. The b/s12, and c/sIV NRP1 isoforms contains the a1a2 and b1b2 domains and most of the b/c linker but no c-domain. Isoform sIII contains the a1a2 domain, the b1 subdomain but only part of the b2 subdomain. The s11 NRP1 isoform contains the a1a2 and b1b2 domains, followed by the portion of the b/c linker encoded by exon 11 and 83 novel amino acids.

In a second aspect of the present invention, following studies in models of ischemic retinopathies, SEMA3A was surprisingly identified as a modulator of cellular senescence. Indeed an unsuspected mechanism triggered by neurons in devascularized retinal zones was identified where they enter a state of premature cellular senescence and adopt a senescence-associated secretory phenotype (SASP). Data described herein show that secretion of SEMA3B by senescent cells drives paracrine senescence through IRE1a and propagate senescence across the ischemic tissue to various cell types including neurons, microglia and the overlying vasculature (paracrine senescence). Furthermore, sustained exposure to SEMA3A was shown to activate IRE1a, induce senescence and drive the expression of a panel of genes known to be critical for promoting and reinforcing the senescent state such as Pai1, Il6, Il1β, TGF-β and Tp53. SEMA3A was also shown to promote senescence-associated DNA-damage foci expressing γH2AX that are hallmarks of cellular senescence. Notably, and as demonstrated herein, genetic interference against SEMA3A limits senescence and stimulates tissue repair.

The inventors have found that modulating SEMA3A levels or activity enables to control cellular senescence, and the secretion of proteins (typically pro-inflammatory cytokines of the SASP) that are released during cellular senescence. The inventors have found that by inhibiting SEMA3A expression or activity, cellular senescence can be prevented, limited or decreased and induction of SASP can be prevented or reduced. Similarly, increasing SEMA3A activity (e.g., by increasing its expression or by contacting cells with a SEMA3A polypeptide) promotes senescence and induces the SASP.

These data provide evidence for a previously unsuspected role for SEMA3A in modulating autocrine and paracrine senescence through the SASP in pathological processes and uncover the therapeutic benefits of modulating SEMA3A activity in diseases and conditions associated with senescence.

(i) Methods of Inhibiting or Preventing Cellular Senescence by Inhibiting SEMA3A Signalling Cellular senescence, including autocrine and paracrine senescence can be inhibited or prevented by reducing SEMA3A activity (i.e., SEMA3A cellular signalling). SEMA3A activity can be inhibited by a number of approaches. Inhibition of SEMA3A cellular activity may be done directly by (i) reducing SEMA3A nucleic acid or protein expression, (ii) by inhibiting its secretion by the cell; or (iii) by sequestering secreted SEMA3A in order to inhibit it's binding to its receptor on the cell surface; thereby preventing intracellular signalling, activation of IRE1α and initiation and/or propagation of cellular senescence. Non-limiting examples of agents and approaches for inhibiting SEMA3A activity include (i) antibodies against SEMA3A; (ii) antibodies against one of its receptor (i.e., competing with SEMA3A binding to its receptor); (iii) antisense and RNAi methods for reducing SEMA3A expression; and/or (iv) use of a soluble receptor or fragment thereof, acting as a functional SEMA3A trap.

The present invention thus provides a method of inhibiting or preventing cellular senescence of a cell or induction of the senescence-associated secretory phenotype (SASP) in a cell comprising reducing SEMA3A level or activity.

The present invention also concerns a method of inhibiting or preventing cellular senescence of a cell or induction of the senescence-associated secretory phenotype (SASP) in a cell comprising contacting said cell with a SEMA3A antagonist.

Also provided is a method of inhibiting or preventing cellular senescence or induction of the senescence-associated secretory phenotype in cells of a subject comprising administering to said subject an effective amount of a SEMA3A antagonist.

As used herein the term "SEMA3A inhibitor" or "SEMA3A antagonist" refers to an agent able to reduce or block SEMA3A-mediated cell signaling associated with SEMA3A induction of the SASP and SEMA3A induced cellular senescence. The "SEMA3A inhibitor" or "SEMA3A antagonist" of the present invention binds to or interacts with the SEMA3A polypeptide or SEMA3A nucleic acid (SEMA3A gene or mRNA) in order to reduce SEMA3A polypeptide expression or interaction with its cognate receptor) such that SEMA3A-mediated cell signaling is reduced or abrogated. Non-limiting examples include an agent which reduces or blocks the expression (transcription or translation) of SEMA3A, an agent able to reduce or block SEMA3A secretion or an agent able to reduce or block SEMA3A binding to its receptor NRP1. Without being so limited, the agent can be natural or synthetic and can be a protein/polypeptide, such as but not limited to, an antibody that specifically binds to SEMA3A or NRP1 receptor; a soluble NRP1 polypeptide or fragment thereof (e.g., an NRP1 trap which binds to SEMA3A), a peptide, a small molecule, a polynucleotide such as but not limited to an antisense or a shRNA specific to SEMA3A nucleic acid sequence encoding a SEMA3A protein or functional variant or fragment thereof.

The above methods may be useful in treating or preventing diseases or conditions in which cellular senescence is detrimental such as various age-related conditions (e.g., sarcopenia, neurodegeneration, thinning of the epidermis, skin wrinkling, hair loss and greying hair, cataract and other diseases of old age), chronic obstructive pulmonary disease (COPD), idiopathic pulmonary fibrosis (IPF), atherosclerosis, osteoarthritis, osteoporosis and Parkinson's disease, glaucoma, intestinal bowel disease, intervertebral disc degeneration, brain aneurysm, aortic aneurysm, pancreatic fibrosis and cystic fibrosis. Inhibition or prevention of cellular senescence may also be useful during and/or after cancer treatment to alleviate side effects of chemotherapy/radiotherapy which include for example, metabolic dysfunction, accelerated aging, increased risk of cancer later in life. In embodiments, the senescence-associated diseases or conditions which are encompassed by the present invention exclude ocular diseases (e.g., retinal vascular diseases (ischemic retinopathies, macular edema)), inflammation, cerebral ischemia, stroke or cancer.

a. Antibodies.

In a particular aspect of the present invention, SEMA3A activity (e.g., SEMA3A-induced IRE1α activation) can be inhibited by using SEMA3A antibodies. These antibodies bind to SEMA3A in such a way that it inhibits its binding to its cognate receptor, NRP1, thereby preventing SEMA3A-mediated cellular signaling (79, 80).

Alternatively, antibodies directly targeting the NRP1 receptor, which block the binding of SEMA3A to NRP1 may also be used. In a particular aspect of the present invention, antibodies targeting NRP1 block SEMA3A binding to the receptor but do not substantially interfere with VEGF binding to NRP1. In an embodiment, the NRP1 antibody binds to the a1a2 (A) domain of the NRP1 polypeptide.

As used herein, the term "SEMA3A antibody" refers to an antibody that specifically binds to (interacts with) a SEMA3A protein and displays no substantial binding to other naturally occurring proteins other than the ones sharing the same antigenic determinants as the SEMA3A protein. Similarly, the term "NRP1 antibody" refers to an antibody that specifically binds to (interacts with) a NRP1 protein and displays no substantial binding to other naturally occurring proteins other than the ones sharing the same antigenic determinants as the NRP1 protein. SEMA3A/NRP1 antibodies include polyclonal, monoclonal, humanized as well as chimeric antibodies. The term antibody or immunoglobulin is used in the broadest sense, and covers monoclonal antibodies (including full length monoclonal antibodies), polyclonal antibodies, multispecific antibodies and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies.

Anti-human SEMA3A/NRP1 antibodies have been previously prepared (80) and are also commercially available from various sources including Santa Cruz. In general, techniques for preparing antibodies (including monoclonal antibodies and hybridomas) and for detecting antigens using antibodies are well known in the art and various protocols are well known and readily available.

b. Soluble Receptor or Fragment Thereof

Modulation of Sema3-mediated cellular senescence can be achieved by using naturally occurring soluble NRP1 polypeptides or synthetic NRP1 polypeptides (e.g., produced in vitro in cell lines (recombinantly) or chemically synthesized). As used herein, the terms, "NRP1 trap", or "NRP1 polypeptide trap" encompass a naturally occurring soluble NRP1 polypeptide (e.g., such as NRP1 secreted isoforms shown in FIGS. 17, 19, in Table 2 and in SEQ ID NOs: 44-47, 95 and 96), non-naturally occurring soluble NRP1 polypeptide and synthetic soluble NRP1 polypeptide including any functional soluble fragment of NRP1 or any functional variant of NRP1 which competes with endogenous (cellular, membrane-bound) NRP1 for SEMA3A ligand binding. In an embodiment, the NRP1 traps of the present invention do not exist in nature (i.e., are not naturally occurring) but are "derived" from naturally occurring NRP1 polypeptides (i.e. they are synthetic; e.g., NRP1 traps comprising the extracellular domain of NRP1 isoform 1 (e.g., aa 1-857 of transmembrane (cellular) NRP1) or a fragment or variant thereof). Generally, NRP1 traps of the present invention initially comprise a signal peptide at their N-terminal end (e.g., about amino acids 1-21 of the NRP1 amino acid sequence shown in FIG. 17) which is cleaved upon maturation and secretion by the cells. Accordingly, NRP1 polypeptide traps of the present invention lack amino acids 1-21 when administered as purified polypeptides or when prepared as pharmaceutical compositions comprising a purified or substantially pure form. Similarly, nucleic acids encoding NRP1 traps of the present invention comprise a polynucleotide sequence in 5' which encodes for a signal peptide (e.g., first 63 nucleotides encoding for the first 21 amino acids at the N-terminal end) which will allow the NRP1 trap to be synthesized and secreted by the cells. Depending on the conditions and cell type, the length of the signal peptide removed for secretion may vary. Removal of aa 1-20, 1-21 and 1-27 (see FIGS. 17-18 and for example, SEQ ID NOs: 47, 95 and 96) have been described. In a particular embodiment, the signal peptide corresponds to the first 21 amino acids of the NRP1 polypeptide set forth in FIG. 17 or SEQ ID NO: 47, 95 or 96.

TABLE 1

NRP1 protein domains

| Domain | Amino acid (with reference to SEQ ID NOs 47, 95 and 96) |
|---|---|
| Signal Peptide (SP) | 1-20, 1-21 or 1-27 depending on condition and/or cell type |
| a1 (CUB 1) | From end of signal peptide to about aa 141 |
| a2 (CUB 2) | From about aa 147 to about aa 265 |
| b1 (F5/8 Cl) | From about aa 275 to about aa 424 |
| b2 (F5/8 C2) | From about aa 431 to about aa 583 |
| c (MAM) | From about aa 591 to about aa 859 |
| Transmembrane | From about aa 860 to about 882 |
| Cytoplasmic | From about aa 883 to aa 923 |

Non-limiting examples of NRP1 traps that may be used in accordance with the present invention include naturally occurring soluble NRP1 set forth in SEQ ID NOs; 44-47, 95 and 96, NRP1 traps described in Table 2 below, in FIG. 18, and in WO 2016/03699, which is incorporated herein by reference. Of course, the mature, active form of soluble NRP1 traps which are administered to a subject or contacted with a cell lack the portion of the aa acid sequence corresponding to the signal peptide as well as the transmembrane and cytoplasmic domain normally present in cellular, membrane-bound NRP1.

TABLE 2

Exemplary NRP1 secreted isoforms and exemplary NRP1 traps of the present invention tested for Sema3A binding:

| Trap | Description | Amino acids including SP | Amino acids in mature trap without SP* | Mutation(s) | Deleted aa** with reference to full length NRP1 (FIG. 17) | Binding to SEMA3A | SEQ ID Nos: nts/aa |
|---|---|---|---|---|---|---|---|
| Iso-b | a1a2-b1b2-c (in part) Secreted NRP1 isoform-b/$S_{12}$; 644 amino acids Uniprot O14786-2; Refseq: NP_001019799.1; NM_001024628.2 | 1-644 E642G; F643I; P644K; | About 22-644; E642G; F643I; P644K | | Δ645-923 | Yes | 44 |

TABLE 2-continued

Exemplary NRP1 secreted isoforms and exemplary NRP1 traps of the present invention tested for Sema3A binding:

| Trap | Description | Amino acids including SP | Amino acids in mature trap without SP* | Mutation(s) | Deleted aa** with reference to full length NRP1 (FIG. 17) | Binding to SEMA3A | SEQ ID Nos: nts/aa |
|---|---|---|---|---|---|---|---|
| Iso-c | a1a2-b1b2-c (in part) Secreted NRP1 isoform-c/S$_{IX}$; 609 amino acids Uniprot: O14786 RefSeq: NP_001019800.1; NM001024629.2 | 1-586 and 622-644; E642G; F643I; P644K | About 22-586 and 622-644; E642G; F643I; P644K | | Δ587-621 | Yes | 45 |
| Iso-d | a1a2-b1b2-c (in part) Secreted NRP1 isoform-b/S$_{11}$; 704 amino acids Uniprot: Q5T7F0 | 1-622 and a novel 83 amino acid tail (704 aa) | About 22-704 | | Δ623-923 | Yes | 46 |
| G | a1a2-b1b2-c | 1-856; | About 22-856; | | Δ857-923 | Yes | 67/68 |
| R | a1a2-b1b2-c | 1-856; | About 22-856 | Y297A (VEGF, SEMA3A low) | Δ857-923 | Yes | 69/70 |
| Z | a1a2-b1b2-c | 1-856; | About 22-856 | E319K, D320K (VEGF, SEMA3A low) | Δ857-923 | Yes | 71/72 |
| AB | a1a2-b1b2-c | 1-856; | About 22-856 | E348K, S346A (Sema3A low) | Δ857-923 | No | 73/74 |
| AC | a1a2-b1b2-c | 1-856; | About 22-856 | D320K (VEGF low) | Δ857-923 | Yes | 75/76 |
| O | a1a2-b1b2 | 1-583; | About 22-583; | | Δ584-923 | Yes | 77/78 |
| Q | a1a2-b1b2 | 1-583 | About 22-583 | Y297A (VEGF, SEMA3A low) | Δ584-923 | No | 79/80 |
| M | a1a2-b1 | 1-424; | About 22-424 | | Δ425-923 | Yes | 81/82 |
| P | a1a2-b1 | 1-424 | About 22-424 | Y297A (VEGF, SEMA3A low) | Δ425-923 | No | 83/84 |
| N | a1a2 | 1-265 | About 22-265 | | Δ266-923 | No | 85/86 |
| W | a1a2-b1-c (in part) | 1-430 and 584-795 | About 22-430 and 584-795 | | Δ431-583; Δ796-923 | Yes | 87/88 |
| X | a1a2-b1-c, (in part) | 1-430 and 584-856 | About 22-430 and 584-856 | Y297A (VEGF, SEMA3A low) | Δ431-583; Δ857-923 | No | 89/90 |
| Y | a1a2-c | 1-274 and 584-856 | About 22-274 and 584-856 | | Δ275-583; Δ857-923 | No | 91/92 |
| S | a1a2-b1-c | 1-430 and 584-856 | About 22-430 and 584-856 | | Δ431-583; Δ857-923 | Yes | 93/94 |
| AD | a1a2b1 | 1-424, 561-583 | About 22-424 and 561-583 | D320K (VEGF low) | Δ425-560 Δ584-923 | No | 51/52 |
| AE | a1a2b1b2 | 1-560 | About 22-560 | D320K (VEGF low) | Δ561-923 | No | 53/54 |
| AF | a1a2b2c | 1-280 and 431-856 | About 22-429 and 431-856 | | Δ281-430; Δ857-923 | No | 55/56 |
| AG | a1a2b2 | 1-280, 431-583 and 631-700 | About 22-280, 431-583 and 631-700 | | Δ281-430; Δ584-630; and Δ701-923 | Yes | 57/58 |
| AJ | a2b1b2c | 1-26, 143-630 and 701-856 | About 22-26, 143-630 and 701-856 | | Δ27-142; Δ631-700; Δ857-923 | Yes | 59/60 |
| AK | a2b1b2 | 1-26 and 143-583 | About 22-26 and 143-583 | | Δ27-142 Δ584-923 | Yes | 61/62 |
| AR | a2b1 | 1-26 and 143-424 | About 22-26 and 143-424 | | Δ27-142 Δ425-923 | Yes | 63/64 |
| AS | a2b1c | 1-26, 143-430, and 584-856 | About 22-26, 143-430, and 584-856 | | Δ27-142 Δ431-583 Δ857-923 | Yes | 65/66 |

*may vary depending on cell type/condition because of SP maturation
**numbering with reference to full length NRP1 (including SP)

In an embodiment, the NRP1 trap of the present invention comprises: (i) amino acids 1-856 (preferably in its mature form, from the aa following the signal peptide (e.g., aa 21, 22 or 28) to aa 856) of the human NRP1 polypeptide; (ii) amino acids 1 to 583 (preferably in its mature form, from the aa following the signal peptide (e.g., aa 21, 22 or 28) to aa 583) of the human NRP1 polypeptide; (iii) amino acids 1 to 424 (preferably in its mature form, from the aa following the signal peptide (e.g., aa 21, 22 or 28) to aa 424) of the human NRP1 polypeptide; (iv) amino acids 1 to 265 (preferably in its mature form, from the aa following the signal peptide (e.g., aa 21, 22 or 28) to aa 265) of the human NRP1 polypeptide; (v) amino acids 1 to 430 and 584 to 856 (preferably in its mature form, from the aa following the signal peptide (e.g., aa 21, 22 or 28) to aa 430 and aa 584 to aa 856) of the human NRP1 polypeptide; (vi) amino acids 1 to 274 and 584 to 856 (preferably in its mature form, from the aa following the signal peptide (e.g., aa 21, 22 or 28) to aa 274 and aa 584 to aa 856) of the human NRP1 polypeptide; (vii) amino acids 1 to 430 and 584 to 856 (preferably in its mature form, from the aa following the signal peptide (e.g., aa 21, 22 or 28) to aa 430 and aa 584 to aa 856) of the human NRP1 polypeptide. In embodiments, the NRP1 polypeptide comprises or consists of the amino acid sequence set forth in FIG. 17, SEQ ID NO: 44, 45, 46, 47, 95 or 96 or an allelic variant or functional variant thereof.

Given that NRP1 distinctly regulates the effects of its ligands on signal transduction and cellular responses, it may be advantageous to specifically inhibit of the activity of SEMA3A not that of the others. In a particular embodiment, the NRP1 traps of the present invention may comprise one or more mutation which reduces the ability of NRP1 to bind to for example, VEGF. Such mutation may be used to more specifically modulate the activity of NRP1 associated with the binding of SEMA3A, with fewer effects on endogenous NRP1 activities associated with other ligands.

Thus, in an embodiment, the NRP1 trap of the present invention is a polypeptide which binds to SEMA3A but not to VEGF. For example the NRP1 trap may comprise the a1 and/or a2 subdomain(s) which bind(s) to SEMA3A but not the b1 and/or b2 subdomain(s) required for VEGF binding (e.g., 1.1, Trap M, Trap N, Trap Y—see Table 2). In an embodiment, the NRP1-derived trap comprises domains a1 and a2 corresponding to amino acids 22 to 275 of the human NRP1 amino acid sequence set forth in FIG. 17. The NRP1 trap may also comprise a mutation (e.g., a deletion or substitution) which abrogates or reduces significantly the binding of VEGF to NRP1 but not that of SEMA3A to NRP1 or may preferentially bind to SEMA3A compared to VEGF (e.g., Trap Z,—see also Tables 2 and 6). Non-limiting examples of such mutation comprise a substitution at the glutamic acid at position 319 and at the aspartic acid at position 320 in NRP1 (e.g., E319K and D320K such as in Trap AC and Z).

In an embodiment, the soluble NRP1 polypeptide or functional variant or fragment thereof (i.e., NRP1 trap) comprises or consists of traps as set forth in FIGS. 17, 18, SEQ ID NO: 44, 45, or 46 or Table 2 or any functional variant thereof which binds to SEMA3A. In embodiments, the soluble NRP1 polypeptide trap comprises or consists of the extracellular domain of a polypeptide set forth in SEQ ID NO: 47, 95 or 96. In embodiments, the NRP1 trap which is used in accordance with the present invention has a binding affinity for SEMA3A which is at least 3 times that for VEGF165. In embodiments, the NRP1 trap which is used in accordance with the present invention has a binding affinity for SEMA3A which is at least 4 times that for VEGF165. In embodiments, the NRP1 trap which is used in accordance with the present invention has a binding affinity for SEMA3A which is at least 5 times that for VEGF165. In embodiments, the NRP1 trap which is used in accordance with the present invention has a binding affinity for SEMA3A which is at least 10 times that for VEGF165. In embodiments, the NRP1 trap which is used in accordance with the present invention has a binding affinity for SEMA3A which is at least 15 times that for VEGF165. In embodiments, the NRP1 trap which is used in accordance with the present invention has a binding affinity for SEMA3A which is at least 18 times that for VEGF165. In embodiments, the NRP1 trap which is used in accordance with the present invention has a binding affinity for SEMA3A which is at least 10 times that for VEGF165. In embodiments, the NRP1 trap which is used in accordance with the present invention has a binding affinity for SEMA3A which is at least 20 times that for VEGF165 (see for example Table 6).

Because the NRP1 traps of the present invention are secreted, they generally lack the transmembrane domain (e.g., corresponding to amino acids residues 860 to 883 of the NRP1 polypeptide sequences shown in FIG. 17) and the cytosolic domain (e.g., corresponding to amino acids residues 884-923 of the NRP1 polypeptide isoform 1 sequences shown in FIG. 17) found in, for example, human NRP1 isoform 1 (SEQ ID NOs: 95, 96, and FIG. 17). In embodiments, the NRP1 traps of the present invention lacks completely or partially domain c of NRP1. NRP1 isoform 1 comprises a larger c domain (see FIG. 17), while that of isoforms b and c is shorter.

As noted above, the present invention also encompasses the use of functional variants and functional fragments of the NRP1 polypeptide traps described herein in the methods described herein. Functional variants are derived from "wild-type" (native) human NRP1 polypeptides sequences (including any allelic variations naturally found in the population, i.e., allelic variants). Accordingly, as used herein, a "functional variant" or "functional fragment" refers to any NRP1 derivative having substantially the same biological activities with respect to cellular senescence as the NRP1 traps of the present invention (i.e., are capable of reducing or preventing induction of the SASP and cellular senescence). Hence, functional derivatives include but are not limited to, proteins which differ from the NRP1 polypeptide traps disclosed herein by any modifications, and/or amino acid substitutions, deletions, additions (e.g., intra-sequence insertions) or carboxyl-terminal fusions which do not significantly decrease the intended biological effects of the NRP1 traps of the present invention (e.g., inhibition or prevention of SEMA3A-mediated cellular senescence or inhibition or prevention of SEMA3A-dependent propagation of cellular senescence through the SASP and ultimately inhibition of IRE1α activation and RNAse activity, etc.). Modifications can occur anywhere including in the polypeptide backbone, (i.e., the amino acid sequence), the amino acid side chains and the amino or carboxy termini as long as the modifications do not substantially negatively affect the intended function of the NRP1 trap of the present invention (i.e., the variant is a functional variant which is capable of binding and sequestering SEMA3A polypeptide (e.g., naturally occurring human soluble NRP1 isoforms or an NRP1 trap corresponding to a polypeptide fragment of the extracellular domain of "wild-type" human NRP1 such as those exemplified in Table 2 and FIG. 18).

Table 3 provides examples of amino acids that may be modified (changed or altered) in NRP1 traps of the present invention. Preferably, the modification(s) in the functional variant (i) is a conservative substitution made in accordance with Table 3 below, (ii) corresponds to a functional allelic or polymorphic variation found in the population; or (iii) corresponds to an amino acid variation found in an ortholog of the human NRP1 polypeptide. Several orthologs of the NRP1 protein are known in the art. For example, by comparing the human NRP1 polypeptide sequence with the NRP1 polypeptide sequences from other known orthologs (e.g., mouse and rat-see FIG. 17), the person skilled in the art can easily identify the conserved residues and those which vary between species and hence can identify the amino acids that may be modified without substantial effect on the desired biological activity (e.g., inhibition or prevention of cellular senescence or inhibition or prevention of propagation of cellular senescence through the SASP). Non-limiting Examples of such amino acids are provided in Table 4.

TABLE 3

Exemplary conservative substitutions

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

TABLE 4

Non-limiting examples of amino acids that may be altered in the soluble NRP1 polypeptides/NRP1 traps of the present invention.

| WT Amino acid* | Domain | Exemplary substitution(s) |
|---|---|---|
| V11 | a1 | Threonine |
| V15 | a1 | alanine |
| P18 | a1 | Leucine |
| N24 | a1 | Serine |
| E26 | a1 | Lysine |
| D29 | a1 | Glycine |
| S35 | a1 | Asparagine |
| D62 | a1 | Glutamic acid |
| M68 | a1 | Isoleucine |
| F90 | a1 | Isoleucine |
| N96 | a1 | Glycine |
| H98 | a1 | Arginine |
| F99 | a1 | Leucine |
| R100 | a1 | Tryptophan |
| P110 | a1 | Serine |
| T153 | a2 | Alanine |
| S155 | a2 | Threonine |
| S170 | a2 | Cysteine |
| V177 | a2 | Isoleucine |
| P196 | a2 | Glutamine |
| M204 | a2 | Valine |
| D219 | a2 | Glutamic acid |

TABLE 4-continued

Non-limiting examples of amino acids that may be altered in the soluble NRP1 polypeptides/NRP1 traps of the present invention.

| WT Amino acid* | Domain | Exemplary substitution(s) |
|---|---|---|
| I242 | a2 | Valine |
| 269 | a2 | Isoleucine |
| 298 | b1 | Glycine |
| A303 | b1 | valine |
| N323 | b1 | Lysine |
| K359 | b1 | Arginine |
| I360 | b1 | Valine |
| V362 | b1 | Isoleucine |
| T371 | b1 | Serine |
| I372 | b1 | Leucine |
| P378 | b1 | Alanine |
| V379 | b1 | Isoleucine |
| L380 | b1 | Isoleucine |
| V392 | b1 | Phenylalanine, leucine |
| A393 | b1 | Glycine |
| P396 | b1 | Proline, serine |
| A409 | b1 | Valine |
| T410 | b1 | Serine |
| S449 | b2 | Alanine |
| G453 | b2 | Alanine |
| S469 | b2 | Threonine |
| A476 | b2 | Serine |
| S479 | b2 | Proline |
| I481 | b2 | Threonine |
| I487 | b2 | Valine |
| E491 | b2 | Aspartic acid |
| I498 | b2 | Valine |
| G518 | b2 | Alanine |
| M528 | b2 | Threonine |
| A553 | b2 | Alanine |
| P555 | b2 | Serine, threonine |
| A556 | b2 | Proline |
| G572 | b2 | Serine |
| A587 | c | Valine |
| L599 | c | Proline |
| D601 | c | Histidine |
| V634 | c | Isoleucine |
| N667 | c | Serine |
| 669 | c | Alanine |
| K672 | c | Arginine |
| S674 | c | Arginine |
| N717 | c | Serine |
| R741 | c | Histidine |
| A755 | c | Valine |
| I756 | c | Valine |
| S805 | c | Proline |
| A813 | c | Threonine |
| P820 | c | Threonine |
| G835 | c | deletion |
| E838 | c | Lysine |
| E854 | c | Aspartic acid |
| T916 | cytoplasmic | Proline |
| T919 | cytoplasmic | Asparagine |
| A179 | a2 | Valine |

*with ref. to FIG. 17 and SEQ ID NO: 96

Other functional variants of NRP1 traps of the present invention may be made by introducing one or more mutations corresponding to natural (allelic) variants detected in the population. These natural variants can be readily identified using well-known publicly available databases such as through the NCBI, GeneCard; HOMIM and Ensembl websites.

In embodiments, the functional variant of the NRP1 trap of the present invention comprises or consists of amino acids 1-857 of SEQ ID NO: 47 or a functional fragment thereof. In embodiments, the functional variant comprises one or more conservative amino acid substitutions located at one or more amino acid positions set forth in Table 4. In embodiments, the amino acid substitution is as set forth in Table 4. In embodiments, The soluble NRP1 polypeptide trap or functional fragment or variant (allelic variant) thereof of the present invention may comprise one or more additional polypeptide domain(s) to increase synthesis, purification, stability and/or bioavailability. For example, NRP1 traps of the present invention may include a FC domain (or part thereof such as the human FC domain) or a purification tag (e.g., a 6×-histidine tag). Such additional polypeptide domain(s) may be linked directly or indirectly (through a linker) to the soluble NRP1 polypeptide or functional fragment or variant thereof. In an embodiment the one or more additional domain is at the C-terminal end of the NRP1 polypeptide trap. In an embodiment the one or more additional domain is at the N-terminal end of the NRP1 polypeptide trap.

The soluble NRP1 polypeptide or functional variant or fragment thereof of the present invention may optionally include one or more polypeptide linkers. Such linkers may be used to link one or more additional polypeptide domain(s) to the soluble polypeptide of the present invention (e.g., a polypeptide domain which increases the stability of the polypeptide in vivo and/or a domain which facilitates purification of the polypeptide). Linker sequence may optionally include peptidase or protease cleavage sites which may be used to remove one or more polypeptide fragments or domains (e.g., removal of purification tag prior to in vivo administration of the soluble NRP1 polypeptides or functional variant or fragment thereof). One non-limiting example of a linker or domain which enables cleavage of the polypeptide and removal of, for example, polypeptide domain(s) (e.g., 6×his tag purification domain) includes a polypeptide comprising a TEV protease cleavage site (e.g., EXXYXQ\G or S, where \ denotes the cleavage site, SEQ ID NOs: 97 and 98). Many other TEV cleavage sites are known and many other protease/peptidase cleavage sites are known to the skilled person and may be introduced in the polypeptides of the present invention to optionally remove one or more polypeptide domains or fragments.

Polypeptide linkers may also be used to replace totally or partially domains which are normally found in the wild-type NRP1 polypeptide but which are absent in the soluble NRP1 polypeptide or functional variant or fragment thereof of the present invention. For example, in the NRP1 traps of the present invention, synthetic linkers may replace totally or partially subdomains a1, a2, b1, b2 and c. The length of the linker may correspond to the entire length of the domain removed or to a portion of it. Such linkers may increase protein folding, stability or binding to NRP1 ligands. Non-limiting examples of NRP1 traps comprising linkers are described in WO2016/033699, which is incorporated herein by reference. One non-limiting example of a useful polypeptide linker is a polyarginine polypeptide. Other linkers are known in the art and may be used in accordance with the present invention.

Thus, the present invention further provides soluble NRP1 polypeptides or functional variants or fragments thereof, nucleic acids encoding the soluble NRP1 polypeptides or functional variants or fragments thereof, vectors comprising the nucleic acids and host cells comprising the nucleic acids or vectors.

c. Inhibition of SEMA3A Expression

Various approaches are available for decreasing SEMA3A expression and thus SEMA3A-mediated cellular senescence. Non-limiting example includes the use of small hairpin shRNA (RNAi), antisense, ribozymes, TAL effectors targeting the SEMA3A promoter, CRISPR/Cas 9/Cpf1 systems or the like.

Expression of shRNAs or similar inhibitory RNAs in cells can be obtained by delivery of plasmids or through viral (e.g., lentiviral vector) or bacterial vectors. Non-limiting examples of shRNAs that may be used to inhibit SEMA3A expression are provided in Table 9 (see Example 11).

Therefore, in alternative embodiments, the invention provides antisense, shRNA molecules (iRNA) and ribozymes for exogenous administration to effect the degradation and/or inhibition of the translation of mRNA of interest. Preferably, the antisense, shRNA molecules and ribozymes target mammalian (preferably human) SEMA3A. An exemplary method of screening for antisense and ribozyme nucleic acids that may be used to provide such molecules as SEMA3A inhibitors of the invention is disclosed in U.S. Pat. No. 5,932,435.

In a further embodiment, expression of a nucleic acid encoding a polypeptide of interest (SEMA3A or NRP1), or a fragment thereof, may be inhibited or prevented using RNA interference (RNAi) technology, a type of post-transcriptional gene silencing. Examples of therapeutic antisense oligonucleotide applications and additional information about antisense molecules, shRNAs and RNAi technologies are provided above in relation to the inhibition of IRE1α and apply to the same extent to the inhibition of SEMA3A expression.

Accordingly, in an embodiment expression of a nucleic acid encoding a polypeptide of interest (SEMA3A or NRP1), or a fragment thereof, may be inhibited by introducing into or generating within a cell an siRNA or siRNA-like molecule corresponding to a nucleic acid encoding a polypeptide of interest (e.g. SEMA3A), or a fragment thereof, or to an nucleic acid homologous thereto.

(ii) Methods of Promoting Cellular Senescence by Increasing SEMA3A Activity

Cellular senescence, including autocrine and paracrine senescence can be promoted or induced by stimulating or increasing SEMA3A activity (i.e., SEMA3A cellular signaling). SEMA3A activity can be increased by a number of approaches including by increasing the expression of SEMA3A in a cell or by contacting a cell with a SEMA3A polypeptide or functional fragment or variant thereof.

Methods of promoting cellular senescence may be useful in diseases and conditions where senescence has beneficial effects such as tissue repair, cancer, renal fibrosis, wound healing, liver fibrosis, myocardial infarction cardiac fibrosis, atherosclerosis and pulmonary hypertension.

6. Modulation of Lipid Parameters

Applicants have found that the NRP1 gene is involved in the control of lipid metabolism (fat uptake/storage/accumulation) and that administration of a soluble NRP1 polypeptide or fragment thereof (e.g., NRP1 trap) significantly reduces diet-induced weight gain and improves lipid parameters, with benefits (or with concomitant positive effects) on blood glucose levels and insulin sensitivity.

Accordingly, in a further aspect, the present invention provides a method of altering a lipid parameter in a subject comprising modulating the expression and/or activity of the NRP1 gene and/or its associated NRP1 protein (e.g., transmembrane isoform 1). In a particular aspect, the method comprises administering to the subject a compound or composition which reduces or inhibits the expression and/or activity of the NRP1 protein. In embodiments, the method comprises administering to the subject (a) a soluble NRP1 polypeptide or fragment thereof (e.g., an NRP1 trap); (b) an NRP1 antibody; or (c) a composition comprising (a) and/or (b) together with a pharmaceutically acceptable carrier.

As used herein, the expression "disease or condition associated with fat accumulation" comprises any disease or condition which is caused by fat accumulation or considered comorbidity to fat accumulation (e.g., diet-induced overweight or obesity). A comorbidity is a medical condition whose prevalence highly increases (i.e., the risk of suffering from such additional disease or condition increases) in the presence of the original condition (e.g., fat accumulation; overweight or obesity). The term can indicate either a condition existing simultaneously with the original metabolic condition (e.g., fat accumulation) or a risk of developing such comorbid condition. The disease or condition associated with fat accumulation is said to be caused by, or otherwise related to fat accumulation in the subject. Diseases and conditions associated with fat accumulation include: high BMI; obesity; metabolic syndrome; NAFLD; cardiovascular diseases (CVD; heart diseases (e.g., congestive heart failure); coronary artery disease (hypercholesterolemia and atherosclerosis) pulmonary embolism, dyslipidemia and stroke); hypertension and Type II Diabetes mellitus (TI-IDM). In embodiments, the fat accumulation corresponds to a BMI greater than or equal to 25 kg/m$^2$. In another embodiment, the fat accumulation corresponds to a BMI greater than or equal to 30 kg/m$^2$.

Body composition parameters associated with fat accumulation are well known in the art. Such body composition parameters include visceral fat area (VFA), body mass index (BMI), waist to hip ratio (WHR); waist-to-height ratio, waist circumference (WC); arm circumference (AC), conicity index, percent body fat (PBF), triceps skin fold, subscapular skin fold, white adipose tissue (WAT) level; and brown adipose (BAT) tissue level.

Modulation of NRP1-mediated lipid metabolism can be achieved using naturally occurring soluble NRP1 polypeptides or synthetic (e.g., recombinantly produced or chemically synthesized) NRP1 polypeptides described herein.

7. Compositions/Formulations

The active ingredient(s) (e.g., one or more SASP inhibitor including one or more IRE1α inhibitors, an inhibitor of SEMA3A (e.g., an NRP1 trap), etc.) can be provided in a pharmaceutical composition. Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. The pharmaceutical compositions can include other medicinal or pharmaceutical agents, carriers, adjuvants, such as preserving, stabilizing, wetting or emulsifying agents, solution promoters, salts for regulating the osmotic pressure, and/or buffers. Proper formulation is dependent upon the route of administration chosen. For injection, the agents of the invention may be formulated in aqueous solutions, preferably in physiologically compatible buffers such as Hanks's solution, Ringer's solution, or physiological saline buffer. Methods well known in the art for making formulations can be found in, for example, Remington: The Science and Practice of Pharmacy, (20th ed.) ed. A. R. Gennaro A R., 2000, Lippencott Williams & Wilkins.

In embodiments, the compositions of the present invention are formulated for delivery to the eye e.g., eye drops or ocular injections. For ocular administration, the compounds can be formulated readily by combining the active compounds with pharmaceutically acceptable carriers suitable for ocular administration, as well known in the art. In embodiments, the carrier is a carrier which is not naturally found in mixtures with the compounds/agents/inhibitors of the present invention (i.e., a non-naturally occurring carrier).

For example, the pharmaceutical compositions can be formulated for topical administration, intravitreal administration, intracameral administration, subconjunctival administration, subtenon administration, retrobulbar administration, posterior juxtascleral administration, or a combination thereof. In some embodiments, the pharmaceutical compositions are formulated for topical administration. In some embodiments, the pharmaceutical compositions are formulated for intravitreal administration.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Alternatively, other delivery systems for pharmaceutical compounds may be employed. Liposomes and emulsions are well known examples of delivery vehicles. Particularly useful delivery system for periocular drug delivery (e.g., in the prevention and/or treatment or ocular diseases such as retinal diseases) include the transscleral absorption pathway which is considered one of the safest means of achieving consistent therapeutic drug concentrations in the inner coat of the posterior segment.

Effective dosage. Pharmaceutical compositions suitable for use in the present invention include compositions wherein the active ingredient(s) is/are contained in an effective amount to achieve the intended purpose. More specifically, a therapeutically effective amount means an amount effective to prevent development of or to alleviate at least one of the existing symptoms of the subject being treated. Determination of the effective amounts is well within the capability of those skilled in the art.

In embodiments, the effective dose of the compound(s) used in accordance with the present invention inhibits cellular senescence or propagation of cellular senescence (through the SASP) sufficiently to reduce or prevent at least one symptom or physiological effect associated with cellular senescence in diseases and conditions described herein (e.g., ocular vascular diseases and other diseases and conditions described herein). Certain compounds which have such activity can be identified by in vitro assays that determine the dose-dependent inhibition of SASP and/or IRE1α.

Alternatively, in other embodiments. the effective dose of the compound(s) used in accordance with the present invention is sufficient to induce or increases the SASP and cause cellular senescence.

For any compound used in the method of the invention, the therapeutically effective dose can be estimated initially from cellular assays. For example, a dose can be formulated in cellular and animal models to achieve a circulating concentration range that includes the IC50 as determined in cellular assays (i e., the concentration of the test compound which achieves a half-maximal inhibition of the cellular signaling function of SASP and/or IRE1α, (usually in response to inflammatory mediators such as Il-1β or other activating stimulus such as hypoxia, ischemia, cellular stress, ER stress).

A therapeutically effective amount refers to that amount of the compound that results in amelioration of symptoms in a subject. Similarly, a prophylactically effective amount refers to the amount necessary to prevent or delay symptoms in a patient (e.g., vascular hyperpermeability, spotted and/or blurry vision, pericytes loss, macular edema, retinal swelling, blood retinal barrier leakage, pathological neovascularization, reduced vascular repair, etc.). Toxicity and therapeutic efficacy of such compounds can be determined by standard pharmaceutical procedures in cell cultures or experimental animals, e.g., determining the maximum tolerated dose (MTD) and the ED (effective dose for 50% maximal response). The dose ratio between toxic and therapeutic effects is the therapeutic index and it can be expressed as the ratio between MTD and ED50. Compounds which exhibit high therapeutic indices are preferred. The exact formulation, route of administration and dosage can be chosen by the individual physician in view of the patient's condition.

Dosage amount and interval may be adjusted individually to provide levels of the active compound which are sufficient to maintain the desired modulating effects, or minimal effective concentration (MEC). The MEC will vary for each compound but can be estimated from in vitro data; e. g. the concentration necessary to achieve substantial inhibition of SASP and/or IRE1α expression or activity (e.g., secretion of cytokines, proteases and growth factors associated with the SASP, ribonuclease activity activation and processing of XBP1s) Dosages necessary to achieve the MEC will depend on individual characteristics and route of administration.

Definitions

In order to provide clear and consistent understanding of the terms in the instant application, the following additional definitions are provided.

The articles "a," "an" and "the" are used herein to refer to one or to more than one (i.e., to at least one) of the grammatical object of the article.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

For the recitation of numeric ranges herein, each intervening number there between with the same degree of precision is explicitly contemplated. For example, for the range of 18-20, the numbers 18, 19 and 20 are explicitly contemplated, and for the range 6.0-7.0, the number 6.0, 6.1, 6.2, 6.3, 6.4, 6.5, 6.6, 6.7, 6.8, 6.9, and 7.0 are explicitly contemplated. The terms "such as" are used herein to mean, and is used interchangeably with, the phrase "such as but not limited to".

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Practice of the methods, as well as preparation and use of the products and compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Green and Sambrook MOLECULAR CLONING: A LABORATORY MANUAL, 4th edition, Cold Spring Harbor Laboratory Press, 2014; Ausubel et al., CURRENT PROTOCOLS IN MOLECULAR BIOLOGY, John Wiley & Sons, New York, 2003 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "treat/treating/treatment" and "prevent/preventing/prevention" as used herein, refer to eliciting the desired biological response, i.e., a therapeutic and prophylactic effect, respectively. In accordance with the subject invention, the therapeutic effect comprises an amelioration of symptoms, and/or a reduction in the severity of the disease or condition (e.g., vascular eye disease), following administration of a pharmaceutical composition or compound (e.g., SASP inhibitor) of the present invention.

As used herein the term "preventing" or "prevention" in reference to diseases or conditions associated with senescence is meant to refer to a reduction in the progression or a delayed onset of at least one symptom associated with the disease or condition or one feature of cellular senescence.

Described herein are methods for modulating cellular senescence. As used herein, "cellular senescence" refers to a condition of a cell in which the cell is viable and metabolically active but has either lost the ability to proliferate or remains part of the tissue architecture but is unable to function/communicate properly with the rest of the tissue (i.e., it becomes dormant). Cellular senescence may increase with age or exposure to factors that induce DNA damage, such as mutation or chromosomal damage, or that induces a DNA damage response or disruption of chromatin structure resulting in changes in gene expression, such as genes associated with SASP. Senescence is thought to be a result of DNA or chromosomal insults including telomere shortening, chromosomal aneuploidy, DNA strand breaks, DNA chemical modification (e.g. alkylation), or triggering of a DNA damage response (DDR). Cellular senescence may be caused by, for example, ischemia, oncogene activation (through DDR) DNA damaging compounds such as chemotherapeutic agents, or DNA damaging radiation such as ionizing and UV radiation. Senescence may be caused by various other treatment regimes, such as corticoid treatment, anti-retroviral treatment, treatment with PPARγ agonists, treatment with xanthine oxidase inhibitors, treatment with bisphosphonates, treatment with antiprotozoal agents, and treatment with inflammatory agents. Senescence may also be caused by metabolic imbalance such as increased caloric intake, insulin resistance, type II diabetes, hyperinsulinemia, high fat diets, high protein diets, ER-stress response (UPR response, as demonstrated herein) and alterations in gut microbiota associated with these diseases. Senescent cells develop a distinctive secretome including metalloproteases, growth factors and inflammatory cytokines, a process named senescence-associated secretory phenotype (SASP) (37), which can propagate senescence to the surrounding tissue in a cell autonomous and non-cell-autonomous (paracrine) fashion (38-40). Thus, paracrine cellular senescence may be induced in cells as a consequence of the senescence-associated secretory phenotype (SASP). Paracrine senescence refers to a state of heightened secretion of proteins, such as pro-inflammatory cytokines (SASP), by senescent cells.

In various embodiments, the cellular senescence is caused by: (a) ischemia; (b) ageing of the cell; (c) DNA damage to the cell; (d) contact with a chemotherapeutic agent; (e) Irradiating the cell with DNA damaging radiation; (f) contacting the cell with an anti-retroviral agent; (g) contacting the cell with a proinflammatory agent; (h) contacting the cell with a DNA damaging agent; (i) contacting the cell with an agent that disrupts chromatin structure; (j) telomere erosion; (k) hypoxia; (I) oncogene activation; (m) telomere dysfunction and (o) any combination of at least two of (a) to (m).

Cells that have undergone cellular senescence may exhibit one or more of the following characteristics: growth arrest, formation of γ-H2AX (a phosphorylated form of the histone variant H2AX) nuclear foci; a rise in the level of p16INK4A; a rise in the expression level of p21 (CipI/Waf1); increased activity of senescence-associated β-galactosidase; production of senescence-associated heterochromatic foci (SAHF); loss of proliferation; trimethylation of histone 3 lysine 9 (H3K9me3); endoplasmic reticulum stress and induction of the unfolded protein response (UPR); increased level and/or activation of tp53; increased number and size of PML nuclear bodies; activation of IRE1α; increased glucose consumption; increased expression and/or secretion of pro-inflammatory cytokines, proteases and growth factors, of the "senescence-associated secretory phenotype" (SASP) (which may include, but is not limited to, Pai1, IL-6, IL-7, IL-1α, IL-1β, IL-8, TGF-β1, MCP-2, MCP4, MIP-Ia, MIP-3a, eotaxin-3, GM-CSF, MIF, EGF, FGF, HGF, VEGF, KGF, PIGH, NGF, MMP1, MMP3, MMP12, MMP13, MMP14, IGFBP2, IGFBP3, IGFBP4, IGFBP6, IGFBP7, fibronectin, cathepsin B, TIMP-2); lack of expression of Ki67; enlarged and flatten cell morphology; persistent DNA damage response (DDR) signaling; and formation of DNA segments with chromatin alterations reinforcing senescence (DNA-SCARS), which are nuclear foci which may contain DDR proteins such as phospho-ATM and ATR substrates. Cells that have undergone cellular senescence typically have increased levels of p16INK4a expression relative to the level of P16INK4a expression in cells that have not undergone cellular senescence. Also, cells that have undergone cellular senescence typically have increased levels of SA-β-Gal activity relative to that of cells that have not undergone cellular senescence.

As used herein, a "senescent cell" or a "cell harboring a senescent phenotype" refers to a cell having at least one of the following features: (i) growth arrest, (ii) enlarged and flatten cell morphology, (iii) DNA damage foci in the nucleus, (iv) secretion of growth factors proteases, cytokines and other factors defined as the senescence-associated secretory phenotypes (SASP) (e.g., PAI1, TNFAAIP2, IGFBP3, VIM, CDKN1A, FN1, CDKN2B, RRAS, IRF7, HSPA2, TES, CTGF, CCND1, ESM1, THBS1, S100A11, RAB31, IGFBP5, IL6, IL1β, TGFβ1, VEGFA, TP53), (v) senescence-associated β-galactosidase (SA-β-gal) activity (which partly reflects the increase in lysosomal mass), (vi) expression of the tumor suppressor p16INK4a (which may activate pRB and cause the formation of senescence-associated heterochromatin foci (SAHF)); (vii) SEMA3A expression; (viii) IRE1a activation (S724 phosphorylation) and increase splicing of XBP1s and/or (ix) increase expression of γH2AX, PML and/or p53 activation. In embodiments, a "senescent cell" is a cell having at least the features: (i), (ii) and/or (ii), (v), (vi) and (ix). In embodiments, the senescence is secondary to cellular ischemia. In embodiments, the senescence is paracrine senescence. In embodiments, the senescence is senescence after differentiation. In embodiments, the senescence is premature senescence. In embodiments, the premature senescence in characterized by an increase in the expression and/or RNAse activity of IRE1α. In embodiments, the senescence is retinal senescence. In embodiments, the senescence is microglial senescence. In embodiments, the senescence is characterized by (i) increased expression and/or activity of P16INK4a, Tp53, IRE1a, Cdkn1a Cdkn2a and/or senescence associated beta-gal activity; (ii) expression of γH2Ax and/or PML; and/or (iii) the expression of the senescence-associated secretory phenotype (SASP). In embodiments, the SASP comprises the secretion of IL-1β, IL-6, Pai1, TGFβ1, IRE1a and/or VEGF-.a. In embodiments, the above-mentioned SASP is secondary to cellular ischemia.

In embodiments, the above-noted cell is a terminally differentiated cell. In embodiments, the cell is a neuron, a microglial cell, a myeloid cell, a monocyte, a macrophage, an endothelial cell, a hepatic cell, a fat cell, a fibroblast, and/or retinal cell. In embodiments, the cell has suffered from cellular ischemia. In embodiments, the cell is a retinal ganglion cell. In embodiments, the cell is a retinal ganglion neuron. In embodiments, the cell is a vascular cell. In embodiments, the cell is a vascular endothelial cell. In embodiments, the cell is an avascular cell (i.e., it is located in an avascular area/region). In embodiments, the cell is an hepatic stellate cell. In embodiments, the cell is a microvascular endothelial cell. In particular embodiments, the cell is not an ocular cell. In particular embodiments, the cell is not a retinal cell. In embodiments, the cell is a mammalian cell. In embodiments, the cell is a human cell.

As used herein, "cellular ischemia" refers to a restriction in oxygen and/or nutrients (e.g., glucose) supply needed for cellular metabolism (to keep tissue alive) as well as inadequate removal of metabolic wastes. It includes local anemia in a given part of a body sometimes resulting from congestion (such as vasoconstriction, thrombosis or embolism). Ischemia can be partial (poor perfusion) or total. Ischemia is generally caused by problems with blood vessels (e.g., embolism, thrombosis (e.g., of an atherosclerotic artery), trauma, aneurysm, cardiomyopathies, hypoglycemia, radiotherapy, hypotension, anemia etc.) with resultant damage to or dysfunction of tissue.

The term "effective amount," as applied to the compound(s), biologics and pharmaceutical compositions described herein, means the quantity necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage can occur depending upon the condition of the subject being treated, and the physician or other individual administering treatment will, in any event, determine the appropriate dose for an individual patient.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid/polynucleotide sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 98% or 99% identical. As used herein, a given percentage of homology between sequences denotes the degree of sequence identity in optimally aligned sequences. An "unrelated" or "non-homologous" sequence shares less than 40% identity, though preferably less than about 25% identity, with any of the nucleic acids and polypeptides disclosed herein.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 98%, or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, WI, U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. For example, In embodiments, the compound of the present invention is an antisense/RNAi or shRNA that hybridizes to an NRP1 or SEMA3A nucleic acid sequence (preferably a human sequence).

The present invention is illustrated in further details by the following non-limiting examples.

Example 1

Retinal Ischemia Triggers Cellular Senescence

In order to elucidate the cellular processes triggered subsequent to vascular degeneration in ischemic retinopathies, we subjected mouse pups to a model of oxygen-induced retinopathy (OIR) that yields avascular neural zones similar to those observed in DR and ROP (27). Mouse pups were exposed to 75% oxygen from postnatal day (P) 7 to 12 to induce vaso-obliteration and returned to ambient air where maximal pre-retinal neovascularization is reached at P17 (27) (FIG. 1A). We then performed an unbiased transcriptomic analysis by high throughput RNA-sequencing of retinas at P14 OIR (when pathological pre-retinal angiogenesis commences) and carried out Gene Set Enrichment Analysis (GSEA) to identify defined gene expression patterns that were modulated. As expected, we found a strong positive correlation in clusters of inflammation (normalized enrichment score (NES)=1.58; false discovery rate (FDRq)

Figure 1B:
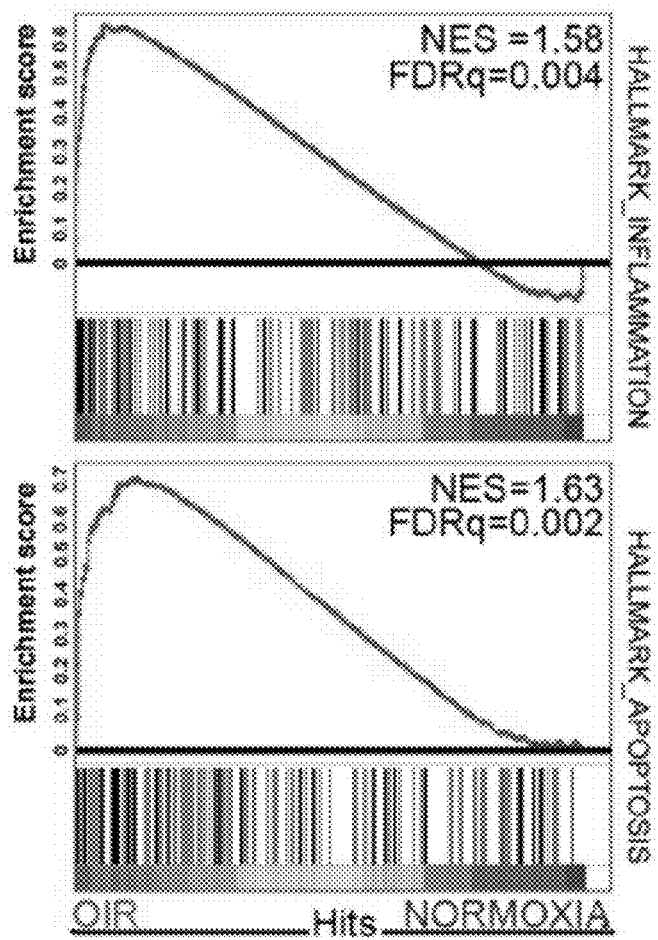
Figure 1C:
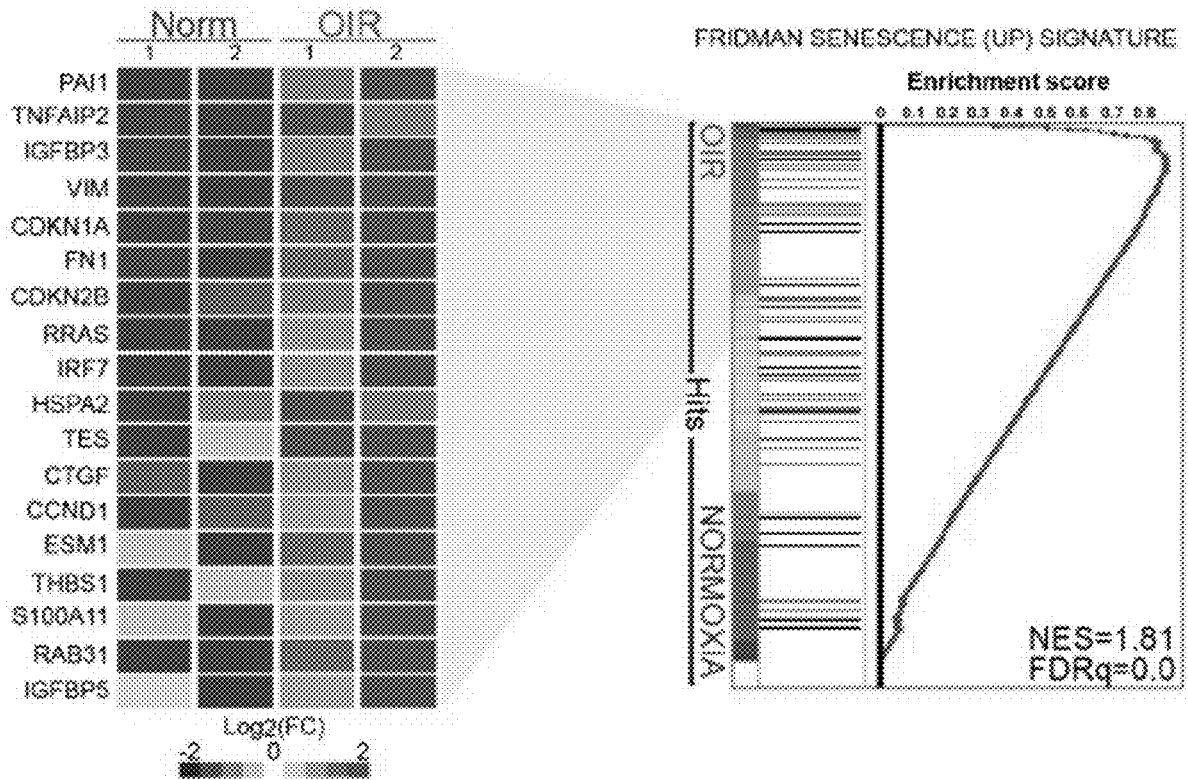

=0.004) and apoptosis (NES=1.63; FDRq=0.002) (FIG. 1B). Given the vastly post-mitotic nature of the neural retina, we also unexpectedly noticed a significant enrichment in the Fridman senescence signature (28) cluster (NES=1.81; FDRq=0.0) (FIG. 1C).

Figure 1D:
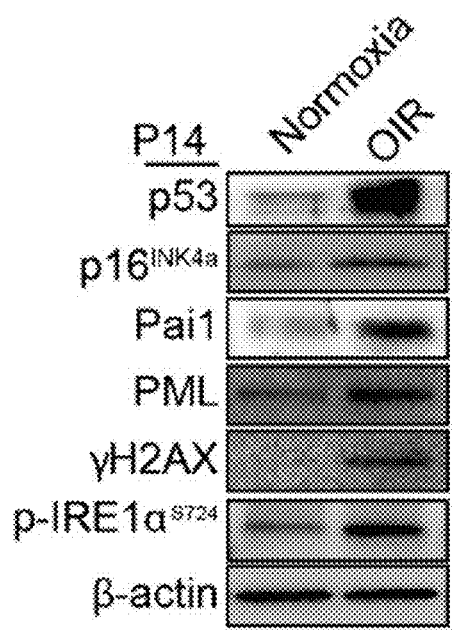
Figure 1E:
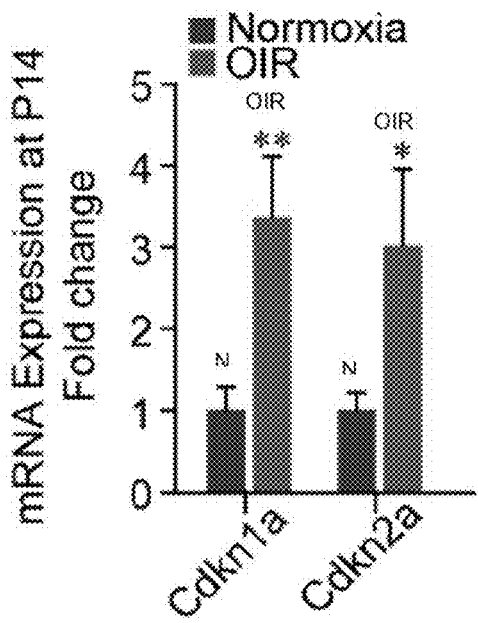

Cellular senescence is a permanent state of cell cycle arrest in which a cell remains viable and metabolically active (29). In a predominantly post-mitotic tissue such as the retina, senescence may be triggered through a DNA damage response or stimulation of tumor suppressor networks reported to be activated in ischemic retinas (30). A senescent state may thus protect retinal cells from low metabolic supply associated with ischemia and help escape hypoxia-associated cell death. Induction of senescence during OIR was further supported by upregulation of classical senescence-associated proteins, such as p53, p16$^{INK4a}$, Pai1, PML, γH2AX and activation of the ER-stress effector inositol requiring enzyme 1α (IRE1α), which has been suggested to promote cellular senescence (31) (FIG. 1D), and significantly increased transcript levels of cyclin-dependent kinase inhibitors (CDKi) Cdkn1a and Cdkn2a in OIR retinas (FIG. 1E).

Figure 10A:
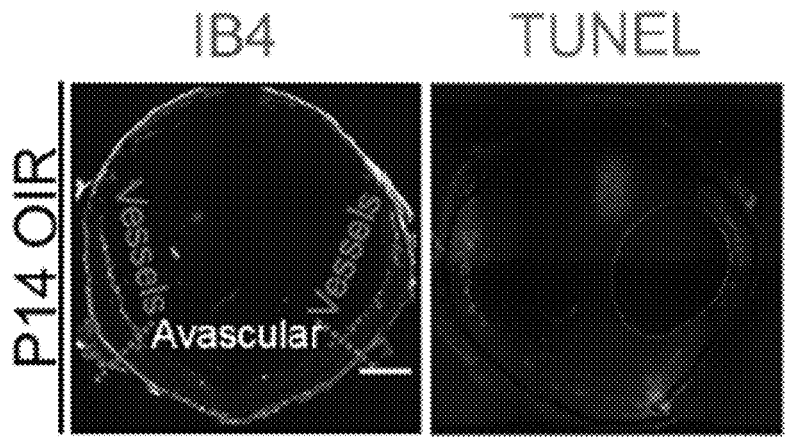
FIGS. 10A-F show that induction of retinal cellular senescence during OIR and in an STZ model of type I diabetes.

To determine which cells were triggering a program of senescence during OIR, we performed senescence-associated β-galactosidase (SA-β-gal) staining on retinal flatmounts at P14. Counterstaining with Isolectin B4 (IB4) revealed that senescent cells resided predominantly in avascular zones (36.99% of cells are SA-β-gal$^+$) compared to vascularized areas (18.79%; P<0.0001). Low numbers of SA-β-gal$^+$ cells were also found in control normoxic retinas (FIGS. 1F and G). In line, analysis of sagittal retinal sections revealed significantly elevated SA-β-gal staining in devascularized areas of the retinal ganglion cell layer (GCL) (10.77% vs 0.3%; P=0.0167) and to a lesser extent in the inner nuclear layer (INL) (2.61% vs 0.45%; P=0.0342) (FIGS. 1H and I). Both layers are intimately associated with the inner retinal vasculature that degenerates in ischemic retinopathies. Because of the hypoxic/oxidative and inflammatory nature of the ischemic retina (32) and GSEA of apoptotic genes in FIG. 1B, we further sought to establish which cells were undergoing apoptotic death during OIR. Terminal deoxynucleotidyl transferase-mediated biotinylated dUTP nick end labeling (TUNEL) revealed a predominance of apoptotic cells in the INL (FIG. 1J) and mostly in the periphery (FIG. 10A). Taken together (FIG. 1J), these data reveal a mutually exclusive pattern of retinal cellular senescence and apoptosis, where cells of the GCL associated with the central zone primarily adopt a senescent phenotype while cells of INL are more susceptible to apoptosis.

Example 2

Figure 2C:
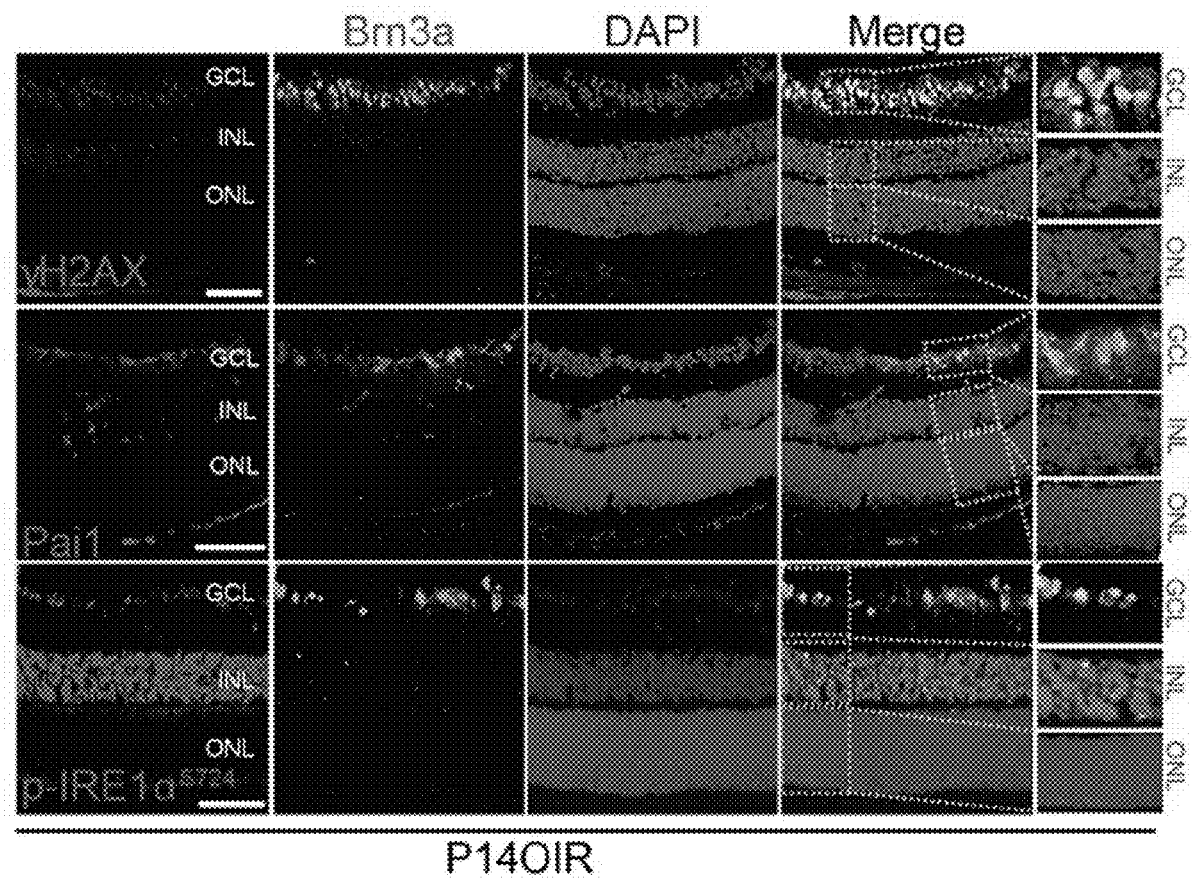
Figure 2D:
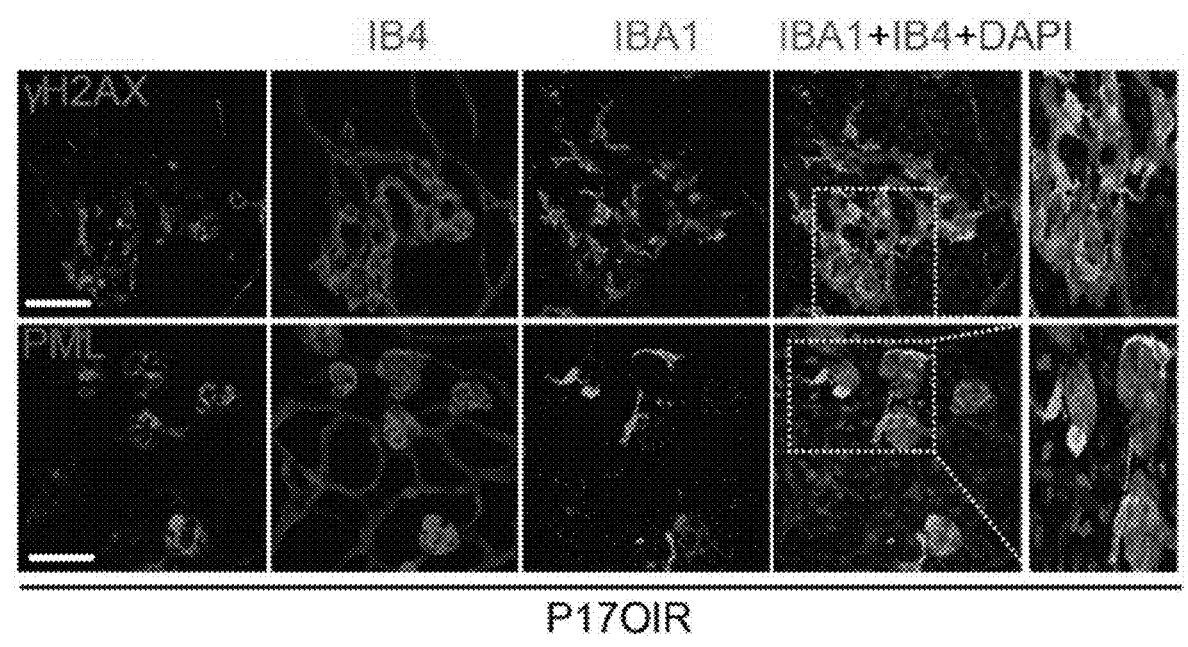
Figure 10B:
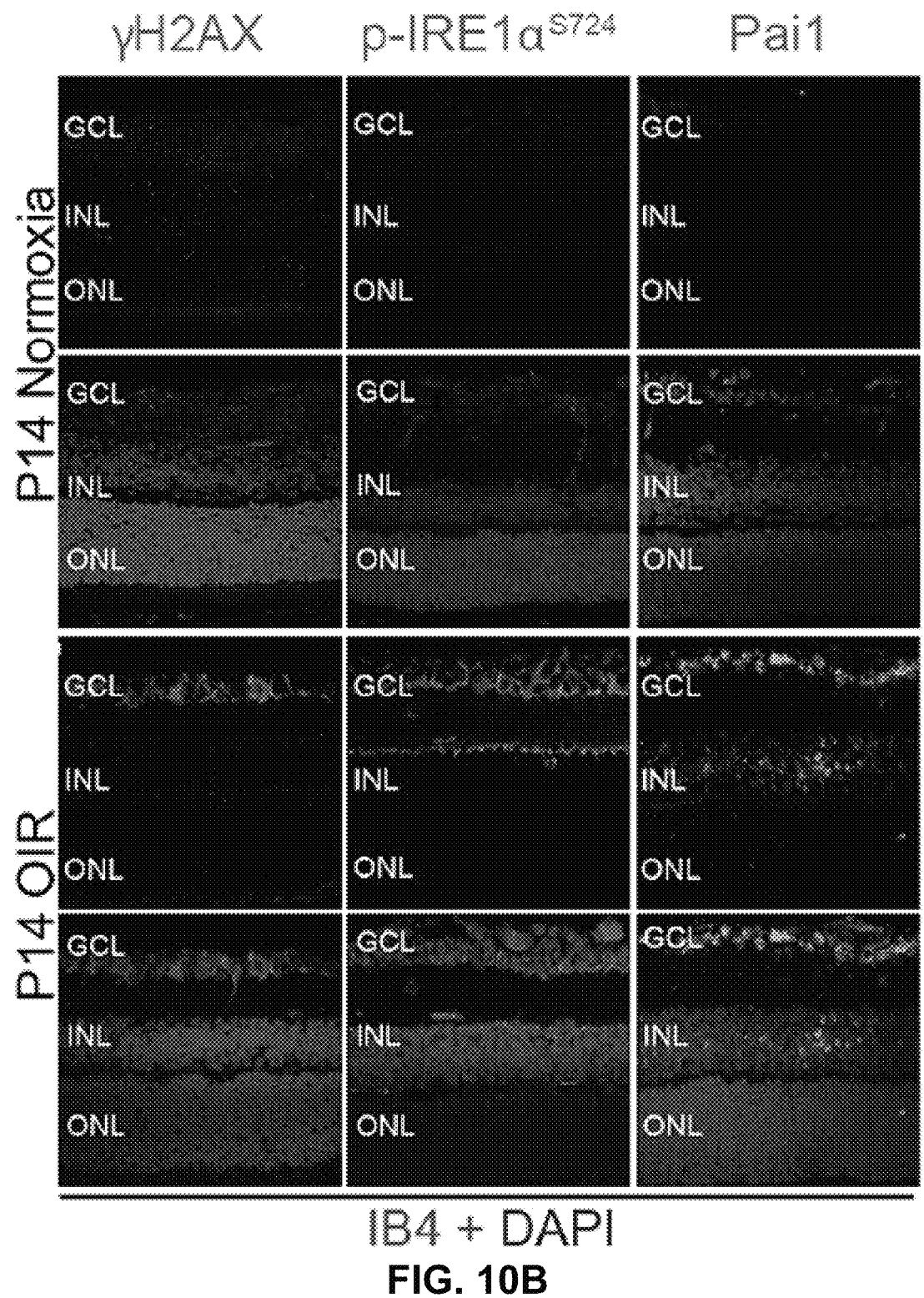
Figures 10C, 10D:
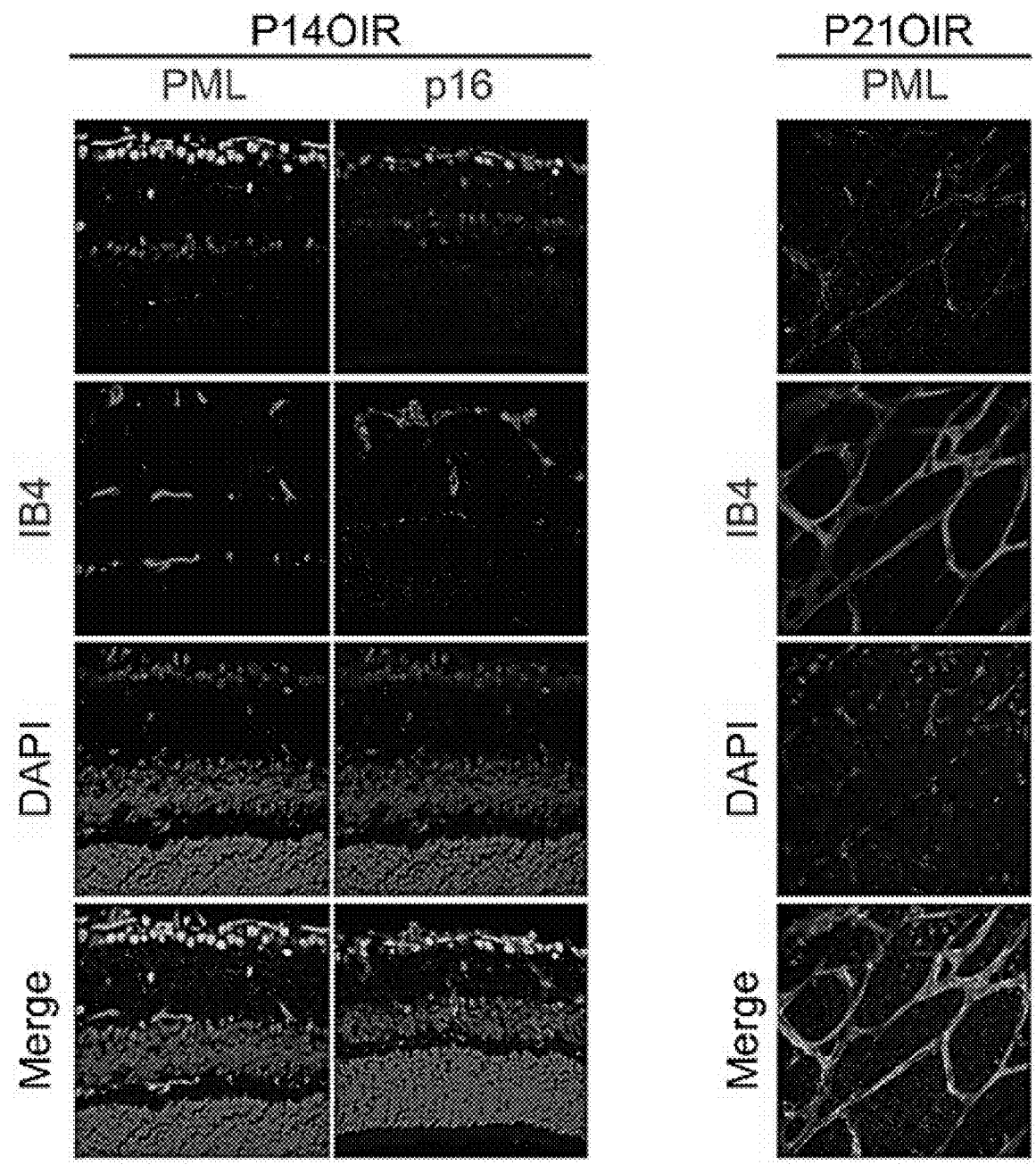
Figure 10E:
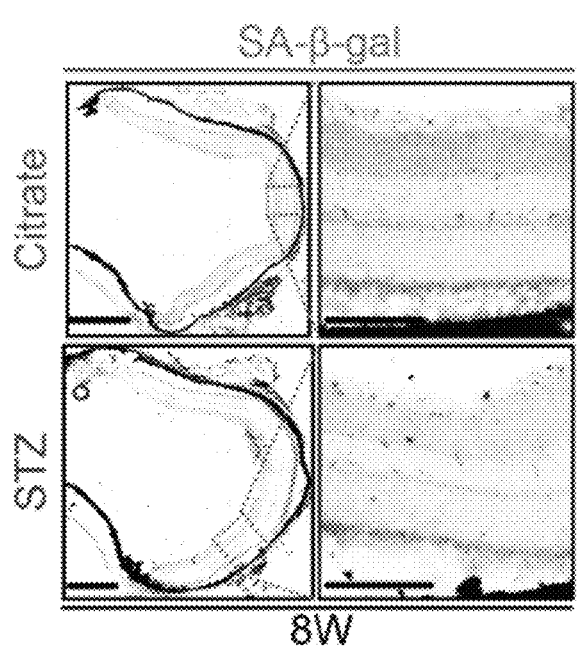
Figure 10F:
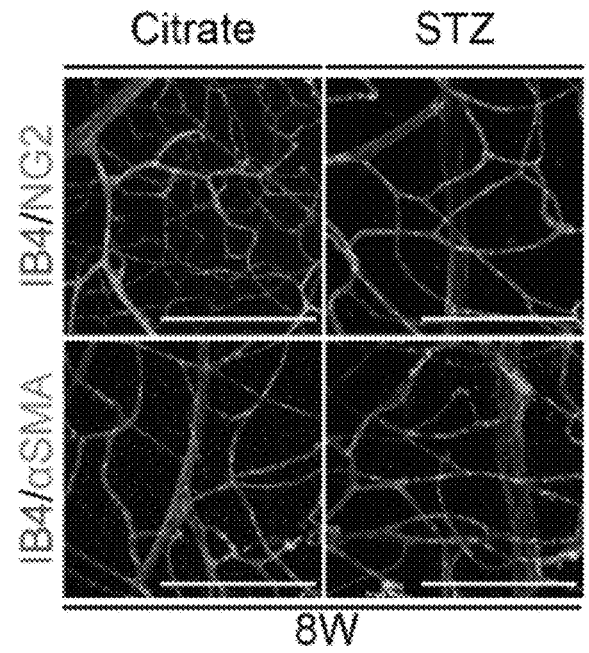
Figure 11A:
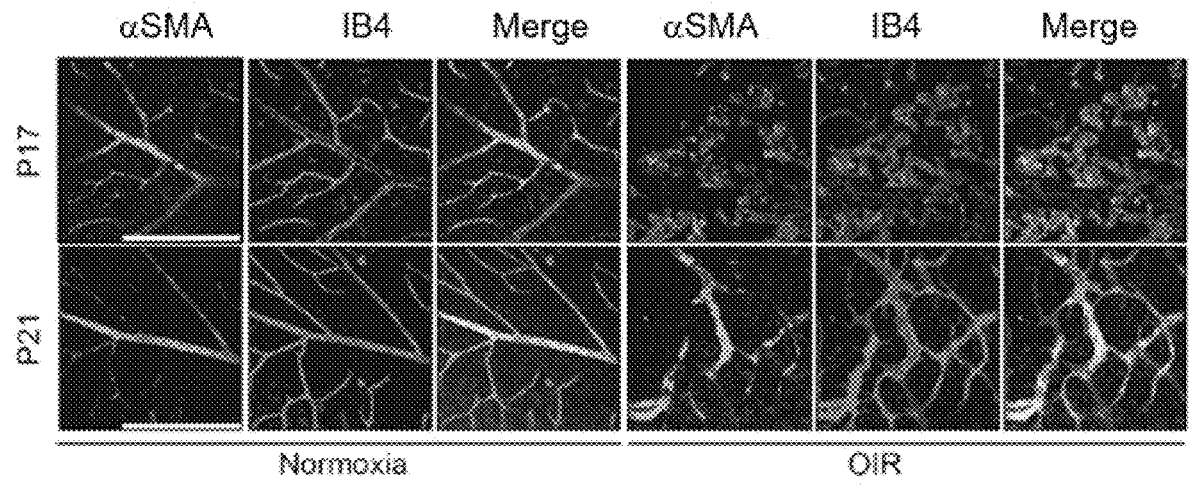
FIGS. 11A-B show vascular coverage during OIR. Representative confocal immunofluorescence of retinal flatmounts stained for α-SMA (FIG. 11A) or NG2 (FIG. 11B), isolectin B4 (IB4), at P17 and P21 during normoxia and OIR. Scale bars represent 200 μm.
Figure 11B:
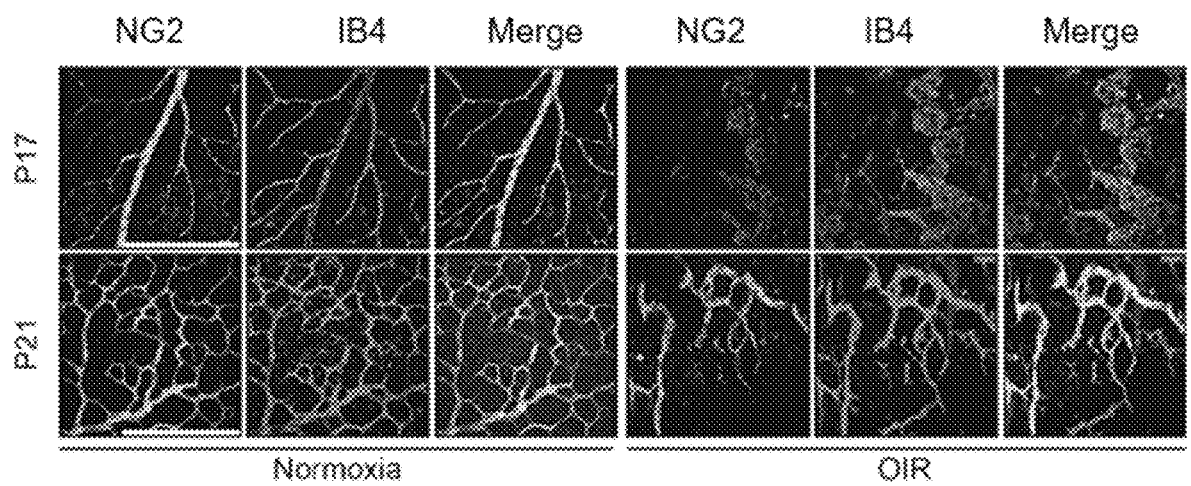

Retinopathy Triggers a Senescence-Associated Secretory Phenotype which Propagates Cellular Senescence The SASP typically reinforces senescence in autocrine and paracrine manners, heightens inflammation and has detrimental effects on tissue microenvironment (34). We interrogated whether the cellular senescence initially observed in the GCL at P14 during OIR (FIG. 1J) propagates to other cell populations of the retina. Initial SA-β-gal staining at P14 in OIR is concentrated in avascular areas (FIGS. 2A and B left panels) and centered on retinal ganglion neurons (RGCs) as substantiated by colocalization of Brn3a+ RGCs with markers of senescence (γH2AX, Pai1 and p-IRE1α$^{S724}$) (FIG. 2C). At this early time point, there is absence of senescence-associated labeling in vessels (FIGS. 10B and C). At P17, during maximal neovascularization, cellular senescence localizes to pathological vascular tufts (FIGS. 2A and B middle panels) and retinal microglia as evidenced by co-labeling of senescence markers γH2AX or PML with IB4 (vessels) and IBA1 (microglia) (FIG. 2D). This vasculature is tortuous and leaky (35) and less stable with less pericyte coverage (FIGS. 11A, B) (36). By P21 of OIR, when retinal vasculature has regenerated, SA-β-gal staining is predominantly confined to vascular cells (FIGS. 2A and B right panels, FIG. 10D). At this later time point, pericyte coverage is re-instated (FIGS. 11A, B). In addition, we observed SA-β-gal stained cells in the GCL of mice at 8 weeks of a streptozotocin-induced model of Type I Diabetes Mellitus (FIGS. 10E, F). The presence of retinal senescence in the STZ model is particularly important given that the OIR model is conducted in mouse pups and angiogenic responses diverge according to age (37). These finding support the presence of cellular senescence in a wide range of ocular vasculopathies. Given that the OIR model is a well-known and established model for ocular vascular pathologies, further studies were conducted in this model. Nevertheless, we observed a transient accumulation of senescent cells in different subcellular populations of the retina in different models of retinopathies. The dynamically evolving pattern of cellular senescence as a function of disease progression supports paracrine senescence.

Figure 2E:
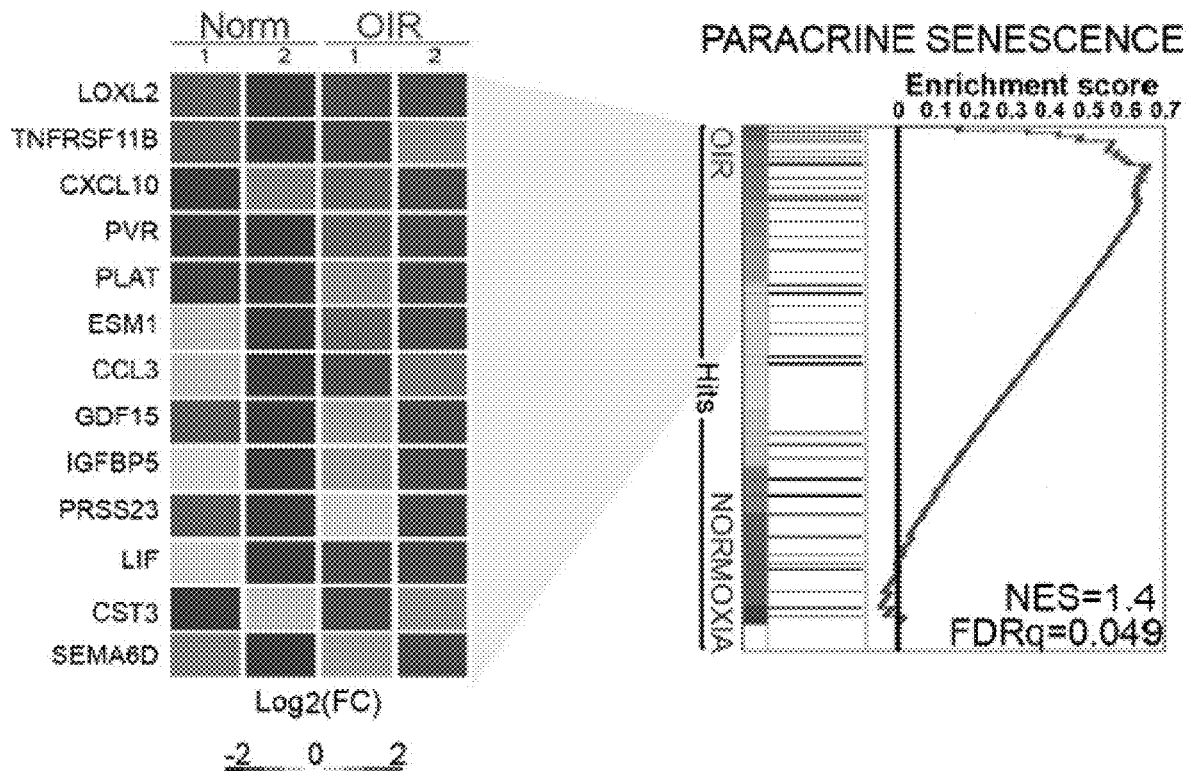
Figure 2F:
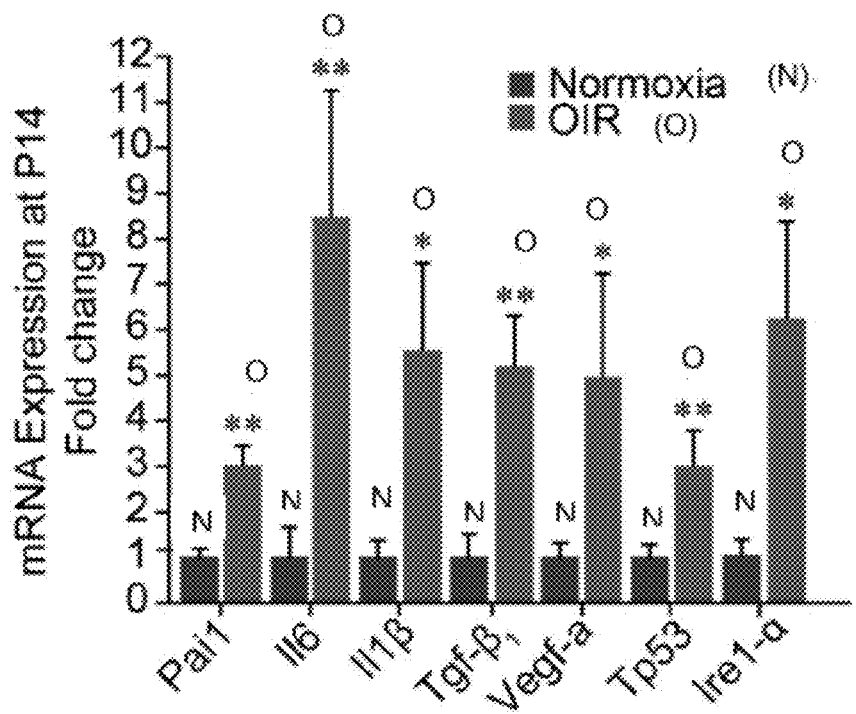

Senescent cells develop a distinctive secretome including metalloproteases, growth factors and inflammatory cytokines, a process named senescence-associated secretory phenotype (SASP) (39), which can propagate senescence to the surrounding tissue in a cell autonomous and non-cell-autonomous (paracrine) fashion (40-42). Heatmap and GSEA of OIR retinas also identified a positive correlation between retinal ischemia and paracrine senescence-associated genes (NES=1.4; FDRq=0.049) (FIG. 2E). Elevated expression of SASP-associated cytokines in OIR was confirmed by RT-qPCR for Pai1, Il6, Il1β, Tgf-β1, Vegf-a, as well as IRE1α, and the tumor suppressor Tp53 (FIG. 2F), suggesting that several cytokines central to pathological angiogenesis may originate from senescent retinal cells.

Example 3

Secretion of Sema3A by Senescent Cells Drives Paracrine Senescence

Figure 3A:
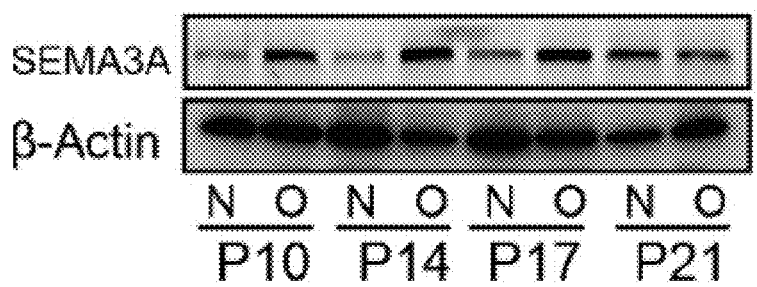
FIGS. 3A-Q show that SEMA3A mediates senescence and paracrine senescence.
Figure 5A:
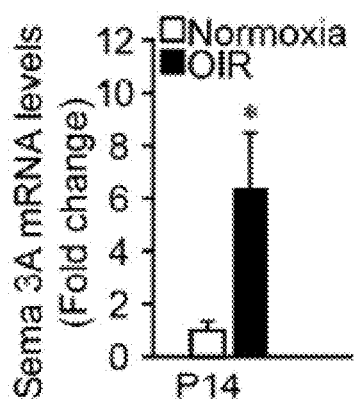
FIGS. 5A-H show that SEMA3A is secreted by senescent cells and triggers paracrine senescence in human retinal microvasculature endothelial cells. Relative mRNA levels of SEMA3A in P14 (FIG. 5A) and P17, P21 (FIG. 5B) retinas (normoxia vs OIR) measured by RT-qPCR.
Figure 5B:
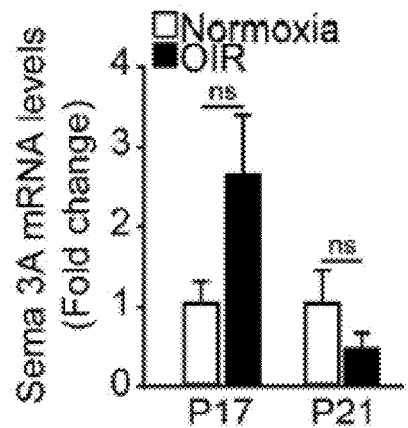

Given the spread of cellular senescence, we sought to identify factors that drive this process in OIR. An effector molecule associated with retinal ischemia that has been suggested to perturb cell cycle (43) is the classical guidance molecule Semaphorin 3A (SEMA3A). SEMA3A is induced throughout the vaso-obliterative and vaso-proliferative phases of OIR (44) and is secreted by hypoxic neurons to deviate regenerating blood vessels and metabolic supply towards less affected regions of the retina (44, 45). Given that expression of SEMA3A is temporally consistent with markers associated with senescent cells during progression of retinopathy (FIG. 3A, FIGS. 5A and B), we questioned whether SEMA3A contributed to propagating paracrine senescence.

Figure 3B:
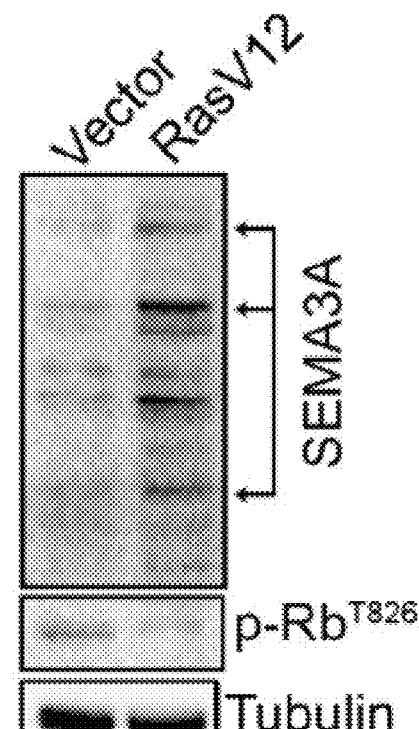
FIG. 3B: Immunoblot analysis of SEMA3A protein levels during Ras-induced senescence in Mouse Embryonic Fibroblasts (MEFs). Cell lysates from MEFs retrovirally transduced with H-RasV12 oncogene or control empty vector harvested 14 days post-selection.
Figure 3C:
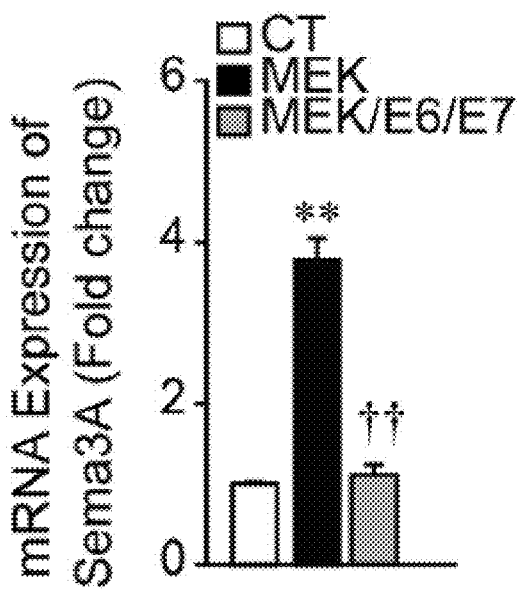
FIG. 3C: SEMA3A transcript levels in human normal diploid fibroblasts (IMR90) retrovirally transduced with empty vector, MEK1 alone or MEK and human papillomavirus oncoproteins E6 and E7. Data are from GEO profile GSE2487 (77) ($P<0.05$ CT compared to MEK and ††$P<0.05$ MEK compared to MEK/E6/E7).
Figure 3D:
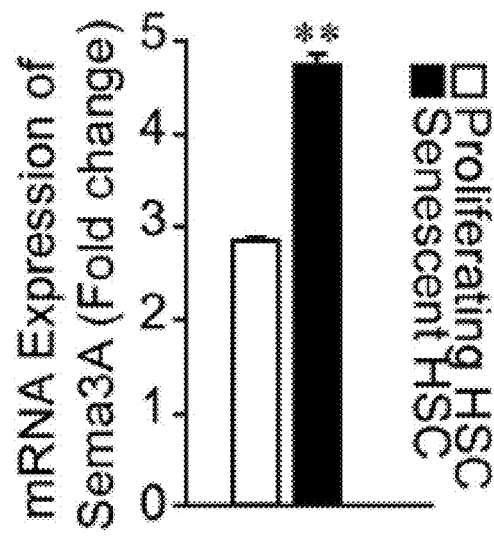
FIG. 3D: SEMA3A transcript levels in proliferating or senescent cultured primary human activated hepatic stellate cells (HSC) ($P=0.027$). Data are from GEO profile GSE11954 (78).
Figure 3E:
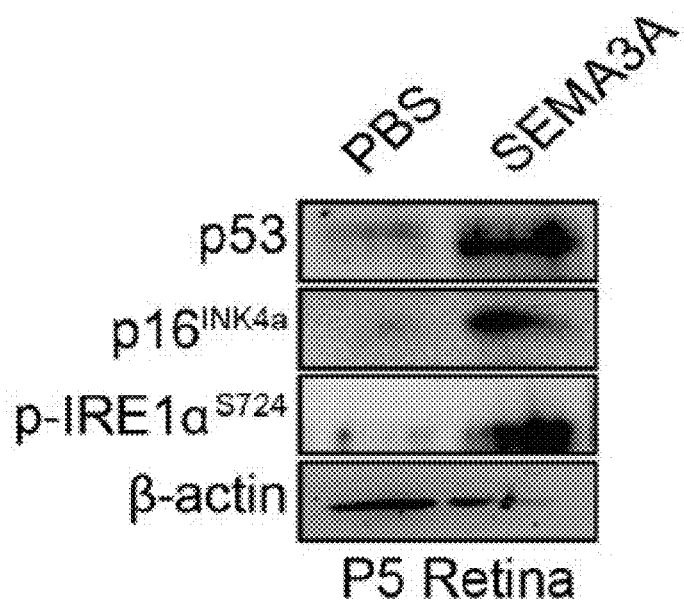
FIG. 3E: Retina from P5 pups that received intravitreal injection of recombinant SEMA3A (100 ng/ml) at P2, and harvested at P5, were subjected to immunoblot analysis against senescence markers and SA-β-gal staining of sagittal cryosections (FIG. 3F).
Figure 3F:
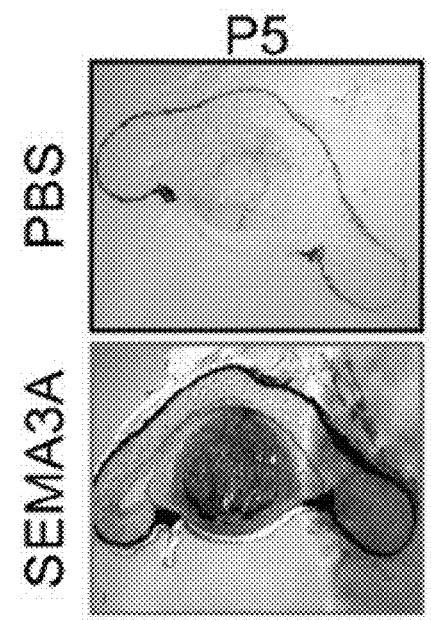
FIG. 3G: Cell cycle distribution profiles of SEMA3A-treated (100 and 500 ng/ml) HRMECs (human retinal microvascular endothelial cells) obtained by FACS analysis 7 days after treatment ($P<0.0001$; Two-way ANOVA)
FIG. 3H: Trans endothelial resistance measured in real time by electric cell impedance sensing (ECIS) demonstrated that SEMA3A reduced endothelial cell proliferation (3-7 days) ($0.048>P>0.009$)).
FIG. 3I: HRMEC, retinal neurons (661W) and J774 (macrophages-like cells) stimulated with recombinant SEMA3A (100 ng/ml) or vehicle (CT) for 7 days, stained for SA-β-gal and quantification in FIG. 3J. (n=3 separate experiments), $P<0.005$ and *$P<0.0001$ from two-tailed Student's t test J.
FIG. 3K: Conditioned medium (CM) was collected from senescent retinal neurons (661W) and macrophage-like, J774 cells grown for 7 days after $H_2O_2$ stimulation (150 μM, 2 h). Senescent cells were stained with SA-β-gal (right) and the level of secreted SEMA3A (S3A) protein in CM was evaluated by immunoblot (left).
FIG. 3L: SA-β-gal staining of neuronal 661W cells infected with the indicated vectors (Lv.sh_GFP or Lv.sh_SEMA3A) and treated with $H_2O_2$ or vehicle (CT). Senescence was evaluated after 7 days of treatment.
FIG. 3M: Quantification of percentage of SA-β-gal positive cells treated as in (J). (n=3 independent experiments). *$P<0.005$, $H_2O_2$-treated sh_GFP cells compared to untreated sh_GFP cells; and †$P<0.005$, $H_2O_2$-treated sh_S3A cells compared to $H_2O_2$-treated sh_GFP cells, from two-tailed Student's t-test. Data are presented as mean±SEM.
FIG. 3N: Induction of paracrine senescence (CM from senescent or not neuron precursor cells ((661W) see FIG. (I)) in HRMEC was evaluated after 7 days by SA-β-gal staining.
FIG. 3O: Quantification of percentage of SA-β-gal positive cells treated as in (1) with CM from the senescent 661W cells.
FIG. 3P: IB4 and SA-β-gal staining of retinas from P14 OIR mice injected intravitreally at P12 with Lv.sh_S3A or Lv.sh_GFP and quantified in FIG. 3Q (***$P<0.0001$)

First, evidence for a potential contribution of SEMA3A to paracrine senescence stemmed from observations that senescence-inducing oncogenes such as RasV12 (FIG. 3B) and MEK (FIG. 3C) trigger production of SEMA3A, as do stress-induced senescent human hepatic stellate cells (HSC) (FIG. 3D). In addition, intravitreal injection of recombinant SEMA3A in P5 pups induced a marked increase of p53, p16INK4a and IRE1α (FIG. 3E) accompanied by a marked augmentation of SA-β-gal staining (FIG. 3F).

Figure 3G:
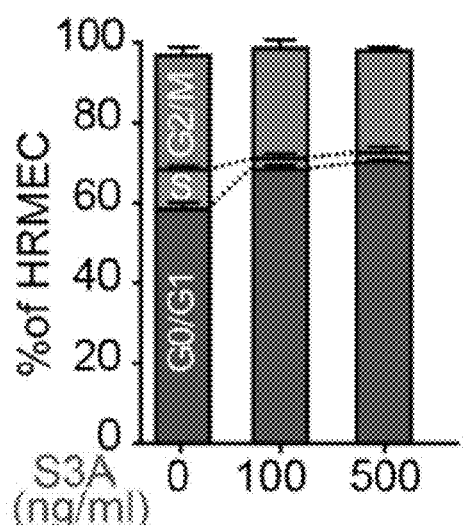
Figure 3H:
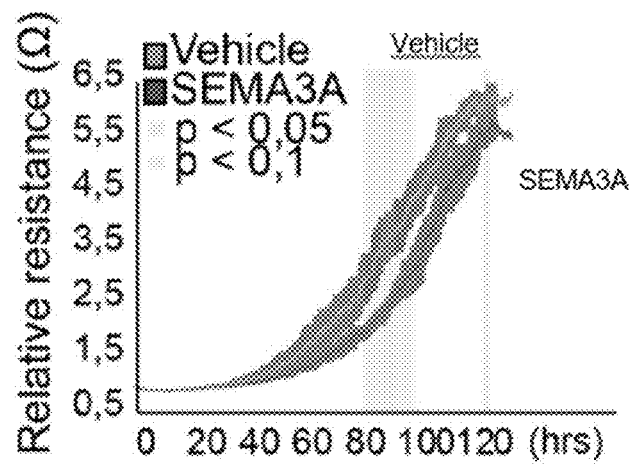

Ultimately, exposure of HRMECs to SEMA3A for 7 days (mimicking the first week of OIR) increased cell cycle arrest in G0/G1 while significantly reducing the S phase (FIG. 3G) and stunted normal endothelial cell growth as measured by electric cell impedance sensing (ECIS) (FIG. 3H).

Figure 3I:
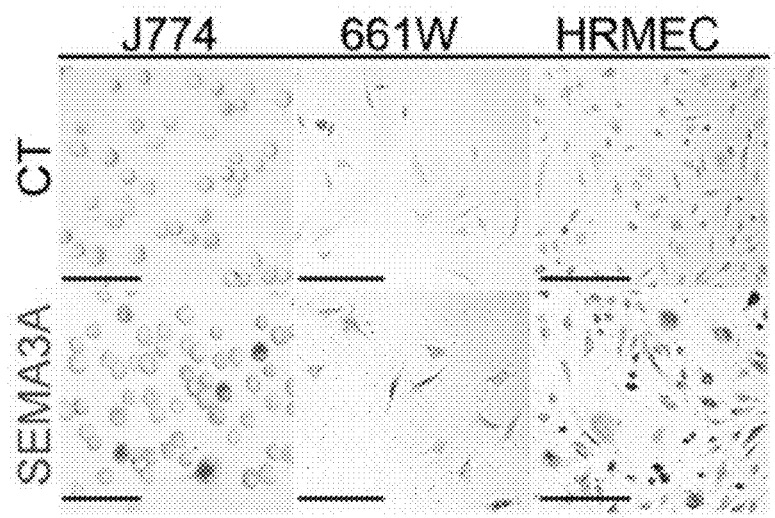
Figure 3J:
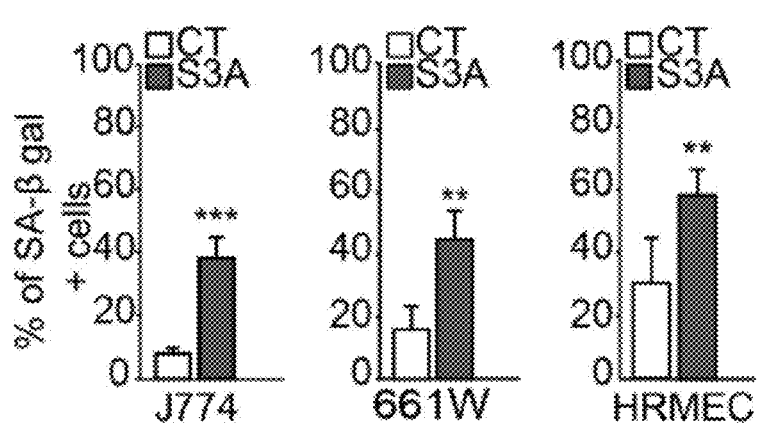
Figure 3K:
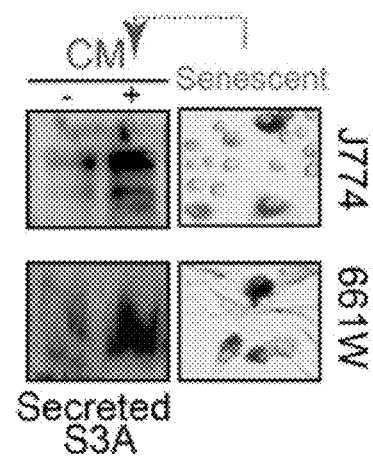

A role for SEMA3A in driving senescence is further substantiated by direct exposure of cells to recombinant SEMA3A, which induces senescence, in macrophage-like J774 cells ($P<0.0001$), in a cell line of retinal neurons (661W photoreceptors used to model retinal neurons) (46) ($P<0.001$) and in HRMECs ($P<0.001$) (FIGS. 3I and J). In addition, $H_2O_2$-driven-senescence which mimics the oxidative environment in retinopathy (3), triggered secretion of SEMA3A in cell lines that model populations entering senescence in retinopathy such as macrophage-like J774 cells (J774) and neuronal 661W cells (FIG. 3K).

Figure 3L:
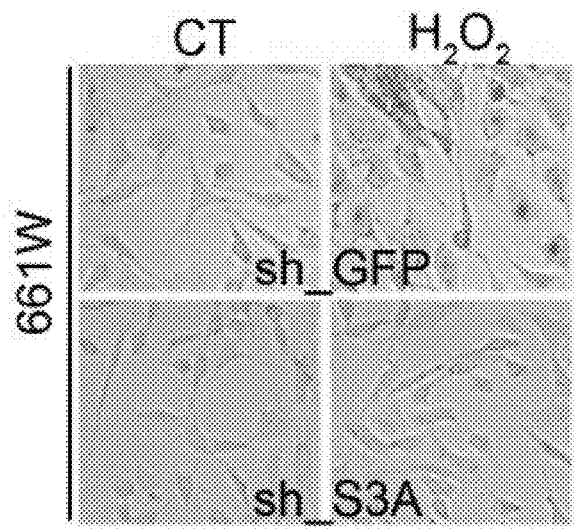
Figure 3M:
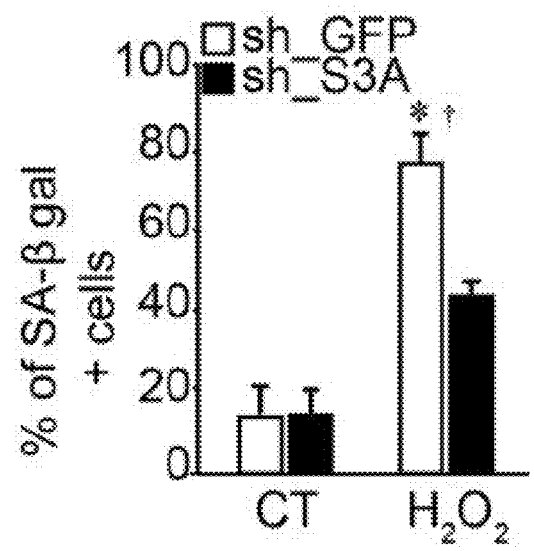
Figure 3N:
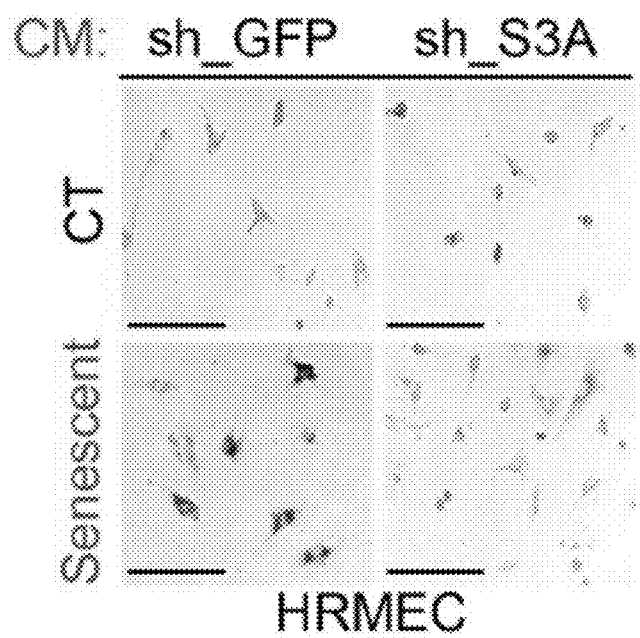
Figure 3O:
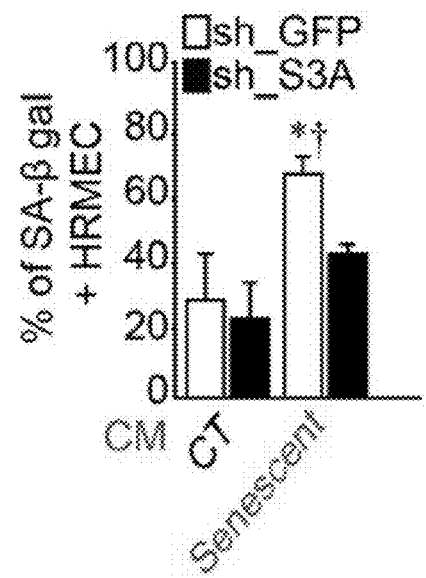
Figure 3P:
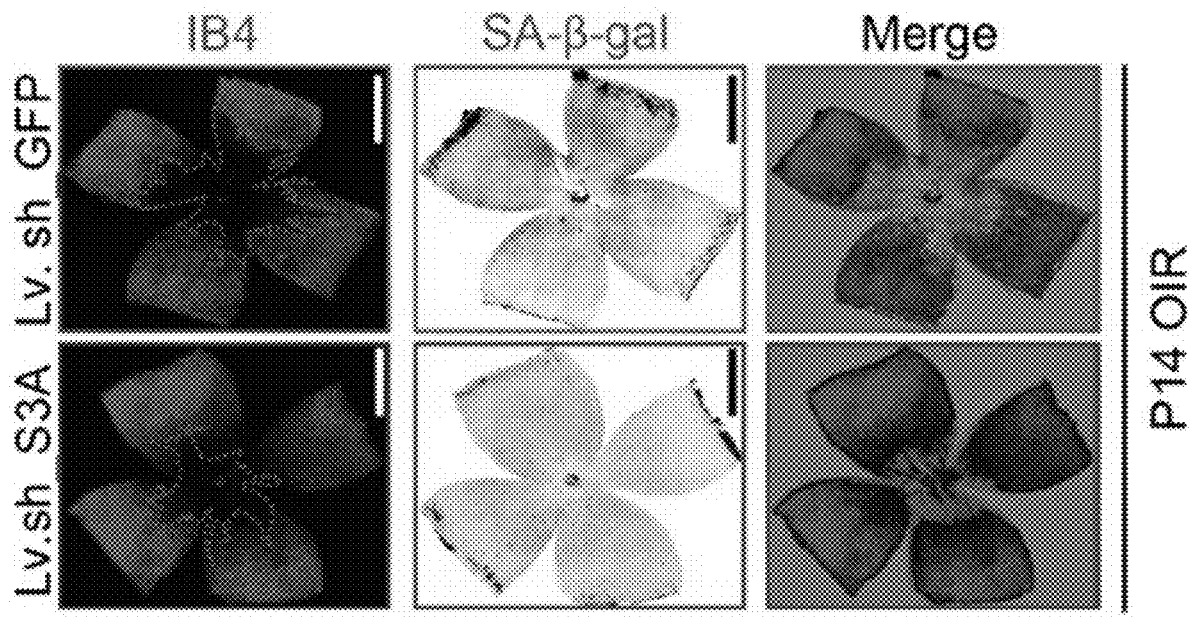
Figure 3Q:
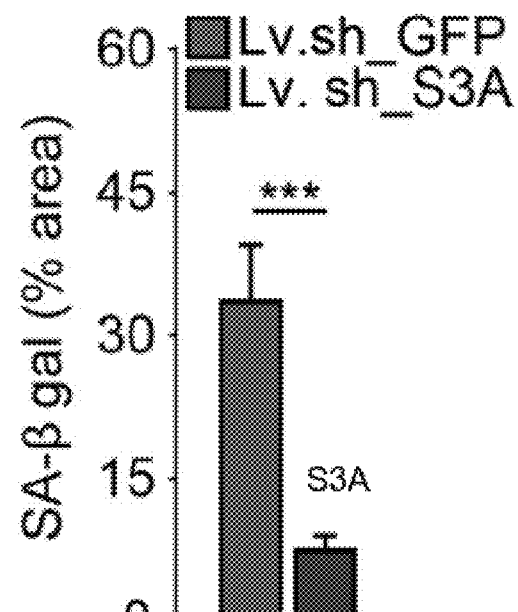
Figure 5C:
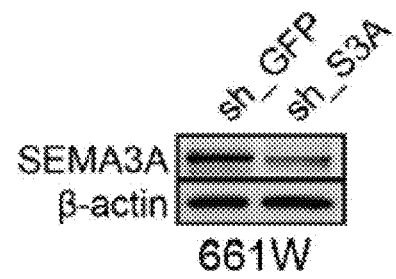
Figure 5D:
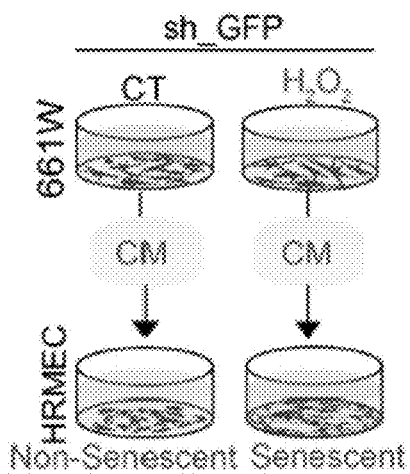
Figure 5E:
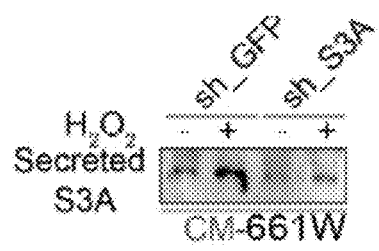
Figure 5F:
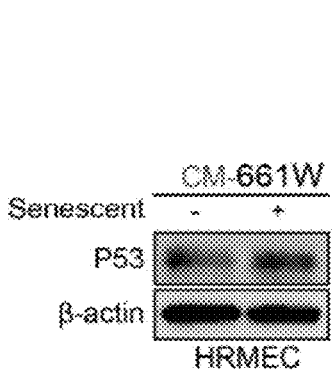
Figure 5G:
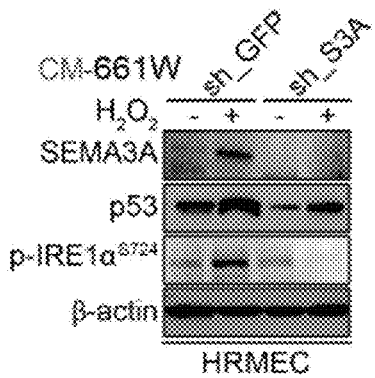

To verify the potential involvement of neuron-derived SEMA3A in driving paracrine endothelial cell senescence, we exposed Human retinal microvascular endothelial cells (HRMECs) to conditioned medium (CM) from senescent 661W cells (FIGS. 3L and M) in which Sema3a was silenced by lentiviral (Lv) vectors carrying small hairpin RNAs (shRNAs) (44, 47). Efficacy of this approach was demonstrated (FIGS. 5C-E). CM from the senescent retinal neuron cell line, effectively propagated senescence in a paracrine fashion given induction of SA-β-gal expression in 68% of HRMECs ($P<0.005$) (FIG. 3N left panels, O), highlighting that factors secreted by senescent cells have the propensity to stimulate senescence in neighboring cells. Conversely, CM from Sema3a-deficient senescent retinal neuron precursor cells triggered significantly less paracrine senescence in HRMEC cells ($P<0.005$) (FIG. 3N right panel, O). In parallel, incubation of HRMECs with conditioned medium (CM) from senescent neuron precursors was sufficient to activate p53 in a SEMA3A-dependent manner (FIGS. 5F and G). Interestingly, downregulating SEMA3A by intravitreal administration of Lv.sh_Sema3a at P12 of OIR significantly diminished the number of senescent SA-β-gal positive retinal cells by 75%, at P14 underscoring the critical contribution of SEMA3A to senescence during OIR (FIGS. 3P and Q). Together, these data provide evidence for production of SEMA3A during cellular senescence and its contribution in propagating paracrine senescence.

Example 4

Enrichment of ER-Stress Transcripts in Retinopathy

Figure 4A:
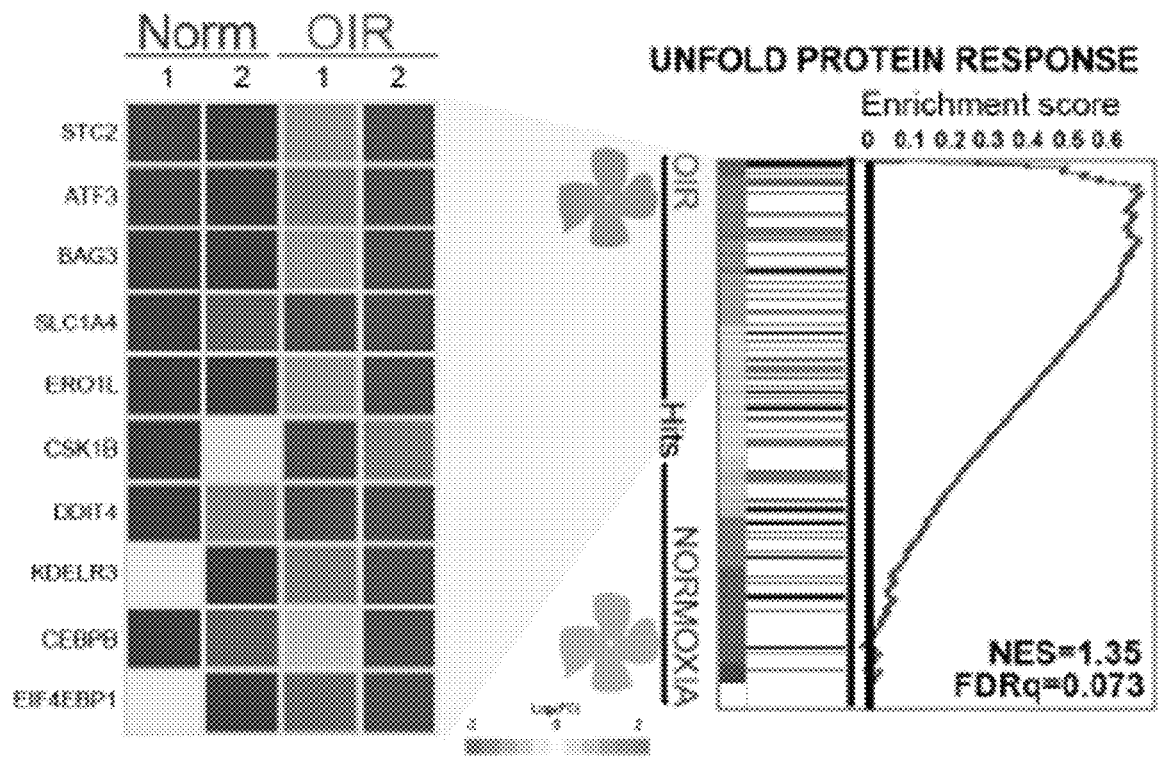
FIGS. 4A-C show Heatmap and GSEA for signatures of the unfolded protein response in P14 OIR vs normoxic retinas.
Figure 5H:
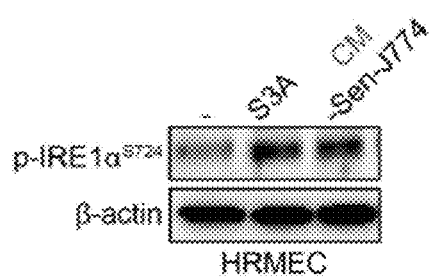

Pathways of the unfolded protein response (UPR) triggered under conditions of ER-stress can provide cells with adaptive mechanisms to survive during metabolic imbalances such as ischemia (48, 49). As supported by Applicant's findings, activation of ER-stress may help drive premature senescence. Transcriptomic analysis of retinas subjected to OIR revealed significant GSEA enrichment in transcripts related to the UPR (NES=1.41; FDRq=0.047) (FIG. 4A). Given that SEMA3A was shown to activate the IRE1α branch of the UPR (FIG. 3E and FIG. 5H), we interrogated on the contribution of IRE1α to premature senescence in ischemic retinas.

Figure 4B:
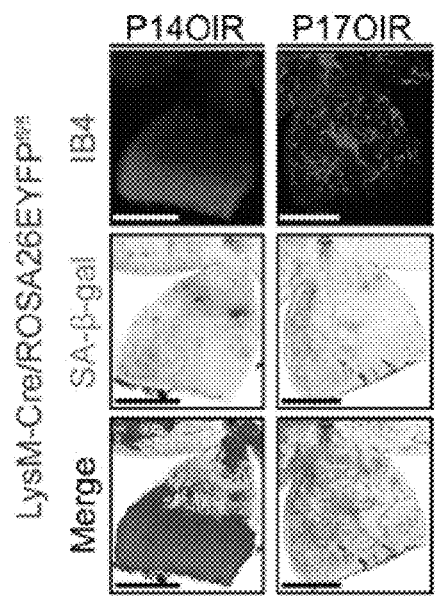
Figure 4C:
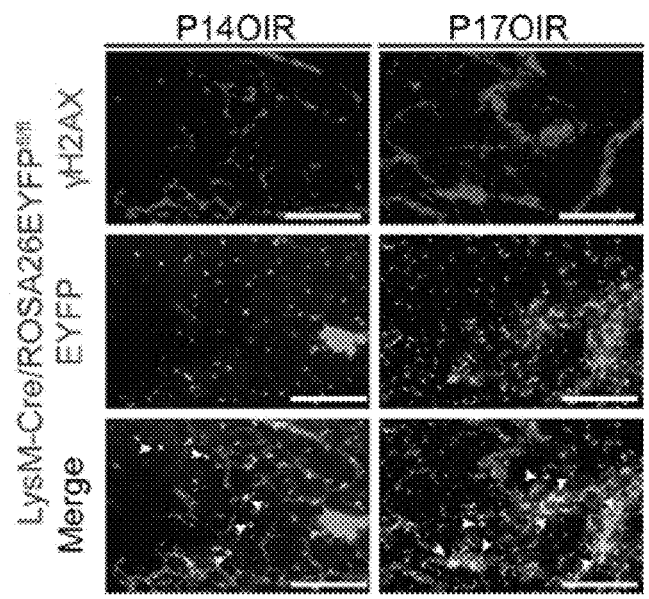

During ischemic retinopathy, there is a substantial implication of microglia and infiltration of myeloid cells that express microglial markers. We crossed myeloid-driver LysM-Cre mice with ROSA26EYFP" and observed SA-β-gal staining in avascular zones (FIG. 4B) rich in EFYP+ myeloid/microglial cells (FIG. 4C). EFYP+ microglia also stained with senescence-associated DNA damage marker γH2AX and preferentially localized to the vascular/avascular border of P14 OIR retinas and to sites of pathological angiogenesis (tufts) at P17 (FIG. 4C).

Example 5

Figure 6A:
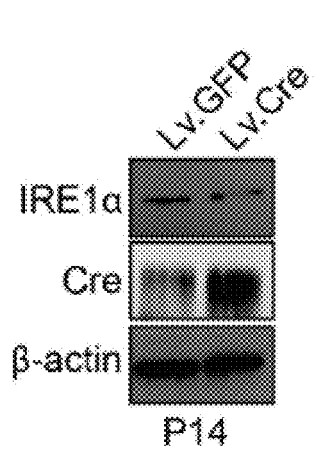
Figure 6B:
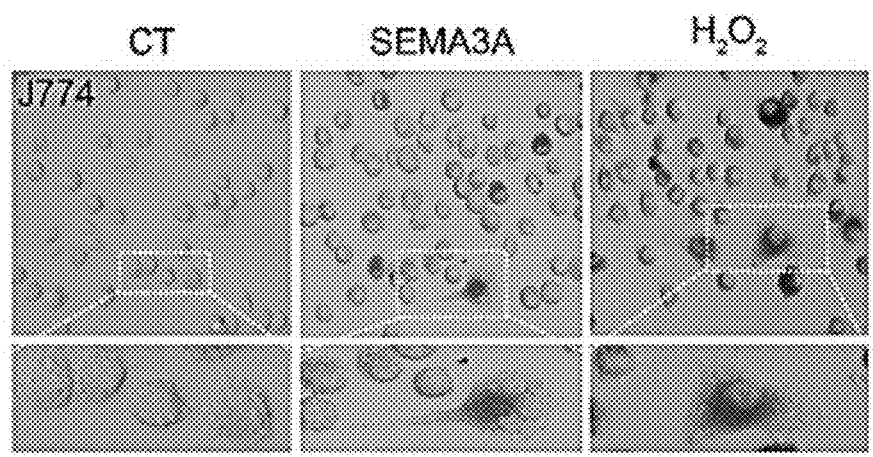
Figure 6C:
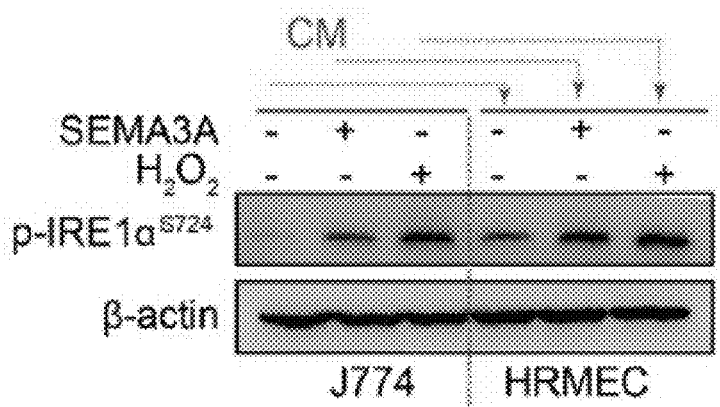
Figure 6D:
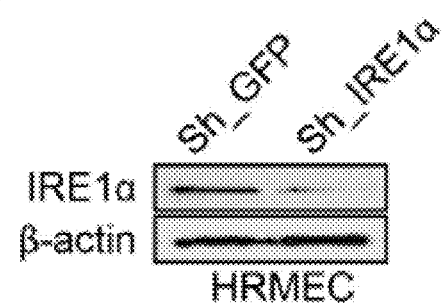
Figure 7C:
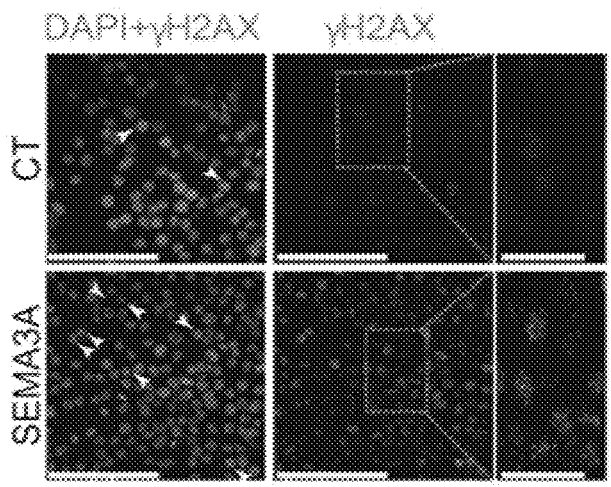

Sema3a Activates Ire1α and the Rnase Activity of Ire1α Contributes to Senescence IRE1α is a type I transmembrane protein that possesses both a serine/threonine kinase domain and a distinct endoribonuclease domain on its cytosolic terminus (54, 55). Through its RNase activity, also termed IRE1α-dependent decay (RIDD), it preferentially targets mRNAs encoding proteins that traverse the ER-Golgi secretory pathway (56). In light of SEMA3A driving senescence through IRE1α (FIGS. 2, 3), we next investigated which catalytic arm was accountable for this physiological response. Given that we established that myeloid cells become senescent with retinal ischemia, we used J774 macrophage/monocyte cells and confirmed that sustained exposure to SEMA3A activated IRE1α (FIG. 7A), induced senescence (FIG. 6B) and drove expression of a panel of genes known to be critical for promoting and reinforcing the senescent state, such as Pai1, Il6, Il1β, TGF-β and Tp53 (FIG. 7B). In addition, SEMA3A promoted senescence-associated DNA-damage foci expressing γH2AX (FIG. 7C) that are hallmarks of cellular senescence (57). Similarly, shRNA-mediated knockdown of IRE1α in endothelial cells prevented SEMA3A-driven senescence (FIGS. 6D and E).

Figure 7D:
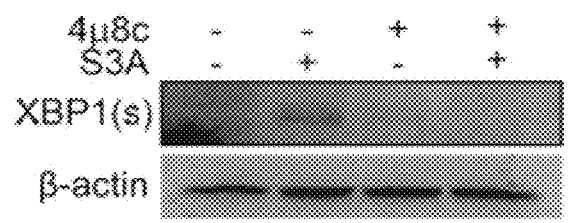
Figure 7E:
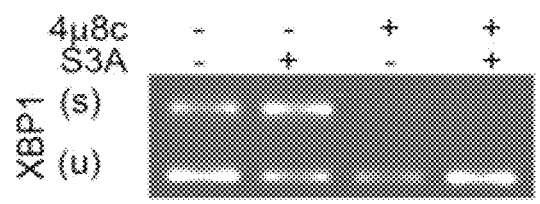
Figure 7F:
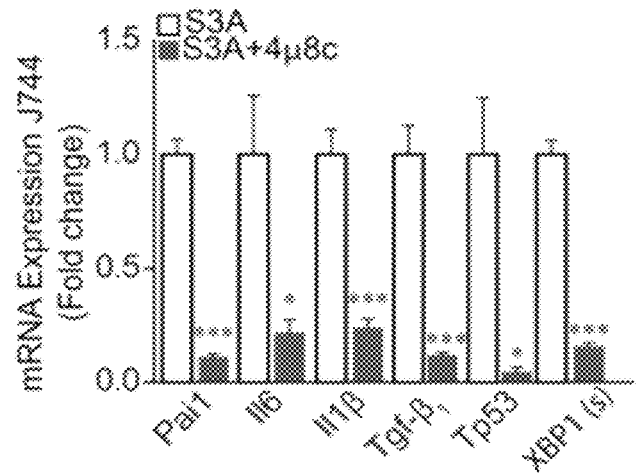

To determine whether SEMA3A-driven senescence was occurring through IRE1α's kinase or RNAse activity, the selective cell-permeable coumarin o-hydroxyaldehyde pharmacological inhibitor of IRE1α's endoribonuclease activity, 4μ8c, was used. Exposure to 4μ8c (FIG. 7D) prevented SEMA3A-induced growth arrest and abrogated SEMA3A-induced senescence (data not shown). In support, 4μ8c also prevented SEMA3A-mediated splicing and activation of the IRE1α effector X-box Binding protein-1 (XBP1) (FIGS. 7D and E). Ultimately, pharmacological inhibition of the endoribonuclease activity of IRE1α inhibited production of specific senescence-associated genes Vegf-a, Tgf-β1, Il-1β, Il-6, Pai-1, Tp53 while there is no effect on Tnf-α or IRE1α itself (FIG. 7F). These data highlight the importance of the endoribonuclease activity of IRE1α in triggering senescence.

Example 6

Metformin Abrogates the SASP and Pathological Retinal Angiogenesis

Figure 8A:
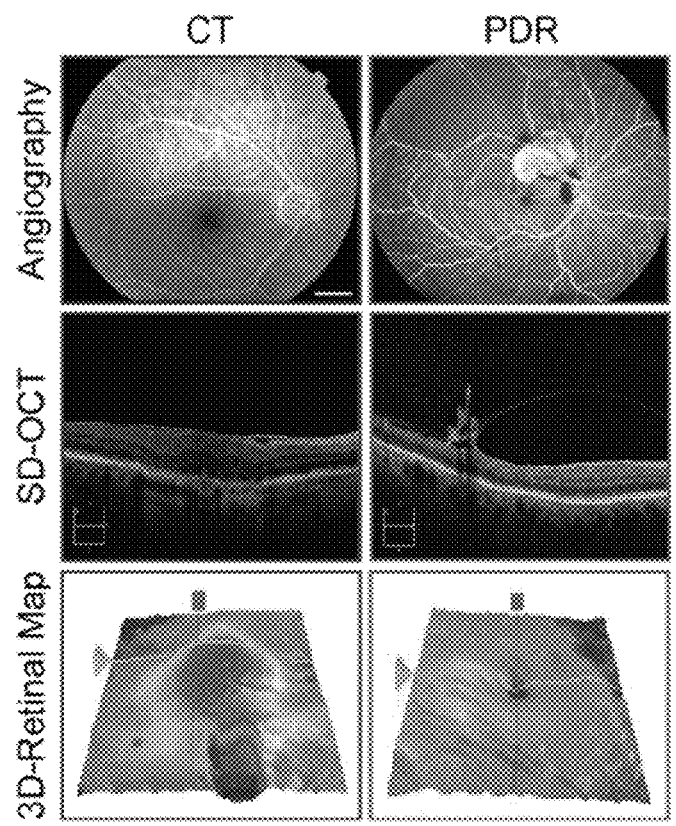
FIGS. 8A-K show that Metformin abrogates the SASP and pathological retinal angiogenesis.
Figure 8B:
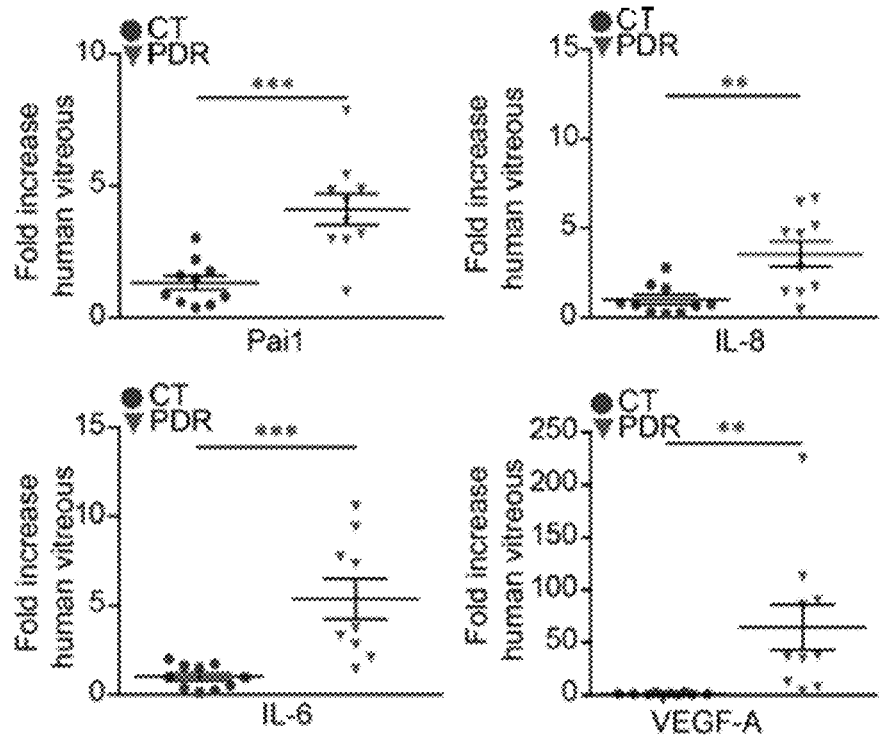
Figure 8C:
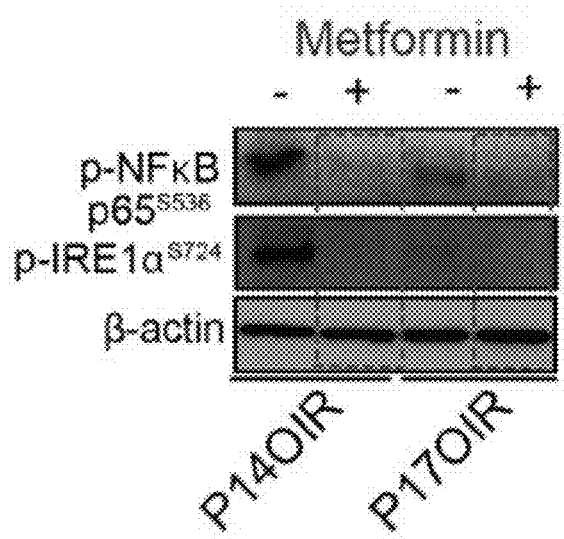
Figure 8D:
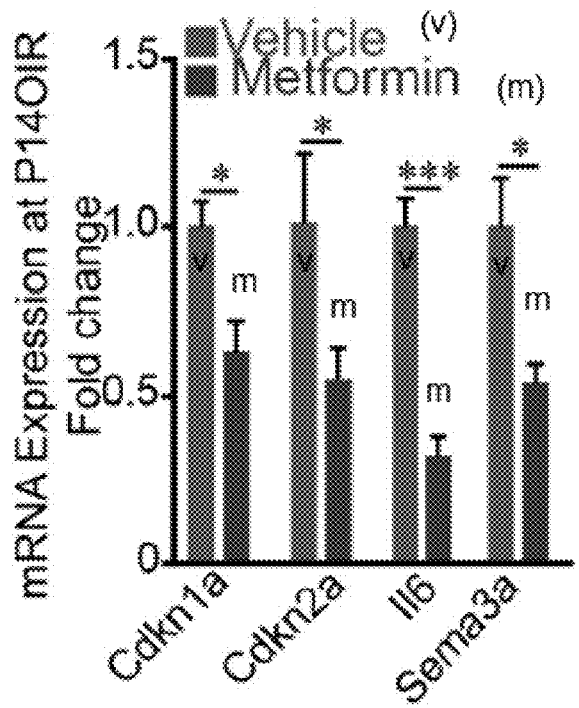
Figure 8E:
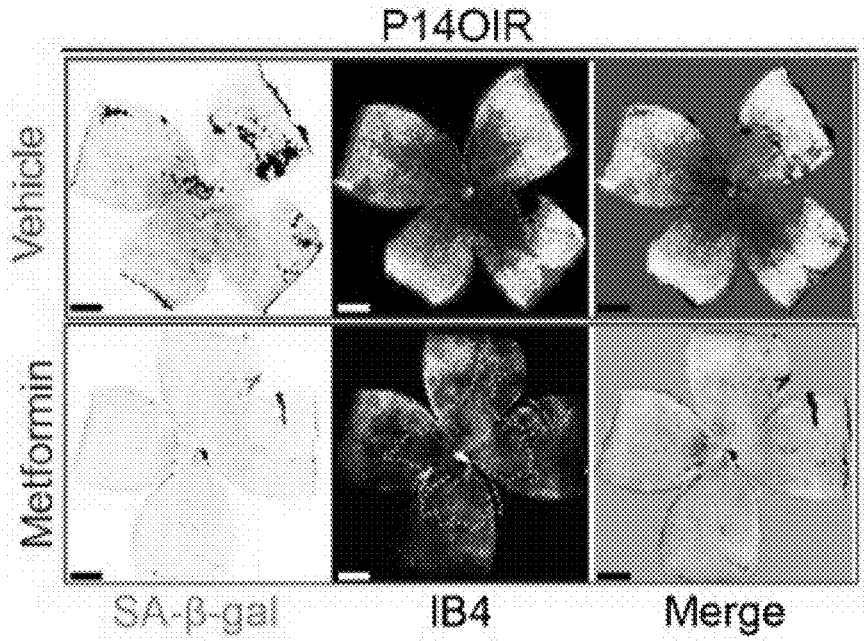
Figure 8F:
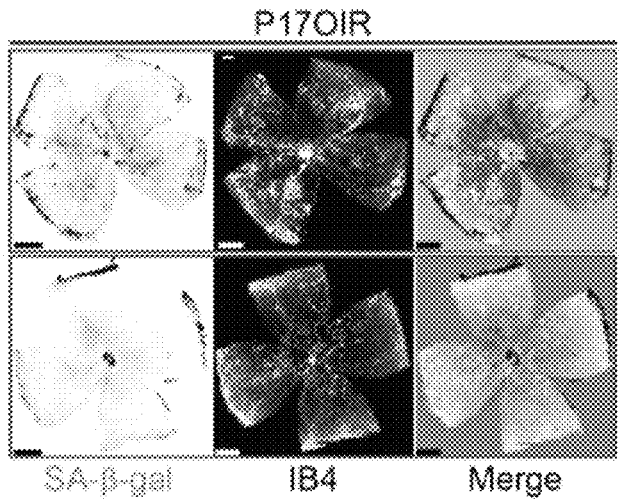
Figure 8G:
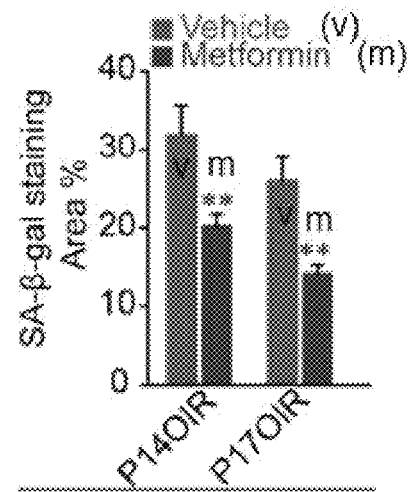
Figures 12A, 12B:
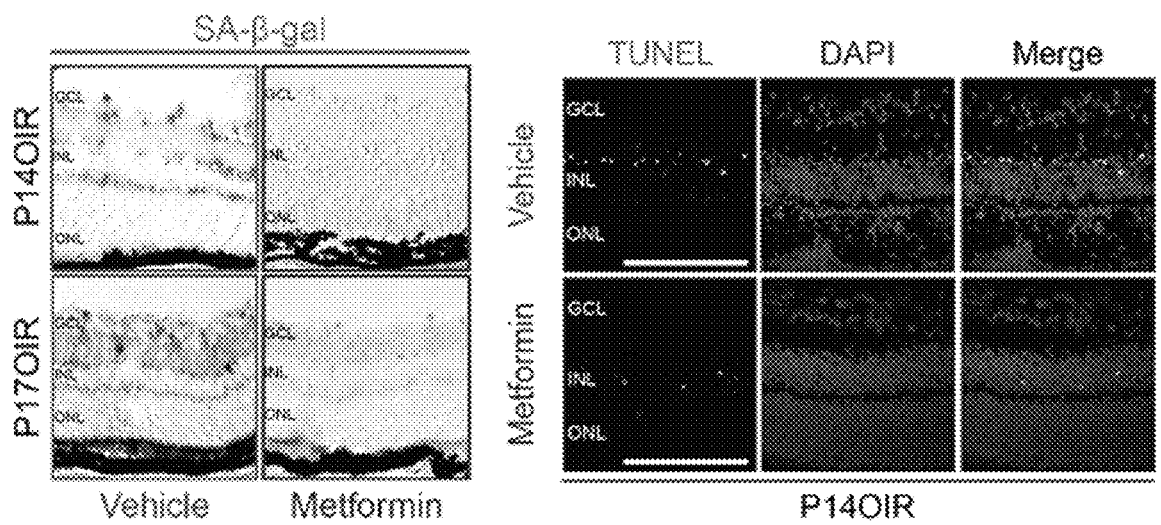
FIGS. 12A-C show that metformin inhibits senescence during OIR.
Figure 13A:
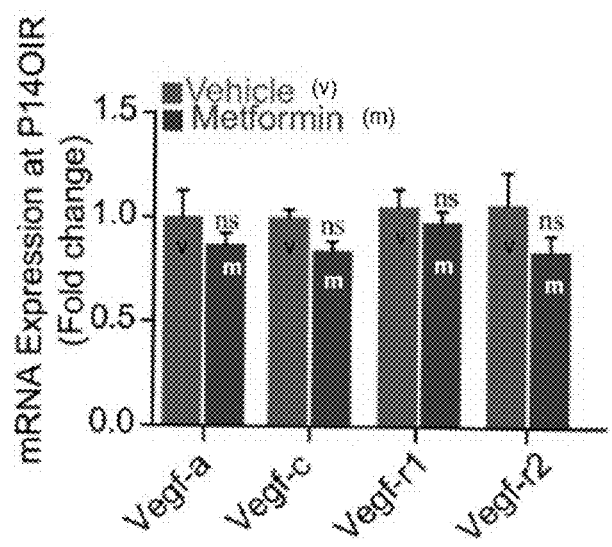
FIGS. 13A-B show genes unaffected by Metformin and Aflibercept in OIR.

To establish the clinical relevance of therapeutic inhibition of the SASP and paracrine senescence in ischemic retinopathy, we assessed levels of key SASP proteins in the vitreous of patients suffering from active proliferative diabetic retinopathy (PDR). Angiography and spectral-domain optical coherence tomography (SD-OCT) were performed, and three-dimensional (3D) retinal maps were generated to evaluate the extent of retinal damage (FIG. 8A). Undiluted vitreous was obtained from patients with PDR and control patients with nonvascular pathology such as epiretinal membrane and macular hole that showed only non-diabetes-related retinal damage. Detailed characteristics of patients are included in Table 1. Evaluation of vitreal SASP proteins by multiplex magnetic bead-based immunoassays revealed significant increases in senescence-associated factors Pai-1 (P=0.0004) IL-6 (P=0.001), IL-8 (P=0.0037) and VEGF-A (P=0.0085) in patients with PDR (FIG. 8B). Given the association between paracrine senescence and retinopathy (FIGS. 1C and 3E), we sought to therapeutically modulate the SASP and assess outcome on pathological retinal angiogenesis. In this regard, the widely used biguanide antidiabetic drug metformin has been reported to reduce the SASP without interfering with the growth arrest program (58). A single intravitreal injection of metformin at P12 attenuated NF-κB and IRE1α activation in mouse retinas subjected to OIR (FIG. 8C). This lead to a significant decrease in IL6, Cdkn1a, Cdkn2a and Sema3A as determined by RT-qPCR (FIG. 8D) and translated into a significant decrease in SA-β-gal at P14 (P=0.0086) (FIGS. 8E and G and FIG. 12A) and P17 (P=0.0036) (FIGS. 8F and G and FIG. 12A). Components of the VEGF signaling pathway were not affected (FIG. 13A). We elected to perform intravitreal injections of metformin given that systemic administration interfered with mouse weight gain and hence could be a confounding factor (32).

TABLE 5

Clinical characteristics of patients having undergone vitreous biopsy.

| Sample | Sex female (F) Male (M) | Age | Patient condition |
|---|---|---|---|
| C1 | M | 82 | Macular Hole (MH) |
| 2 | F | 62 | Epiretinal membrane (ERM) |
| 3 | F | 69 | ERM-control / pseudo TM |
| C4 | M | 75 | MH-Cataract |
| C5 | M | 77 | Retinal Detachment |
| C6 | M | 69 | ERM |
| C7 | M | 68 | ERM |
| C8 | M | 81 | ERM |
| C9 | M | 70 | ERM |
| C10 | F | 65 | MH |
| P1 | F | 78 | Proliferative Diabetic Retinopathy (PDR) |
| P2 | F | 72 | PDR |
| P3 | F | 69 | PDR |
| P4 | M | 36 | PDR |
| P5 | F | 70 | PDR |
| P6 | F | 74 | PDR |
| P7 | F | 67 | PDR |
| P8 | M | 69 | PDR |
| P9 | F | 70 | PDR |
| P10 | M | 45 | PDR |

Figure 8H:
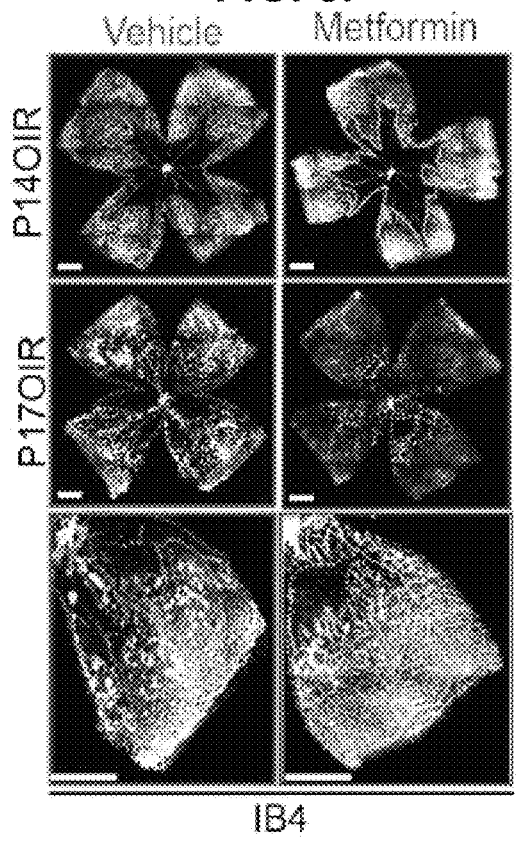
Figure 8I:
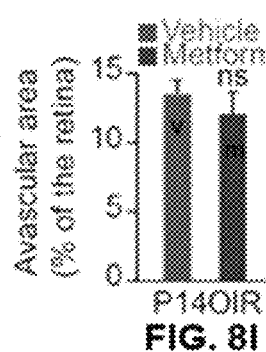
Figure 8J:
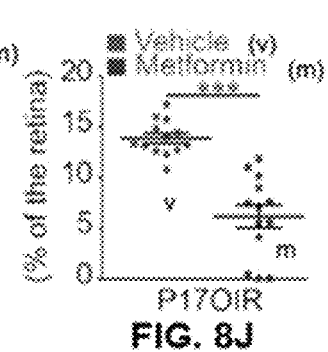
Figure 8K:
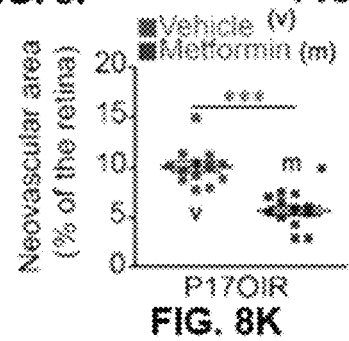
Figure 12C:
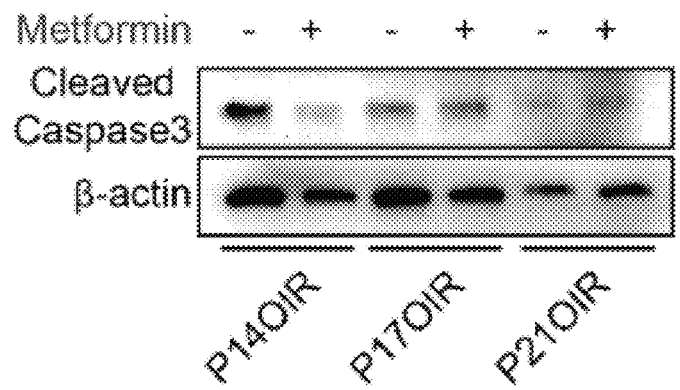

We next determined if treatment with metformin and subsequent inhibition of the SASP would result in increased apoptosis. TUNEL staining revealed that treatment with metformin lowered the number of apoptotic cells in the INL layer when compared to vehicle-treated retinas without aggravating apoptosis in cells of the GCL (FIG. 12B). Findings were confirmed by Western blotting of retinas for cleaved caspase-3 during different stages of retinopathy (FIG. 12C). Ultimately, intravitreal injection of metformin enhanced vascular regeneration more than 2-fold as assessed at P17 (P<0.0001) (FIGS. 8H and J) and suppressed pathological neovascularization by half (P<0.0001) (FIGS. 8H, K). It is important to note that administering metformin via systemic paths did not show any benefits on pathological retinal angiogenesis underscoring the need for local intravitreal administration. Taken together, these data support the therapeutic inhibition of the SASP with biguanides such as metformin in the treatment of pathological ocular angiogenesis (pathological neovascularization).

Example 7

Figure 9A:
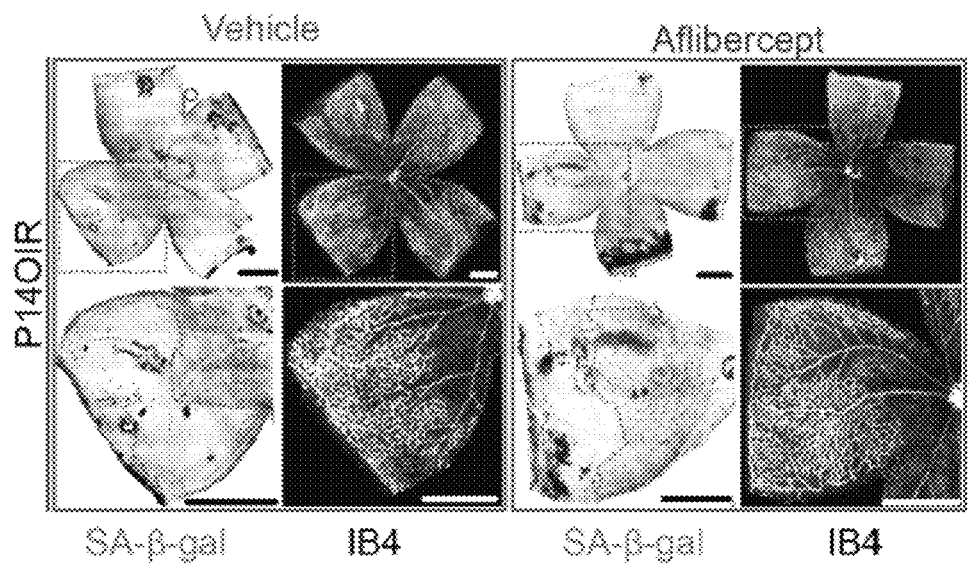
FIGS. 9A-G show that Aflibercept abrogates pathological angiogenesis without promoting vascular repair or cellular senescence. Representative P14 (FIG. 9A) and P17 (FIG. 9C) OIR flatmount retinas labeled with IB4 and SA-β-gal of mice intravitreally injected with Aflibercept or vehicle at P12. Quantification of percentage SA-β-gal stained area in P14 (FIG. 9B) and P17 (FIG. 9D) OIR mice treated as in FIG. 9A or FIG. 9C. (P=0.3087 at P14, (n=13-14); P=0.1580 at P17 (n=13); Aflibercept compared with vehicle-injected retinas). Quantification of avascular areas at P14 (P=0.4897, n=11-13) (FIG. 9E) and P17 (P=0.9502, n=6-7) (FIG. 9F) of OIR. Pre-retinal neovascularization was assessed at P17 OIR (FIG. 9G). Results are expressed as percentage of avascular or neovascular area versus the whole retinal area (*P=0.0207, n=5-6); Aflibercept compared to vehicle-injected retinas n=5-6)). Horizontal bars represent mean value of percentage, and dots represent individual values. Scale bars are 500 μm. Data are presented as mean±SEM.
Figure 9B:
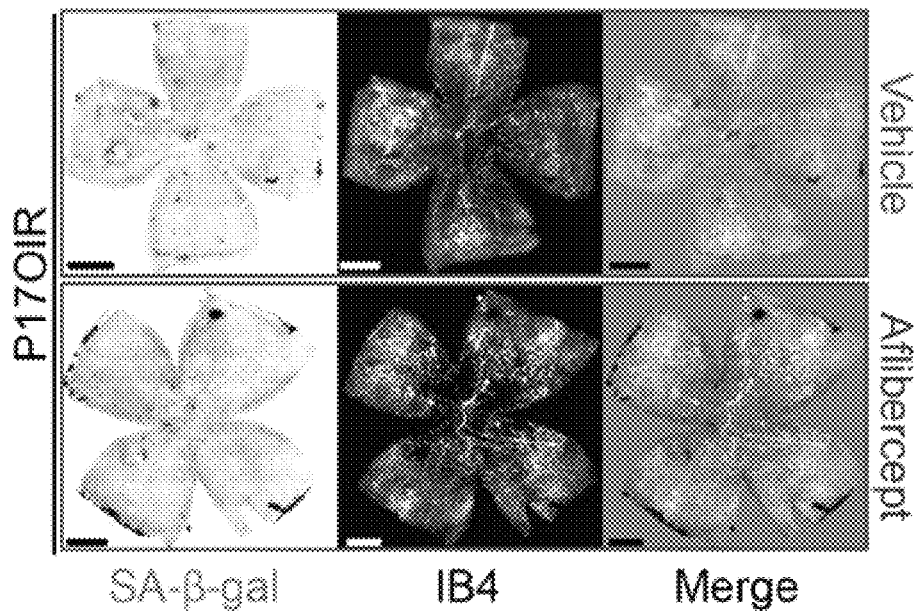
Figure 9C:
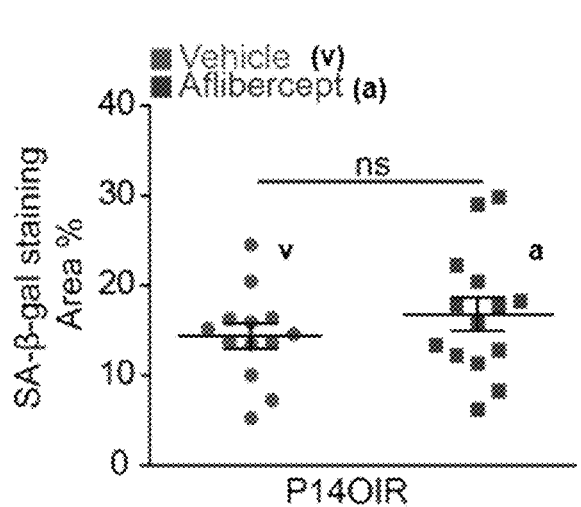
Figure 9D:
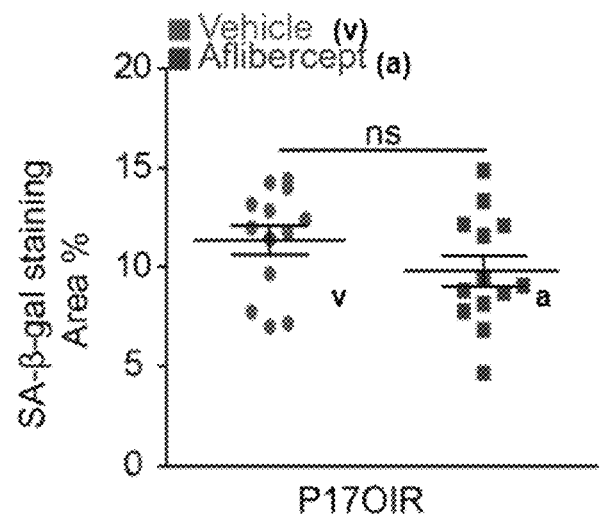
Figure 9E:
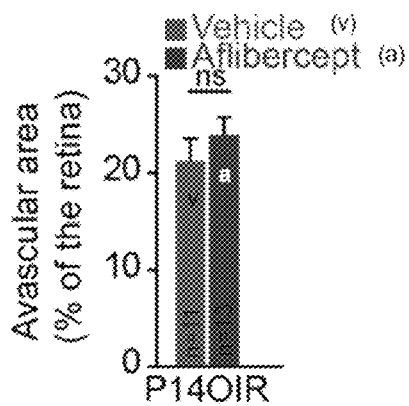
Figure 9F:
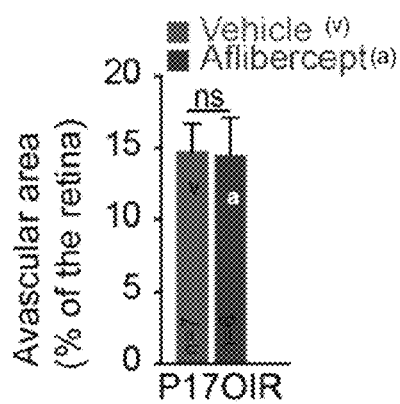
Figure 9G:
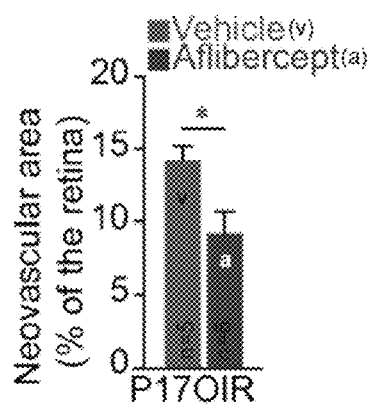
Figure 13B:
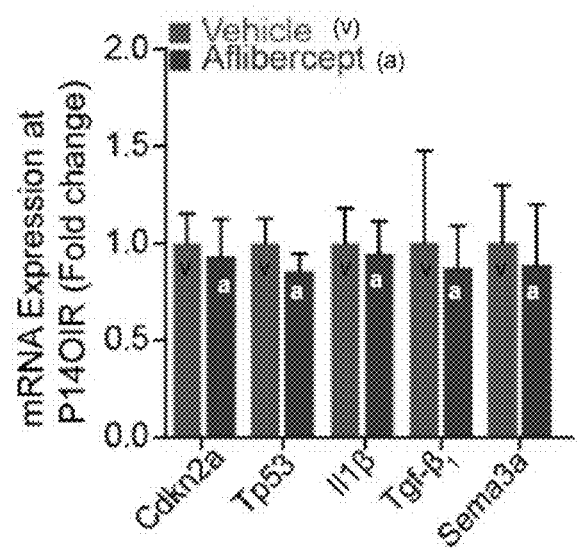

VEGF Trap-Eye Abrogates Pathological Retinal Angiogenesis Yet does not Increase Vascular Regeneration or Reduce Senescence We next determined if currently used anti-VEGF treatments such as VEGF trap-eye (Aflibercept) (59, 60) influenced retinal senescence during retinopathy (60). Aflibercept is a recombinant fusion protein made-up of the extracellular domains of human VEGF receptors 1 and 2 and an Fc portion. As such, it binds at least VEGF-A and Placental Growth factor (PLGF) (59). Intravitreal injection of Aflibercept at P12 of OIR did not significantly influence SA-β-gal staining at P14 (P=0.3087) (FIGS. 9A, B) or P17 (P=0.1580) (FIGS. 9C, D). Interestingly, in contrast to treatment with metformin which reduces the SASP and augments vascular regeneration, Aflibercept does not modulate rates of vascular regeneration at P14 (P=0.4897) (FIGS. 9A, C) or P17 (P=0.9502) (FIGS. 8B, D), nor drivers of senescence (FIG. 13B). As expected, intravitreal injection of Aflibercept lead to a marked decrease in neovascularization at P17 OIR (P=0.0207) (FIG. 9G), (*P<0.001)). Hence, treatment with Aflibercept does not relieve retinal ischemia or senescence nor enhance retinal vascular repair, and only directly blocks pathological neovascularization. Together, these data further strengthen the link between cellular senescence and ischemia-driven pathological angiogenesis.

Example 8

Preparation of Soluble Sema3A Neutralizing Traps

High affinity traps to inhibit/neutralize SEMA3A were generated. These traps were derived from Neuropilin 1 (NRP1) and were optionally coupled to 6x-His tag or FC proteins (see FIG. 18 and Table 2). Various variants comprising either the entire NRP1 extracellular domain or functional variants capable of maintaining SEMA3A binding were generated. Traps containing a b1 domain (which binds to VEGF) and including a neutralizing VEGF$_{165}$ mutation were generated. The traps were shown to be highly expressed and secreted in transformed human cells. Simple purification and formulation protocols were developed to produce trap samples for structure-activity relationships (SAR) and in vivo efficacies studies.
Methods
Cell culture and material. The human Neuropilin 1 (GenBank™ accession NM_003873, SEQ ID NO: 66) was acquired from Origene Inc. The Origen clone comprises a conservative mutation at amino acid 140 which changes the leucine for an isoleucine. The 293T (ATCC) cells were grown in Dulbecco's modified Eagle's medium supplemented with 10% fetal calf serum. The pFUSE-hIgG1-Fc1 vector was purchased from InvivoGen Inc.
Cloning. The extracellular domain of Neuropilin-1 (residues 1-856), or portions of it, were PCR amplified from Origene clone RC217035 using the Phusion™ high fidelity polymerase (New England Biolabs) and cloned in the EcoR1-BgIII of pFUSE-hIgG1-Fc1 in frame with the human FC-1 coding sequence. Constructs coding for the soluble versions of the traps were generated by inserting a sequence coding for a TEV protease cleavage site followed by 6xHis residues and a stop codon upstream of the FC coding portion of the corresponding FC constructs. Additional deletions (b1, b1b2) or VEGF165 binding mutations (e.g., Y297A) were introduced using the Q5 site directed mutagenesis kit (NEB). All constructs sequences were verified by Sanger sequencing (Genome Quebec).

Evaluation of traps' expression in human cells. Constructs coding for the mouse and human traps were transfected in 293T cells. Cells were grown for 48 hrs post transfection in FreeStyle™ 293 medium (Invitrogen). Cell lysates were prepared from 293T cells 48 hours post-transfections. Cells were extensively washed with PBS and lysed in ice cold lysis buffer (50 mM HEPES pH7.5, 150 mM NaCL, 1.5 mM MgCl2, 1% Triton X-100 and 10% glycerol) supplemented with standard amounts of protease inhibitors (AEBSF, TPCK, TLCK, aprotinin, leupeptin, pepstatin and E64, Sigma). Cell lysates were cleared by micro centrifugation (12000 g, 20 minutes). Lysates concentrations were determined by standard micro BCA (Sigma). Equal amounts of protein were loaded on 5-20% PAGE-SDS gradient gels and transfered to PVDF (Amersham). Cleared conditioned media from transfected cells were incubated with either Protein A sepharose (Pharmacia) or Talon resin (Clontech) for FC or 6xHis tag. Resins were washed with PBS and diluted in 2×PAGE-SDS sample buffer prior to gel separation and transfer. The antibody used in immunoblottings were the anti-human Neuropilin-1 (Cell signaling), the mouse monoclonal anti-6×-HIS (In Vitrogen) and the reporter HRP linked anti-human, mouse and rabbit IgG (BioRAD). All antibodies were used at a 1/2000 dilution. Chemiluminescent signal was captured using a Fuji imaging system after incubation of membranes with ECL (Amersham).

Traps expression and purification. 293-T cells were transfected with plasmids encoding the various traps by either the Polyethylamine (PEI) or the calcium phosphate precipitation standard transfections methods. The next day cells were washed twice with serum free media and fed with serum free complete media (Free style 293 media, InVitrogen). Conditioned medium were collected after 60-72 hrs of growth in serum free media and cleared from cellular debris by swing bucket centrifugation (2000 RPM, 20 minutes). FC traps were purified from conditioned media of transfected 293T cells by passage on Protein A or G sepharose (Pharmacia) followed by extensive washes with PBS and elutions with 0.1 M glycine pH 3.0. Elution fractions were neutralised immediately by the addition of 1/10 volume 1 M Tris pH 8 and 1/10 volume of 10×PBS pH 7.4. Soluble 6×HIS tagged traps were purified from conditioned media of transfected 293T cell by passage on Talon agarose (Clontech) followed by extensive washes with PBS and stepwise imidazole elutions (Range 10-150 uM typically). Samples of purification fractions of traps were analysed on 5-15% or 5-20% gradient PAGE-SDS gels. Gel were stained using the Safely Blue staining kit (InVitrogen).

Sterile formulation of purified traps for in vivo injections. Purifications elution fractions from 40 ml of conditioned media were pooled and diluted to a total volume of 10 ml in PBS. Diluted trap proteins were sterilized by filtration through a 0.2 uM low protein binding filter (Progene). Protein solutions were concentrated and buffer exchanged with PBS on sterile PES concentration devices (Pierce, nominal MWCO 30 KD). Sterile concentrated Traps samples (~30-50 ul) were analysed and stained on PAGE-SDS as described above.

Example 9

Affinity of Traps for Sema3A

Production of AP-VEGF$_{165}$. the coding sequence of the human VEGF165 variant 1 (NM_001025366) was sub-cloned in the pAPtag5 vector (GenHunter), in-frame with an Alkaline Phosphatase domain (AP-VEGF165). HEK293T cells were transfected with the AP-VEGF165 construct using a polyethylenimine (PEI) transfection method. Following the overnight transfection step, cells were cultured for an additional 60 hr in serum free media (In vitrogen). The cell media were collected and concentrated on a PES device (Pierce). The concentrated AP-VEGF165 ligand was analysed on PAGE-SDS and quantified using SimplyBlue safe stain (Life technologies).

Sema 3A and AP-VEGF$_{165}$ binding assays. Saturation curves for the determinations of KD of binding to SEMA 3A or VEGF165 were obtained as follow. Wells of high protein binding 96 well plates (Maxisorp, Nunc) were coated with purified traps diluted in PBS and blocked afterward with binding buffer (PBS containing 2% casein and 0.05% Tween 20). The SEMA3A-FC (R&D systems) or AP-VEGF165 ligands were diluted in binding buffer over an extensive range of concentrations and added to wells. Following an overnight incubation, wells were washed with PBS containing 0.05% tween. Bound SEMA3a-FC was detected using an HRP-linked anti-Human IgG (Biorad) and ECL substrate (Pierce). Alternatively, bound AP-VEGF165 was detected using CPD star substrate (Roche). The Chemiluminescent signal was acquired on a TECAN reader. Dissociation constant (KD) were determined by non-linear curve fitting using the Graph Pad prism software.

The relative affinity of traps of the present invention to SEMA3A and VEGF has been assessed. Traps were prepared as described in Example 8. Schematic representation of traps tested (without HIS or FC tags) is also provided in FIG. 18.

TABLE 6

Dissociation constant of SEMA3A and VEGF for various traps

| NRP1 Trap | SEMA 3A-FC binding (nM) | VEGF165 binding (nM) |
|---|---|---|
| G | 0.8 | 6.75 |
| O | 1.05 | N.D. |
| M | 0.95 | 20.13 |
| N | >1000 | >250 |
| R | 6.15 | N.D. |
| W | 1.14 | 20.73 |
| Y | >750 | N.D. |
| Z | 4.44 | 66.96 |
| AB | N.D. | 29.51 |
| AC | 4 | No binding |
| Q | No binding | N.D. |
| P | No binding | N.D. |
| X | No binding | N.D. |
| S | N.D. | 24.6 |
| AD | No binding | No binding |
| AE | No binding | No binding |
| AF | No binding | N.D. |
| AJ | 2.4 | N.D. |
| Ak | 4.4 | N.D. |

The soluble NRP1 traps tested generally bind more efficiently to SEMA3A than VEGF. Such preference for SEMA3A was found surprising since SEMA3A and VEGF are considered to normally have the same general affinity for NRP1. Applicants have also surprisingly found that introduction of a mutation at position 297 (Y297A) in NRP1 not only inhibits binding to VEGF but also to NRP1. Such mutation was previously though to be associated with Increased affinity for SEMA3A may be advantageous in conditions where SEMA3A inhibition is preferred over inhibition of VEGF. As inhibition of VEGF using VEGF inhibitors such as bevacizumab has been suggested to induce cellular senescence in colorectal cancer cells in vitro and in vivo (Hasan et al., 2011 Int. J. Cancer 1; 129(9):2115-2123), the use of NRP1 traps having a reduced affinity for VEGF may be preferred in the context of senescence associated diseases and conditions. Furthermore, NRP1 traps preferably interacting with Sema3a over VEGF are expected to show reduced side effects associated with inhibition of VEGF cell signaling.

Example 10

Attenuation of Cellular Senescence by NRP1 Traps

Mice subjected to OIR were intravitreally injected with NRP1 traps G or M or with vehicle at P12 and retinas were monitored for cellular senescence. As shown in FIG. 20, quantification of SA-β-gal staining of P17 OIR flatmount retinas reveals a significant attenuation of cellular senescence when mice receive a single injection of Trap M or Trap G, with Trap M being more effective in inhibiting cellular senescence. Interestingly, Trap M, has a kd for SEMA3A which is about 20×greater than for VEGF, while the preference for SEMA3A for trap G is much less important (see Table 6).

Example 11

Experimental Procedures

Animals. All studies were performed according to the Association for Research in Vision and Ophthalmology (ARVO) Statement for the Use of Animals in Ophthalmic and Vision Research and were approved by the Animal Care Committee of the University of Montreal in agreement with the guidelines established by the Canadian Council on Animal Care. C57Bl/6 wild-type (WT) were purchased from The Jackson Laboratory. LyzM-Cre (Lyz2$^{tm1(cre)|flo/J}$; no. 004781) were purchased from The Jackson Laboratory. (C57Bl/6 WT, LysM-Cre, and LysM-Cre/ROSA26EYFP$^{fl/f}$, we generated mice with EYFP-expressing cells of myeloid lineage (71).

O2-induced retinopathy. Mouse pups from different strains (C57Bl/6 WT, LyzM-Cre, LysM-Cre/IRE1$^{fl/fl}$, LysM-Cre/IRE1$^{+/+}$, IRE1$^{fl/fl}$ and LysM-Cre/ROSA26EYFP$^{fl/fl}$), and their fostering mothers (CD1, Charles River) were exposed to 75% 02 from postnatal day 7 (P7) to day 12 and returned to room air. This model serves as a proxy to human ocular neovascular diseases such as ROP and diabetic retinopathy characterized by a late phase of destructive pathological angiogenesis (72, 73). Upon return to room air, hypoxia-driven neovascularization (NV) develops from P14 onwards (27). We enucleated eyes at different time points and dissected the retinas for mRNA, protein assays or flatmounting.

RNA-Seq samples preparation and sequencing. Total RNA was isolated from retinas using the RNeasy Mini Kit (QIAGEN). The mRNA was then purified from 1 μg of total RNA using the Dynabeads® mRNA DIRECT™ Micro Kit (Thermo Fisher SCIENTIFIC). Whole transcriptome libraries were prepared using the Ion Total RNA-seq Kit v2. The yield and size distribution of the amplified libraries were assessed with an Agilent Bioanalyzer using a DNA 1000 Kit. Sequencing was performed on an Ion Chef™ Instrument (Ion Torrent™, Thermo Fisher SCIENTIFIC).

cDNA Library Construction and Sequencing. Analysis was performed using the Torrent Suite software v4.4 (Thermo Fisher) and the whole Transcriptome Analysis Plugin v 4.2-r7 (Thermo Fisher). The whole Transcriptome Analysis Plugin aligns reads on mouse reference genome (mm10) using Tophat2 then unmapped reads are aligned using Bowtie2 and merged together. FPKM are calculated using Cufflinks.

Gene Set enrichment Analysis (GSEA). Gene set enrichment analysis was conducted using GSEA v2.2.1 software provided by Broad Institute of MIT and Harvard University. We used GSEA to validate correlation between molecular signatures in phenotype of interest. Enrichment analysis was conducted with log 2-normalized Fragment Per Kilobase of transcript per Million (FPKM) data generated by the ToPhat/Cuffdiff command pipeline: FPKM values were converted as ratios (FPKM x/[FPKM Normoxia]mean), then log 2 normalized (log 2[ratio]) and median centered (log 2 ratio−[log 2 ratio Normoxia]mean).

Default parameters were changed as follow: Gene sets of interest were found in a catalog of functional annotated gene sets from Molecular signature database (MSigDB); Phenotype was permutated 1000 times; Phenotype label was defined as 'OIR' vs 'Normoxia'; gene sets smaller than 15 and larger than 500 were excluded from the analysis; statistic used to score hits was defined as 'weighted p2', and the class separation metric used was 't Test'.

Semi-quantitative and Real-time PCR analysis. We isolated RNA using the GenElute™ Mammalian Total RNA Miniprep Kit (Sigma) and performed a digestion with DNase I to prevent amplification of genomic DNA. We reversed transcribed the RNA using M-MLV reverse transcriptase and analyzed gene expression using SybrGreen™ in an ABI Biosystems Real-Time PCR machine. β-actin was used as a reference gene. Primers sequences are displayed in Table 7. We investigated the splicing of XBP-1 by incubating the XBP-1 semi-quantitative PCR product with 0.4 U/μL of PstI enzyme for 5 hrs at 37° C. followed by separation on 2.5% agarose gel.

TABLE 7

Primers.

| Target | Forward primer | SEQ ID NO: | Reverse primer | SEQ ID NO: |
|---|---|---|---|---|
| β-actin | GACGGCCAGGTCATCACTATTG | 1 | CCACAGGATTCCATACCCAAGA | 17 |
| Il1β | CTGGTACATCAGCACCTCACA | 2 | GAGCTCCTTAACATGCCCTG | 18 |
| Il6 | CTCTGGGAAATCGTGGAAATG | 3 | AAGTGCATCATCGTTGTTCATACA | 19 |
| Ire1α | CCGAACGTGATCCGCTACTTCT | 4 | CGCAAAGTCCTTCTGCTCCACA | 20 |

TABLE 7-continued

Primers.

| Target | Forward primer | SEQ ID NO: | Reverse primer | SEQ ID NO: |
|---|---|---|---|---|
| Cdkn2a | GGCCAATCCCAAGAGCAGAG | 5 | GCCACATGCTAGACACGCTA | 21 |
| Cdkn1a | CTCCACTGCTGCTTCCTGAG | 6 | TGCTGAGCTCATGCCCTTTG | 22 |
| TP53 | CCGTGTTGGTTCATCCCTGTA | 7 | TTTTGGATTTTTAAGACAGAGTCTTTGTA | 23 |
| Pai1 | TGACGTCGTGGAACTGC | 8 | GAAAGACTTGTGAAGTCGGC | 24 |
| SEMA3A | GGGACTTCGCTATCTTCAGAAC | 9 | GGCGTGCTTTTAGGAATGTTG | 25 |
| Tgf-β | GGACTCTCCACCTGCAAGAC | 10 | CATAGATGGCGTTGTTGCGG | 26 |
| XPB1-s | CTGAGTCCGAATCAGGTCCAG | 11 | GTCCATGGGAAGATGTTCTGG | 27 |
| Tnf-α | CGCGACGTGGAACTGGCAGAA | 12 | CTTGGTGGTTTGCTACGACGTGGG | 28 |
| Vegfa | GCCCTGAGTCAAGAGGACAG | 13 | CTCCTAGGCCCCTCAGAAGT | 29 |
| Vegfc | CAAGGCTTTTGAAGGCAAAG | 14 | AGAAGGTGTTTGTGGCTGCT | 30 |
| Vegfr-1 | GTCACAGATGTGCCGAATGG | 15 | TGAGCGTGATCAGCTCCAGG | 31 |
| Vegfr-2 | GGCGGTGGTGACAGTATCTT | 16 | GTCACTGACAGAGGCGATGA | 32 |

Flow Cytometry Analysis. Human retinal microvascular endothelial cells (HRMEC) cell cycle analysis (P1 biolegend) were performed according to the manufacturer's instructions and as previously reported (43). Briefly, HRMEC (1×10⁶) were seeded in 6-well plates and incubated for 7 days with SEMA3A, 100 and 500 ng/ml. The samples were analyzed by flow cytometry. FACS was performed on a LSRII (BD Biosciences) device and data were analysed using FlowJo software (version 7.6.5).

Electric Cell-substrate Impedance Sensing (ECIS) Proliferation assay. Real-time analysis of trans-endothelial electric resistance was performed by plating 5000 HRMECs/ml were seeded onto 8W10E+ standard 8-well arrays (Applied BioPhysics, NY). Cells were allowed to grow leading to a capacitance of less than 10 nF. Cells were starved for 5 Hours with endothelial basal media (EBM-2, Lonza) and then treated with 100 ng/ml SEMA3A or vehicle (EBM-2) for 120 h and impedance was measured using an ECIS Zθ impedance instrument (Applied BioPhysics, NY). Measurements were taken for 120 h post treatment.

Human samples. We obtained approval of human clinical protocol and informed consent form by Maisonneuve-Rosemont Hospital (HMR) ethics committee (Ref. CER: 10059) and recruitment of patients for local core vitreal biopsy sampling from patients afflicted with proliferative retinopathies. The entire procedure was performed as an outpatient procedure in the minor procedure room within the ambulatory clinic from the Department of Ophthalmology at Maisonneuve-Rosemont Hospital. All instruments were opened and handled in a sterile manner. The study conforms to the tenets of the Helsinki declaration.

Vitrectomy. All patients previously diagnosed with PDR were followed and operated by a single vitreoretinal surgeon (FAR). Control patients were undergoing surgical treatment for non-vascular pathology (ERM or MH) by the same surgeon. In an operating room setting, patients underwent surgery under local retro/peribulbar anesthesia. A 5% povidone-iodine solution was used to clean the periocular skin and topical instillation into the eye and within the cul-de-sac was left in place for 5 minutes. Three-port 25-gauge transconjunctival pars plana vitrectomy was performed through 25-gauge valved cannulas (Alcon). Under microscope visualization using a wide-angle viewing system (Resight, Zeiss), undiluted vitreous was collected with a 25-gauge vitrector. After vitreous biopsy, the infusion line was opened and vitrectomy and membrane peeling was performed in the usual fashion to treat diabetic vitreous hemorrhage and tractional retinal detachment. This was followed by panretinal endolaser photocoagulation, fluid-air exchange, and intravitreal anti-VEGF injection.

Quantification of Cytokines by Multiplex. Vitreous samples were frozen on dry ice and immediately after biopsy were stored at −80°. Vitreous samples were centrifuged at 15000×g for 5 minutes at 4° C. prior to analysis. Pai1, VEGF, IL-6, IL-8. A multiplex panel (Cancer Panel 1 from Bio-rad) used according to the manufacturer's protocol. The Luminex assay was analyzed using a Bio-Plex 200 array reader (Bio-rad). A quantitative determination of the respective analytes was achieved by comparing the raw data obtained from the patient samples with a standard curve. A total of 4 cytokines (Croa, Grob and IL-1β) had to be excluded because of detection limit.

Immunofluorescence (IF). To localize protein expression, eyes were enucleated from mice and fixed in 4% paraformaldehyde for 4 h at RT and incubated in 30% sucrose overnight and then frozen in OCT compound. We then embedded the whole eye in optimal cutting temperature compound at −20° C. and performed 12 um sections. We carried out IF experiments and visualized sections with an epifluorescent microscope (Zeiss Axiolmager) or confocal microscope (Olympus confocal FV1000).

For visualization of pan-retinal vasculature, dissected retinas were flatmounted and incubated overnight with Rhodamine labeled *Griffonia (Bandeiraea) Simplicifolia* Lectin I (Vector Laboratories, Inc.) in 1 mM $CaCl_2$) in PBS for retinal vasculature. The extent of avascular area or neovascularization area at P17 using ImageJ and the SWIFT-NV method (74).

For Protein localization, flatmounted retinas were incubated with different antibodies as indicated. For in vitro IF, cultured cells were plated on 0.1% gelatin-coated coverslips and serum-starved overnight and stimulated for 7 days with SEMA3A (100 ng/ml). Cells were washed briefly with cold PBS and fixed for 20 minutes in PBS containing 3.5% paraformaldehyde. Cells were rinsed with PBS and permeabilized with 0.3% Triton in PBS for 5 minutes. Fixed cells were blocked with 1% BSA and then incubated for 1 hour with primary antibodies in 0.1% BSA in PBS. Bound primary antibodies were visualized after 1 hour of incubation using Alexa Fluor secondary antibody. Coverslips were mounted using Fluoromount (Sigma-Aldrich) and analyzed by confocal microscope (Olympus confocal FV1000). Samples were viewed with a ×63/1.4 NA oil or ×30 objective. Images were assembled using Photoshop CS4 (Adobe Systems). For all antibodies used for immunohistochemistry, see Table 8.

TABLE 8

Antibodies

| Target | Clone | Company | Catalogue no. | Application | Dilution/WB | Dilution/IHC |
|---|---|---|---|---|---|---|
| Phospho-NF-kB | p65, Ser536 | Cell Signaling Technology | 3031 | WB | 1/250 | |
| β-actin | | MEDIMABS | MM-0164-P | WB | 1/2000 | |
| P-IRE1α | S724 | Santa Cruz Biotechnology | ab48187 | WB | 1/500 | 1/100 |
| IRE1α (tot) | 14C10 | Cell Signaling Technology | 3294 | WB | 1/250 | |
| NF-kappaB | L8F6 | Cell Signaling Technology | 6956 | WB | 1/250 | 1/100 |
| P16 | F-12 | Santa Cruz Biotechnology | sc1661 | WB | 1/500 | 1/100 |
| P21 | C-19 Sc-397 | Santa Cruz Biotechnology | L1913 | WB | 1/500 | |
| P53 | FL-393 sc-6243 | Santa Cruz Biotechnology | B2013 | WB | 1/500 | |
| SEMA 3A | ab23393 | Abcam | GR26629-13 | WB | 1/50 | |
| Pai I | H-135 Sc-8979 | Santa Cruz Biotechnology | E2214 | WB | 1/500 | 1/100 |
| XBP1 | M-186 Sc-7160 | Santa Cruz Biotechnology | G2415 | WB | 1/500 | |
| H2AX (8Hydroxyguanosine) | 15A3 | Abcam | ab62623 | WB | 1/1000 | 1/100 |
| Cre-recombinase | 2D8 | millipore | MAB3120 | WB | 1/500 | 1/100 |
| IBA1 | | Wako | | IHC | | 1/200 |
| Cleaved caspase-3 | (Asp175) | Cell Signaling | | WB | 1/1000 | |
| Brn3a | C-20 | Santa Cruz Biotechnology | Sc-31984 | IHC | | 1/200 |
| α-SMA | Gr43049-4 | Abcam | ab7817 | IHC | | 1/200 |
| NG2 | | Abcam | ab50009 | IHC | | 1/100 |

Senescence-associated β-galactosidase (SA-β-gal) assay. Senescence-associated β-galactosidase assays were carried out as described previously (57, 75)

Figure 14:
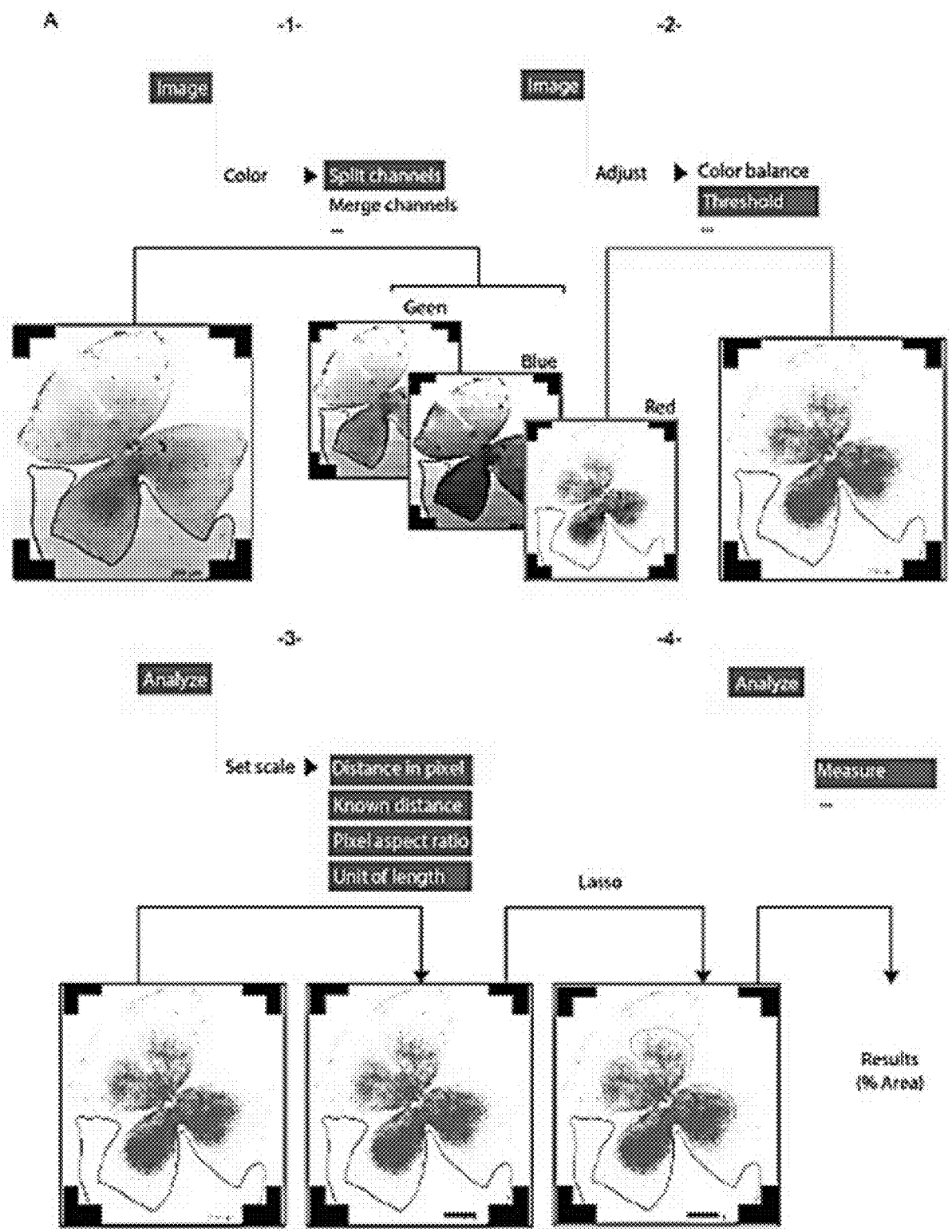
FIG. 14 shows how the quantification of retinal SA-β-gal is performed. Schematic description of quantification of SA-β-gal staining on flatmount retinas (or sagittal eye sections) using Image J software analysis.

Quantification of SA-β-gal in vivo. Senescence-associated β-galactosidase staining in flatmount retinas or sagittal eye sections were analyzed using Image J software as described in FIG. 14.

Lentivirus production. Lentiviral vectors (HIV-1 derived) were prepared by transfecting HEK293T cells HEK293T cells (Invitrogen) as previously described by us and others (35, 44, 76) with a vector plasmid containing Cre, green fluorescent protein GFP or the small hairpin RNAs (Sh_RNAs) against SEMA3A, IRE1α or GFP (see Table 9 below) together with the third-generation packaging plasmids pVSVG, pMDL, and pREV (Open Biosystems). Approximately $10^7$ cells were seeded and transfected with the above plasmids in DMEM complete medium (Invitrogen) and incubated for 30 hours. Subsequently, supernatant was replaced with fresh complete DMEM medium and incubated for an additional 30 hours. Secreted virus was collected and ultracentrifuged at 50000 g, resuspended in PBS, aliquoted, and stored at −80° C.

Intravitreal injections. P2, P10 or P12 C57BL/6 pups were anesthetized with 3.0% isoflurane and injected in the vitreous chamber with 0.5 µL of lentivirus (see "Lentivirus production"), recombinant SEMA3A (100 ng/µL), metformin (10 µg/µL) or Aflibercept (10 µg/uL) using a 10-µL Hamilton syringe fitted with a 50-gauge glass capillary tip. Approximately 254±11.0 ng/µL of lentivirus Sh_GFP and 323.3±15.3 ng/µL containing Sh_Sema3a, Lv.Cre (15.0 ng/mL), Lv.GFP (15.0 ng/mL) was injected. Virus titers were assessed with the p24 ELISA kit (ZeptoMetrix). The titers of the lentiviruses used were (in ng p24) LV.Sh_RNA IRE1α (8.52 ng/mL), and LV.Sh_RNA.GFP (8.47 ng/mL).

TABLE 9 shRNAs

| Target | Ref. | Antisense target sequence (in Mature antisense sequence T changed to U) | SEQ ID NO: |
|---|---|---|---|
| hSEMA3A | TRON0000058138 | AAATCCTTGATATTAACCAGG | 33 |
| hSEMA3A | TRON0000058139 | TTTCCCGTAAATATCACACCG | 34 |

TABLE 9 -continued shRNAs

| Target | Ref. | Antisense target sequence (in Mature antisense sequence T changed to U) | SEQ ID NO: |
|---|---|---|---|
| hSEMA3A | TRON0000058142 | TTGAAACTACTTTAAGAACGG | 35 |
| hSEMA3A | TRON0000058140 | AAATTAGCACATTCTTTCAGG | 36 |
| mSEMA3A | TRON0000067328 | AAATTGCCAATATACCAAGGC | 37 |
| mSEMA3A | TRON0000067331 | AATGAGCTGCATGAAGTCTCG | 38 |
| mSEMA3A | TRON0000067330 | AAATTGGCACATTCTTTCAGG | 39 |
| mSEMA3A | TRON0000067329 | TTCATTAGGAATACATCCTGC | 40 |
| mSEMA3A | TRON0000067332 | TTATTTATAGGAAACACTGGG | 41 |
| IRE1α | | AACGCCACCCATCCAACCA | 42 |
| shGFP | | GCAAGCTGACCCTGAAGTTCAT | 43 |

Preparation of conditioned media (CM). Human retinal microvascular endothelial cells (HRMECs), retinal neuron 661W photoreceptor cells and Mouse macrophages (J774A.1 cell line) were incubated for 7 days with recombinant SEMA3A (100 ng/µL), $H_2O_2$ (150 µM for 2 h) 48 h after transfection or not as indicated in each experiment. Supernatants were centrifuged and filtered and then frozen for subsequent use. For Western Blot on CM was concentrated using ultra centrifugal amicon filter unit from Millipore.

Western blotting. We enucleated eyes at varying time points and rapidly dissected and homogenized retinas for assessment of retinal protein levels. Protein concentration from retinal homogenate and cell lysates were assessed by BCA assay (Sigma), and then 30 µg of protein analyzed for each condition by standard SDS-PAGE technique. Antibodies used for Western-blotting are listed in Table 8 above.

Statistical analyses. We used Students T-test and ANOVA, where appropriate. A P<0.005 and P<0.05, respectively was considered statistically different using Prism, version 5 software (GraphPad).

Recombinant proteins used. Recombinant human Semaphorin 3A (from murine myeloma cell line, NS0) (R&D Systems) concentration used in vitro 100 and 500 ng/ml and 100 ng/ml in vivo.

Materials. Metformin, assay (RIPA) buffer, protease inhibitor cocktail, and phosphatase inhibitors were purchased from Sigma Chemicals. Aflibercept (Eylea™) was purchased from Bayer. 4µ8c inhibitor was from Torcis (Biosciences).

Plasmids and generation of Stable Cell Lines and Transfections. We stably transfected 661W cells and HRMECs (Open Biosystems) cells with 500 ng of Sh_RNA plasmids targeting, Sema3a, IRE1α respectively and an unrelated sh_RNA (sh_GFP) for 16 hr at 37_C using Lipofectamine™ 2000 following the manufacturer's directions. We generated stable cell lines by selecting with 2 mg of puromycin over 2 weeks. Expression plasmids for GFP, IRE1α WT, dominant-negative mutant of IRE1α, the RNase dead mutant K907A in J774 cells using Lipofectamine™ 2000. Plasmids for IRE1α were obtained from Addgene (Fumihiko Urano: plasmids #20744 and #20745).

Example 12

Experimental Procedures for Examples 13-15

Mice. All studies were performed according to the guidelines of the Canadian Council on Animal Care and were approved by the Animal Care Committee of the University of Montreal. C57131/6 wildtype mice, LysM-Cre mice (B6.129P2-Lyz2$^{tm1(cre)/fo}$/J; no.004781), and Neuropilin-1 floxed mice (B6.129(SJL)-NRP1$^{tm2Ddg}$/J; no. 005247), were purchased from The Jackson Laboratory and bred in house. Diets: HFD: 60% fat calories, BioSery F3282; control feed: 2018 Teklad Global 18% protein rodent diet.

Fluorescence-activated Cell Sorting (FACS) of adipose tissue macrophages Retroperitoneal fat pads were collected, weighted and homogenized in DMEM F12 medium then incubated with 1 mg/mL of collagenase D (Sigma) at 37° C. for 45 minutes. EDTA was then added at a concentration of 10 mM and the mix was incubated for an extra 5 minutes. Homogenates were then filtered with a 70-µm cell strainer and centrifuged. Pellets were resuspended and incubated in lysis buffer (10 mM KCHO$_3$; 150 mM; NH$_4$Cl; 0.1 mM EDTA) for 5 minutes at room temperature and centrifuged. Pellets were resuspended in 1×PBS and filtered with a 100-µm cell strainer. Cell suspensions were incubated with Zombie Aqua Fixable Viability Kit (BioLegend) for 15 minutes at room temperature. Cells were then incubated with LEAF purified anti-mouse CD16/32 (Biolegend) for 15 minutes at room temperature to block Fc receptors. Cells were then incubated for 25 minutes at 4° C. with the following antibodies: Brilliant Violet 785 anti-mouse CD45.2 (BioLegend), Brilliant Violet 711 anti-mouse/human CD11b (BioLegend), APC/CY7 anti-mouse Ly-6G (BioLegend), Pe/Cy7 anti-mouse F4/80 (BioLegend), PE antimouse CD11c (BioLegend), FITC anti-mouse Ly-6C (BioLegend) and APC anti-mouse CD304 (Neuropilin-1) or APC Rat IgG2a, κ Isotype Ctrl (BioLegend). For analysis of CD206 expression, permeabilisation and fixation of the cells was done using the Cytofix/Cytoperm kit (BD Bioscience) at 4° C. for 20 minutes. Cells were then incubated with Rat serum (Cedarlane) for 25 minutes at 4° C. in order to block intracellular receptors. Cells were finally stained with Brilliant Violet 421 anti-mouse CD206 (MMR) (BioLegend) for 25 minutes at 4° C. FACS was performed on a Fortessa (BD Biosciences) device, and data were analyzed using FlowJo software (version 7.6.5).

In vivo BODIPY uptake. In vivo BODIPY intake assays were performed on LysM-Cre-NRP1$^{+/+}$ and LysM-Cre-NRP1$^{fl/fl}$ male mice fed with HFD for 10 weeks. Mice were starved for four hours before administrating an intraperitoneal injection of 100 µL of 30 µM BODIPY™ 500/510 C1, C12 in 1% BSA. Mice were euthanized 3 hours following BODIPY™ injection. The blood was collected by cardiac puncture, and the plasma was subsequently separated by centrifugation. Samples of heart, liver and white adipose tissue were collected and homogenized in 1×RIPA buffer (Cell Signaling). BODIPY™ fluorescence of homogenates and plasma was read with Infinite M1000 Pro reader (Tecan) at a wavelength emission of 488 nm and excitation at 525 nm and normalized to protein concentration (quantified with QuantiPro™ BCA assay kit from Sigma).

Primary macrophages culture 8-12 week old LysM-Cre-NRP1$^{+/+}$ and LysM-Cre-NRP1$^{fl/fl}$ mice were anesthetized with 2% isoflurane in 2 L/min oxygen and then euthanized by cervical dislocation. Then, a small incision in abdominal skin of mouse was performed. Skin was pulled to each size of the mouse and peritoneal cavity was washed with 5 ml of PBS plus 3% FBS for 2 min. Then, the harvested cells were centrifuged for 5 min at 1000 rpm, resuspended in medium (DMEM F12 plus 10% FBS and 1% Streptomycin/Penicillin) and plated. After 1 h of culture at 37° C. under a 5% CO$_2$ atmosphere the medium was changed and cells were cultured for the next 24 h in the same conditions before use in BODIPY uptake, pHrodo phagocytosis assay, or Oil Red-O staining.

Quantitative RT-PCR (qPCR) analysis. RNA extraction was performed with 100-500 mg of frozen (−80° C.) RP-WAT following the Trizol Reagent Protocol (Invitrogen). Total RNA (1 µg) was reverse transcribed according to the manufacturer's instructions (iScript cDNA synthesis kit, Bio-Rad). qPCR was performed using SYBR Green (Bio-Rad) and 40 ng cDNA per reaction (7500 Real-Time PCR System, Applied Biosystem). Expression levels were normalized to the expression of b-actin. Primers (Integrated DNA Technologies) sequences are listed as follows:

TABLE 10

Sequences of primers used for qRT-PCR

| Genes | Forward (5'→3') Sequence | SEQ ID NO: | Reverse (5'→3') Sequence | SEQ ID NO: |
|---|---|---|---|---|
| NRP1 | ACCCACATTTCG ATTTGGAG | 99 | TTCATAGCGGAT GGAAAACC | 100 |

TABLE 10-continued

Sequences of primers used for qRT-PCR

| Genes | Forward (5'→3') Sequence | SEQ ID NO: | Reverse (5'→3') Sequence | SEQ ID NO: |
|---|---|---|---|---|
| SEMA3a | GCTCCTGCTCCG TAGCCTGC | 101 | TCGGCGTTGCTT TCGGTCCC | 102 |
| SEMA3e | TCTGCAACCATC CA | 103 | ACCACAAGAGGG AAGCACAGAC | 104 |
| TGFb | GGACTCTCCACC TGCAAGAC | 105 | CATAGATGGCGT TGTTGCGG | 106 |
| VEGFa | GCCCTGAGTCAA GAGGACAG | 107 | CTCCTAGGCCCC TCAGAAGT | 108 |
| VEGFb | TCTGAGCATGGA ACTCATGG | 109 | TCTGCATTCACA TTGGCTGT | 110 |

ImmGen skyline dataset. Immunological Genome Project data Phase 1 (GEO accession code GSE15907) and phase 2 (GSE37448) were extracted and normalized in R by Robust Multi array Average (RMA), antiLog values were plotted.

Immunohistochemistry (IHC). RPWAT tissue was fixed in 4% PFA for 48 hours then incubated in 20% methanol for 10 minutes and rinsed in PBS. 1 hour blocking in 3% BSA (Hyclone, GE)+0.3% Triton™ X-100 (Sigma) preceded overnight incubation with Rhodamine-labeled *Griffonia (Bandeiraea) Simplicifolia* Lectin I (Vector Laboratories Inc.), anti-rat F4/80 (Donkey IgG; eBioscience), anti-rabbit Perilipin (Donkey IgG; Abcam), anti-rat Neuropilin-1 antibody, (Donkey IgG; R&D Systems) at 4° C. Alexa-Fluor secondary antibodies were incubated for two hours at 20° C. The RPWAT was then mounted onto a microscope slide and images were taken by confocal microscope.

Macrophage BODIPY intake. Macrophages extracted from LysMCRE-NRP1$^{+/+}$ and LysMCRE-NRP1$^{fl/fl}$ were seeded in 48 well plates at $1\times10^5$ cells/well. BODIPY 500/510 C1, C12 (Life technologies) was added at a concentration of 0.5 and 1 µg/mL, incubated at room temperature for five minutes, then put on ice. Wells were washed with cold PBS then fixed with 1% paraformaldehyde (Electron Microscopy Science). Fluorescence was read with an Infinite M1000 Pro reader (Tecan) at a wavelength emission of 488 nm and 525 nm excitation. Cells were then stained with DAPI (Life Technologies) at a concentration of 1/20000 and fluorescence measured at 358 nm excitation, 461 nm emission.

pHrodo phagocytosis assay. Macrophages extracted from LysMCRE-NRP1$^{+/+}$ and LysMCRE-NRP1$^{fl/fl}$ were seeded in 96 well plates at $1\times10^5$ cells/well. pHrodo® Green Zymosan Bioparticles Conjugate® (Life Technologies) was resuspended at a concentration of 0.5 mg/mL in FluoroBrite™ DMEM Media+10% FBS+1% PenStrep. 100 µL of the bioparticle resuspension was added to the cells and empty wells as a negative control. Cells were incubated 90 minutes at 37° C., and pH/phagocytosis-dependent fluorescence was detected on a TECAN plate reader at 509 nm excitation and 533 nm emission. Net phagocytosis was calculated by subtracting negative control fluorescence from that of the experimental samples.

Oil Red-O staining and quantification. Cultured adipocytes and peritoneal macrophages were washed in PBS and fixed in 10% PFA for 30 minutes and rinsed. Cells were then incubated for 60 minutes with twice filtered 0.3% Oil Red-O solution and rinsed. Pictures were taken under light microscopy at a 10× magnification for the adipocytes and 63× for the macrophages. Lipid droplet quantification was performed using the Limit of threshold method from ImageJ.

Weight gain in presence of adeno Trap M protocol. C57Bl6/J mice at 6-8 weeks of age were separated in 6 groups (Regular diet+Saline, Regular diet+adeno Trap M, Regular diet+adeno GFP, High fat diet+Saline, High fat diet+adeno Trap M, High fat diet+adeno GFP). Mice were intravenously injected (tail vein) with saline, Adeno-Trap M or Adeno GFP ($0.25\times10^{10}$ PFU/injection). Half of these mice were fed a high fat diet and the other half a regular diet and weighed at weekly intervals.

Figure 26:
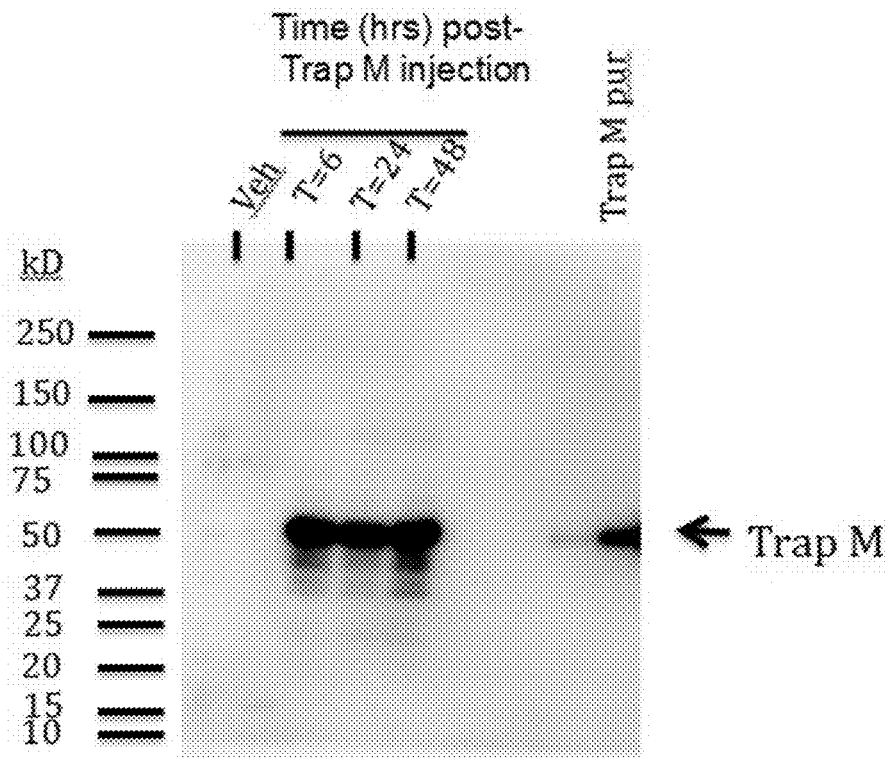
FIG. 26 shows analysis of pharmacodynamic properties of Trap M following systemic injection. C57l316 mice (aged 6-8 weeks) were intravenously tail vein injected with purified Traps M (0.5 mg/kg dose), and serum samples were collected 6, 24 and 48 hrs post injection. Traps M captured from approximatively 75 ul serum using IMAC sepharose was detected by immunoblotting with an anti-human NRP1 (cubAI domain)
Figure 27:
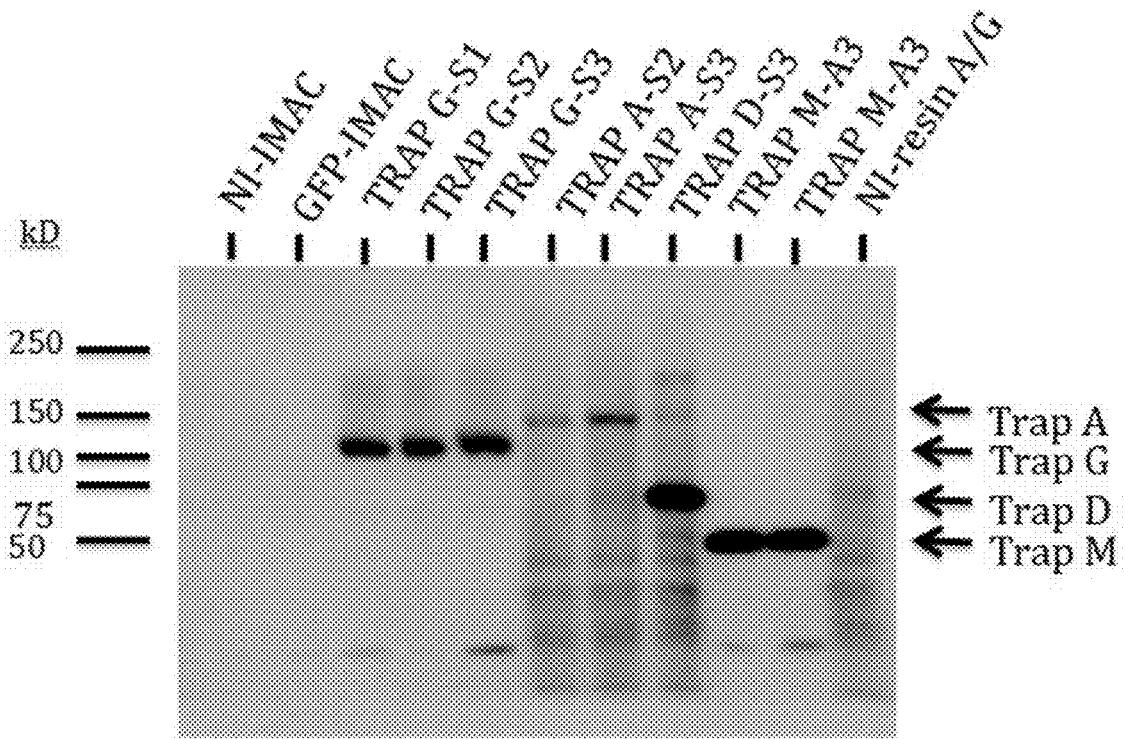
FIG. 27 shows Cos cell expression of traps G, A, D and M following transduction with adenovirus stocks. Cos cells were transduced with the indicated adenovirus stocks. Traps G and M were purified from transduced cells supernatants using IMAC sepharose while Traps A and D were enriched using protein A/G sepharose. Traps were detected by immunoblotting with an anti-human NRP1 (cubAI domain). Legends: NI) supernatant from non-infected Cos cells, GFP supernatant from Adeno-Green fluorescent protein (GFP) infected Cos cells S1) Lipofectamine™ 2000 transfection adenovirus stock, S2) Effectene transfection adenovirus stock, S3) PEI transfection adenovirus stock, A2) Adenovirus stock amplification round 2, A3) Adenovirus stock amplification round 3. Where specifies purification were done with IMAC sepharose (IMAC) or Protein A/G sepharose (A/G)
Figure 28:
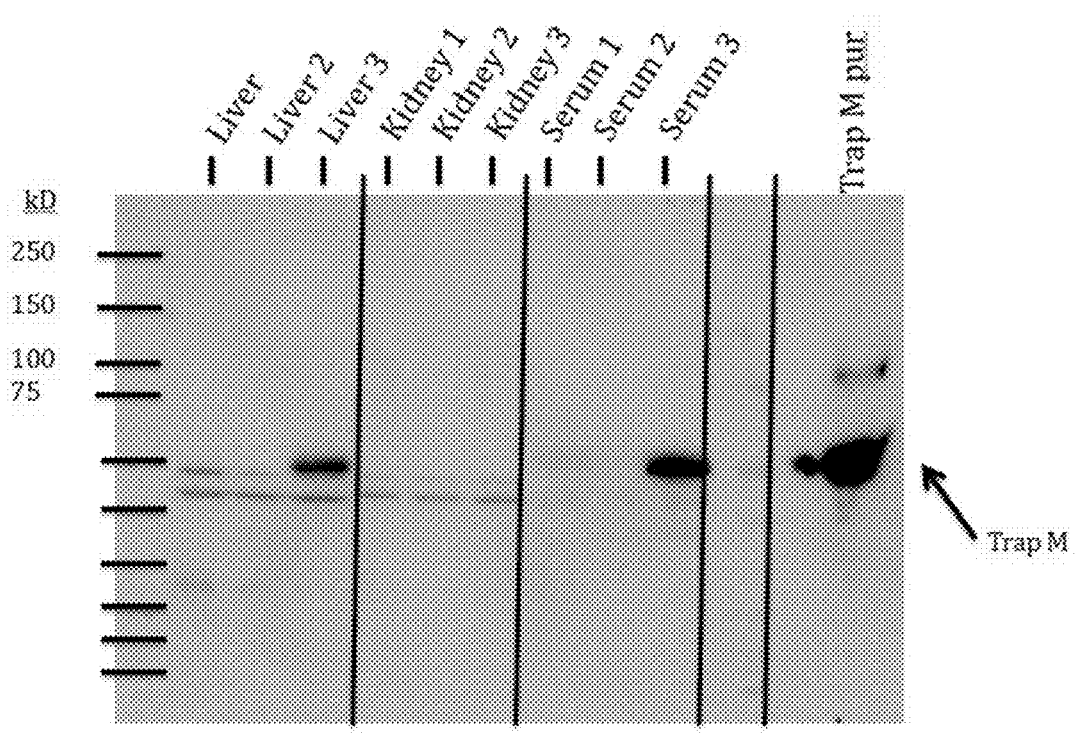
FIG. 28 shows analysis of the pharmacological distribution of Trap M following systemic infection with the Adeno-virus-Trap M construct. C57l316 mice (aged 6-8 weeks) were intravenously tail vein injected with adenovirus-Trap M or control adenovirus-GFP stocks. Mice were sacrificed 2 weeks post infection and serum, kidneys and liver tissues were collected and stored at −80° C. until analysis. Trap M was captured from serum (approximatively 75 ul) or tissues lysates from kidney or liver (approximatively 40 mg) lysed in PBS/2% triton x-100 using IMAC sepharose and was detected by immunoblotting with an anti-human NRP1 (cubAI domain). Legend; 1) Non-infected mice, 2) Adeno-GFP infected mice and 3) Adeno-Trap M infected mice.
Figure 29:
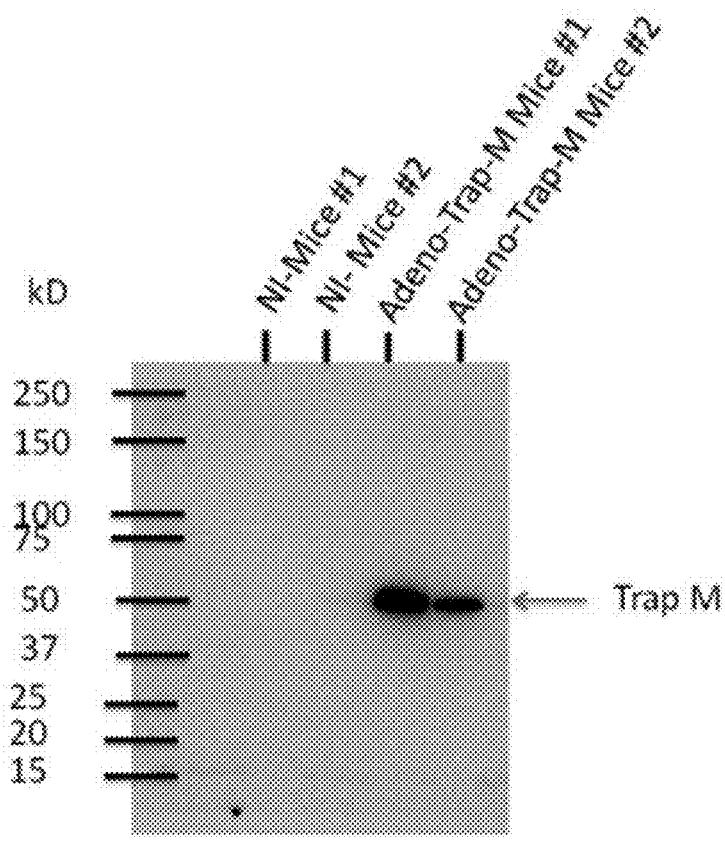
FIG. 29 shows the expression of trap M two weeks post adenovirus infection. Trap M was captured from blood (approximatively 25 ul) lysed in PBS 2% triton X-100 using IMAC sepharose and was detected by immunoblotting with an anti-human NRP1 (cubAI domain). Legend; NI: Non-infected mice.

Two and eight weeks after injections, a drop of blood was taken from the tail. The presence of Trap M was assessed in the blood by immunoprecipitation using an anti-His antibody (see FIGS. 26, 28 and 29).

Figure 25A:
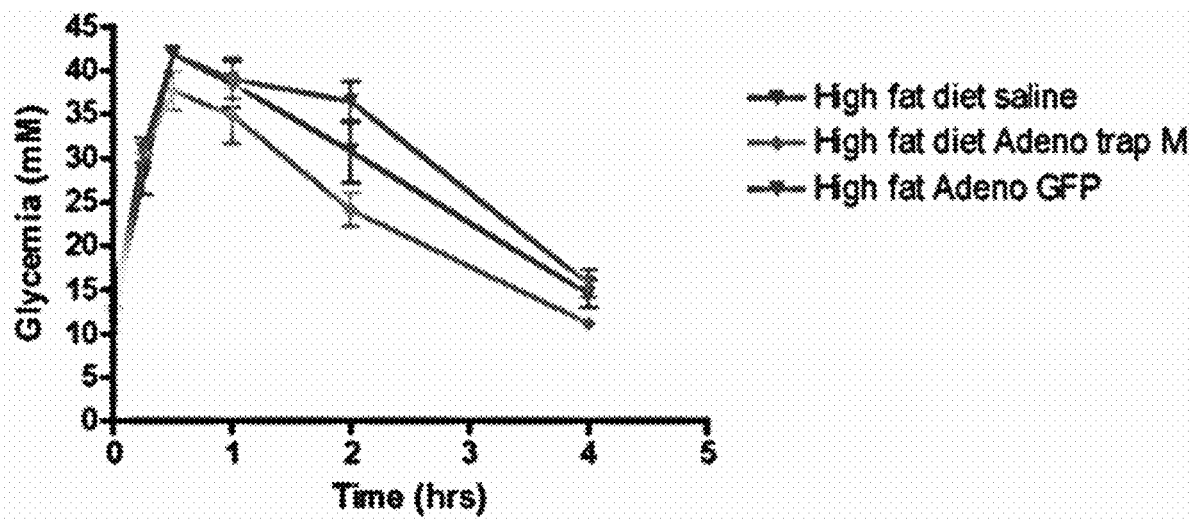
FIGS. 25A-B show Glucose tolerance test in mice expressing Trap M.

Glucose Tolerance Test (GTT). C57Bl6/J mice at 6-8 weeks of age were intravenously injected with saline or Adeno-Trap M ($0.25\times10^{10}$ PFU/injection). Mice were fed a high fat diet right after injection. Glycemia was assessed at baseline, 15, 30, 60, 120 and 240 minutes following intraperitoneal injection of 2 g of D-glucose/kg. Measurements recorded are shown in FIG. 25 (N=5, and N.S means not significant in Two-way Anova Bonferroni posttest).

Insulin Tolerance Test (ITT). Mice were starved 5.5 hours (in the morning). Blood glucose was measured at baseline, 30, 60 and 120 minutes following intraperitoneal injection of 0.75 U/kg of insulin.

In vivo BODIPY™ uptake. In vivo BODIPY™ intake assays were performed on LysM-Cre-NRP1+/+ and LysM-Cre-NRP1fl/fl male mice fed with HFD for 10 weeks. Mice were starved for four hours before administrating an intraperitoneal injection of 100 µL of 30 µM BODIPY 500/510 C1, C12 (Life technologies) in 1% BSA (Hyclone, GE). Mice were euthanized 3 hours following BODIPY injection. The blood was collected by cardiac puncture, and the plasma was subsequently separated by centrifugation. Samples of heart, liver and white adipose tissue were collected and homogenized in 1×RIPA buffer (Cell Signaling). BODIPY fluorescence of homogenates and plasma was read with Infinite M1000 Pro reader (TECAN) at a wavelength emission of 488 nm and excitation at 525 nm and normalized to protein concentration (quantified with QuantiPro™ BCA assay kit from Sigma).

Oil Red O stain and quantification. Cultured adipocytes and peritoneal macrophages were washed in PBS and fixed in 10% PFA for 30 minutes and rinsed. Cells were then incubated for 60 minutes with twice filtered 0.3% Oil Red-O (Sigma) solution and rinsed. Pictures were taken under light microscopy at a 10× magnification for the adipocytes and 63× for the macrophages. Lipid droplet quantification was performed using the limit of threshold method from ImageJ.

Adenovirus production. Traps AD and AE were derived from Trap M and O (previously described WO2016/033699) by introduction of the VEGF165 binding mutant residue D320K using the Q5 site directed mutagenesis kit (New England Biolabs). Adenovirus trap constructs were generated by first sub-cloning the coding sequences of Traps M, G, A and D into the EcoRI-EcoRV site of pENTR1A (Life technologies) followed by LR clonase homologous recombination in the destination vector pAd/CMV/V5-DEST (Life technologies). The current set of constructs are referred to as pAdeno-Trap A, C, G or M and pAdeno-GFP. All constructs insert sequences were verified by Sanger sequencing (Genome Quebec). All junction regions generated after trap coding sequence recombination into pAD/CMV/V5-dest were sequenced as well.

Statistical analyses. Data are presented as mean±SEM. A 2-tailed Student's t test and ANOVA were used, where appropriate, to compare the different groups. P<0.05 was considered statistically different.

Example 13

NRP1-Expressing Macrophages Accumulate in Adipose Tissue During Diet-Induced Obesity Upon Diet-induced obesity (D10), necrotic adipocytes release Fatty acids (FA) are partially taken up by surrounding macrophages forming crown-like structures. In view of the importance of macrophages in lipid metabolism and obesity, the expression profiles of NRP1 in myeloid cells were analyzed using data from the immunological consortium ImmGen (Heng and Painter, 2008). Expression of NRP1 was most robust in adipose tissue macrophages (ATMs) compared to other steady state tissue-resident macrophages, monocytes and neutrophils (FIG. 21A). This data pointed to a potential role of NRP1+ macrophages in adipose tissue homeostasis.

Figure 21D:
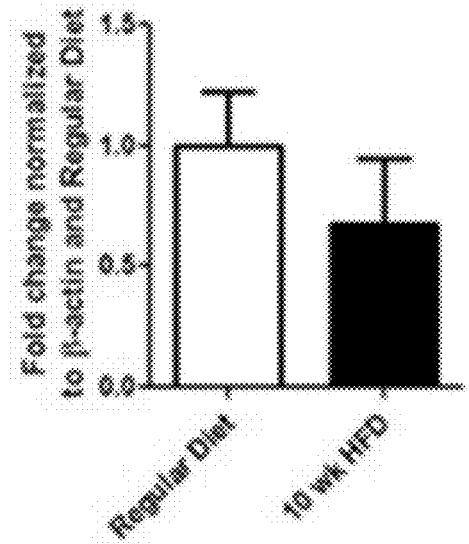
Figure 21E:
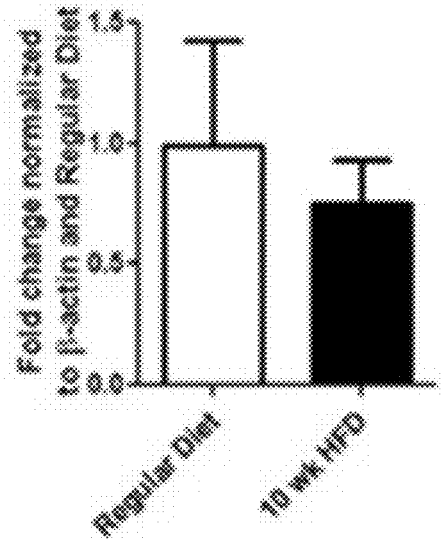
Figure 21F:
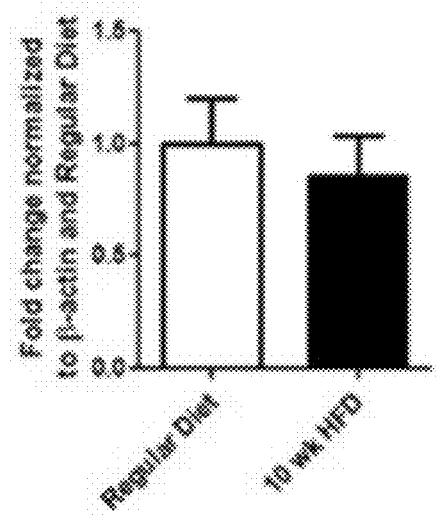
Figure 21G:
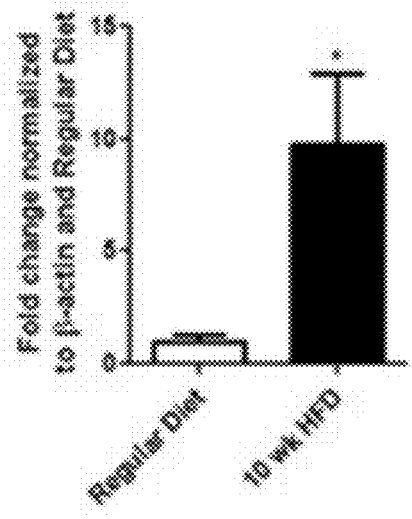

Therefore C57BL/6 mice were placed on high fat diet (HFD; 60% fat calories) for 10 weeks starting at 8 weeks of life and ATM populations were investigated by Fluorescence-activated Cell Sorting (FACS). In accordance with other studies, an increased presence of ATMs was detected in adipose tissue of HFD-fed mice when compared to age matched controls on regular diet (RD; 18% fat calories) (FIG. 21B). This was paralleled by a proportionate increase in NRP1+ ATMs (FIG. 21C). Immunohistochemistry (IHC) of retroperitoneal white adipose tissue (RPWAT) from both 10 week HFD-fed mice and age matched RD mice confirmed robust expression of NRP1 on macrophages and vessels (data not shown). After 22 weeks of HFD, NRP1 localized to crown-like structures, which correspond to clusters of phagocytic macrophages surrounding dying and dead adipocytes (data not shown). Of the NRP1 ligands investigated, only Transforming Growth Factor Beta 1 (Tgfb1) rose significantly in the retroperitoneal white adipose tissue (RPWAT) of HFD-fed mice (FIG. 21G), while Semaphorin-3A (Sema3a), Vascular Endothelial Growth Factor-A (Vegfa) or -B (Vegfb) were unaffected (FIGS. 21D-F). Together, these data demonstrate robust expression of NRP1 in ATMs and suggest accretion of NRP1+ macrophages in adipose tissue during HFD-induced weight gain.

Example 14

NRP1 Promotes Fatty Acid Uptake and Phagocytosis by Macrophages

Figure 22A:
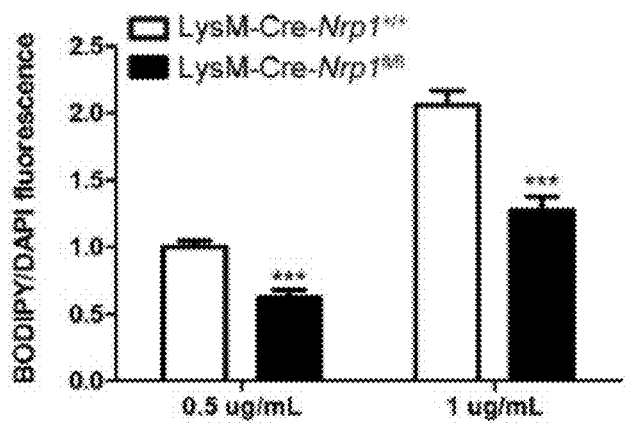
Figure 22B:
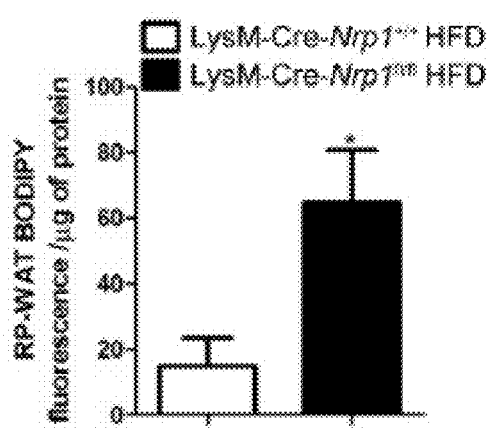
Figure 22C:
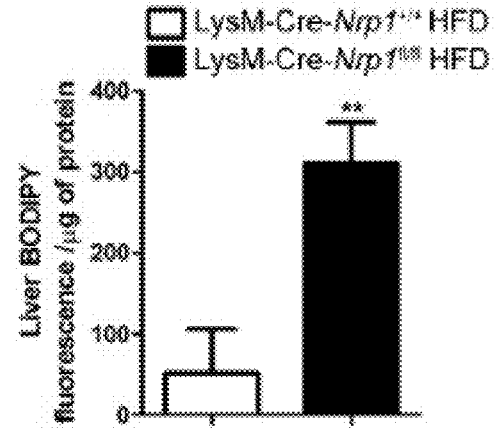
Figure 22D:
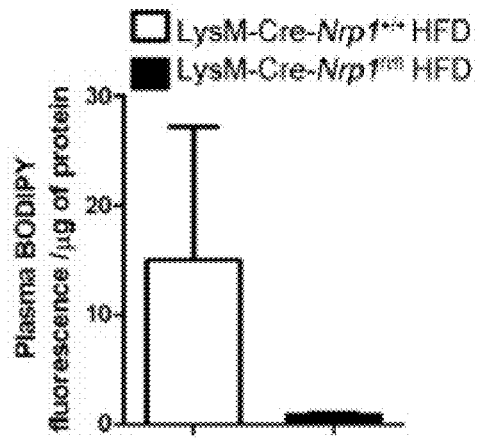
Figure 22E:
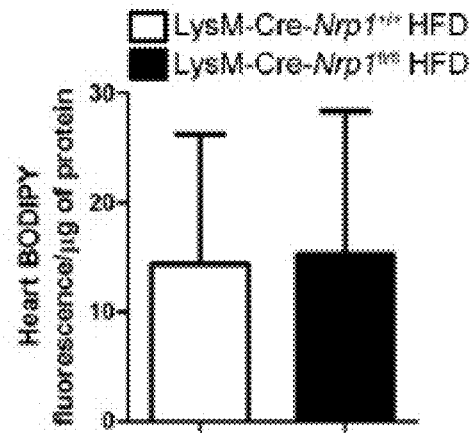

In obesity, long chain Fatty acid (FA) uptake is upregulated in adipocytes (Berk et al., 1999; Petrescu et al., 2005). To elucidate the role of NRP1$^+$ macrophages in adipose tissue homeostasis and weight gain, a LysM-CRE-NRP1$^{fl/fl}$ mouse line was generated with NRP1 specifically ablated in cells of myeloid lineage (Dejda et al., 2014). The uptake of a long chain FA analogue (C1-BODIPY-C12, an 18-carbon FA) was therefore measured in LysM-Cre-NRP1$^{fl/fl}$ and control LysM-Cre-NRP1$^{+/+}$ macrophages. NRP1-deficient macrophages took up significantly less FAs than control macrophages during acute exposure (FIG. 22A). In addition, systemic administration of C1-C12 BODIPY revealed significantly elevated levels of the tagged FAs in RPWAT and liver of LysM-Cre-NRP1$^{fl/fl}$ mice (FIGS. 22 B, C) when compared to plasma and heart (FIGS. 22 D, E) solidifying the role of NRP1$^+$ macrophages in lipid uptake.

To determine if NRP1 affected lipid sequestering in macrophages, neutral lipids within macrophages were stained with Oil Red O. Oil Red O stain was significantly reduced in LysM-Cre-NRP1$^{fl/fl}$ macrophages incubated in adipocyte-conditioned medium (FIGS. 22F-G). Because adipocyte and macrophage media differ in glucose and insulin concentration, we assessed if the decrease in internalized lipids in NRP1-deficient macrophages also occurred in non-conditioned media, including adipocyte medium with and without insulin, as well as macrophage medium. In all conditions, NRP1$^-$ macrophages sequestered significantly fewer neutral lipids than controls (FIGS. 22 H-K).

Figure 23:
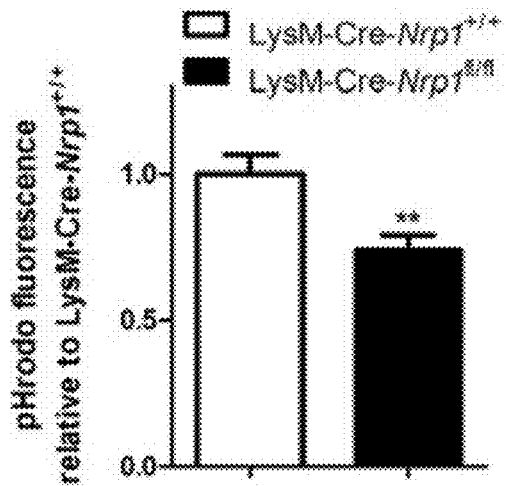
FIG. 23 shows that macrophages lacking NRP1 have a decreased phagocytic capacity. Phagocytosis was measured with the pHrodo green zymosan bioparticles conjugate in LysM-Cre-NRP1$^{fl/fl}$ and control macrophages. pHrodo fluorescence was detected in control and LysM-Cre-NRP1$^{fl/fl}$ macrophages (n=8 per group). Data represented as mean±S.E.M. Student's unpaired t-test, **p<0.01.

As adipocyte death increases in obese mice and humans, it lures macrophages to necrotic sites in order to phagocytose cellular debris and sequester released lipids (Cinti et al., 2005). Having observed reduced lipid uptake in NRP1 deficient macrophages, we questioned whether their phagocytic capacities were also compromised. Phagocytosis was measured with the pHrodo green zymosan bioparticles conjugate in LysM-Cre-NRP1$^{fl/fl}$ and control macrophages, and found that macrophages lacking NRP1 had a decreased phagocytic capacity (FIG. 23).

In summary, the above results demonstrate that NRP1 deficient macrophages have impaired FA uptake and phagocytic capacity.

Example 15

NRP1 Trap Reduces Weight Gain Associated with High Fat Diet

The effect of an NRP1 trap on weight gain was assessed. An adeno virus expressing a soluble NRP1 trap comprising domains a1, a2 and b1 of NRP1 (Trap M, see Table 2); Adeno GFP; or saline (control) was administered to male mice and at the same time mice were switched from a regular diet to a high fat diet (HFD, T0). Weight gain was monitored over a period of 10 weeks. Data are presented as mean±SEM. Student's unpaired t-test, *p<0.05, **p<0.01, Saline vs Adeno Trap M, Two-way Anova, Bonferroni posttest, wherein N=5.

Figure 24:
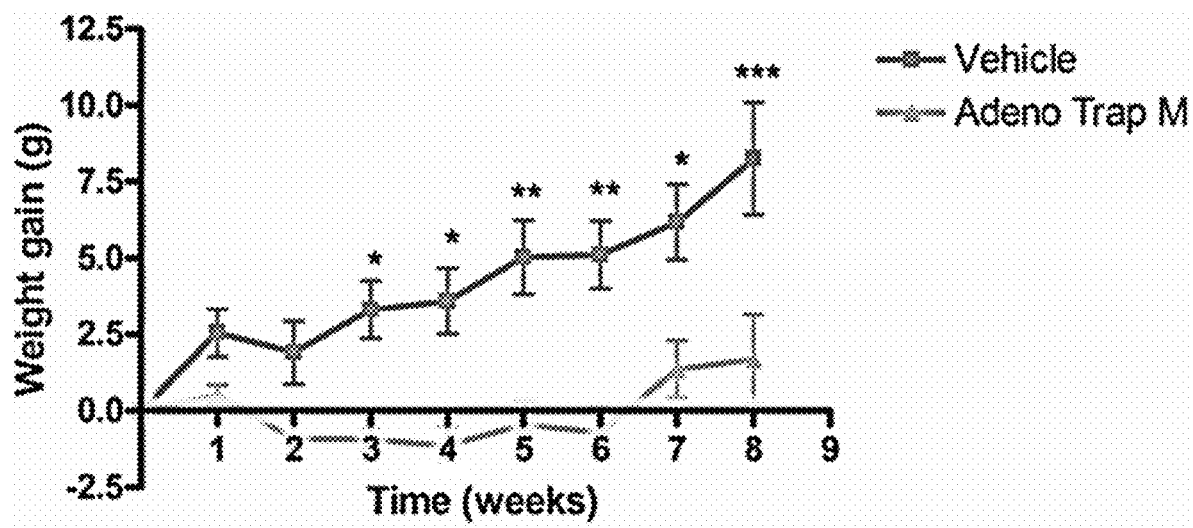
FIG. 24 shows that NRP1 polypeptide trap prevents weight gain in mice fed a high fat diet (see Example 4). The effect of an NRP1 trap on weight gain was assessed. An adeno virus expressing a soluble NRP1 trap comprising domains a1, a2 and b1 of NRP1 (Trap M, FIG. 9A); Adeno GFP; or saline (control) was administered to male mice and at the same time mice were switched from a regular diet to a high fat diet (HFD, TO). Weight gain was monitored over a period of 10 weeks. Data are presented as mean±SEM. Student's unpaired t-test, *$p<0.05$, **$p<0.01$, Saline vs Adeno Trap M, Two-way Anova, Bonferroni posttest, wherein N=5.

As shown in FIG. 24, administration of NRP1 prevented weight gain in mice. The increase in weight gain observed at weeks 7 and 8 coincides with a decrease in circulating adenovirus expressing NRP1-trap. Surprisingly, prevention of weight gain was more important in male mice than in female mice (data not shown).

Figure 25B:
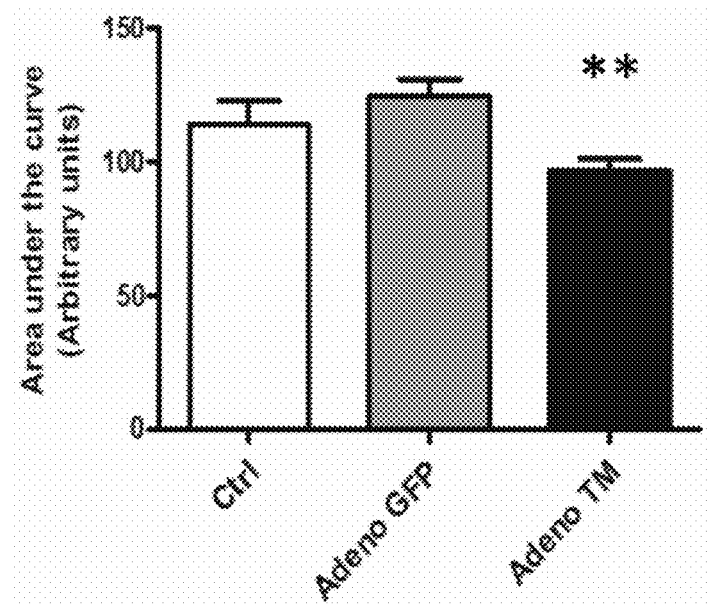

The effect of NRP1 traps on glucose tolerance was also assessed. Six to height (6-8) weeks old C57B16/J mice were intravenously injected with saline, Adeno GFP or Adeno Trap M and fed a high fat diet right after injection. Glycemia was assessed at different time-points after intraperitoneal injection of 2 g of glucose/kg mice. As shown in FIG. 25B mice treated with Adeno Trap M were more tolerant to glucose than mice treated with saline or Adeno GFP.

TABLE 11

SEQ ID NOs. of sequences disclosed herein

| SEQ ID NO: | DNA/PRT | Description |
| --- | --- | --- |
| 1-32 | DNA | Oligos listed in Table 6 |
| 33-43 | DNA | shRNAs target sequence listed in Table 9 |
| 44-46 | PRT | Human soluble Neuropilin-1 (NRP1) protein sequences shoen in FIG. 19 and described in Table 2 |
| 47 | PRT | Consensus sequence (variant) derived from alignment of FIG. 17 and known variants. |
| 48 | PRT | Mouse NRP1 precursor FIG. 17 |
| 49 | PRT | Rat NRP1 precursor FIG. 17 |
| 50 | PRT | Human Sema3A precursor protein shown in FIG. 16 |
| 51, 53, 55, 57, 59, 61, 63, 65, 67, 69, 71, 73, 75, 77, 79, 81, 83, 85, 87, 89, 91 and 93 | DNA | Traps AD, AE, AF, AG, AJ, AK, AR, AS, G, R, Z, AB, AC, O, Q, M, P, N, W, X, Y and S (see Table 2)-Includes signal peptide |
| 52, 54, 56, 58, 60, 62, 64, 66, 68, 70, 72, 74, 76, 78, 80, 82, 84, 86, 88, 90, 92 and 94 | PRT | Traps AD, AE, AF, AG, AJ, AK, AR, AS, G, R, Z, AB, AC, O, Q, M, P, N, W, X, Y and S (see Table 2) |
| 95 | PRT1 | Human NRP1 isoform 1, full length (cellular form) |
| 96 | PRT1 | NRP1 functional variant (Origen sequence), full length (cellular form) |
| 97-98 | PRT1 | Exemplary peptide sequences recognized by TEV protease |
| 99-110 | DNA | qRT-PCR primers set forth in Table 10 |

The scope of the claims should not be limited by the preferred embodiments set forth in the examples, but should be given the broadest interpretation consistent with the description as a whole.

REFERENCES

1. P. Sapieha et al., Proliferative retinopathies: angiogenesis that blinds. Int J Biochem Cell Biol 42, 5-12 (2010).
2. L. P. Aiello et al., Suppression of retinal neovascularization in vivo by inhibition of vascular endothelial growth factor (VEGF) using soluble VEGF-receptor chimeric proteins. Proc Natl Acad Sci USA 92, 10457-10461 (1995).
3. L. Aiello, Perspectives on diabetic retinopathy. American journal of ophthalmology 136, 122-135 (2003).
4. M. E. Hartnett, J. Penn, Mechanisms and management of retinopathy of prematurity. The New England Journal of Medicine 367, 2515-2526 (2012).
5. A. Hellström, L. E. H. Smith, O. Dammann, Retinopathy of prematurity. The Lancet—British Edition 382, 1445-1457 (2013).
6. J. H. Kempen et al., The prevalence of diabetic retinopathy among adults in the United States. Arch Ophthalmol 122, 552-563 (2004).
7. D. A. Antonetti, R. Klein, T. W. Gardner, Diabetic retinopathy. N Engl J Med 366, 1227-1239 (2012).
8. H. Sakai, Y. Tani, E. Shirasawa, Y. Shirao, K. Kawasaki, Development of electroretinographic alterations in streptozotocin-induced diabetes in rats. Ophthalmic Res 27, 57-63 (1995).
9. H. A. Hancock, T. W. Kraft, Oscillatory potential analysis and ERGs of normal and diabetic rats. Invest Ophthalmol Vis Sci 45, 1002-1008 (2004).
10. K. Shinoda et al., Early electroretinographic features of streptozotocin-induced diabetic retinopathy. Clin Experiment Ophthalmol 35, 847-854 (2007).
11. A. J. Barber et al., The Ins2Akita mouse as a model of early retinal complications in diabetes. Invest Ophthalmol Vis Sci 46, 2210-2218 (2005).
12. A. J. Barber et al., Neural apoptosis in the retina during experimental and human diabetes. Early onset and effect of insulin. J Clin Invest 102, 783-791 (1998).
13. M. J. Gastinger, A. R. Kunselman, E. E. Conboy, S. K. Bronson, A. J. Barber, Dendrite remodeling and other abnormalities in the retinal ganglion cells of Ins2 Akita diabetic mice. Invest Ophthalmol Vis Sci 49, 2635-2642 (2008).
14. V. Asnaghi, C. Gerhardinger, T. Hoehn, A. Adeboje, M. Lorenzi, A role for the polyol pathway in the early neuroretinal apoptosis and glial changes induced by diabetes in the rat. Diabetes 52, 506-511 (2003).
15. T. S. Kern, A. J. Barber, Retinal ganglion cells in diabetes. J Physiol 586, 4401-4408 (2008).
16. P. Sapieha et al., Omega-3 polyunsaturated fatty acids preserve retinal function in type 2 diabetic mice. Nutr Diabetes 2, e36 (2012).
17. D. Munoz-Espin et al., Programmed cell senescence during mammalian embryonic development. Cell 155, 1104-1118 (2013).
18. M. Storer et al., Senescence is a developmental mechanism that contributes to embryonic growth and patterning. Cell 155, 1119-1130 (2013).
19. D. Munoz-Espin, M. Serrano, Cellular senescence: from physiology to pathology. Nat Rev Mol Cell Biol 15, 482-496 (2014).
20. M. Demaria et al., An essential role for senescent cells in optimal wound healing through secretion of PDGF-AA. Dev Cell 31, 722-733 (2014).
21. D. J. Baker et al., Naturally occurring p16(Ink4a)-positive cells shorten healthy lifespan. Nature 530, 184-189 (2016).
22. D. J. Baker et al., Clearance of p16Ink4a-positive senescent cells delays ageing-associated disorders. Nature 479, 232-236 (2011).
23. B. G. Childs, M. Durk, D. J. Baker, J. M. van Deursen, Cellular senescence in aging and age-related disease: from mechanisms to therapy. Nat Med 21, 1424-1435 (2015).

24. O. Moiseeva et al., Metformin inhibits the senescence-associated secretory phenotype by interfering with IKK/NF-κB activation. Aging cell 12, 489-498 (2013).
25. L. E. Smith et al., Oxygen-induced retinopathy in the mouse. Invest Ophthalmol Vis Sci 35, 101-111 (1994).
26. J. Acosta et al., A complex secretory program orchestrated by the inflammasome controls paracrine senescence. Nature Cell Biology 15, 978-990 (2013).
27. J. Campisi, F. d'Adda di Fagagna, Cellular senescence: when bad things happen to good cells. Nat Rev Mol Cell Biol 8, 729-740 (2007).
28. Y. Okuno, A. Nakamura-Ishizu, K. Otsu, T. Suda, Y. Kubota, Pathological neoangiogenesis depends on oxidative stress regulation by ATM. Nat Med 18, 1208-1216 (2012).
29. C. Denoyelle et al., Anti-oncogenic role of the endoplasmic reticulum differentially activated by mutations in the MAPK pathway. Nat Cell Biol 8, 1053-1063 (2006).
30. A. Stahl et al., Postnatal Weight Gain Modifies Severity and Functional Outcome of Oxygen-Induced Proliferative Retinopathy. Am J Pathol.
31. A. Dorfman, O. Dembinska, S. Chemtob, P. Lachapelle, Early manifestations of postnatal hyperoxia on the retinal structure and function of the neonatal rat. Invest Ophthalmol Vis Sci 49, 458-466 (2008).
32. P. Perez Mancera, A. R. J. Young, M. Narita, Inside and out: the activities of senescence in cancer. Nature Reviews. Cancer 14, 547-558 (2014).
33. F. Binet et al., Neuronal ER Stress Impedes Myeloid-Cell-Induced Vascular Regeneration through IRE1alpha Degradation of Netrin-1. Cell Metab 17, 353-371 (2013).
34. R. Cao et al., VEGFR1-mediated pericyte ablation links VEGF and PIGF to cancer-associated retinopathy. Proc Natl Acad Sci USA 107, 856-861 (2010).
35. J. Honek et al., Modulation of age-related insulin sensitivity by VEGF-dependent vascular plasticity in adipose tissues. Proc Natl Acad Sci USA 111, 14906-14911 (2014).
36. C. M. Beausejour et al., Reversal of human cellular senescence: roles of the p53 and p16 pathways. EMBO J 22, 4212-4222 (2003).
37. J.-P. Coppé, P.-Y. Desprez, A. Krtolica, J. Campisi, The senescence-associated secretory phenotype: the dark side of tumor suppression. Annual review of pathology 5, 99-118 (2010).
38. J. Acosta et al., Chemokine signaling via the CXCR2 receptor reinforces senescence. Cell 133, 1006-1018 (2008).
39. T. Kuilman et al., Oncogene-induced senescence relayed by an interleukin-dependent inflammatory network. Cell 133, 1019-1031 (2008).
40. N. Wajapeyee, R. Serra, X. Zhu, M. Mahalingam, M. Green, Oncogenic BRAF induces senescence and apoptosis through pathways mediated by the secreted protein IGFBP7. Cell 132, 363-374 (2008).
41. Y. Bai et al., Effects of semaphorin 3A on retinal pigment epithelial cell activity. Investigative ophthalmology & visual science 54, 6628-6638 (2013).
42. J.-S. Joyal et al., Ischemic neurons prevent vascular regeneration of neural tissue by secreting semaphorin 3A. Blood 117, 6024-6035 (2011).
43. P. Sapieha, Eyeing central neurons in vascular growth and reparative angiogenesis. Blood 120, 2182-2194 (2012).
44. A. F. Thompson, M. E. Crowe, C. J. Lieven, L. A. Levin, Induction of Neuronal Morphology in the 661W Cone Photoreceptor Cell Line with Staurosporine. PLoS One 10, e0145270 (2015).
45. A. Cerani et al., Neuron-derived semaphorin 3A is an early inducer of vascular permeability in diabetic retinopathy via neuropilin-1. Cell metabolism 18, 505-518 (2013).
46. F. Binet, P. Sapieha, ER Stress and Angiogenesis. Cell Metab, (2015).
47. I. Tabas, D. Ron, Integrating the mechanisms of apoptosis induced by endoplasmic reticulum stress. Nat Cell Biol 13, 184-190 (2011).
48. K. Zhang et al., The unfolded protein response transducer IRE1α prevents ER stress-induced hepatic steatosis. EMBO Journal 30, 1357-1375 (2011).
49. P. Sapieha et al., The succinate receptor GPR91 in neurons has a major role in retinal angiogenesis. Nat Med 14, 1067-1076 (2008).
50. Y. Wei et al., Nrf2 in ischemic neurons promotes retinal vascular regeneration through regulation of semaphorin 6A. Proceedings of the National Academy of Sciences of the United States of America 112, E6927-6936 (2015).
51. A. Dejda et al., Neuropilin-1 mediates myeloid cell chemoattraction and influences retinal neuroimmune crosstalk. Journal of Clinical Investigation 124, 4807-4822 (2014).
52. M. Schroder, R. J. Kaufman, The mammalian unfolded protein response. Annu Rev Biochem 74, 739-789 (2005).
53. P. Walter, D. Ron, The unfolded protein response: from stress pathway to homeostatic regulation. Science 334, 1081-1086 (2011).
54. J. Hollien, J. S. Weissman, Decay of Endoplasmic Reticulum-Localized mRNAs During the Unfolded Protein Response. Science 313, 104-107 (2006).
55. F. A. Mallette, M. F. Gaumont-Leclerc, G. Ferbeyre, The DNA damage signaling pathway is a critical mediator of oncogene-induced senescence. Genes Dev 21, 43-48 (2007).
56. O. Moiseeva, X. Deschênes Simard, M. Pollak, G. Ferbeyre, Metformin, aging and cancer. Aging 5, 330-331 (2013).
57. J. Holash et al., VEGF-Trap: a VEGF blocker with potent antitumor effects. Proc Natl Acad Sci USA 99, 11393-11398 (2002).
58. J. S. Heier et al., Intravitreal aflibercept (VEGF trap-eye) in wet age-related macular degeneration. Ophthalmology 119, 2537-2548 (2012).
59. M. Chopp, Z. G. Zhang, Q. Jiang, Neurogenesis, angiogenesis, and MRI indices of functional recovery from stroke. Stroke 38, 827-831 (2007).
60. L. Li et al., Angiogenesis and improved cerebral blood flow in the ischemic boundary area detected by MRI after administration of sildenafil to rats with embolic stroke. Brain Res 1132, 185-192 (2007).
61. L. Hayflick, P. S. Moorhead, The serial cultivation of human diploid cell strains. Exp Cell Res 25, 585-621 (1961).
62. M. M. Edwards et al., The deletion of MathS disrupts retinal blood vessel and glial development in mice. Exp Eye Res, (2011).
63. K. Okabe et al., Neurons limit angiogenesis by titrating VEGF in retina. Cell 159, 584-596 (2014).
64. Y. Usui et al., Neurovascular crosstalk between interneurons and capillaries is required for vision. J Clin Invest 125, 2335-2346 (2015).

65. C. D. Wiley, J. Campisi, From Ancient Pathways to Aging Cells-Connecting Metabolism and Cellular Senescence. Cell Metab 23, 1013-1021 (2016).
66. J. R. Dorr et al., Synthetic lethal metabolic targeting of cellular senescence in cancer therapy. Nature 501, 421-425 (2013).
67. J. P. Coppe, K. Kauser, J. Campisi, C. M. Beausejour, Secretion of vascular endothelial growth factor by primary human fibroblasts at senescence. J Biol Chem 281, 29568-29574 (2006).
68. F. Martinon, X. Chen, A. H. Lee, L. H. Glimcher, TLR activation of the transcription factor XBP1 regulates innate immune responses in macrophages. Nat Immunol 11, 411-418 (2010).
69. Q. Qiu et al., Toll-like receptor-mediated IRE1alpha activation as a therapeutic target for inflammatory arthritis. EMBO J 32, 2477-2490 (2013).
70. E. Check Hayden, Anti-ageing pill pushed as bona fide drug. Nature 522, 265-266 (2015).
71. B. E. Clausen, C. Burkhardt, W. Reith, R. Renkawitz, I. Forster, Conditional gene targeting in macrophages and granulocytes using LysMcre mice. Transgenic Res 8, 265-277 (1999).
72. P. Sapieha et al., Retinopathy of prematurity: understanding ischemic retinal vasculopathies at an extreme of life. J Clin Invest 120, 3022-3032 (2010).
73. A. Stahl et al., The mouse retina as an angiogenesis model. Invest Ophthalmol Vis Sci 51, 2813-2826 (2010).
74. A. Stahl et al., Computer-aided quantification of retinal neovascularization. Angiogenesis 12, 297-301 (2009).
75. G. P. Dimri et al., A biomarker that identifies senescent human cells in culture and in aging skin in vivo. Proc Natl Acad Sci USA 92, 9363-9367 (1995).
76. T. Dull et al., A third-generation lentivirus vector with a conditional packaging system. J Virol 72, 8463-8471 (1998).
77. M. Collado et al., Tumour biology: senescence in premalignant tumours. Nature 436, 642 (2005).
78. V. Krizhanovsky et al., Senescence of activated stellate cells limits liver fibrosis. Cell 134, 657-667 (2008).
79. Antipenko A et al. (2003) Structure of the semaphorin-3A receptor binding module. Neuron 39: 589-598.
80. Shirvan A. et al., (2002). Anti-semaphorin 3A Antibodies Rescue Retinal Ganglion Cells from Cell Death following Optic Nerve Axotomy. JBC 277 (51): 49799-49807.
81. Hasan et al. (2011) Inhibition of VEGF induces cellular senescence in colorectal cancer cells. Int. J. Cancer 1; 129(9):2115-2123.

The invention claimed is:

1. A method for treating a disease or condition associated with premature senescence of retinal neurons in a subject in need thereof comprising administering to the subject an effective amount of
   (i) a soluble Neuropilin-1 (NRP1) polypeptide that binds Semaphorin 3A (SEMA3A), wherein the soluble NRP1 polypeptide consists of an amino acid sequence having at least 95% identity with SEQ ID NO:82 and does not comprise the b2 and c domains of native human NRP1, or
   (ii) a fusion protein comprising a soluble NRP1 polypeptide consisting of an amino acid sequence having at least 95% identity with SEQ ID NO:82 and that does not comprise the b2 and c domains of native human NRP1, fused to a fragment crystallizable (Fc) domain, and wherein said disease or condition associated with premature senescence of retinal neurons is glaucoma.

2. The method of claim 1, wherein the soluble NRP1 polypeptide consists of the amino acid sequence of SEQ ID NO: 82.

3. The method of claim 1, wherein the soluble NRP1 polypeptide is fused to a fragment crystallizable (Fc) domain.

4. The method of claim 3, wherein the Fc domain is fused to the carboxy-terminal end of the soluble NRP1 polypeptide.

5. The method of claim 3, wherein the soluble NRP1 polypeptide and the Fc domain are fused via a linker.

6. The method of claim 1, wherein the senescence is paracrine senescence.

7. The method of claim 1, wherein the senescence is secondary to ischemia.

8. The method of claim 1, wherein the soluble NRP1 polypeptide or fusion protein is formulated in a pharmaceutical composition that further comprises one or more pharmaceutically acceptable excipients.

9. The method of claim 1, wherein the soluble NRP1 polypeptide or fusion protein is administered in the eye of the subject.

10. The method of claim 9, wherein the soluble NRP1 polypeptide or fusion protein is administered in the form of eye drops or ocular injections.

11. The method of claim 10, wherein the ocular injections are intravitreal injections.

12. The method of claim 3, wherein the Fc domain is fused to the amino-terminal end of the soluble NRP1 polypeptide.

* * * * *